United States Patent
Wang

(10) Patent No.: US 10,227,312 B2
(45) Date of Patent: Mar. 12, 2019

(54) GLUCOSYLCERAMIDE SYNTHASE INHIBITORS FOR THE TREATMENT OF DISEASES

(71) Applicant: BIOMARIN PHARMACEUTICAL INC., Novato, CA (US)

(72) Inventor: Bing Wang, San Jose, CA (US)

(73) Assignee: BIOMARIN PHARMACEUTICAL INC., Novato, CA (US)

(*) Notice: Subject to any disclaimer, the term of this patent is extended or adjusted under 35 U.S.C. 154(b) by 0 days.

(21) Appl. No.: 15/556,786

(22) PCT Filed: Mar. 10, 2016

(86) PCT No.: PCT/US2016/021706
§ 371 (c)(1),
(2) Date: Sep. 8, 2017

(87) PCT Pub. No.: WO2016/145153
PCT Pub. Date: Sep. 15, 2016

(65) Prior Publication Data
US 2018/0044302 A1    Feb. 15, 2018

Related U.S. Application Data

(60) Provisional application No. 62/131,703, filed on Mar. 11, 2015.

(51) Int. Cl.
| | |
|---|---|
| *C07D 265/02* | (2006.01) |
| *C07D 217/26* | (2006.01) |
| *C07D 311/76* | (2006.01) |
| *C07D 311/94* | (2006.01) |
| *C07D 409/04* | (2006.01) |
| *C07D 413/12* | (2006.01) |
| *C07D 495/04* | (2006.01) |
| *C07D 498/04* | (2006.01) |

(52) U.S. Cl.
CPC ......... *C07D 265/02* (2013.01); *C07D 217/26* (2013.01); *C07D 311/76* (2013.01); *C07D 409/04* (2013.01); *C07D 413/12* (2013.01); *C07D 495/04* (2013.01); *C07D 498/04* (2013.01)

(58) Field of Classification Search
CPC .. C07D 265/02; C07D 217/26; C07D 311/76; C07D 311/94
See application file for complete search history.

(56) References Cited

U.S. PATENT DOCUMENTS

2010/0256216 A1* 10/2010 Siegel ............... C07D 295/125
514/422

FOREIGN PATENT DOCUMENTS

| WO | WO 2009117150 A2 | 9/2009 |
|---|---|---|
| WO | WO 2010014554 A1 | 2/2010 |
| WO | WO 2010039256 A1 | 4/2010 |
| WO | WO 2015065937 A1 | 5/2015 |

OTHER PUBLICATIONS

Hajj et al., "Novel Mechanisms of Action of Classical Chemotherapeutic Agents on Sphigolipid Pathway," Biol. Chem., 2015, 396(6-7): 669-679, Feb. 20, 2015.

* cited by examiner

*Primary Examiner* — Laura L Stockton
(74) *Attorney, Agent, or Firm* — Jones Day

(57) ABSTRACT

Described herein are compounds of Formula I, methods of making such compounds, pharmaceutical compositions and medicaments containing such compounds, and methods of using such compounds to treat or prevent diseases or conditions associated with the enzyme glucosylceramide synthase (GCS).

18 Claims, No Drawings

GLUCOSYLCERAMIDE SYNTHASE INHIBITORS FOR THE TREATMENT OF DISEASES

CROSS REFERENCE

The present application is a U.S. National Stage filing under 35 U.S.C. § 371 of International Application No. PCT/US2016/021706, filed Mar. 10, 2016, which claims the benefit of priority of U.S. Provisional Application No. 62/131,703, filed Mar. 11, 2015, the contents of each of which applications are incorporated herein by reference in their entireties.

FIELD

Described herein are compounds, methods of making such compounds, pharmaceutical compositions and medicaments containing such compounds, and methods of using such compounds to treat or prevent diseases or conditions associated with the enzyme glucosylceramide synthase (GCS).

BACKGROUND

Glucosylceramide synthase (GCS) is a key enzyme which catalyzes the initial glycosylation step in the biosynthesis of glucosylceramide-based glycosphingolipids (GSLs) namely via the transfer of glucose from UDP-glucose (UDP-Glc) to ceramide to form glucosylceramide. GCS is a transmembrane, type III integral protein localized in the cis/medial golgi. Glycosphingolipids (GSLs) are believed to be integral in many cell membrane events, including cellular interactions, signaling, and trafficking. Synthesis of GSL structures has been shown (*Proc. Natl. Acad. Sci USA* 1999, 96(16), 9142-9147) to be essential for embryonic development and for the differentiation of some tissues. Ceramide plays a central role in sphingolipid metabolism, and downregulation of GCS activity has been shown to have marked effects on the sphingolipid pattern with diminished expression of glycosphingolipids. Sphingolipids have a role in physiological as well as pathological cardiovascular conditions. In particular, sphingolipids and their regulating enzymes appear to play a role in adaptive responses to chronic hypoxia in the neonatal rat heart (*Prostaglandins & Other Lipid Mediators* 2005, 78(1-4), 249-263).

GCS inhibitors have been proposed for the treatment of a variety of diseases (see, for example, WO2005068426). Such diseases include glycolipid storage diseases (e.g., Tay Sachs, Sandhoffs, GM1 gangliosidosis, Niemanns-Pick, and Fabry diseases), diseases associated with glycolipid accumulation (e.g., Gaucher disease), diseases that cause renal hypertrophy or hyperplasia such as diabetic nephropathy, diseases that cause hyperglycemia or hyperinsulinemia, cancers in which glycolipid synthesis is abnormal, infectious diseases caused by organisms which use cell surface glycolipids as receptors, infectious diseases in which synthesis of glucosylceramide is essential or important, diseases in which excessive glycolipid synthesis occurs (e.g., atherosclerosis, polycystic kidney disease, and renal hypertrophy), neuronal disorders, neuronal injury, inflammatory diseases or disorders associated with macrophage recruitment and activation (e.g., rheumatoid arthritis, Crohn's disease, asthma and sepsis), pain (see WO2008011483—neuropathic pain, inflammatory pain, headache pain, somatic pain, visceral pain, referred pain), cognitive disorders (see WO2008/109286—agnosia; amnesia; aphasia; an apraxia; delirium; dementia including AIDS dementia complex, Binswanger's disease, dementia with Lewy Bodies, frontotemporal dementia, mild cognitive impairment, multi-infarct dementia, Pick's disease, semantic dementia, senile dementia, and vascular dementia; and learning disorders including Asperger's syndrome, attention deficit disorder, attention deficit hyperactivity disorder, autism, childhood disintegrative disorder, and Rett syndrome), neurodegenerative disorders (such as Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, and senile dementia (Alzheimer type), glomerular disease, and diabetes mellitus and obesity (see WO 2006053043)). Renal hypertrophy induced by diabetes is associated with enhanced synthesis of glycosphingolipids such as glucosylceramide and ganglioside $GM_3$, which accumulate in the kidney of rats (*J. Clin. Invest.* 1993, 91(3), 797).

It has been shown that overexpression of GCS is implicated in multi-drug resistance and disrupts ceramide-induced apoptosis. For example, Turzanski et al. (*Experimental Hematology* 2005, 33(1), 62-72) have shown that ceramide induces apoptosis in acute myeloid leukemia (AML) cells and that P-glycoprotein (p-gp) confers resistance to ceramide-induced apoptosis, with modulation of the ceramide-glucosylceramide pathway making a marked contribution to this resistance in TF-I cells. Thus, GCS inhibitors can be useful for treatment of proliferative disorders (such as cancer) by inducing apoptosis in diseased cells.

Sandhoff (or type 2 GM2 gangliosidosis) is caused by a deficiency in β-hexosaminidase A and B activity which leads to an accumulation of the ganglioside $GM_2$ and other glycolipids causing damage to the central nervous system and eventually is lethal (*PLoS One* 2011, 6(6), e21758). Tay-Sachs disease (or $GM_2$ gangliosidosis) is caused by a deficiency in β-hexosaminidase A which lead to an accumulation of gangliosides in the brain's nerve cells eventually leading to their premature death. Intravenous injection of the missing enzyme(s) is not a viable option as of the enzymes does cross the blood-brain barrier (*Genetics in Medicine* 2009, 1(6), 425). Glucosylceramide synthase is a key enzyme in the synthesis of glucosylceramide and other glycosphingolipids. Its inhibition can decrease the amount of the glycosphingolipids which accumulate in Sandhoff disease.

Fabry disease is caused by loss of activity of the lysosomal hydrolase α-galactosidase which leads to an accumulation of glycosphingolipids (particularly globotriaosylceramide) causing pain, renal disease and failure, cerebral vascular disease, and myocardial infarction (*Kidney International* 2000, 57, 446). One treatment strategy is to provide the defective enzyme to the patient; however, enzyme replacement therapy can only slow the progression of the disease and is not a cure. An alternative or complementary strategy is one where glucosylceramide synthase, a key enzyme in the synthesis of glycosphingolipids, is inhibited with a small molecule thus decreasing the amount of globotriaosylceramide and other glucosylceramide-based lipids that need to be broken down by hydrolase α-galactosidase.

Gaucher disease is caused by a defect in the enzyme lysosomal glucocerebrosidase which is responsible for catalyzing the breakdown of glucosylceramide which then accumulates in tissues of affected people (*J. Org. Chem.* 2007, 72(4), 1088) causing liver malfunction, skeletal disorders, painful bone lesions, hypersplenism, pancytopenia, and neurological symptoms (convulsions, hypertonia, mental retardation, apnea, dementia, and ocular muscle apraxia). One treatment strategy is to provide the defective enzyme to the patient; however, enzyme replacement therapy is not suitable for all patients and does not address the neurological manifestations of the disease for those with type 2 and type 3. An alternative or complementary strategy is one where glucosylceramide synthase is inhibited with small molecules thus decreasing the amount of glucosylceramide that needs to be broken down by glucocerebrosidase.

Nonalcoholic fatty liver disease (NALD) is a disease where fat accumulates in the liver of people who drink little or no alcohol and results in inflammation and scarring of the liver which can progress to liver failure. Inhibition of glucosylceramide synthase in ob/ob mice lowered glucose levels, lowered liver/body weight ratio, decreased the accumulation of triglycerides, and prevented and reversed steatosis (*Hepatology* 2009, 50(1), 85-93). Thus GCS inhibitors are useful for the prevention and treatment of NALD.

Polycystic kidney disease (PKD) is a genetic disease characterized by noncancerous cysts which are filled with fluid and cause the kidneys to enlarge which can result in a decrease in quality of life (e.g., headaches, high blood pressure, back and side pain, colon problems, mitral valve prolapsed, and kidney stones) and can be life-threatening (e.g., kidney failure, aneurysm in the brain, and high blood pressure which can lead to heart disease and stroke). PKD can also damage the liver, spleen, pancreas, vasculature, testes, seminal vesicles, and intestines. Glucosylceramide and ganglioside $GM_3$ levels in the kidney are higher than in normal tissue (*Nat Med* 2010, 16(7), 788). Thus, blocking the synthesis of glucosylceramide with an inhibitor of GCS can be useful in the treatment of PKD to reduce new cyst formation (partial or complete inhibition of cystogenesis), reduce cyst mass, reduce the size and number of cysts, and/or reduce the severity of the symptoms associated. All current treatments for PKD address symptoms and do not treat the underlying cause of the disease (*Nat Med* 2010, 16(7), 788).

SUMMARY

In one aspect, provided is a compound of Formula I:

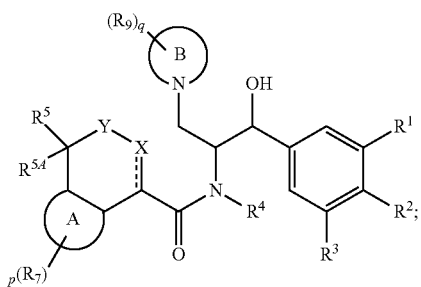

Formula I where:
$R^1$ is H; or $R^1$ and $R^2$ together form —$OCH_2CH_2O$—;
$R^2$ is $C_{3-6}$ cycloalkyloxy or 3-6 membered heterocycloalkyloxy;
$R^3$ is H or halogen;
$R^4$ is H or $C_{1-4}$ alkyl;
$R^5$ and $R^{5A}$ are each independently H or $C_{1-4}$ alkyl;
X is N or O, and when X is N, the dashed line is a bond to form a double bond, and when X is O, the dashed line is not a bond to form a single bond;
Y is $C(R^6)_2$, or O; with the proviso that X and Y are not both O;
$R^6$ at each occurrence is independently H or $C_{1-4}$ alkyl;
Ring A is phenylene, naphthylene, or 5-10 membered heteroarylene;
$R^7$ at each occurrence is independently halogen, $C_{1-6}$ alkyl, $C_{1-6}$ alkoxy, $C_{3-6}$ cycloalkyloxy, ($C_{3-6}$ cycloalkyl)$C_{1-6}$ alkoxy, phenyl, or 5-6 membered heteroaryl, wherein the phenyl and heteroaryl are each optionally substituted with 1, 2, or 3 $R^8$;
p is 0, 1, or 2;
$R^8$ at each occurrence is independently halogen, cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl;
Ring B is a 4-6 membered heterocycloalkyl ring;
$R^9$ at each occurrence is independently halogen, $OR^{10}$, or $N(R^{10})_2$;
$R^{10}$ at each occurrence is independently H or $C_{1-4}$ alkyl;
q is 0, 1, 2, 3, or 4; and
optionally a single stereoisomer or mixture of stereoisomers thereof and
additionally optionally a pharmaceutically acceptable salt thereof.

In a further aspect, provided is a pharmaceutical composition comprising:
1) a Compound of Formula I optionally as a single stereoisomer or mixture of stereoisomers thereof and additionally optionally as a pharmaceutically acceptable salt thereof, and
2) a pharmaceutically acceptable excipient.

In a further aspect, provided is a method of treating a disease or disorder comprising administering a Compound of Formula I, optionally as a single stereoisomer or mixture of stereoisomers thereof and additionally optionally as a pharmaceutically acceptable salt thereof, or the pharmaceutical composition thereof additionally comprising a pharmaceutically acceptable excipient.

DETAILED DESCRIPTION

Abbreviations

| Abbreviation | Meaning |
|---|---|
| aq | aqueous |
| Boc | tert-butoxycarbonyl |
| CBz | carbobenzyloxy |
| conc | concentrated |
| DCM | dichloromethane |
| DIPEA | diisoproylethylamine |
| DMF | dimethylformamide |
| DMP | Dess-Martin periodinane |
| DMSO | dimethyl sulfoxide |
| EDCI | 1-ethyl-3-(3-dimethylaminopropyl)carbodiimide |
| h | hours |
| HATU | O-(7-azabenzotriazol-1-yl)-N,N,N',N'-tetramethyluronium hexafluorophosphate |
| HOBt | hydroxybenzotriazole |
| LC-MS | liquid chromatography - mass spectrometry |
| LDA | lithium diisopropyl amide |
| mg | milligram |
| mHz | megahertz |
| mL | milliliter |
| μL | microliter |
| Ms | mesyl |
| NBS | N-bromosuccinimide |
| NMP | N-methyl pyrrolidone |
| NMR | nuclear magnetic resonance |

-continued

| Abbreviation | Meaning |
|---|---|
| rt or RT | room temperature |
| sat | saturated |
| TBDMS | tert-butyldimethylsilyl |
| TFA | trifluoroacetic acid |
| THF | tetrahydrofuran |
| TLC | thin layer chromatography |

Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used throughout this application and the appended claims, the following terms have the following meanings:

"About" preceding a numerical value refers to a range of values ±10% of the value specified.

"Acceptable" with respect to a formulation, composition or ingredient, as used herein, means having no persistent detrimental effect on the general health of the subject being treated.

"Alkoxy" means an —OR group where R is alkyl, as defined herein. Illustrative examples include, but are not limited to, methoxy, ethoxy, propoxy, 2-propoxy, butoxy, tert-butoxy, pentyloxy, and hexyloxy.

"Alkyl" means a straight or branched saturated hydrocarbon radical containing from 1-10 carbon atoms, in another example 1-6 carbon atoms. Illustrative examples include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

"Alkylamino" means a —NHR radical where R is alkyl as defined herein, e.g., methylamino, ethylamino, n-, iso-propylamino, n-, iso-, tert-butylamino, and the like.

"Alkylaminocarbonyl" means a —C(O)R group where R is alkylamino, as defined herein.

"Amino" means an —NH$_2$ group.

"Aminocarbonyl" means a —C(O)R group where R is amino, as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Phenylene" means a divalent radical formed by removal of a hydrogen atom from phenyl.

"Naphthylene" means a divalent radical formed by removal of a hydrogen atom from naphthyl.

"Indanylene" means a divalent radical formed by removal of a hydrogen atom from indanyl.

"Cycloalkyl" means a monocyclic or fused bicyclic, saturated or partially unsaturated (but not aromatic), hydrocarbon radical of three to ten carbon ring atoms. Fused bicyclic hydrocarbon radical includes bridged rings. Cycloalkyl includes spirocycloalkyl rings. Unless stated otherwise, the valency of the group may be located on any atom of any ring within the radical, valency rules permitting. One or two ring carbon atoms may be replaced by a —C(O)—, —C(S)—, or —C(=NH)— group.

In certain embodiments, cycloalkyl groups include but are not limited to:

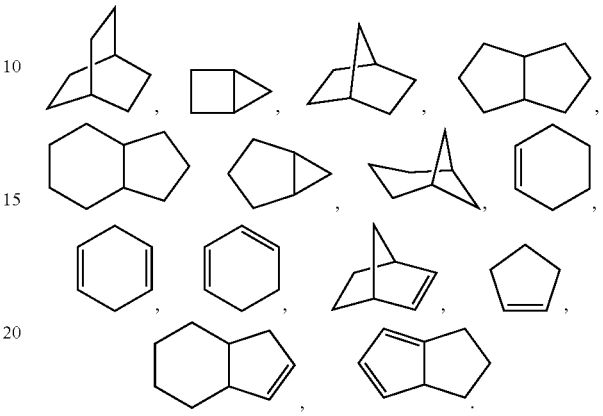

"Cycloalkyloxy" means an —OR group where R is cycloalkyl, as defined herein.

"(Cycloalkyl)alkoxy" means an —OR group where R is alkyl, as defined herein, where the R is substituted by a cycloalkyl group, as defined herein. Illustrative examples include, but are not limited to, cyclohexylmethoxy, cyclohexylethoxy, cyclohexylpropoxy, cyclohexyl-2-propoxy, cyclohexylbutoxy, cyclohexyltert-butoxy, cyclohexylpentyloxy, cyclohexylhexyloxy, cyclopentylmethoxy, cyclopentylethoxy, cyclopentylpropoxy, cyclopentyl-2-propoxy, cyclopentylbutoxy, cyclopentyltert-butoxy, cyclopentylpentyloxy, and cyclopentylhexyloxy.

"Dialkylamino" means an —NRR' radical where R and R' are independently alkyl as defined herein, e.g., dimethylamino, diethylamino, N,N-methylpropylamino or N,N-methylethylamino, and the like.

"Dialkylaminocarbonyl" means a —C(O)R group where R is dialkylamino, as defined herein.

"Halo" or "halogen" means a fluoro, chloro, bromo, or iodo group.

"Haloalkoxy" means an alkoxy group, as defined herein, substituted with one or more halo atoms. In certain embodiments, the alkoxy group is substituted with 1, 2, 3, 4 or 5 halo atoms; or with 1, 2, or 3 halo atoms; or with one halo atom.

"Heteroaryl" means monocyclic, fused bicyclic, or fused tricyclic, radical of 5 to 14 ring atoms containing one or more, in another example one, two, three, or four ring heteroatoms independently selected from —O—, —S(O)$_n$— (n is 0, 1, or 2), —N—, —N(H)—, and N-oxide, and the remaining ring atoms being carbon, wherein the ring comprising a monocyclic radical is aromatic and wherein at least one of the fused rings comprising a bicyclic or tricyclic radical is aromatic (but does not have to be a ring which contains a heteroatom, e.g. 2,3-dihydrobenzo[b][1,4]dioxin-6-yl). One or two ring carbon atoms of any nonaromatic rings comprising a bicyclic or tricyclic radical may be replaced by a —C(O)—, —C(S)—, or —C(=NH)— group. Fused bicyclic radical includes bridged ring systems. Unless stated otherwise, the valency may be located on any atom of any ring of the heteroaryl group, valency rules permitting.

"Heteroarylene" means a divalent radical formed by removal of a hydrogen atom from heteroaryl, as defined herein.

In certain embodiments, heteroaryl includes, but is not limited to, triazolyl, tetrazolyl, pyrrolyl, imidazolyl, thienyl, furanyl, pyrazolyl, oxazolyl, isooxazolyl, oxadiazolyl, thiadiazolyl, indolyl, 2,3-dihydro-1H-indolyl (including, for example, 2,3-dihydro-1H-indol-2-yl or 2,3-dihydro-1H-indol-5-yl, and the like), indazolyl, phthalimidyl, benzimidazolyl, benzoxazolyl, benzofuranyl, benzothienyl, benzopyranyl, benzothiazolyl, pyridinyl, pyrazinyl, pyrimidinyl, pyridazinyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), pyrrolo[1,2-b]pyridazinyl, imidazo[1,2-a]pyridinyl, thiazolyl, benzo[d][1,3]dioxolyl, 2,3-dihydrobenzo[b][1,4]dioxinyl, furo[2,3-d]thiazolyl, thieno[2,3-d]oxazolyl, thieno[3,2-b]furanyl, furo[2,3-d]pyrimidinyl, furo[3,2-b]pyridinyl, furo[3,2-c]pyridinyl, 6,7-dihydro-5H-cyclopenta[b]pyridinyl, and 7,8-dihydro-6H-cyclopenta[g]quinoxalinyl.

"Benzothiophenylene" means a divalent radical formed by removal of a hydrogen atom of benzothiophenyl.

"Indazolylene" means a divalent radical formed by removal of a hydrogen atom of indazolyl.

"Quinolylene" means a divalent radical formed by removal of a hydrogen atom of quinolylene.

"Heterocycloalkyl" means a saturated or partially unsaturated (but not aromatic) monovalent monocyclic group of 3 to 9 ring atoms or a saturated or partially unsaturated (but not aromatic) monovalent fused bicyclic group of 5 to 12 ring atoms in which one or more heteroatoms, for example one, two, three, or four ring heteroatoms, independently selected from —O—, —S(O)$_n$— (n is 0, 1, or 2), —N═, —NH—, and N-oxide, the remaining ring atoms being carbon. One or two ring carbon atoms may be replaced by a —C(O)—, —C(S)—, or —C(═NH)— group. Fused bicyclic radical includes bridged ring systems. Unless otherwise stated, the valency of the group may be located on any atom of any ring within the radical, valency rules permitting.

In certain embodiments, heterocycloalkyl includes, but is not limited to, azetidinyl, pyrrolidinyl, 2-oxopyrrolidinyl, 2,5-dihydro-1H-pyrrolinyl, 2,5-dioxo-1H-pyrrolyl, 2,5-dioxo-pyrrolidinyl, 2,5-dihydro-1H-pyrrolyl, piperidinyl, 2-oxopiperidinyl, 4-piperidonyl, morpholinyl, piperazinyl, 2-oxopiperazinyl, dioxopiperazinyl, pyranyl, tetrahydropyranyl, tetrahydrothiopyranyl, 1,3-dioxinyl, 1,3-dioxanyl, 1,4-dioxinyl, 1,4-dioxanyl, thiomorpholinyl, thiamorpholinyl, perhydroazepinyl, pyrazolidinyl, imidazolinyl, imidazolidinyl, 2,4-dioxo-imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, 2-azaspiro[3.3]heptanyl, 7-azabicyclo[2.2.1]heptanyl, and 8-azabicyclo[3.2.1]octanyl, and N-oxide (for example 1-oxido-pyrrolidin-1-yl) thereof.

"Heterocycloalkyloxy" means an —OR group where R is heterocycloalkyl, as defined herein.

"Stereoisomers" include (but are not limited to) geometric isomers, enantiomers, diastereomers, and mixtures of geometric isomers, enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic column.

As used herein, "amelioration" of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

"Excipient" or "pharmaceutically acceptable excipient" means a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

"Pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt are not specifically limited as far as it can be used in medicaments. Examples of a salt that the compounds described herein forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid: organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

"Subject" refers to a mammal, but not limited to, a human, primate, monkey, cow, pig, sheep, goat, horse, dog, cat, rabbit, rat, or mouse. The terms "subject" and "patient" are used interchangeably herein in reference, for example, to a mammalian subject, such as a human. In certain embodiments, the subject is a human.

"Treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

EMBODIMENTS

The following paragraphs present a number of embodiments of the compounds disclosed herein, where the appropriate substituents are independently selected as set forth in in the Summary and hereafter. Thus, provided are compounds of the recited formulae as defined by any combination of the broader and narrower definitions of these substituents as set forth herein. In each instance the embodiment includes both the recited compound(s) as well as a single stereoisomer or mixture of stereoisomers thereof, as well as a pharmaceutically acceptable salt thereof.

The compounds described herein, as well as their corresponding pharmaceutically acceptable salts thereof, can exist in isotopically-labeled form, in which one or more atoms of the compounds are replaced by an atom having the same atomic number but an atomic mass different from the atomic mass usually found in nature. Examples of isotopes that can be incorporated into compounds described herein include isotopes of hydrogen, carbon, nitrogen, oxygen, phosphorous, sulfur, fluorine, and chloride, such as $^2$H (deuterium), $^3$H (tritium), $^{13}$C, $^{14}$C, $^{15}$N, $^{17}$O, $^{18}$O, $^{31}$P, $^{32}$P, $^{35}$S, $^{18}$F, and $^{36}$Cl, respectively. Isotopically labeled compounds described herein, as well as pharmaceutically acceptable salts thereof, generally can be prepared by carrying out the procedures disclosed in the Schemes and/or in the Examples and Preparations herein, by substituting a readily available isotopically labeled reagent for a non-isotopically labeled reagent.

In one aspect, provided is a compound of Formula I:

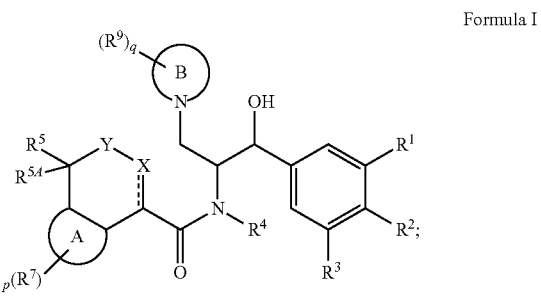

Formula I wherein
$R^1$ is H; or $R^1$ and $R^2$ together form —OCH$_2$CH$_2$O—;
$R^2$ is $C_{3-6}$ cycloalkyloxy or 3-6 membered heterocycloalkyloxy;
$R^3$ is H or halogen;
$R^4$ is H or $C_{1-4}$ alkyl;
$R^5$ and $R^{5A}$ are each independently H or $C_{1-4}$ alkyl;
X is N or O, and when X is N, the dashed line is a bond to form a double bond, and when X is O, the dashed line is not a bond to form a single bond;
Y is $C(R^6)_2$, or O; with the proviso that X and Y are not both O;
$R^6$ at each occurrence is independently H or $C_{1-4}$ alkyl;
Ring A is phenylene, naphthylene, or 5-10 membered heteroarylene;
$R^7$ at each occurrence is independently halogen, $C_{1-6}$ alkyl, $C_{1-6}$ alkoxy, $C_{3-6}$ cycloalkyloxy, $(C_{3-6}$ cycloalkyl)$C_{1-6}$ alkoxy, phenyl, or 5-6 membered heteroaryl, wherein the phenyl and heteroaryl are each optionally substituted with 1, 2, or 3 $R^8$;
p is 0, 1, or 2;
$R^8$ at each occurrence is independently halogen, cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$alkylaminocarbonyl, or $C_{1-6}$ dialkylaminocarbonyl;
Ring B is a 4-6 membered heterocycloalkyl ring;
$R^9$ at each occurrence is independently halogen, OR$^{10}$, or N(R$^{10}$)$_2$;
$R^{10}$ at each occurrence is independently H or $C_{1-4}$ alkyl;
q is 0, 1, 2, 3, or 4; and
optionally a single stereoisomer or mixture of stereoisomers thereof, and
additionally optionally a pharmaceutically acceptable salt thereof.

In another aspect, provided is a compound of Formula I:

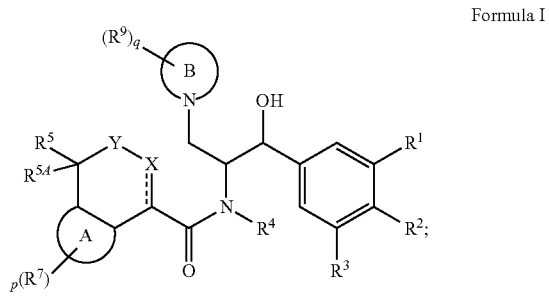

Formula I wherein
$R^1$ is H; or $R^1$ and $R^2$ together form —OCH$_2$CH$_2$O—;
$R^2$ is C$_{3-6}$ cycloalkyloxy or 3-6 membered heterocycloalkyloxy;
$R^3$ is H or halogen;
$R^4$ is H or C$_{1-4}$ alkyl;
$R^5$ and $R^{5A}$ are each independently H or C$_{1-4}$ alkyl;
X is N or O, and when X is N, the dashed line is a bond to form a double bond, and when X is O, the dashed line is not a bond to form a single bond;
Y is C(R$^6$)$_2$, or O; with the proviso that X and Y are not both O;
$R^6$ at each occurrence is independently H or C$_{1-4}$ alkyl;
Ring A is phenylene, naphthylene, or 5-10 membered heteroarylene;
$R^7$ at each occurrence is independently halogen, C$_{1-6}$ alkyl, phenyl, or 5-6 membered heteroaryl, wherein the phenyl and heteroaryl are each optionally substituted with 1, 2, or 3 R$^8$;
p is 0, 1, or 2;
$R^8$ at each occurrence is independently halogen, cyano, amino, C$_{1-6}$ alkylamino, C$_{1-6}$ dialkylamino, C$_{1-6}$ alkyl, C$_{1-6}$ alkoxy, C$_{1-6}$haloalkoxy, aminocarbonyl, C$_{1-6}$ alkylaminocarbonyl, or C$_{1-6}$ dialkylaminocarbonyl;
Ring B is a 4-6 membered heterocycloalkyl ring;
$R^9$ at each occurrence is independently halogen, OR$^{10}$, or N(R$^{10}$)$_2$;
$R^{10}$ at each occurrence is independently H or C$_{1-4}$ alkyl;
q is 0, 1, 2, 3, or 4; and
optionally a single stereoisomer or mixture of stereoisomers thereof, and
additionally optionally a pharmaceutically acceptable salt thereof.

In some embodiments, the compound of Formula I is that wherein

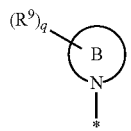

is selected from

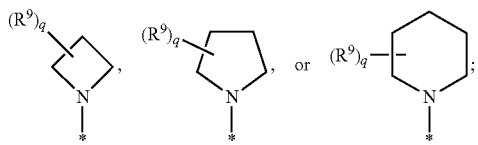

wherein the asterisk indicates the point of attachment to the rest of the molecule.

In some embodiments, the compound of Formula I is that wherein p is 0, 1, or 2; or p is 0 or 1; or p is 1 or 2; or p is 0; or p is 1; or p is 2.

In some embodiments, the compound of Formula I is that wherein q is 0, 1, 2, 3 or 4; or q is 0, 1, 2 or 3; or q is 0, 1 or 2; or q is 0 or 1; or q is 0; or q is 1; or q is 2; or q is 3; or q is 4. In some embodiments, the compound of Formula I is that wherein q is 1, 2, 3 or 4; or q is 2, 3 or 4; or q is 3 or 4; or q is 4. In some embodiments, the compound of Formula I is that wherein q is 0, 1, or 2; or q is 0 or 1; or q is 1 or 2; or q is 0; or q is 1; or q is 2.

In some embodiments, the compound of Formula I is that wherein Ring A is bicyclic; or Ring A is bicyclic with 1-3 nitrogen atoms; or Ring A is bicyclic with 1-2 nitrogen atoms. In some embodiments, Ring A is phenylene, naphthylene, benzothiophenylene, indazolylene, or quinolylene. In some embodiments, Ring A is phenylene and $R^7$ is phenyl or thienyl, each substituted with halogen. In some embodiments, $R^7$ is phenyl substituted with halogen, or thienyl substituted with Cl. In some embodiments, $R^7$ is phenyl substituted with halogen. In some embodiments, $R^7$ is thienyl substituted with Cl.

In some embodiments, the compound of Formula I is that wherein Ring A is phenylene and $R^7$ is C$_{1-6}$ alkoxy, C$_{3-6}$ cycloalkyloxy, or (C$_{3-6}$ cycloalkyl)C$_{1-6}$ alkoxy. In some embodiments, Ring A is phenylene and $R^7$ is alkoxy. In some embodiments, Ring A is phenylene and $R^7$ is cycloalkoxy. In some embodiments, Ring A is phenylene and $R^7$ is cycloalkylalkoxy. In some embodiments, Ring A is phenylene and $R^7$ is cyclohexylmethoxy.

In some embodiments, Ring A is phenylene, naphthylene, or 5-10 membered heteroarylene; where the phenylene is substituted with phenyl, or 5-6 membered heteroaryl, wherein the phenyl and heteroaryl are each optionally substituted with 1, 2, or 3 R$^8$; and the naphthylene and heteroarylene are each independently substituted with 1 or 2 halogen or C$_{1-6}$ alkyl. In some embodiments, Ring A is phenylene substituted with phenyl or 5-6 membered heteroaryl, wherein the phenyl and heteroaryl are each independently optionally substituted with 1, 2, or 3 R$^8$. In some embodiments, Ring A is naphthylene or 5-10 membered heteroarylene, where the naphthylene and heteroarylene are each independently optionally substituted with 1 or 2 halogen, C$_{1-6}$ alkyl.

In some embodiments, Ring A is phenylene; where the phenylene is substituted with C$_{1-6}$ alkoxy, C$_{3-6}$ cycloalkyloxy, (C$_{3-6}$ cycloalkyl)C$_{1-6}$ alkoxy, phenyl, or 5-6 membered heteroaryl, wherein the phenyl and heteroaryl are each optionally optionally substituted with 1, 2, or 3 R$^8$. In some embodiments, Ring A is phenylene substituted with C$_{3-6}$ cycloalkyloxy, (C$_{3-6}$ cycloalkyl)C$_{1-6}$ alkoxy, phenyl, or 5-6 membered heteroaryl, wherein the phenyl and heteroaryl are each independently optionally substituted with 1, 2, or 3 R$^8$.

In some embodiments, the compound of Formula I is according to Formula I(a) or Formula I(b):

Formula I(b)

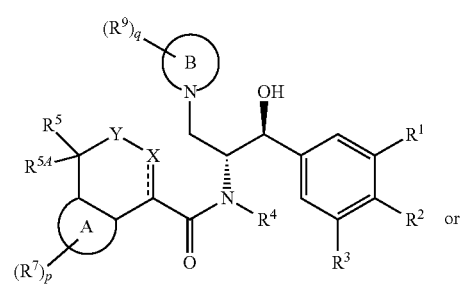

or

Formula I(a)

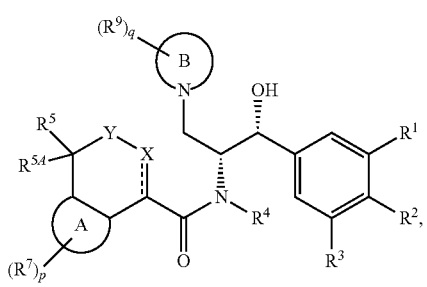

optionally as a single stereoisomer or mixture of stereoisomers thereof and additionally optionally as a pharmaceutically acceptable salt thereof.

In some embodiments, the compound of Formula I is according to Formula II, Formula II(a), or Formula II(b):

Formula II

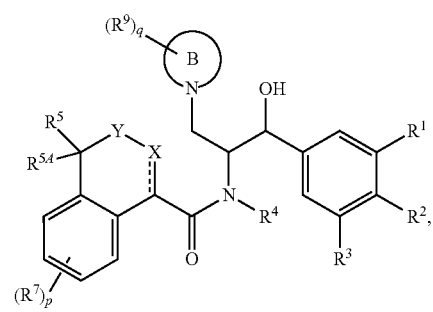

Formula II(a)

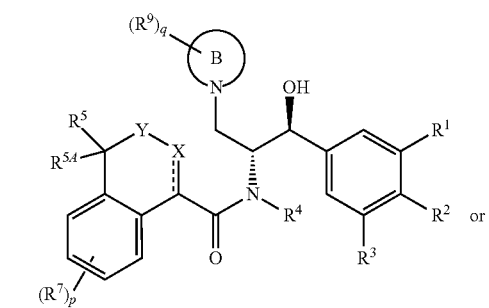

or

Formula II(b)

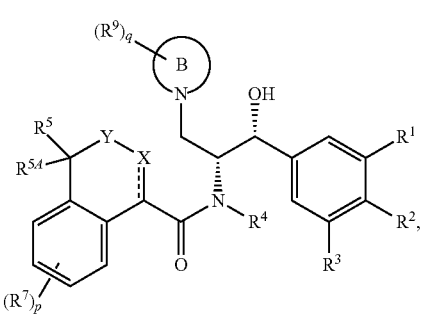

optionally as a single stereoisomer or mixture of stereoisomers thereof and additionally optionally as a pharmaceutically acceptable salt thereof.

In some embodiments, the compound of Formula I is according to Formula III, Formula III(a), or Formula III(b):

Formula III

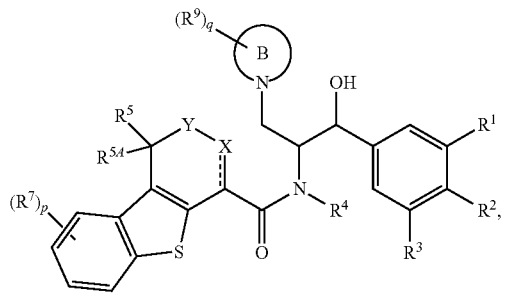

Formula III(a)

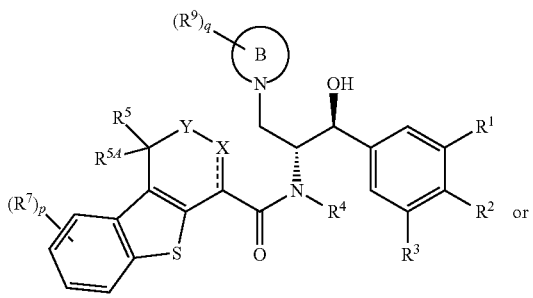

or

Formula III(b)

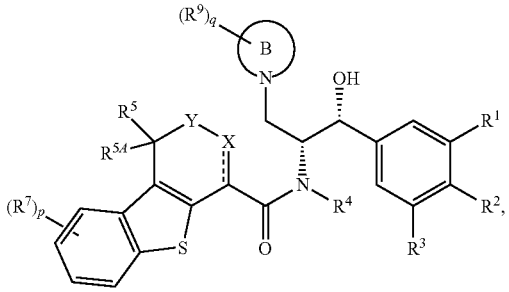

optionally as a single stereoisomer or mixture of stereoisomers thereof and additionally optionally as a pharmaceutically acceptable salt thereof.

In some embodiments, the compound of Formula I is according to Formula IV, Formula IV(a), or Formula IV(b):

Formula IV

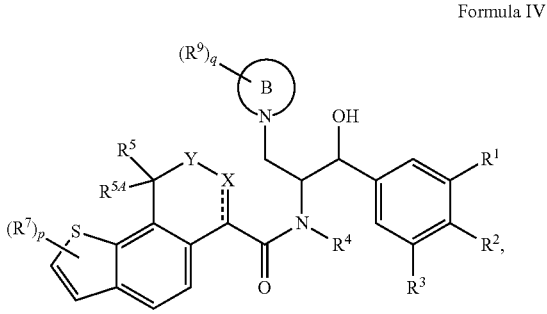

Formula IV(a)

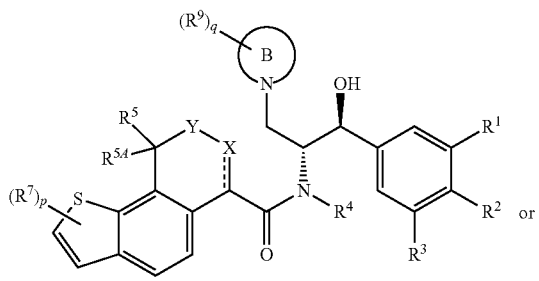

or

Formula IV(b)

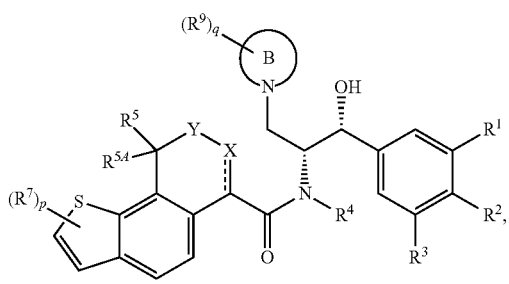

optionally as a single stereoisomer or mixture of stereoisomers thereof and additionally optionally as a pharmaceutically acceptable salt thereof.

In some embodiments, the compound of Formula I is according to Formula V, Formula V(a), or Formula V(b):

Formula V

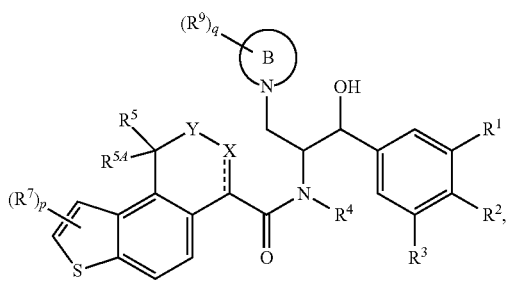

Formula V(a)

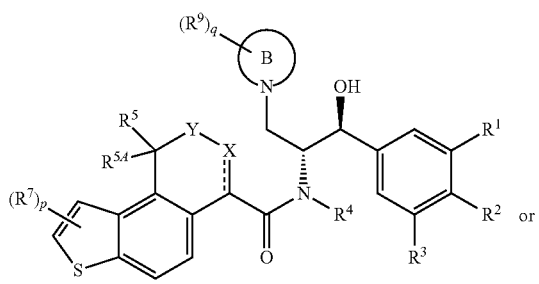

or

Formula V(b)

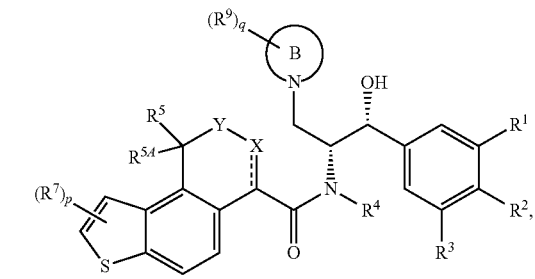

optionally as a single stereoisomer or mixture of stereoisomers thereof and additionally optionally as a pharmaceutically acceptable salt thereof.

In some embodiments, the compound of Formula I is according to Formula VI, Formula VI(a), or Formula VI(b):

Formula VI

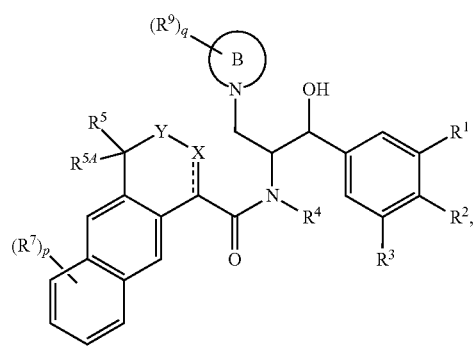

Formula VI(a)

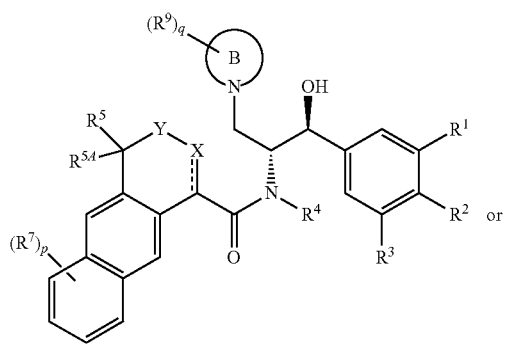

or

Formula VI(b)

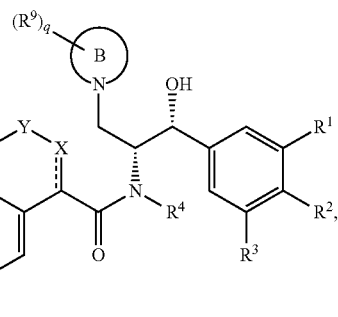

optionally as a single stereoisomer or mixture of stereoisomers thereof and additionally optionally as a pharmaceutically acceptable salt thereof.

In some embodiments, the compound of Formula I is according to Formula VII, Formula VII(a), or Formula VII(b):

Formula VII

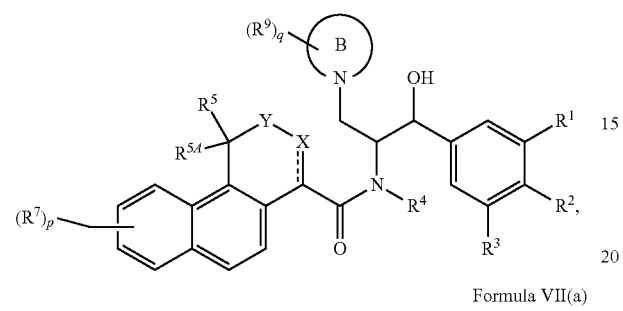

Formula VII(a)

Formula VII(b)

optionally as a single stereoisomer or mixture of stereoisomers thereof and additionally optionally as a pharmaceutically acceptable salt thereof.

In some embodiments, the compound of Formula I is according to Formula VIII, Formula VIII(a), or Formula VIII(b):

Formula VIII

Formula VIII(a)

Formula VIII(b)

optionally as a single stereoisomer or mixture of stereoisomers thereof and additionally optionally as a pharmaceutically acceptable salt thereof.

In some embodiments, the compound of Formula I is according to Formula IX, Formula IX(a), or Formula IX(b):

Formula IX

Formula IX(a)

-continued

Formula IX(b)

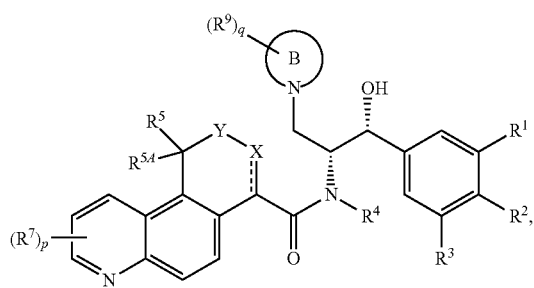

optionally as a single stereoisomer or mixture of stereoisomers thereof and additionally optionally as a pharmaceutically acceptable salt thereof.

In some embodiments, the compound of Formula I is according to Formula X, Formula X(a), or Formula X(b):

Formula X

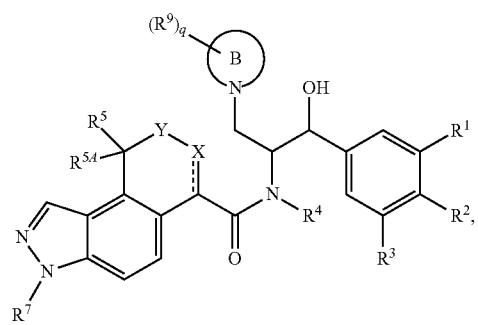

Formula X(a)

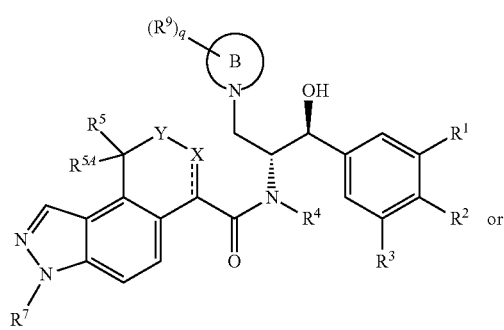

Formula X(b)

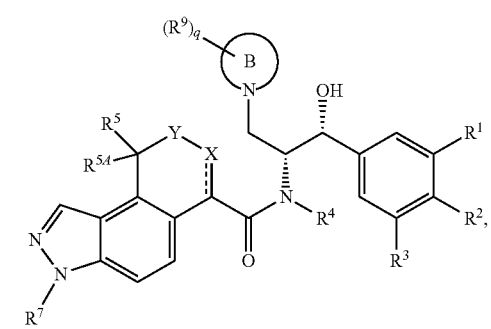

optionally as a single stereoisomer or mixture of stereoisomers thereof and additionally optionally as a pharmaceutically acceptable salt thereof.

In some embodiments, the compound of Formula I is according to Formula XI, Formula XI(a), or Formula XI(b):

Formula XI

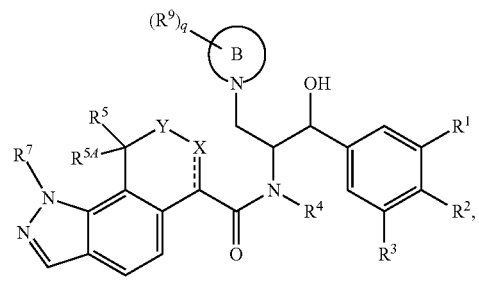

Formula XI(a)

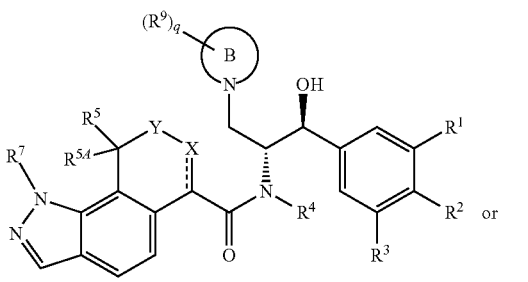

Formula XI(b)

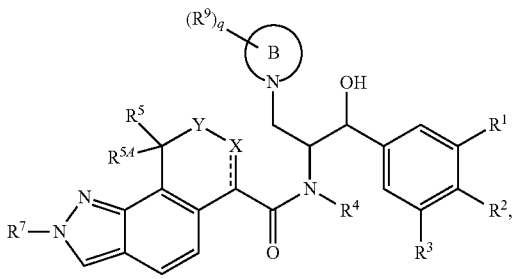

optionally as a single stereoisomer or mixture of stereoisomers thereof and additionally optionally as a pharmaceutically acceptable salt thereof.

In some embodiments, the compound of Formula I is according to Formula XII, Formula XII(a), or Formula XII(b):

Formula XII

Formula XII(a)

optionally as a single stereoisomer or mixture of stereoisomers thereof and additionally optionally as a pharmaceutically acceptable salt thereof.

In some embodiments, the compound of Formula I is that wherein p is 0 or 1.

In some embodiments, the compound of Formula I is that wherein q is 0.

In some embodiments, the compound of Formula I is according to Formula XIII, Formula XIII(a) or Formula XIII(b):

Formula XIII

Formula XIII(a)

Formula XIII(b)

wherein n is 1 or 2;

$R^1$ is H; or $R^1$ and $R^2$ together form —OCH$_2$CH$_2$O—;

$R^2$ is $C_{3-6}$ cycloalkyloxy;

$R^3$ is H, Cl, or F;

$R^4$ is H or $C_{1-4}$ alkyl;

$R^5$ and $R^{5A}$ are each independently H or $C_{1-4}$ alkyl;

X is N or O, and when X is N, the dashed line is a bond to form a double bond, and when X is O, the dashed line is not a bond to form a single bond;

Y is CH$_2$, CH(C$_{1-4}$ alkyl), C(C$_{1-4}$ alkyl)$_2$, or O; with the proviso that X and Y are not both O;

Ring A is phenylene, naphthylene, benzothiophenylene, indazolylene, or quinolylene;

$R^7$ is Cl, F, $C_{1-6}$ alkyl, cyclohexylmethoxy, phenyl, or thienyl, where the cyclohexylmethoxy, phenyl, and thienyl are each optionally substituted with $R^8$;

$R^8$ is Cl, F, or $C_{1-6}$ alkyl; and optionally a single stereoisomer or mixture of stereoisomers thereof and additionally optionally a pharmaceutically acceptable salt thereof.

In some embodiments, the compound of Formula I is according to Formula XIII, Formula XIII(a) or Formula XIII(b):

Formula XIII

Formula XIII(a)

-continued

Formula XIII(b)

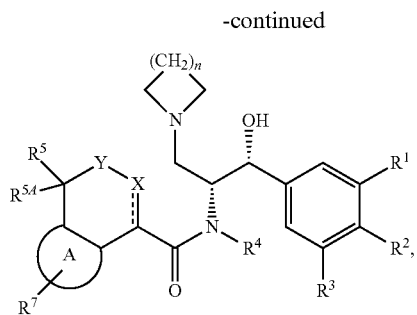

wherein
n is 1 or 2;
$R^1$ is H; or $R^1$ and $R^2$ together form —OCH$_2$CH$_2$O—;
$R^2$ is $C_{3-6}$ cycloalkyloxy;
$R^3$ is H, Cl, or F;
$R^4$ is H or $C_{1-4}$ alkyl;
$R^5$ and $R^{5A}$ are each independently H or $C_{1-4}$ alkyl;
X is N or O, and when X is N, the dashed line is a bond to form a double bond, and when X is O, the dashed line is not a bond to form a single bond;
Y is CH$_2$, CH($C_{1-4}$ alkyl), C($C_{1-4}$ alkyl)$_2$, or O; with the proviso that X and Y are not both O;
Ring A is phenylene, naphthylene, benzothiophenylene, indazolylene, or quinolylene;
$R^7$ is Cl, F, $C_{1-6}$ alkyl, phenyl, or thienyl, where the phenyl and thienyl are each optionally substituted with $R^8$;
$R^8$ is Cl, F, or $C_{1-6}$ alkyl; and
optionally a single stereoisomer or mixture of stereoisomers thereof and additionally
optionally a pharmaceutically acceptable salt thereof.

In some embodiments, the compound of Formula XIII, Formula XIII(a) or Formula XIII(b) is that where the Ring A is phenylene, naphthylene or benzothiophenylene. In some embodiments, the compound of Formula XIII, Formula XIII(a) or Formula XIII(b) is that where the Ring A is indazolylene or quinolylene.

In some embodiments, $R^1$ is H. In some embodiments, $R^1$ and $R^2$ together form —OCH$_2$CH$_2$O—.

In some embodiments, $R^3$ is H. In some embodiments, $R^3$ is halogen; or $R^3$ is Cl or F; or $R^3$ is Cl; or $R^3$ is F.

In some embodiments, $R^4$ is H. In some embodiments, $R^4$ is $C_{1-4}$ alkyl; or $R^4$ is methyl, ethyl, propyl or butyl; or $R^4$ is methyl, ethyl, or propyl; or $R^4$ is methyl or ethyl; or $R^4$ is methyl.

In some embodiments, $R^5$ and $R^{5A}$ are each H. In some embodiments, one of $R^5$ or $R^{5A}$ is H and the other is $C_{1-4}$ alkyl; or the other is methyl, ethyl, propyl or butyl; or the other is methyl, ethyl, or propyl; or the other is methyl or ethyl; or the other is methyl. In some embodiments, both of $R^5$ or $R^{5A}$ are $C_{1-4}$ alkyl; or one is methyl or ethyl and the other is methyl, ethyl, propyl or butyl; or one is methyl or ethyl and the other is methyl, ethyl, or propyl; or one is methyl or ethyl and the other is methyl or ethyl; or one is methyl and the other is methyl or ethyl. In some embodiments, both of $R^5$ or $R^{5A}$ are methyl.

In some embodiments, $R^7$ at each occurrence is independently Cl, F, $C_{1-6}$ alkyl, phenyl, or 5-6 membered heteroaryl, wherein the phenyl and heteroaryl are each optionally substituted with 1, 2, or 3 $R^8$; or the phenyl and heteroaryl are each substituted with Cl or F. In some embodiments, $R^7$ at each occurrence is independently Cl, F, methyl, ethyl, propyl, butyl, phenyl, or 5-6 membered heteroaryl, wherein the phenyl and heteroaryl are each substituted with $R^8$; or the phenyl and heteroaryl are each substituted with Cl or F. In some embodiments, $R^7$ at each occurrence is independently Cl, F, methyl, phenyl, or 5 membered heteroaryl, wherein the phenyl and heteroaryl are each substituted with $R^8$; or the phenyl and heteroaryl are each substituted with Cl or F. In some embodiments, $R^7$ at each occurrence is independently Cl, F, methyl, phenyl, or thienyl, wherein the phenyl and thienyl are each substituted with $R^8$. In some embodiments, $R^7$ at each occurrence is independently Cl, F, methyl, phenyl, or thienyl, wherein the phenyl is substituted with F and the thienyl is substituted with Cl. In some embodiments, $R^7$ at each occurrence is independently Cl or F. In some embodiments, $R^7$ at each occurrence is independently phenyl or thienyl, wherein the phenyl and thienyl are each substituted with $R^8$. In some embodiments, $R^7$ at each occurrence is independently phenyl or thienyl, wherein the phenyl and thienyl are each substituted with Cl or F. In some embodiments, $R^7$ at each occurrence is independently phenyl or thienyl, wherein the phenyl is substituted with F and the thienyl is substituted with Cl.

In some embodiments, $R^7$ at each occurrence is independently Cl, F, $C_{1-6}$ alkyl, $C_{1-6}$ alkoxy, $C_{3-6}$ cycloalkyloxy, ($C_{3-6}$ cycloalkyl)$C_{1-6}$ alkoxy, phenyl, or 5-6 membered heteroaryl, wherein the cycloalkyloxy, (cycloalkyl)alkoxy, phenyl and heteroaryl are each optionally substituted with 1, 2, or 3 $R^8$; or the cycloalkyloxy, (cycloalkyl)alkoxy, phenyl and heteroaryl are each optionally substituted with Cl or F. In some embodiments, $R^7$ at each occurrence is independently Cl, F, methyl, ethyl, propyl, butyl, $C_{3-6}$ cycloalkyloxy, ($C_{3-6}$ cycloalkyl)$C_{1-6}$ alkoxy, phenyl, or 5-6 membered heteroaryl, wherein the cycloalkyloxy, (cycloalkyl)alkoxy, phenyl and heteroaryl are each optionally substituted with $R^8$; or the cycloalkyloxy, (cycloalkyl)alkoxy, phenyl and heteroaryl are each optionally substituted with Cl or F. In some embodiments, $R^7$ at each occurrence is independently Cl, F, methyl, cycloalkyloxy, (cycloalkyl)alkoxy, phenyl, or 5 membered heteroaryl, wherein the cycloalkyloxy, (cycloalkyl)alkoxy, phenyl and heteroaryl are each optionally substituted with $R^8$; or the cycloalkyloxy, (cycloalkyl)alkoxy, phenyl and heteroaryl are each optionally substituted with Cl or F. In some embodiments, $R^7$ at each occurrence is independently Cl, F, methyl, cyclohexylmethoxy, phenyl, or thienyl, wherein the cyclohexylmethoxy, phenyl and thienyl are each optionally substituted with $R^8$. In some embodiments, $R^7$ at each occurrence is independently Cl, F, methyl, cyclohexylmethoxy, phenyl, or thienyl, wherein the cyclohexylmethoxy, phenyl and thienyl are each substituted with $R^8$. In some embodiments, $R^7$ at each occurrence is independently Cl, F, methyl, cyclohexylmethoxy, phenyl, or thienyl, wherein the cyclohexylmethoxy is unsubstituted, the phenyl is substituted with F, and the thienyl is substituted with Cl. In some embodiments, $R^7$ at each occurrence is independently Cl or F. In some embodiments, $R^7$ at each occurrence is independently cyclohexylmethoxy, phenyl or thienyl, wherein the cyclohexylmethoxy is unsubstituted, and the phenyl and thienyl are each substituted with $R^8$. In some embodiments, $R^7$ at each occurrence is independently cyclohexylmethoxy, phenyl or thienyl, wherein the cyclohexylmethoxy is unsubstituted, and the phenyl and thienyl are each substituted with Cl or F. In some embodiments, $R^7$ at each occurrence is independently cyclohexylmethoxy, phenyl or thienyl, wherein the cyclohexylmethoxy is unsubstituted, the phenyl is substituted with F, and the thienyl is substituted with Cl.

In some embodiments, $R^8$ at each occurrence is independently halogen; or $R^8$ at each occurrence is independently Cl or F. In some embodiments, $R^8$ at each occurrence is independently cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl. In some embodiments, $R^8$ at each occurrence is independently amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl. In some embodiments, $R^8$ at each occurrence is independently amino, $C_{1-6}$ alkylamino, $C_{1-6}$ dialkylamino, $C_{1-6}$ alkyl, $C_{1-6}$ alkoxy, or $C_{1-6}$ haloalkoxy. In some embodiments, $R^8$ at each occurrence is independently aminocarbonyl, $C_{1-6}$ alkylaminocarbonyl, or $C_{1-6}$ dialkylaminocarbonyl.

In some embodiments, X is N and the dashed line is a bond to form a double bond. In some embodiments, the compound of Formula I is that where X is O and the dashed line is not a bond to form a single bond.

In some embodiments, Y is $C(R^6)_2$, where each $R^6$ is H; or one $R^6$ is H and the other is $C_{1-4}$ alkyl; or each $R^6$ is $C_{1-4}$ alkyl. In some embodiments, Y is $C(R^6)_2$, where one $R^6$ is H and the other is methyl. In some embodiments, Y is $C(R^6)_2$, where $R^6$ is methyl. In some embodiments, Y is O.

In some embodiments, the —Y—X= moiety comprises —O—N=, —CH($CH_3$)—N=, or —C($CH_3$)$_2$—N=. In some embodiments, the —Y—X= moiety comprises —O—N=. In some embodiments, the —Y—X= moiety comprises —CH$_2$—N=, —CH($CH_3$)—N=, or —C($CH_3$)$_2$—N=. In some embodiments, the —Y—X= moiety is —C($CH_3$)$_2$—N=. In some embodiments, the —Y—X— moiety comprises —CH($CH_3$)—O—, or —C($CH_3$)$_2$—O—. In some embodiments, the —Y—X— moiety comprises —CH$_2$—O—.

In some embodiments, Ring A is phenylene or naphthylene, where the phenylene is optionally substituted with phenyl or 5-6 membered heteroaryl, where the phenyl and 5-6 membered heteroaryl are each independently optionally substituted with Cl or F; and the naphthylene is optionally substituted with Cl or F. In some embodiments, Ring A is phenylene or naphthylene, where the phenylene is optionally substituted with phenyl or thienyl, where the phenyl and thienyl are each independently optionally substituted with Cl or F; and the naphthylene is optionally substituted with Cl or F. In some embodiments, Ring A is phenylene or naphthylene, where the phenylene is optionally substituted with fluorophenyl or thienyl substituted with chloro, and the naphthylene is optionally substituted with chloro or fluoro; or the naphthylene is optionally substituted with fluoro.

In some embodiments, Ring A is phenylene substituted with phenyl or 5-6 membered heteroaryl, where the phenyl or heteroaryl are optionally substituted with chloro or fluoro; or the phenyl is substituted with fluoro and the heteroaryl is optionally substituted with chloro. In some embodiments, Ring A is phenylene substituted with phenyl or 6 membered heteroaryl, where the phenyl or heteroaryl are optionally substituted with chloro or fluoro; or the phenyl is substituted with fluoro and the heteroaryl is optionally substituted with chloro. In some embodiments, Ring A is phenylene substituted with phenyl or 5 membered heteroaryl, where the phenyl or heteroaryl are optionally substituted with chloro or fluoro; or the phenyl is substituted with fluoro and the heteroaryl is optionally substituted with chloro. In some embodiments, Ring A is phenylene substituted with phenyl or thienyl, where the phenyl or thienyl are optionally substituted with chloro or fluoro. In some embodiments, Ring A is phenylene substituted with fluorophenyl or chlorothienyl. In some embodiments, Ring A is phenylene substituted with fluorophenyl. In some embodiments, Ring A is phenylene substituted with chlorothienyl.

In some embodiments, Ring A is phenylene, which is optionally substituted with 1 or 2 $R^7$. In some embodiments, Ring A is phenylene, which is optionally substituted with 1 or 2 $R^7$, where each $R^7$, when present, is independently selected from halogen, $C_{1-6}$ alkyl, phenyl, or 5-6 membered heteroaryl, where each phenyl or 5-6 membered heteroaryl, when present, is optionally and independently substituted with 1, 2, or 3 $R^8$. In some embodiments, Ring A is phenylene which is optionally substituted with 1 or 2 $R^7$, where each $R^7$, when present, is independently selected from halogen, $C_{1-6}$ alkyl, phenyl, or 5-6 membered heteroaryl, where each phenyl or 5-6 membered heteroaryl, when present, is optionally and independently substituted with 1, 2, or 3 $R^8$, where each $R^8$, when present, is selected from halogen, cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl.

In some embodiments, Ring A is phenylene, which is optionally substituted with 1 or 2 $R^7$. In some embodiments, Ring A is phenylene, which is optionally substituted with 1 or 2 $R^7$, where each $R^7$, when present, is independently selected from halogen, $C_{1-6}$ alkyl, $C_{1-6}$ alkoxy, $C_{3-6}$ cycloalkyloxy, ($C_{3-6}$ cycloalkyl)$C_{1-6}$ alkoxy, phenyl, or 5-6 membered heteroaryl, where each $C_{3-6}$ cycloalkyloxy, ($C_{3-6}$ cycloalkyl)$C_{1-6}$ alkoxy, phenyl, or 5-6 membered heteroaryl, when present, is optionally and independently substituted with 1, 2, or 3 $R^8$. In some embodiments, Ring A is phenylene which is optionally substituted with 1 or 2 $R^7$, where each $R^7$, when present, is independently selected from halogen, $C_{1-6}$ alkyl, $C_{1-6}$ alkoxy, $C_{3-6}$ cycloalkyloxy, ($C_{3-6}$ cycloalkyl)$C_{1-6}$ alkoxy, phenyl, or 5-6 membered heteroaryl, where each $C_{3-6}$ cycloalkyloxy, ($C_{3-6}$ cycloalkyl)$C_{1-6}$ alkoxy, phenyl, or 5-6 membered heteroaryl, when present, is optionally and independently substituted with 1, 2, or 3 $R^8$, where each $R^8$, when present, is selected from halogen, cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl.

In some embodiments, Ring A is naphthylene substituted with halogen or $C_{1-6}$ alkyl. In some embodiments, Ring A is naphthylene substituted with Cl, F, methyl, ethyl, propyl, or butyl. In some embodiments, Ring A is naphthylene substituted with Cl, F, or methyl. In some embodiments, Ring A is naphthylene substituted with Cl or F; or the naphthylene is substituted with Cl; or the naphthylene is substituted with F.

In some embodiments, Ring A is naphthylene, which is optionally substituted with 1 or 2 $R^7$. In some embodiments, Ring A is naphthylene, which is optionally substituted with 1 or 2 $R^7$, where each $R^7$, when present, is independently selected from halogen, $C_{1-6}$ alkyl, phenyl, or 5-6 membered heteroaryl, where each phenyl or 5-6 membered heteroaryl, when present, is optionally and independently substituted with 1, 2, or 3 $R^8$. In some embodiments, Ring A is naphthylene, which is optionally substituted with 1 or 2 $R^7$, where each $R^7$, when present, is independently selected from halogen, $C_{1-6}$ alkyl, phenyl, or 5-6 membered heteroaryl, where each phenyl or 5-6 membered heteroaryl, when present, is optionally and independently substituted with 1, 2, or 3 $R^8$, where each $R^8$, when present, is independently selected from halogen, cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl. In some embodiments, Ring A is 5-10 membered heteroarylene, which is optionally substituted with 1 or 2 $R^7$. In some embodiments, Ring A is 5-10 membered heteroarylene, where the 5-10 membered heteroarylene is bicyclic with 1-3 nitrogen atoms, which is optionally substituted with 1 or 2 $R^7$. In some embodiments, Ring A is 5-10 membered heteroarylene, where the 5-10 membered heteroarylene is bicyclic with 1-2 nitrogen atoms, which is optionally substituted with 1 or 2 $R^7$. In some embodiments, Ring A is 5-10 membered heteroarylene, where the 5-10 membered heteroarylene is selected from phenylene, naphthylene, benzothiophenylene, indazolylene, or quinolylene, which is optionally substituted with 1 or 2 $R^7$. In some embodiments, Ring A is 5-10 membered heteroarylene, which is optionally substituted with 1 or 2 $R^7$, where each $R^7$, when present, is independently selected from halogen, $C_{1-6}$ alkyl, phenyl, or 5-6 membered heteroaryl, where each phenyl or 5-6 membered heteroaryl, when present, is optionally and independently substituted with 1, 2, or 3 $R^8$. In some embodiments, Ring A is 5-10 membered heteroarylene, which is optionally substituted with 1 or 2 $R^7$, where each $R^7$, when present is independently selected from halogen, $C_{1-6}$ alkyl, phenyl, or 5-6 membered heteroaryl, where each phenyl or 5-6 membered heteroaryl, when present, is optionally and independently substituted with 1, 2, or 3 $R^8$, where each $R^8$, when present, is selected from halogen, cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl.

In some embodiments, Ring A is benzothiophenylene, indazolylene, or quinolylene substituted with halogen or $C_{1-6}$ alkyl. In some embodiments, Ring A is benzothiophenylene, indazolylene, or quinolylene, where the benzothiophenylene is substituted with halogen, and the indazolylene or quinolylene are substituted with $C_{1-6}$ alkyl. In some embodiments, Ring A is benzothiophenylene, indazolylene, or quinolylene, where the benzothiophenylene is substituted with Cl or F, and the indazolylene or quinolylene are substituted with methyl, ethyl, propyl or butyl. In some embodiments, Ring A is benzothiophenylene, indazolylene, or quinolylene, where the benzothiophenylene is substituted with Cl or F, and the indazolylene or quinolylene are substituted with methyl. In some embodiments, Ring A is benzothiophenylene, indazolylene, or quinolylene, where the benzothiophenylene is substituted with Cl, and the indazolylene or quinolylene are substituted with methyl. In some embodiments, Ring A is benzothiophenylene substituted with Cl or F; or Ring A is benzothiophenylene substituted with Cl. In some embodiments, Ring A is indazolylene or quinolylene, each optionally substituted with $C_{1-4}$ alkyl; or each is optionally substituted with methyl. In some embodiments, Ring A is indazolylene or quinolylene, where the indazolylene is substituted with methyl.

In some embodiments, Ring A is 5-6 membered heteroarylene or 9-10 membered bicyclic heteroarylene, each of which is optionally substituted with halogen or $C_{1-6}$ alkyl. In some embodiments, Ring A is 5-6 membered heteroarylene or 9-10 membered bicyclic heteroarylene, each of which is substituted with Cl, F, methyl, ethyl, propyl or butyl. In some embodiments, Ring A is 5-6 membered heteroarylene substituted with Cl or F; or Ring A is 9-10 membered bicyclic heteroarylene substituted with methyl, ethyl, propyl or butyl. In some embodiments, Ring A is 5-6 membered heteroarylene substituted with Cl, or Ring A is 9-10 membered bicyclic heteroarylene substituted with methyl. In some embodiments, Ring A is 5 membered heteroarylene substituted with Cl, or Ring A is 9-10 membered bicyclic heteroarylene substituted with methyl. In some embodiments, Ring A is thienyl substituted with Cl; indazolylene substituted with methyl; or quinolylene.

In some embodiments, Ring A is 5-6 membered heteroarylene optionally substituted with halogen or $C_{1-6}$ alkyl; or Ring A is 5 membered heteroarylene optionally substituted with halogen or $C_{1-6}$ alkyl; or Ring A is 6 membered heteroarylene optionally substituted with halogen or $C_{1-6}$ alkyl. In some embodiments, Ring A is 5-6 membered heteroarylene substituted with Cl, F, methyl, ethyl, propyl or butyl; or Ring A is 5 membered heteroarylene substituted with Cl, F, methyl, ethyl, propyl or butyl; or Ring A is 6 membered heteroarylene substituted with Cl, F, methyl, ethyl, propyl or butyl. In some embodiments, Ring A is 5-6 membered heteroarylene substituted with Cl or F; or Ring A is 5 membered heteroarylene substituted with Cl or F; or Ring A is 6 membered heteroarylene substituted with Cl or F. In some embodiments, Ring A is 5-6 membered heteroarylene substituted with Cl; or Ring A is 5 membered heteroarylene substituted with Cl. In some embodiments, Ring A is thienyl substituted with Cl.

In some embodiments, Ring A is 9-10 membered bicyclic heteroarylene optionally substituted with halogen or $C_{1-6}$ alkyl; or Ring A is 9-10 membered bicyclic heteroarylene with 1 or 2 ring nitrogen atoms optionally substituted with halogen or $C_{1-6}$ alkyl; or Ring A is 9-10 membered bicyclic heteroarylene with 2 ring nitrogen atoms optionally substituted with halogen or $C_{1-6}$ alkyl; or Ring A is 9-10 membered bicyclic heteroarylene with 1 ring nitrogen atom optionally substituted with halogen or $C_{1-6}$ alkyl. In some embodiments, Ring A is 9-10 membered bicyclic heteroarylene substituted with Cl, F, methyl, ethyl, propyl or butyl; or Ring A is 9-10 membered bicyclic heteroarylene with 1 or 2 ring nitrogen atoms substituted with Cl, F, methyl, ethyl, propyl or butyl; or Ring A is 9-10 membered bicyclic heteroarylene with 2 ring nitrogen atoms substituted with Cl, F, methyl, ethyl, propyl or butyl; or Ring A is 9-10 membered bicyclic heteroarylene with 1 ring nitrogen atom substituted with Cl, F, methyl, ethyl, propyl or butyl. In some embodiments, Ring A is 9-10 membered bicyclic heteroarylene substituted with methyl, ethyl, propyl or butyl; or Ring A is 9-10 membered bicyclic heteroarylene with 1 or 2 ring nitrogen atoms substituted with methyl, ethyl, propyl or butyl; or Ring A is 9-10 membered bicyclic heteroarylene with 2 ring nitrogen atoms substituted with methyl, ethyl, propyl or butyl; or Ring A is 9-10 membered bicyclic heteroarylene with 1 ring nitrogen atom substituted with methyl, ethyl, propyl or butyl. In some embodiments, Ring A is 9-10 membered bicyclic heteroarylene substituted with methyl; or Ring A is 9-10 membered bicyclic heteroarylene with 1 or 2 ring nitrogen atoms substituted with methyl; or Ring A is 9-10 membered bicyclic heteroarylene with 2 ring nitrogen atoms substituted with methyl; or Ring A is 9-10 membered bicyclic heteroarylene with 1 ring nitrogen atom substituted with methyl. In some embodiments, Ring A is indazolylene substituted with methyl, or Ring A is quinolylene.

In some embodiments, Ring A is benzothiophenylene substituted with Cl or F; Ring A is benzothiophenylene substituted with Cl.

In some embodiments, Ring A is indazolylene or quinolylene, each optionally substituted with $C_{1-6}$ alkyl; or Ring A is indazolylene or quinolylene, each optionally substituted with methyl, ethyl, propyl or butyl; or Ring A is indazolylene or quinolylene, each optionally substituted with methyl. In some embodiments, Ring A is indazolylene substituted with methyl, or Ring A is quinolylene. In some embodiments, Ring A is quinolylene.

In some embodiments, Ring A is indazolylene substituted with $C_{1-6}$ alkyl; or Ring A is indazolylene substituted with methyl, ethyl, propyl or butyl. In some embodiments, Ring A is indazolylene substituted with methyl.

In some embodiments, Ring B is a 4-6 membered heterocycloalkyl ring, which is optionally substituted with 1, 2, 3, or 4 $R^9$. In some embodiments, Ring B is a 4-6 membered heterocycloalkyl ring, where the 4-6 membered heterocycloalkyl ring is a 4-6 membered heteroalkyl ring with one nitrogen atom, which is optionally substituted with 1, 2, 3, or 4 $R^9$. In some embodiments, Ring B is a 4-6 membered heterocycloalkyl ring, where the 4-6 membered heterocycloalkyl ring is a 4-6 membered heteroalkyl ring with one nitrogen atom, which is optionally substituted with 1, 2, 3, or 4 $R^9$, where each $R^9$, when present, is independently selected from halogen, $OR^{10}$, or $N(R^{10})_2$. In some embodiments, Ring B is a 4-6 membered heterocycloalkyl ring, where the 4-6 membered heterocycloalkyl ring is a 4-6 membered heteroalkyl ring with one nitrogen atom, which is optionally substituted with 1, 2, 3, or 4 $R^9$, where each $R^9$, when present, is independently selected from halogen, $OR^{10}$, or $N(R^{10})_2$, where each $R^{10}$, when present, is independently selected from H or $C_{1-4}$ alkyl.

In some embodiments, Ring B is a 4-6 membered heterocycloalkyl ring, which is optionally substituted with 1 or 2 $R^9$. In some embodiments, Ring B is a 4-6 membered heterocycloalkyl ring, which is optionally substituted with 1 or 2 groups independently selected from Cl, F, $C_{1-4}$ alkoxy, amino, $C_{1-6}$ alkylamino, and $C_{1-6}$ dialkylamino. In some embodiments, Ring B is a 4-6 membered heterocycloalkyl ring, which is optionally substituted with 1 or 2 groups independently selected from Cl and F. In some embodiments, Ring B is a 4-6 membered heterocycloalkyl ring, which is optionally substituted with 1 or 2 groups independently selected from $C_{1-4}$ alkoxy, amino, $C_{1-6}$ alkylamino, and $C_{1-6}$ dialkylamino.

In some embodiments, Ring B is an azetidine ring, which is optionally substituted with 1 or 2 groups independently selected from Cl, F, $C_{1-4}$ alkoxy, amino, $C_{1-6}$ alkylamino, and $C_{1-6}$ dialkylamino. In some embodiments, Ring B is an azetidine ring, which is optionally substituted with 1 or 2 groups independently selected from Cl and F. In some embodiments, Ring B is an azetidine ring, which is optionally substituted with 1 or 2 groups independently selected from $C_{1-4}$ alkoxy, amino, $C_{1-6}$ alkylamino, and $C_{1-6}$ dialkylamino. In some embodiments, Ring B is an unsubstituted azetidine ring.

In some embodiments, Ring B is a pyrrolidine ring, which is optionally substituted with 1 or 2 groups independently selected from Cl, F, $C_{1-4}$ alkoxy, amino, $C_{1-6}$ alkylamino, and $C_{1-6}$ dialkylamino. In some embodiments, Ring B is a pyrrolidine ring, which is optionally substituted with 1 or 2 groups independently selected from Cl and F. In some embodiments, Ring B is a pyrrolidine ring, which is optionally substituted with 1 or 2 groups independently selected from $C_{1-4}$ alkoxy, amino, $C_{1-6}$ alkylamino, and $C_{1-6}$ dialkylamino. In some embodiments, Ring B is a unsubstituted pyrrolidine ring.

In some embodiments, Ring B is a piperidine ring, which is optionally substituted with 1 or 2 groups independently selected from Cl, F, $C_{1-4}$ alkoxy, amino, $C_{1-6}$ alkylamino, and $C_{1-6}$ dialkylamino. In some embodiments, Ring B is a piperidine ring, which is optionally substituted with 1 or 2 groups independently selected from Cl and F. In some embodiments, Ring B is a piperidine ring, which is optionally substituted with 1 or 2 groups independently selected from $C_{1-4}$ alkoxy, amino, $C_{1-6}$ alkylamino, and $C_{1-6}$ dialkylamino. In some embodiments, Ring B is an unsubstituted piperidine ring.

In some embodiments, the compound of Formula I is according to Formula XIV:

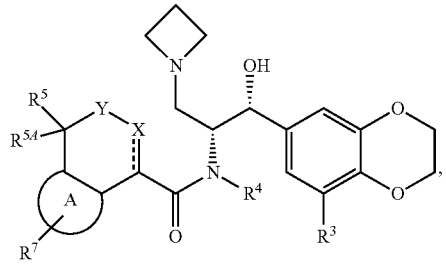

Formula XIV where all groups are as defined in any of the embodiments described herein.

In some embodiments, the compound of Formula I is according to Formula XV:

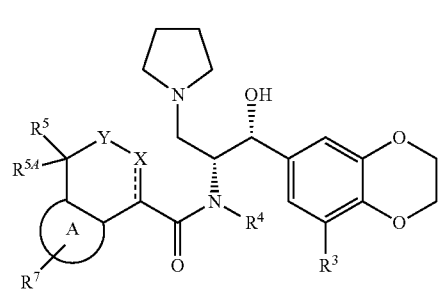

Formula XV where all groups are as defined in any of the embodiments described herein.

In some embodiments, the compound of Formula I is according to Formula XVI:

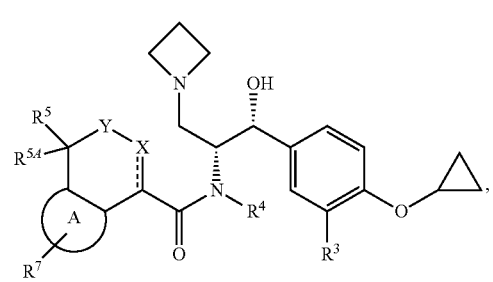

Formula XVI where all groups are as defined in any of the embodiments described herein.

In some embodiments, the compound of Formula I is according to Formula XVII:

Formula XVII

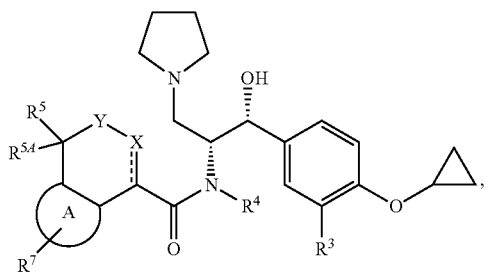

where all groups are as defined in any of the embodiments described herein.

In some embodiments, the compound of Formula I is according to Formula XVIII:

Formula XVIII

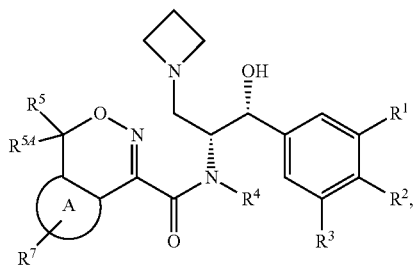

where all groups are as defined in any of the embodiments described herein.

In some embodiments, the compound of Formula I is according to Formula XIX:

Formula XIX

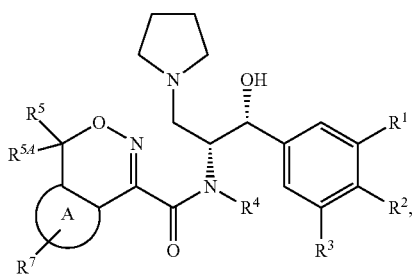

where all groups are as defined in any of the embodiments described herein.

In some embodiments, the compound of Formula I is according to Formula XX:

Formula XX

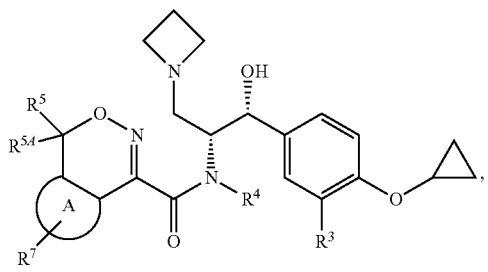

where all groups are as defined in any of the embodiments described herein.

In some embodiments, the compound of Formula I is according to Formula XXI:

Formula XXI

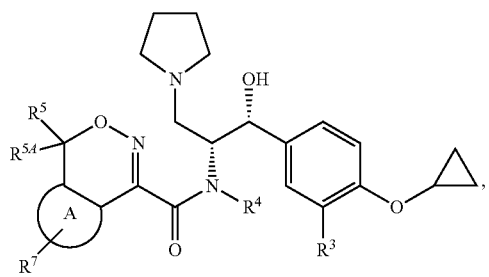

where all groups are as defined in any of the embodiments described herein.

In some embodiments, the compound of Formula I is according to Formula XXII:

Formula XXII

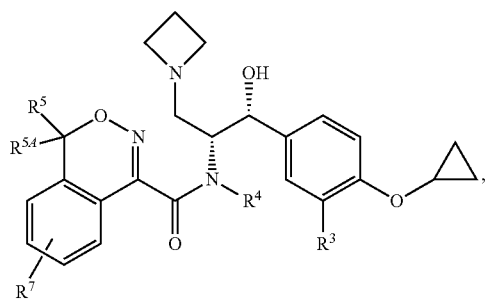

where all groups are as defined in any of the embodiments described herein.

In some embodiments, the compound of Formula I is according to Formula XXIII:

Formula XXIII

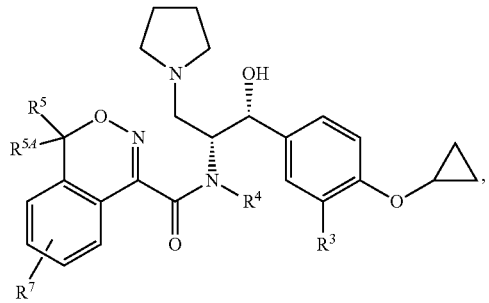

where all groups are as defined in any of the embodiments described herein.

In some embodiments, the compound of Formula I is that wherein Ring A is:

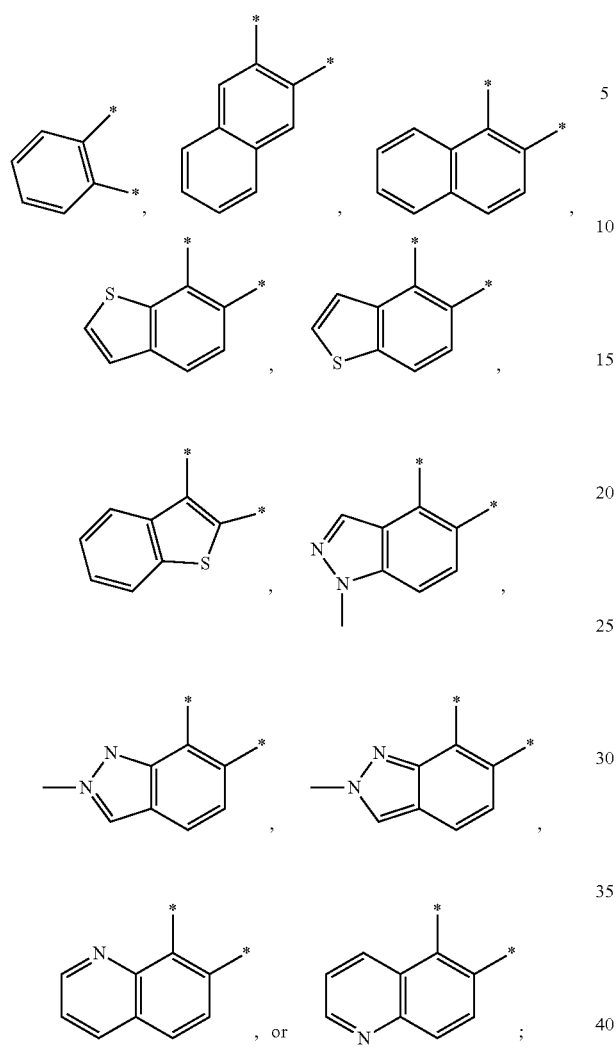
wherein Ring A is optionally independently substituted 0, 1, or 2 R⁷; and wherein the asterisk indicates the point of attachment to the rest of the molecule.
In some embodiments, the compound of Formula I is that wherein
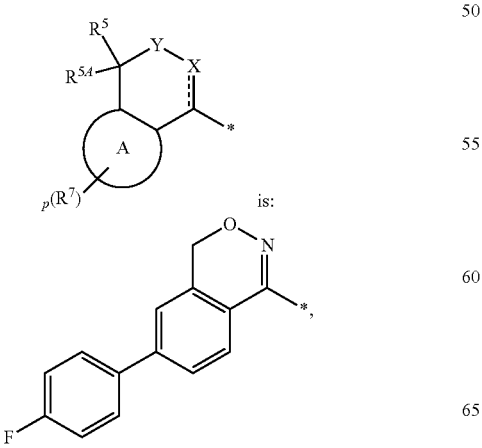
is:
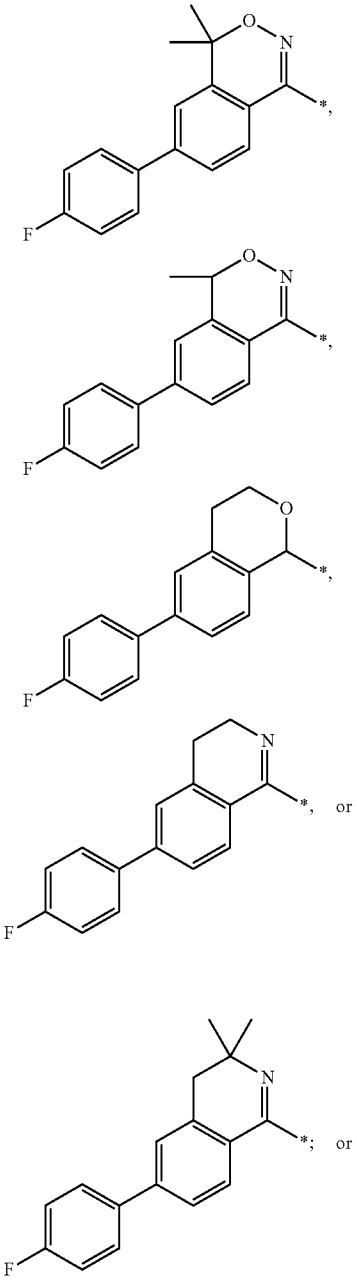

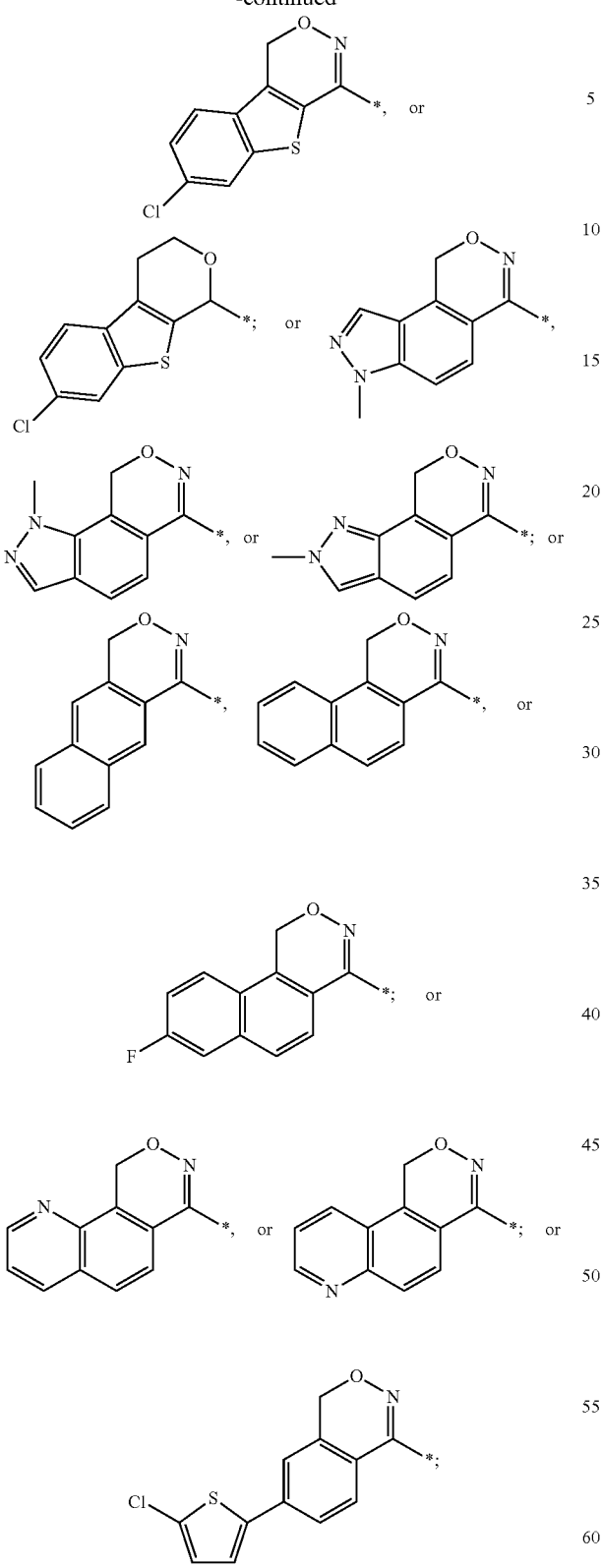
wherein the asterisk indicates the point of attachment to the rest of the molecule.
In some embodiments, the compound of Formula I is that wherein
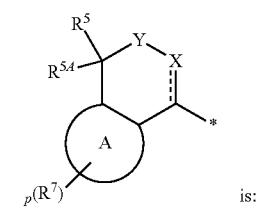
is:

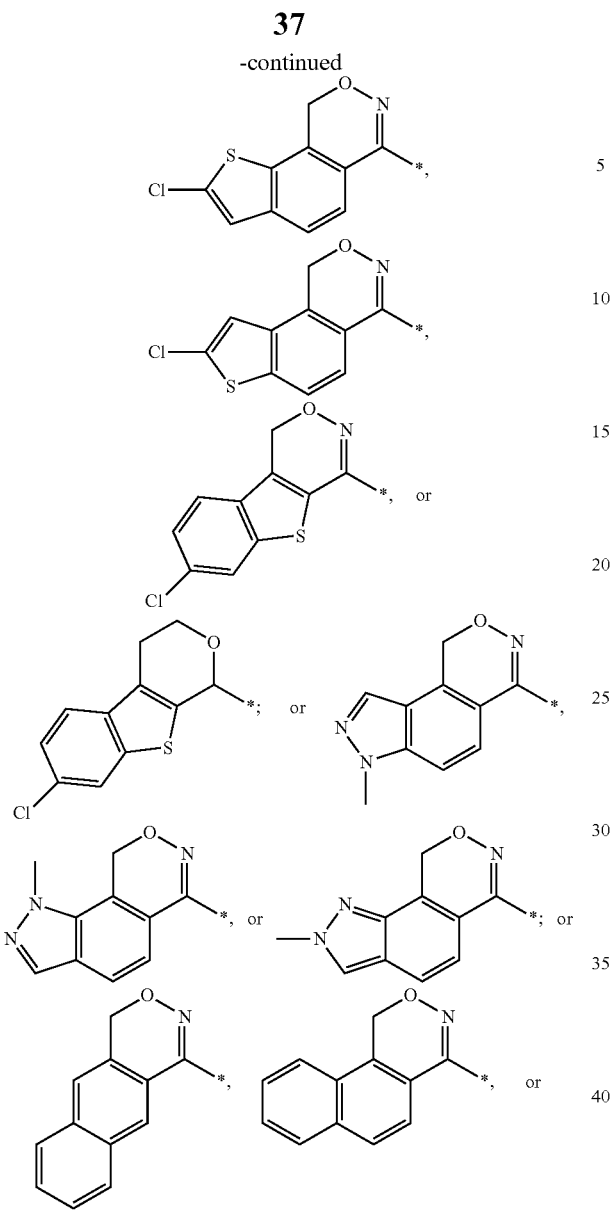
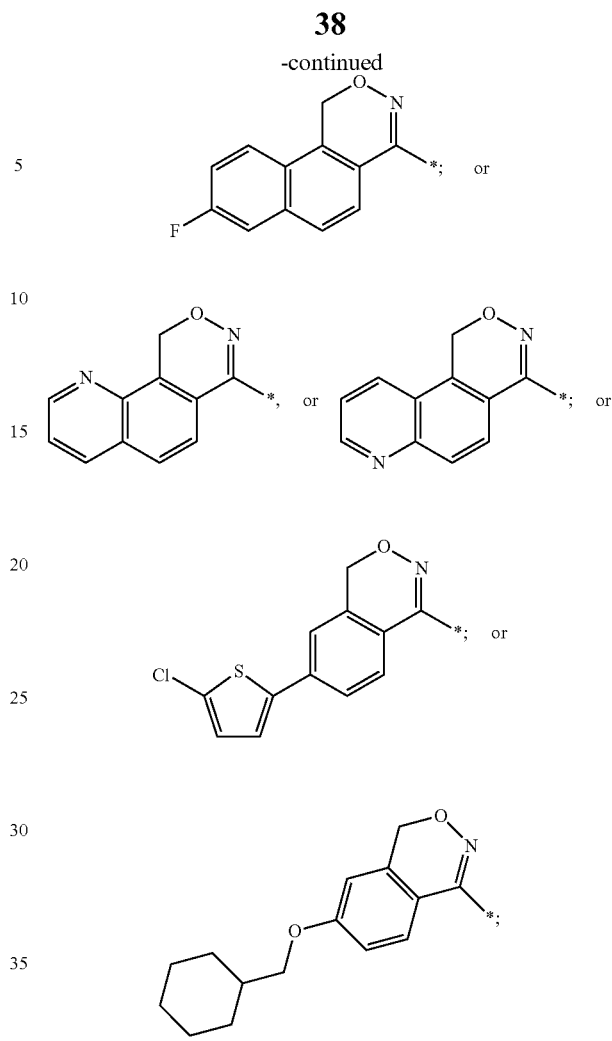

wherein the asterisk indicates the point of attachment to the rest of the molecule.

In some embodiments, the compound of Formula I is according to the compounds in Table 1, where the compound nomenclature was generated by the ChemBioDraw 14.0 program:

TABLE 1

| Example No. | Name | Structure |
|---|---|---|
| 1 | N-((1R,2R)-1-(3-chloro-4-cyclopropoxyphenyl)-1-hydroxy-3-(pyrrolidin-1-yl)propan-2-yl)-7-(4-fluorophenyl)-1H-benzo[d][1,2]oxazine-4-carboxamide | 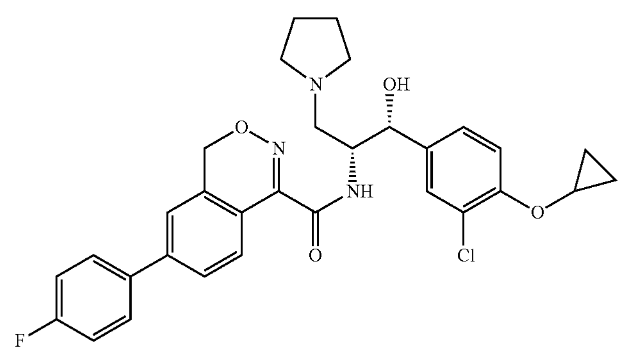 [SMILES: O=C(N[C@H](CN1CCCC1)[C@H](O)c1ccc(OC2CC2)c(Cl)c1)C1=NOCc2cc(-c3ccc(F)cc3)ccc21] |

TABLE 1-continued

| Example No. | Name | Structure |
|---|---|---|
| 2 | N-((1R,2R)-1-(4-cyclopropoxy-3-fluorophenyl)-1-hydroxy-3-(pyrrolidin-1-yl)propan-2-yl)-7-(4-fluorophenyl)-1H-benzo[d][1,2]oxazine-4-carboxamide | 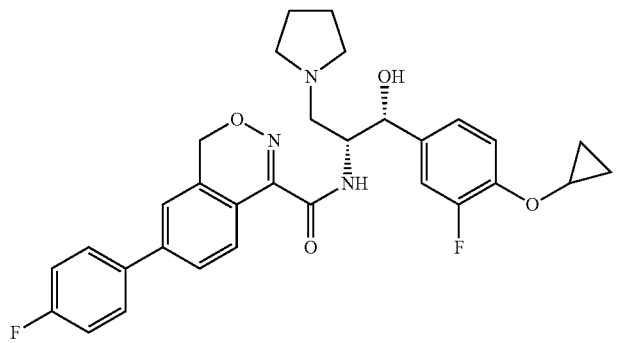 |
| 3 | N-((1R,2R)-1-(8-fluoro-2,3-dihydrobenzo[b][1,4]dioxin-6-yl)-1-hydroxy-3-(pyrrolidin-1-yl)propan-2-yl)-7-(4-fluorophenyl)-1H-benzo[d][1,2]oxazine-4-carboxamide | 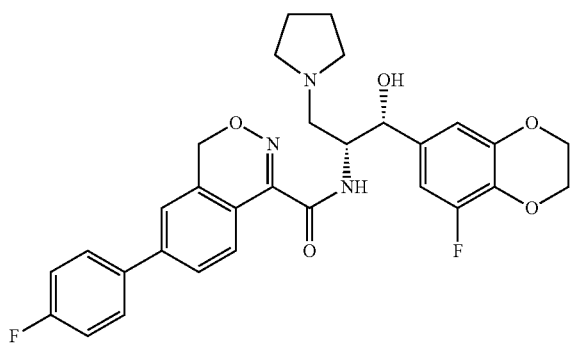 [SMILES: O=C(N[C@H](CN1CCCC1)[C@H](O)c1cc(F)c2c(c1)OCCO2)C1=NOCc2cc(-c3ccc(F)cc3)ccc21] |
| 4 | N-((1R,2R)-1-(4-cyclopropoxyphenyl)-1-hydroxy-3-(pyrrolidin-1-yl)propan-2-yl)-7-(4-fluorophenyl)-1H-benzo[d][1,2]oxazine-4-carboxamide | 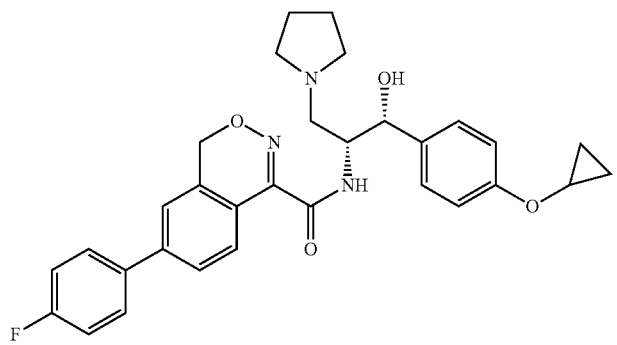 [SMILES: O=C(N[C@H](CN1CCCC1)[C@H](O)c1ccc(OC2CC2)cc1)C1=NOCc2cc(-c3ccc(F)cc3)ccc21] |
| 5 | N-((1R,2R)-3-(azetidin-1-yl)-1-(3-chloro-4-cyclopropoxyphenyl)-1-hydroxypropan-2-yl)-7-(4-fluorophenyl)-1H-benzo[d][1,2]oxazine-4-carboxamide | 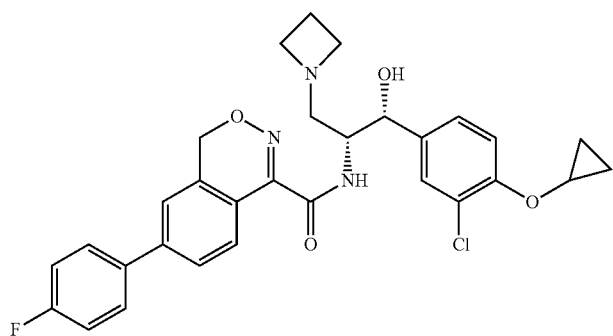 |

TABLE 1-continued

| Example No. | Name | Structure |
|---|---|---|
| 6 | N-((1R,2R)-3-(azetidin-1-yl)-1-(4-cyclopropoxyphenyl)-1-hydroxypropan-2-yl)-7-(4-fluorophenyl)-1H-benzo[d][1,2]oxazine-4-carboxamide | 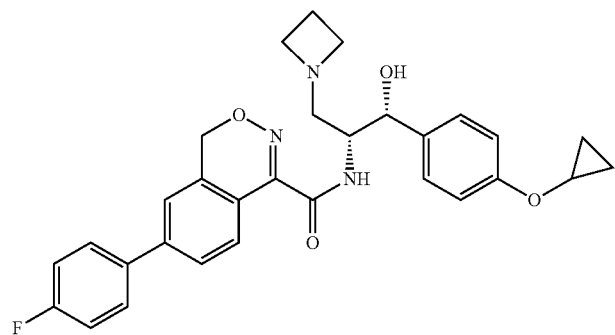 [SMILES: O=C(N[C@H](CN1CCC1)[C@H](O)c1ccc(OC2CC2)cc1)C1=NOCc2cc(-c3ccc(F)cc3)ccc21] |
| 7 | N-((1R,2R)-3-(azetidin-1-yl)-1-(4-cyclopropoxy-3-fluorophenyl)-1-hydroxypropan-2-yl)-7-(4-fluorophenyl)-1H-benzo[d][1,2]oxazine-4-carboxamide | 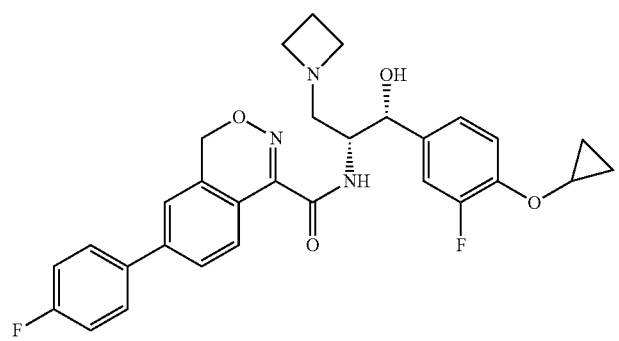 [SMILES: O=C(N[C@H](CN1CCC1)[C@H](O)c1ccc(OC2CC2)c(F)c1)C1=NOCc2cc(-c3ccc(F)cc3)ccc21] |
| 8 | 7-(5-chlorothiophen-2-yl)-N-((1R,2R)-1-(4-cyclopropoxy-3-fluorophenyl)-1-hydroxy-3-(pyrrolidin-1-yl)propan-2-yl)-1H-benzo[d][1,2]oxazine-4-carboxamide | 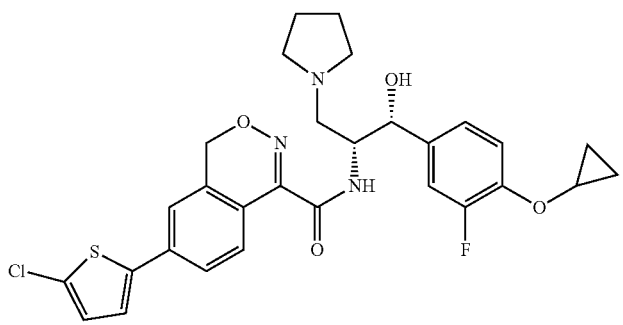 |
| 9 | N-((1R,2R)-3-(azetidin-1-yl)-1-(4-cyclopropoxy-3-fluorophenyl)-1-hydroxypropan-2-yl)-7-(5-chlorothiophen-2-yl)-1H-benzo[d][1,2]oxazine-4-carboxamide | 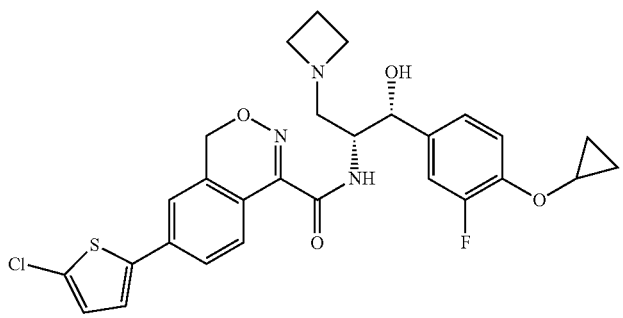 [SMILES: O=C(N[C@H](CN1CCC1)[C@H](O)c1ccc(OC2CC2)c(F)c1)C1=NOCc2cc(-c3ccc(Cl)s3)ccc21] |

TABLE 1-continued

| Example No. | Name | Structure |
|---|---|---|
| 10 | N-((1R,2R)-1-(3-chloro-4-cyclopropoxyphenyl)-1-hydroxy-3-(pyrrolidin-1-yl)propan-2-yl)-7-(5-chlorothiophen-2-yl)-1H-benzo[d][1,2]oxazine-4-carboxamide | 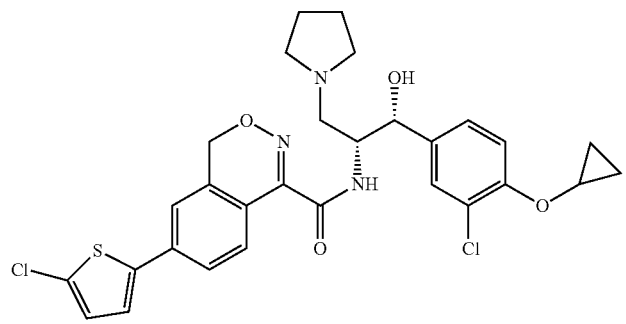 |
| 11 | N-((1R,2R)-3-(azetidin-1-yl)-1-(4-cyclopropoxyphenyl)-1-hydroxypropan-2-yl)-7-(5-chlorothiophen-2-yl)-1H-benzo[d][1,2]oxazine-4-carboxamide | 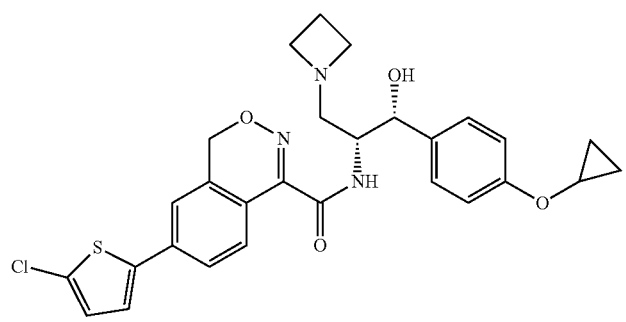 [SMILES: O=C(N[C@H](CN1CCC1)[C@H](O)c1ccc(OC2CC2)cc1)C1=NOCc2cc(-c3ccc(Cl)s3)ccc21] |
| 12 | 7-chloro-N-((1R,2R)-1-(4-cyclopropoxy-3-fluorophenyl)-1-hydroxy-3-(pyrrolidin-1-yl)propan-2-yl)-1H-benzo[4,5]thieno[2,3-d][1,2]oxazine-4-carboxamide | 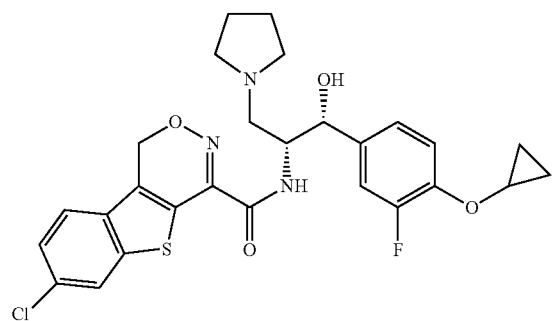 [SMILES: O=C(N[C@H](CN1CCCC1)[C@H](O)c1ccc(OC2CC2)c(F)c1)C1=NOCc2c1sc1cc(Cl)ccc21] |
| 13 | 7-chloro-N-((1R,2R)-1-(3-chloro-4-cyclopropoxyphenyl)-1-hydroxy-3-(pyrrolidin-1-yl)propan-2-yl)-1H-benzo[4,5]thieno[2,3-d][1,2]oxazine-4-carboxamide | 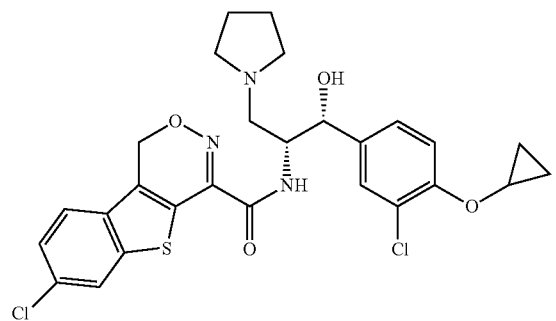 |

TABLE 1-continued

| Example No. | Name | Structure |
|---|---|---|
| 14 | 7-(5-chlorothiophen-2-yl)-N-((1R,2R)-1-(4-cyclopropoxyphenyl)-1-hydroxy-3-(pyrrolidin-1-yl)propan-2-yl)-1H-benzo[d][1,2]oxazine-4-carboxamide | 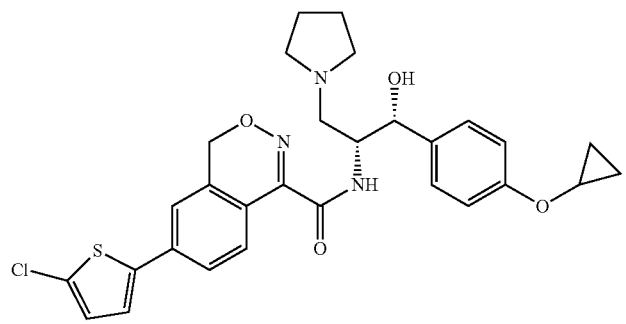 [SMILES: O=C(N[C@H](CN1CCCC1)[C@H](O)c1ccc(OC2CC2)cc1)C1=NOCc2cc(-c3ccc(Cl)s3)ccc21] |
| 15 | N-((1R,2R)-3-(azetidin-1-yl)-1-(4-cyclopropoxy-3-fluorophenyl)-1-hydroxypropan-2-yl)-7-chloro-1H-benzo[4,5]thieno[2,3-d][1,2]oxazine-4-carboxamide | 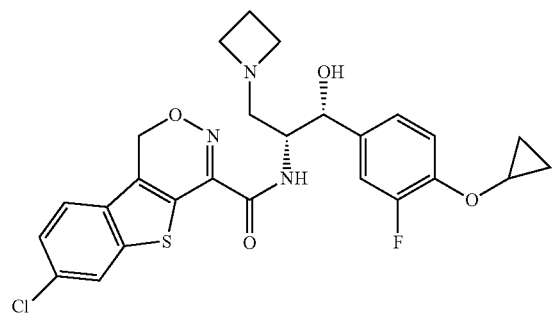 |
| 16 | N-((1R,2R)-3-(azetidin-1-yl)-1-(3-chloro-4-cyclopropoxyphenyl)-1-hydroxypropan-2-yl)-7-chloro-1H-benzo[4,5]thieno[2,3-d][1,2]oxazine-4-carboxamide | 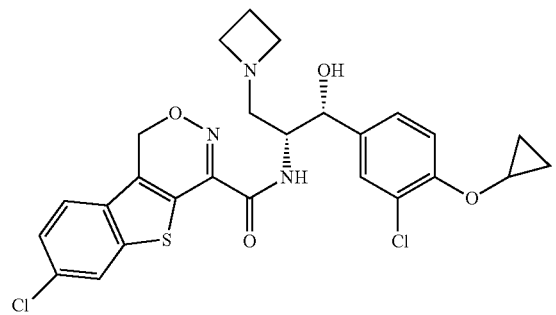 [SMILES: O=C(N[C@H](CN1CCC1)[C@H](O)c1ccc(OC2CC2)c(F)c1)C1=NOCc2c1sc1cc(Cl)ccc21] |
| 17 | N-((1R,2R)-1-(4-cyclopropoxy-3-fluorophenyl)-1-hydroxy-3-(pyrrolidin-1-yl)propan-2-yl)-7-(4-fluorophenyl)-N-methyl-1H-benzo[d][1,2]oxazine-4-carboxamide | 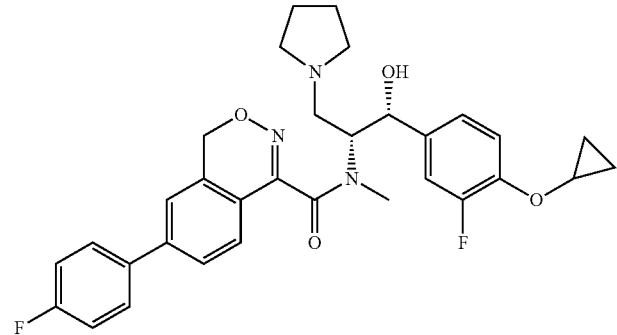 [SMILES: CN(C(=O)C1=NOCc2cc(-c3ccc(F)cc3)ccc21)[C@H](CN1CCCC1)[C@H](O)c1ccc(OC2CC2)c(F)c1] |

TABLE 1-continued

| Example No. | Name | Structure |
|---|---|---|
| 18 | 7-(5-chlorothiophen-2-yl)-N-((1R,2R)-1-(4-cyclopropoxy-3-fluorophenyl)-1-hydroxy-3-(pyrrolidin-1-yl)propan-2-yl)-N-methyl-1H-benzo[d][1,2]oxazine-4-carboxamide | 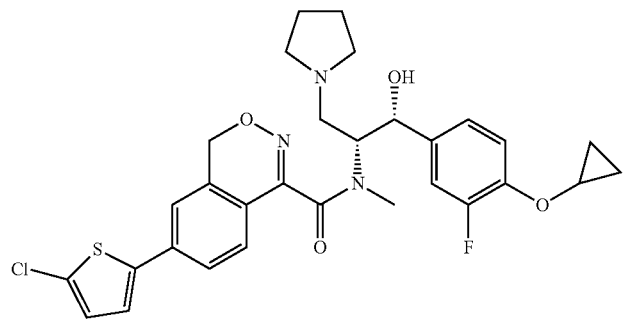 [SMILES: CN(C(=O)C1=NOCc2cc(-c3ccc(Cl)s3)ccc21)[C@H](CN1CCCC1)[C@H](O)c1ccc(OC2CC2)c(F)c1] |
| 19 | N-((1R,2R)-1-(3-chloro-4-cyclopropoxyphenyl)-1-hydroxy-3-(pyrrolidin-1-yl)propan-2-yl)-7-(4-fluorophenyl)-N-methyl-1H-benzo[d][1,2]oxazine-4-carboxamide | 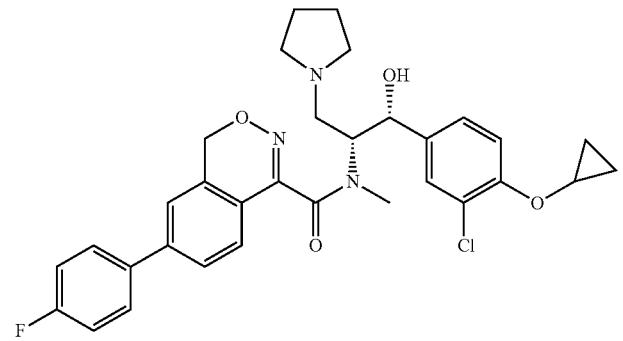 [SMILES: CN(C(=O)C1=NOCc2cc(-c3ccc(F)cc3)ccc21)[C@H](CN1CCCC1)[C@H](O)c1ccc(OC2CC2)c(Cl)c1] |
| 20 | N-((1R,2R)-1-(3-chloro-4-cyclopropoxyphenyl)-1-hydroxy-3-(pyrrolidin-1-yl)propan-2-yl)-1H-naphtho[2,3-d][1,2]oxazine-4-carboxamide | 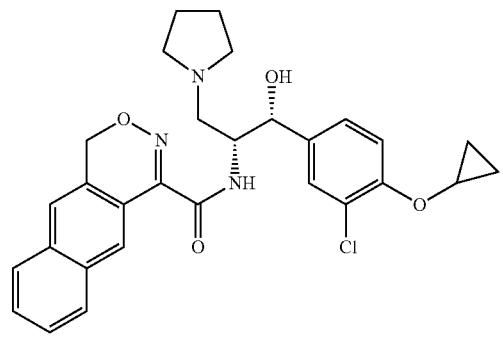 [SMILES: O=C(N[C@H](CN1CCCC1)[C@H](O)c1ccc(OC2CC2)c(Cl)c1)C1=NOCc2cc3ccccc3cc21] |
| 21 | N-((1R,2R)-3-(azetidin-1-yl)-1-(3-chloro-4-cyclopropoxyphenyl)-1-hydroxypropan-2-yl)-7-(4-fluorophenyl)-N-methyl-1H-benzo[d][1,2]oxazine-4-carboxamide | 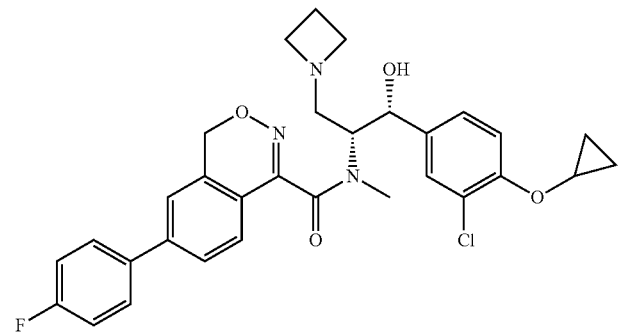 [SMILES: CN(C(=O)C1=NOCc2cc(-c3ccc(F)cc3)ccc21)[C@H](CN1CCC1)[C@H](O)c1ccc(OC2CC2)c(Cl)c1] |

TABLE 1-continued

| Example No. | Name | Structure |
|---|---|---|
| 22 | N-((1R,2R)-1-(3-chloro-4-cyclopropoxyphenyl)-1-hydroxy-3-(pyrrolidin-1-yl)propan-2-yl)-1H-naphtho[2,1-d][1,2]oxazine-4-carboxamide | 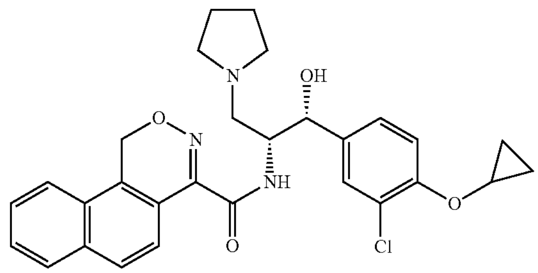 [SMILES: O=C(N[C@H](CN1CCCC1)[C@H](O)c1ccc(OC2CC2)c(Cl)c1)C1=NOCc2c1ccc1ccccc21] |
| 23 | N-((1R,2R)-1-(3-chloro-4-cyclopropoxyphenyl)-1-hydroxy-3-(pyrrolidin-1-yl)propan-2-yl)-7-(4-fluorophenyl)-1,1-dimethyl-1H-benzo[d][1,2]oxazine-4-carboxamide | 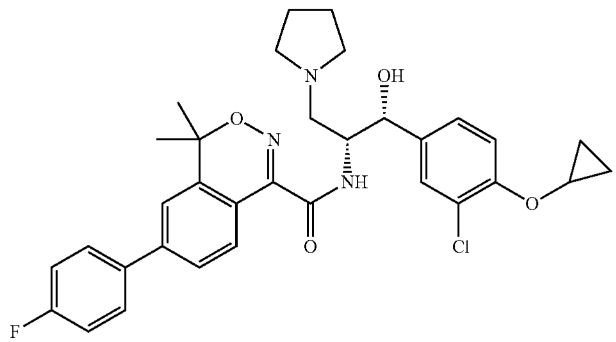 [SMILES: CC1(C)ON=C(C(=O)N[C@H](CN2CCCC2)[C@H](O)c2ccc(OC3CC3)c(Cl)c2)c2ccc(-c3ccc(F)cc3)cc21] |
| 24 | N-((1R,2R)-1-(3-chloro-4-cyclopropoxyphenyl)-1-hydroxy-3-(pyrrolidin-1-yl)propan-2-yl)-7-(4-fluorophenyl)-1-methyl-1H-benzo[d][1,2]oxazine-4-carboxamide | 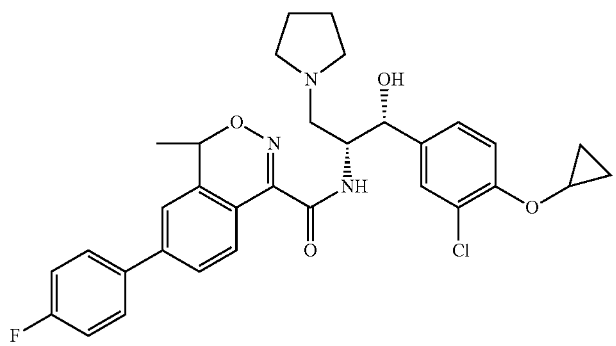 [SMILES: CC1ON=C(C(=O)N[C@H](CN2CCCC2)[C@H](O)c2ccc(OC3CC3)c(Cl)c2)c2ccc(-c3ccc(F)cc3)cc21] |
| 25 | N-((1R,2R)-1-(4-cyclopropoxyphenyl)-1-hydroxy-3-(pyrrolidin-1-yl)propan-2-yl)-1H-naphtho[2,1-d][1,2]oxazine-4-carboxamide | 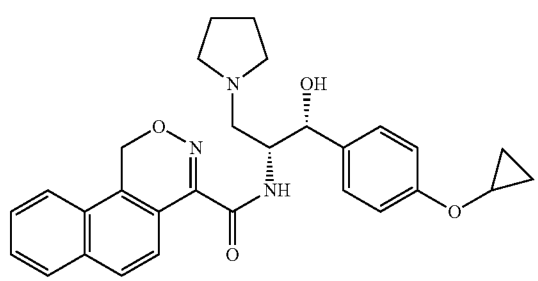 [SMILES: O=C(N[C@H](CN1CCCC1)[C@H](O)c1ccc(OC2CC2)cc1)C1=NOCc2c1ccc1ccccc21] |
| 26 | N-((1R,2R)-3-(azetidin-1-yl)-1-(3-chloro-4-cyclopropoxyphenyl)-1-hydroxypropan-2-yl)-1H-naphtho[2,1-d][1,2]oxazine-4-carboxamide | 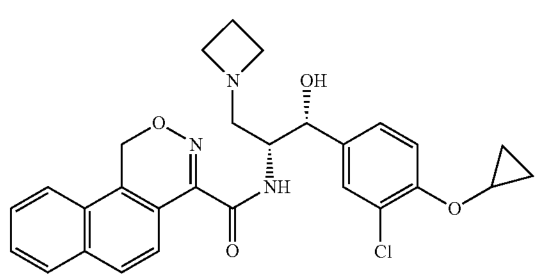 [SMILES: O=C(N[C@H](CN1CCC1)[C@H](O)c1ccc(OC2CC2)c(Cl)c1)C1=NOCc2c1ccc1ccccc21] |

TABLE 1-continued

| Example No. | Name | Structure |
|---|---|---|
| 27 | N-((1R,2R)-1-(3-chloro-4-cyclopropoxyphenyl)-1-hydroxy-3-(pyrrolidin-1-yl)propan-2-yl)-10H-[1,2]oxazino[4,5-h]quinoline-7-carboxamide | 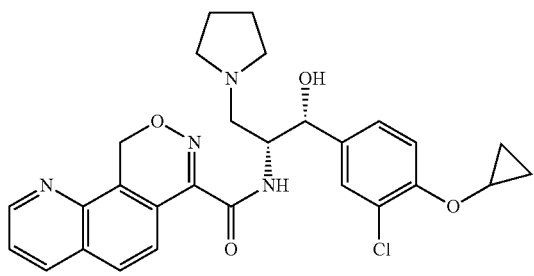 |
| 28 | N-((1R,2R)-1-(3-chloro-4-cyclopropoxyphenyl)-1-hydroxy-3-(pyrrolidin-1-yl)propan-2-yl)-8-fluoro-1H-naphtho[2,1-d][1,2]oxazine-4-carboxamide | 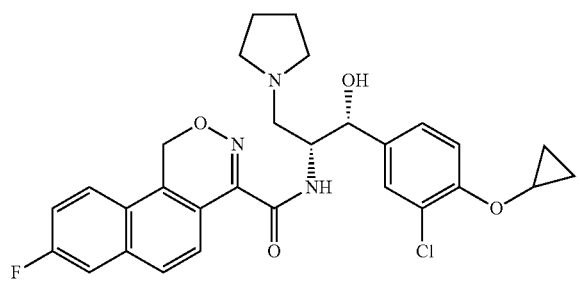 [SMILES: O=C(N[C@H](CN1CCCC1)[C@H](O)c1ccc(OC2CC2)c(Cl)c1)C1=NOCc2c1ccc1cc(F)ccc21] |
| 29 | N-((1R,2R)-1-(4-cyclopropoxyphenyl)-1-hydroxy-3-(pyrrolidin-1-yl)propan-2-yl)-8-fluoro-1H-naphtho[2,1-d][1,2]oxazine-4-carboxamide | 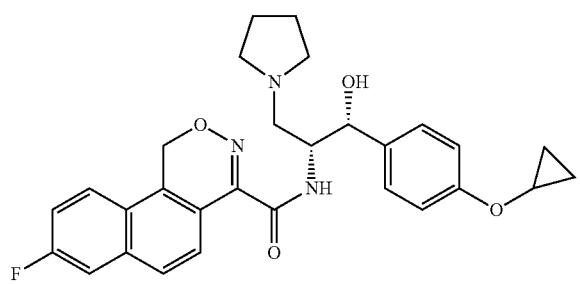 [SMILES: O=C(N[C@H](CN1CCCC1)[C@H](O)c1ccc(OC2CC2)cc1)C1=NOCc2c1ccc1cc(F)ccc21] |
| 30 | N-((1R,2R)-3-(azetidin-1-yl)-1-(3-chloro-4-cyclopropoxyphenyl)-1-hydroxypropan-2-yl)-8-fluoro-1H-naphtho[2,1-d][1,2]oxazine-4-carboxamide | 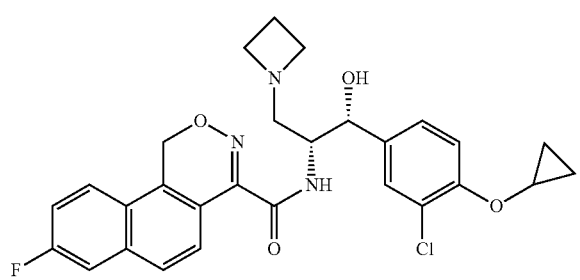 [SMILES: O=C(N[C@H](CN1CCC1)[C@H](O)c1ccc(OC2CC2)c(Cl)c1)C1=NOCc2c1ccc1cc(F)ccc21] |
| 31 | N-((1R,2R)-3-(azetidin-1-yl)-1-(4-cyclopropoxyphenyl)-1-hydroxypropan-2-yl)-8-fluoro-1H-naphtho[2,1-d][1,2]oxazine-4-carboxamide | 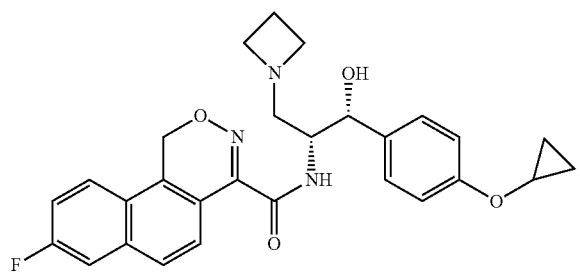 [SMILES: O=C(N[C@H](CN1CCC1)[C@H](O)c1ccc(OC2CC2)cc1)C1=NOCc2c1ccc1cc(F)ccc21] |

TABLE 1-continued

| Example No. | Name | Structure |
|---|---|---|
| 32 | 8-chloro-N-((1R,2R)-1-(3-chloro-4-cyclopropoxyphenyl)-1-hydroxy-3-(pyrrolidin-1-yl)propan-2-yl)-1H-thieno[3',2':3,4]benzo[1,2-d][1,2]oxazine-4-carboxamide | 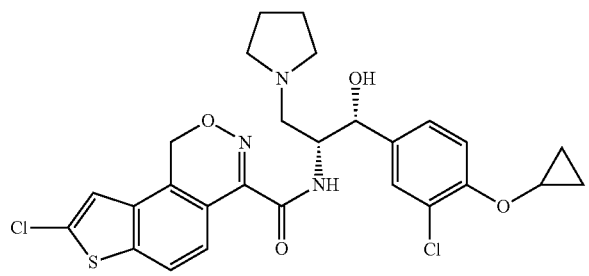 [SMILES: O=C(N[C@H](CN1CCCC1)[C@H](O)c1ccc(OC2CC2)c(Cl)c1)C1=NOCc2c1ccc1sc(Cl)cc21] |
| 33 | N-((1R,2R)-1-(3-chloro-4-cyclopropoxyphenyl)-1-hydroxy-3-(pyrrolidin-1-yl)propan-2-yl)-7-methyl-1,7-dihydro-[1,2]oxazino[5,4-e]indazole-4-carboxamide | 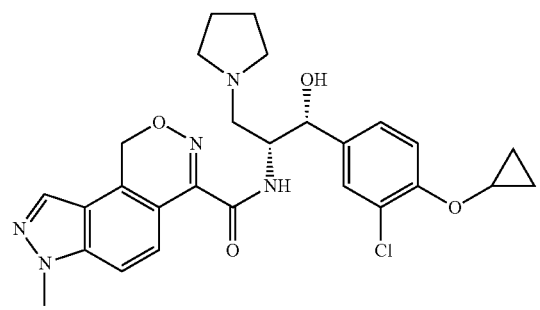 [SMILES: Cn1ncc2c3c(ccc21)C(C(=O)N[C@H](CN1CCCC1)[C@H](O)c1ccc(OC2CC2)c(Cl)c1)=NOC3] |
| 34 | N-((1R,2R)-1-(3-chloro-4-cyclopropoxyphenyl)-1-hydroxy-3-(pyrrolidin-1-yl)propan-2-yl)-1-methyl-1,9-dihydro-[1,2]oxazino[4,5-g]indazole-6-carboxamide | 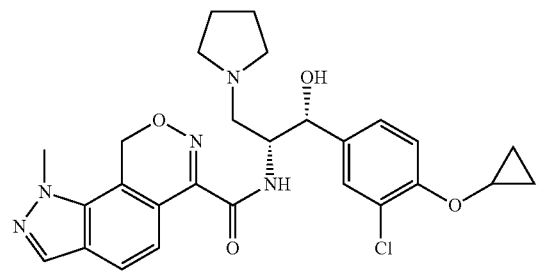 [SMILES: Cn1ncc2ccc3c(c21)CON=C3C(=O)N[C@H](CN1CCCC1)[C@H](O)c1ccc(OC2CC2)c(Cl)c1] |
| 35 | N-((1R,2R)-1-(3-chloro-4-cyclopropoxyphenyl)-1-hydroxy-3-(pyrrolidin-1-yl)propan-2-yl)-2-methyl-2,9-dihydro-[1,2]oxazino[4,5-g]indazole-6-carboxamide | 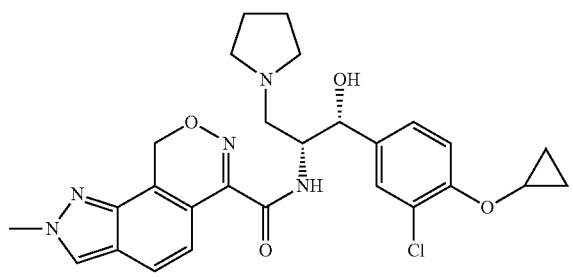 [SMILES: Cn1cc2ccc3c(c2n1)CON=C3C(=O)N[C@H](CN1CCCC1)[C@H](O)c1ccc(OC2CC2)c(Cl)c1] |
| 36 | N-((1R,2R)-1-(3-chloro-4-cyclopropoxyphenyl)-1-hydroxy-3-(pyrrolidin-1-yl)propan-2-yl)-1H-[1,2]oxazino[5,4-f]quinoline-4-carboxamide | 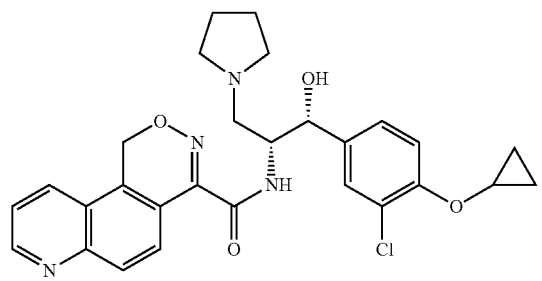 [SMILES: O=C(N[C@H](CN1CCCC1)[C@H](O)c1ccc(OC2CC2)c(Cl)c1)C1=NOCc2c1ccc1ncccc21] |

TABLE 1-continued

| Example No. | Name | Structure |
|---|---|---|
| 37 | 2-chloro-N-((1R,2R)-1-(3-chloro-4-cyclopropoxyphenyl)-1-hydroxy-3-(pyrrolidin-1-yl)propan-2-yl)-9H-thieno[2',3':3,4]benzo[1,2-d][1,2]oxazine-6-carboxamide | 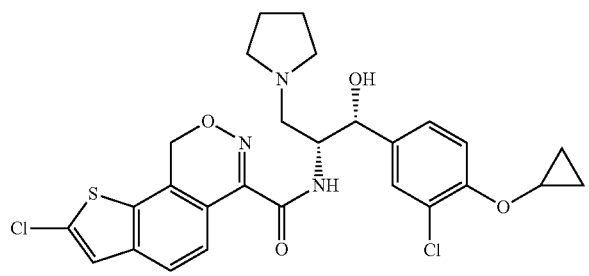 [SMILES: O=C(N[C@H](CN1CCCC1)[C@H](O)c1ccc(OC2CC2)c(Cl)c1)C1=NOCc2c1ccc1cc(Cl)sc21] |
| 38 | N-((1R,2R)-1-(4-cyclopropoxy-3-fluorophenyl)-1-hydroxy-3-(pyrrolidin-1-yl)propan-2-yl)-6-(4-fluorophenyl)-3,4-dihydroisoquinoline-1-carboxamide | 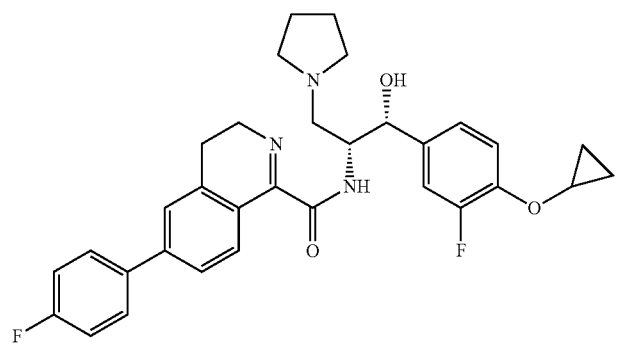 |
| 39 | N-((1R,2R)-1-(3-chloro-4-cyclopropoxyphenyl)-1-hydroxy-3-(pyrrolidin-1-yl)propan-2-yl)-6-(4-fluorophenyl)-N-methyl-3,4-dihydroisoquinoline-1-carboxamide | 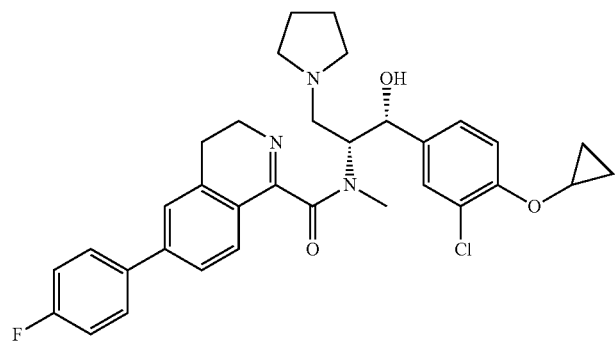 |
| 40 | N-((1R,2R)-3-(azetidin-1-yl)-1-(4-cyclopropoxyphenyl)-1-hydroxypropan-2-yl)-6-(4-fluorophenyl)-3,4-dihydroisoquinoline-1-carboxamide | 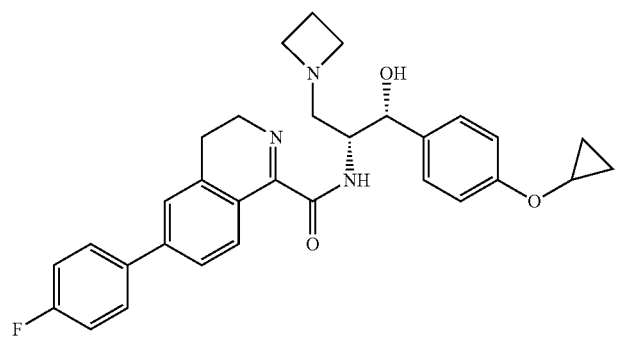 [SMILES: O=C(N[C@H](CN1CCC1)[C@H](O)c1ccc(OC2CC2)cc1)C1=NCCc2cc(-c3ccc(F)cc3)ccc21] |

TABLE 1-continued

| Example No. | Name | Structure |
|---|---|---|
| 41 | N-((1R,2R)-1-(3-chloro-4-cyclopropoxyphenyl)-1-hydroxy-3-(pyrrolidin-1-yl)propan-2-yl)-6-(4-fluorophenyl)-3,3-dimethyl-3,4-dihydroisoquinoline-1-carboxamide | 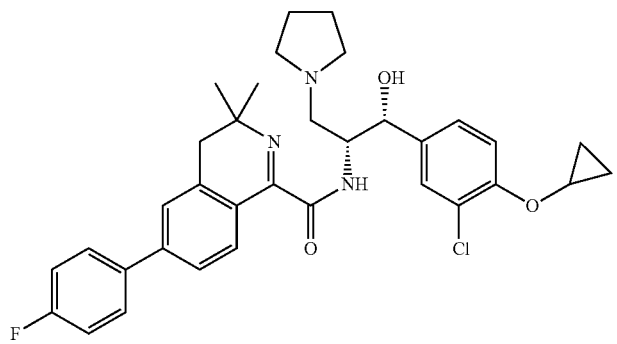 [SMILES: CC1(C)Cc2cc(-c3ccc(F)cc3)ccc2C(C(=O)N[C@H](CN2CCCC2)[C@H](O)c2ccc(OC3CC3)c(Cl)c2)=N1] |
| 42 | N-((1R,2R)-1-(3-chloro-4-cyclopropoxyphenyl)-1-hydroxy-3-(pyrrolidin-1-yl)propan-2-yl)-6-(4-fluorophenyl)isochroman-1-carboxamide | 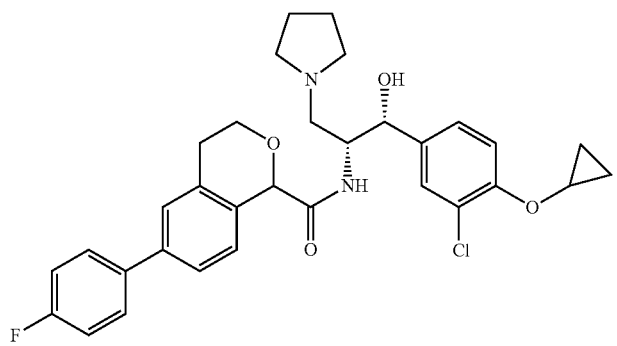 |
| 43 | 7-chloro-N-((1R,2R)-1-(3-chloro-4-cyclopropoxyphenyl)-1-hydroxy-3-(pyrrolidin-1-yl)propan-2-yl)-3,4-dihydro-1H-benzo[4,5]thieno[2,3-c]pyran-1-carboxamide | 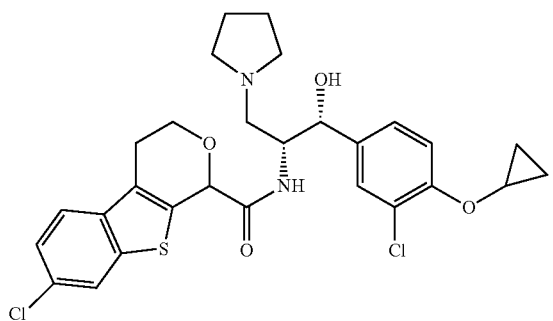 |
| 44 | 8-chloro-N-((1R,2R)-1-(4-cyclopropoxyphenyl)-1-hydroxy-3-(pyrrolidin-1-yl)propan-2-yl)-1H-thieno[3',2':3,4]benzo[1,2-d][1,2]oxazine-4-carboxamide | 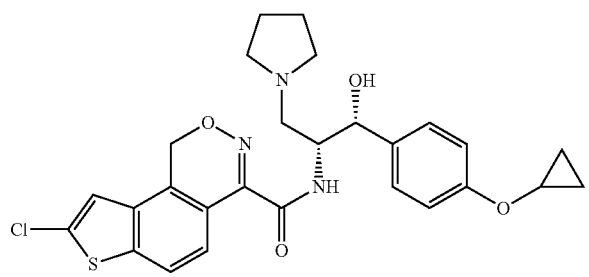 [SMILES: O=C(N[C@H](CN1CCCC1)[C@H](O)c1ccc(OC2CC2)cc1)C1=NOCc2c1ccc1sc(Cl)cc21] |

TABLE 1-continued

| Example No. | Name | Structure |
|---|---|---|
| 45 | N-((1R,2R)-1-(3-chloro-4-cyclopropoxyphenyl)-1-hydroxy-3-(pyrrolidin-1-yl)propan-2-yl)-7-(cyclohexylmethoxy)-1H-benzo[d][1,2]oxazine-4-carboxamide | 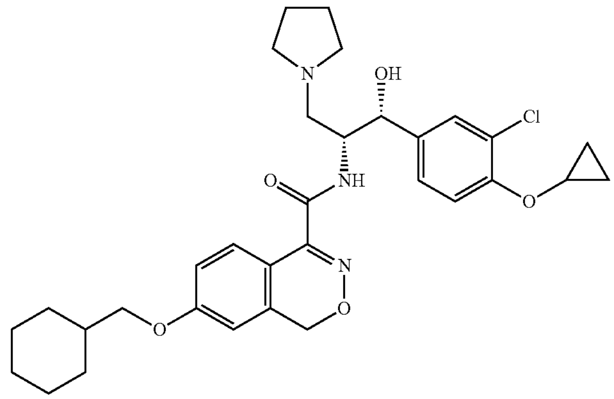 [SMILES: O=C(N[C@H](CN1CCCC1)[C@H](O)c1ccc(OC2CC2)c(Cl)c1)C1=NOCc2cc(OCC3CCCCC3)ccc21] |
| 46 | N-((1R,2R)-1-(4-cyclopropoxy-3-fluorophenyl)-1-hydroxy-3-(pyrrolidin-1-yl)propan-2-yl)-1-methyl-1,9-dihydro[1,2]oxazino[4,5-g]indazole-6-carboxamide | 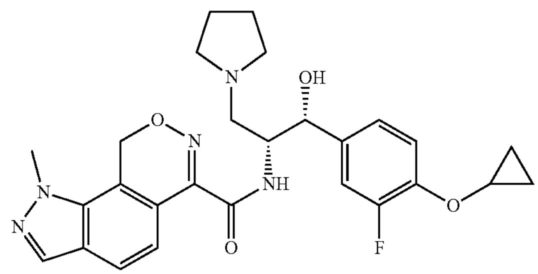 [SMILES: Cn1ncc2ccc3c(c21)CON=C3C(=O)N[C@H](CN1CCCC1)[C@H](O)c1ccc(OC2CC2)c(F)c1] |
| 47 | 2-chloro-N-((1R,2R)-1-(4-cyclopropoxy-3-fluorophenyl)-1-hydroxy-3-(pyrrolidin-1-yl)propan-2-yl)-9H-thieno[2',3':3,4]benzo[1,2-d][1,2]oxazine-6-carboxamide | 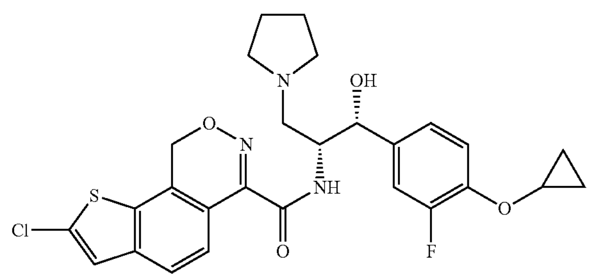 [SMILES: O=C(N[C@H](CN1CCCC1)[C@H](O)c1ccc(OC2CC2)c(F)c1)C1=NOCc2c1ccc1cc(Cl)sc21] |

In some embodiments, the compound is selected from Table 1.

In some embodiments, the compound is selected from the group consisting of the compounds of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, and 43.

In some embodiments, the compound is selected from the group consisting of the compounds of Examples 44, 45, 46, and 47.

In some embodiments, the compound is selected from the group consisting of the compounds of Examples 1, 2, 3, 4, 5, 6, 7, 8, 9, 10, 11, 12, 13, 14, 17, 18, 19, 20, 21, 22, 24, 25, 26, 27, 28, 29, 30, 31, 38, 39, 40, 44, 45, 46, and 47.

In some embodiments, the compound is selected from the group consisting of the compounds of Examples 1, 2, 3, 4, 5, 6, 7, 8, 9, 10, 11, 14, 17, 18, 19, 20, 21, 22, 25, 26, 27, 28, 29, 30, 38, 39, 44, 46, and 47.

In some embodiments, the compound is selected from the group consisting of the compounds of Examples 1, 2, 3, 7, 8, 9, 14, 17, 20, 22, 25, 26, 27, 28, 29, 30, 45, 46, and 47.

In some embodiments, the compound is selected from the group consisting of the compounds of Examples 1, 2, 3, 4, 5, 6, 7, 17, 19, 21, 23, 24, 38, 39, 40, 41, and 42.

In some embodiments, the compound is selected from the group consisting of the compounds of Examples 8, 9, 10, 11, 14, and 18.

In some embodiments, the compound is selected from the group consisting of the compounds of Examples 1, 2, 3, 4, 5, 6, 7, 8, 9, 10, 11, 14, 17, 18, 19, 21, 23, 24, 38, 39, 40, 41, 42, and 45.

In some embodiments, the compound is selected from the group consisting of the compounds of Examples 12, 13, 15, 16, 44 and 47.

In some embodiments, the compound is selected from the group consisting of the compounds of Examples 20, 22, 25, 26, 28, 29, 30, and 31.

In some embodiments, the compound is selected from the group consisting of the compounds of Examples 27, 32, 33, 34, 35, 36, 37, 43, 44, 46, and 47.

In some embodiments, the compound is selected from the group consisting of the compounds of Examples 1, 2, 3, 4, 8, 10, 12, 13, 14, 17, 18, 19, 20, 22, 23, 24, 25, 27, 28, 29, 32, 33, 34, 35, 36, 37, 38, 39, 41, 42, 43, 44, 45, 46, and 47.

In some embodiments, the compound is selected from the group consisting of the compounds of Examples 5, 6, 7, 9, 11, 15, 16, 21, 26, 30, 31, and 40.

In some embodiments, the compound is selected from the group consisting of the compounds of Examples 1, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, and 47.

In some embodiments, the compound is selected from the compound of Example 3.

In some embodiments, the compound is selected from the group consisting of the compounds of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 44, 45, 46, and 47.

In some embodiments, the compound is selected from the group consisting of the compounds of Examples 38, 39, 40, 41, 42, and 43.

In some embodiments, the compound is selected from the group consisting of the compounds of Examples 1, 2, 3, 4, 5, 6, 7, 8, 9, 10, 11, 12, 13, 14, 15, 16, 19, 20, 22, 23, 24, 25, 26, 27, 28, 29, 30, 31, 32, 33, 34, 35, 36, 37, 38, 40, 41, 42, 43, 44, 45, 46, and 47.

In some embodiments, the compound is selected from the group consisting of the compounds of Examples 17, 18, 19, 21, and 38.

Pharmaceutical Administration and Formulation

In some embodiments, provided herein are pharmaceutical compositions comprising a Compound of Formula I, I(b), I(c), or a compound in Table 1, optionally as a single stereoisomer or mixture of stereoisomers thereof and additionally optionally as a pharmaceutically acceptable salt thereof; and a pharmaceutically acceptable excipient.

In some embodiments, the pharmaceutical composition comprises a compound of Formula I, I(a), I(b), II, II(a), II(b), III, III(a), III(b), IV, IV(a), IV(b), V, V(a), V(b), VI, VI(a), VI(b), VII, VII(a), VII(b), VIII, VIII(a), VIII(b), IX, IX(a), IX(b), X, X(a), X(b), XI, XI(a), XI(b), XII, XII(a), XII(b), XIII, XIII(a), XIII(b), XIV, XV, XVI, XVII, XVIII, XIX, XX, XXI, XXII, XXIII or a compound of Table 1; optionally as a single stereoisomer or mixture of stereoisomers thereof and additionally optionally as a pharmaceutically acceptable salt thereof; and one or more pharmaceutically acceptable excipient(s).

In certain embodiments, the compounds presented herein can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

In certain embodiments, the compounds presented herein can be administered in any acceptable solid, semi-solid, liquid or gaseous dosage form. Acceptable dosage forms include, but are not limited to, aerosols, capsules, creams, elixirs, emulsions, gases, gels, grains, liniments, lotions, lozenges, ointments, pastes, powders, solutions, suspensions, syrups and tablets. Acceptable delivery systems include, but are not limited to, biodegradable implants (e.g., poly(DL-lactide), lactide/glycolide copolymers and lactide/caprolactone copolymers), capsules, douches, enemas, inhalers, intrauterine devices, nebulizers, patches, pumps and suppositories. Methods for preparing the dosage forms of the invention are known, or will be apparent, to those skilled in this art; for example, see Remington's Pharmaceutical Sciences, 18th Ed., (Mack Publishing Company, Easton, Pa., 1990).

In certain embodiments, a dosage form of the invention may be comprised solely of a compound of the invention or the compound of the invention may be formulated along with conventional excipients, including pharmaceutical carriers, adjuvants, and/or other medicinal or pharmaceutical agents. Acceptable excipients include, but are not limited to, (a) antiadherents, such as croscarmellose sodium, crospovidone, sodium starch glycolate, microcrystalline cellulose, starch and talc; (b) binders, such as acacia, cellulose, gelatin, hydroxypropyl cellulose, lactose, maltitol, polyethylene glycol, polyvinyl pyrrolidone, sorbitol, starch, sugar, sucrose and xylitol; (c) coatings, such as cellulose, shellac, zein and enteric agents; (d) disintegrants, such as cellulose, cross-linked polyvinyl pyrrolidone, sodium carboxymethyl cellulose, methylcellulose, microcrystalline cellulose, sodium starch glycolate, starch, and alginic acid; (e) diluents or filling agents, such as calcium or sodium carbonate, calcium or sodium phosphate, sugars (such as glucose, lactose, mannitol, sorbitol and sucrose), cellulose, croscarmellose sodium, and povidone; (f) flavoring agents; (g) coloring agents; (h) glidants, such as calcium stearate, colloidal silicon dioxide, glyceryl behenate, glyceryl monostearate, glyceryl palmitostearate, hydrogenated vegetable oil, magnesium stearate, magnesium trisilicate, mineral oil, polyethylene glycols, silicon dioxide, starch, stearate, stearic acid, talc, sodium stearyl fumarate, sodium benzoate and zinc; (i) lubricants, such as calcium stearate, hydrogenated vegetable oils, magnesium stearate, mineral oil, polyethylene glycol, sodium stearyl fumarate, stearin, stearic acid and talc; and (j) preservatives, such as chlorobutanol, citric acid, cysteine, methionine, methyl paraben, phenol, propyl paraben, retinyl palmitate, selenium, sodium citrate, sorbic acid, vitamin A, vitamin C and vitamin E. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed. Capsules may contain any of the excipients listed above, and may additionally contain a semi-solid or liquid carrier, such as a polyethylene glycol or oil. Pharmaceutical carriers include soluble polymers, microparticles made of insoluble or biodegradable natural and synthetic polymers, microcapsules or microspheres, lipoproteins, liposomes and micelles.

In certain embodiments, the pharmaceutical compositions may be in the form of a liquid, such as a solution, suspension, emulsion, syrup, elixir, or other like forms or may be presented as a dry product for reconstitution with water or other suitable vehicle before use. Liquid preparations may contain conventional additives such as (a) liquid diluents, such as water, saline, Ringer's solution, alcohols including monohydric alcohols and polyhydric alcohols such as polyethylene or propylene glycols and their derivatives, glycerin, fixed oils such as synthetic mono or diglycerides, or other solvents; (b) surfactants, suspending agents, or emulsifying agents, such as sodium carboxymethylcellulose, methylcellulose, hydroxypropyl methylcelluose, sodium alginate, polyvinylpyrrolidone, gum tragacanth, gum acacia, polyoxyethylene sorbitan fatty acid esters, saturated polyglycolized glycerides, monoglycerides, fatty acid esters, block copolymers of ethylene oxide and propylene oxide, polyoxyl stearates, ethoxylated castor oils, and ethoxylated hydroxystearic acids; (c) buffers, such as acetates, citrates or phosphates; (d) chelating agents, such as ethylenediaminetetraacetic acid, carbohydrates such as dextran, hydroxyalkylcellulose, hydroxyalkylmethylcellulose, or saturated fatty acids, such as stearic acid; (e) antibacterial agents, such as chlorobutanol, benzyl alcohol, phenol, sorbic acid, or parabens, such as methyl paraben; (f) antioxidants, such as ascorbic acid or sodium bisulfite; (g) isotonic agents, sodium chloride or sugars, such as dextrose; as well as sweetening and flavoring agents, dyes and preservatives.

In certain embodiments, the pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In certain embodiments, the pharmaceutical compositions will contain a therapeutically effective amount of a compound of the invention, as an individual stereoisomer or mixture of stereoisomers, or a pharmaceutically acceptable salt thereof, with the remainder of the pharmaceutical composition comprised of one or more pharmaceutically acceptable excipients. Generally, for oral administration, a compound of the invention, as an individual stereoisomer or mixture of stereoisomers, or a pharmaceutically acceptable salt thereof will comprise from 1% to 99% by weight of a pharmaceutically acceptable composition, with the remainder of the composition comprised of one or more pharmaceutically acceptable excipients. Typically, a compound of the invention, as an individual stereoisomer or mixture of stereoisomers, or a pharmaceutically acceptable salt thereof will comprise from 5% to 75% by weight of a pharmaceutically acceptable composition, with the remainder of the composition comprised of one or more pharmaceutically acceptable excipients. For parenteral administration, a compound of the invention, as an individual stereoisomer or mixture of stereoisomers, or a pharmaceutically acceptable salt thereof will comprise from 0.01% to 1% by weight of a pharmaceutically acceptable composition.

In certain embodiments, a therapeutically effective amount of a compound of the invention will vary depending upon a sundry of factors including the activity, metabolic stability, rate of excretion and duration of action of the compound, the age, weight, general health, sex, diet and species of the subject, the mode and time of administration of the compound, the presence of adjuvants or additional therapeutically active ingredients in a composition, and the severity of the disease for which the therapeutic effect is sought.

In certain embodiments, the compounds presented herein can be administered to human subjects at dosage levels in the range of about 0.1 to about 10,000 mg per day. A normal human adult having a body weight of about 70 kilograms can be administered a dosage in the range of from about 0.15 µg to about 150 mg per kilogram of body weight per day. Typically, a normal adult human will be administered from about 0.1 mg to about 25 mg, or 0.5 mg to about 10 mg per kilogram of body weight per day. The compounds of the invention may be administered in one or more unit dose forms. The unit doses may be administered one to four times a day, or two times a day, or once a day. In an alternate method of describing an effective dose, an oral unit dose is one that is necessary to achieve a blood serum level of about 0.05 to 20 µg/ml or about 1 to 20 µg/ml in a subject The optimum dose of a compound of the invention for a particular subject can be determined by one of ordinary skill in the art.

Uses and Methods of Treatment

In some embodiments, the compounds described herein are used in the preparation or manufacture of medicaments for the treatment of diseases or conditions that are mediated by the enzyme GCS or in which inhibition of the enzyme GCS ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically active metabolite, pharmaceutically acceptable prodrug, or pharmaceutically acceptable solvate thereof, in therapeutically effective amounts to said subject.

In some embodiments, provided is a method of treating or ameliorating a medical condition, comprising administering to a subject in need thereof a compound according to any of the various embodiments described herein or a pharmaceutical composition according to any of the various embodiments described herein.

In some embodiments, provided herein is a method of treating or ameliorating a disease ameliorated by the inhibition of GCS comprising administering to a subject in need of treatment a therapeutically-effective amount of a compound of Formula I, I(a), I(b), II, II(a), II(b), III, III(a), III(b), IV, IV(a), IV(b), V, V(a), V(b), VI, VI(a), VI(b), VII, VII(a), VII(b), VIII, VIII(a), VIII(b), IX, IX(a), IX(b), X, X(a), X(b), XI, XI(a), XI(b), XII, XII(a), XII(b), XIII, XIII(a), XIII(b), XIV, XV, XVI, XVII, XVIII, XVIII, XIX, XX, XXI, XXII, XXIII, or a compound in Table 1; optionally as a single stereoisomer or mixture of stereoisomers thereof and additionally optionally as a pharmaceutically acceptable salt thereof. In some embodiments, the disease is selected from glycolipid storage diseases (e.g., Tay Sachs, Sandhoffs, GM1 gangliosidosis—including type, type 2 and type 3, Niemanns-Pick, and Fabry diseases); diseases associated with glycolipid accumulation (e.g., Gaucher disease); diseases that cause renal hypertrophy or hyperplasia such as diabetic nephropathy; diseases that cause hyperglycemia or hyperinsulemia; cancers in which glycolipid synthesis is abnormal; infectious diseases caused by organisms which use cell surface glycolipids as receptors or in which synthesis of glucosylceramide is essential or important; a metabolic disorder such as atherosclerosis, polycystic kidney disease, renal hypertrophy, diabetes mellitus, and obesity; cancer such as breast cancer, renal adenocarcinoma, brain cancer, neuroblastoma, lung cancer, intestinal cancer, pancreas and prostate cancer; neuronal disorders; neuronal injury; inflammatory diseases or disorders (e.g., rheumatoid arthritis, Crohn's disease, asthma and sepsis), and diabetes mellitus and obesity.

In another embodiment, the disease is a gangliosidosis with central nervous system involvement, e.g., Gaucher's type 2, Gaucher's type 3, Gaucher's type 1 in which patients are at a higher risk for peripheral neuropathy and parkinsonian features, Sandhoff, infantile Sandhoff with peripheral neuropathy, GM1 gangliosidosis type 1, GM1 gangliosidosis type 2, GM1 gangliosidosis type, Tay-Sachs, and GM2 gangliosidosis, AB variant. In another embodiment, the disease is GM1 gangliosidosis type 1, GM1 gangliosidosis type 2, GM1 gangliosidosis type, Tay-Sachs, or GM2 gangliosidosis with AB variant. In another embodiment, the disease is Gaucher's type 2, Gaucher's type 3, Gaucher's type 1 in which patients are at a higher risk for peripheral neuropathy and parkinsonian features. In another embodiment, the disease is Sandhoff or infantile Sandhoff with peripheral neuropathy.

In another embodiment the compounds of Formula I, I(a), I(b), II, II(a), II(b), III, III(a), III(b), IV, IV(a), IV(b), V, V(a), V(b), VI, VI(a), VI(b), VII, VII(a), VII(b), VIII, VIII(a), VIII(b), IX, IX(a), IX(b), X, X(a), X(b), XI, XI(a), XI(b), XII, XII(a), XII(b), XIII, XIII(a), XIII(b), XIV, XV, XVI, XVII, XVIII, XIX, XX, XXI, XXII, XXIII, or a compound in Table 1; optionally as a single stereoisomer or mixture of stereoisomers thereof and additionally optionally as a pharmaceutically acceptable salt thereof is one which crosses the blood brain barrier.

Preparation of Compounds

The following are illustrative examples of how the compounds can be prepared and tested. Although the examples can represent only some embodiments, it should be understood that the following examples are illustrative and not limiting.

In a further aspect, it is provided a method of making a compound, comprising synthesizing a compound as any of the various embodiments described above or below. Examples of the method are further described in the Examples. All synthetic steps outlined herein may be combined with subsequent steps, or may incorporate batches or compounds from previous steps.

Compounds disclosed herein are commercially available or can be readily prepared from commercially available starting materials according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Synthesis of some of the compounds are exemplified in detail below.

In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral axillary, separation of the resulting mixture of diastereomers by recrystallization or chromatography and liberation of the optically pure product from the auxiliary or (2) direct separation of the mixture of optical enantiomers on chiral chromatographic column.

Materials were obtained from commercial suppliers and were used without further purification. Air or moisture sensitive reactions were conducted under argon atmosphere using oven-dried glassware and standard syringe/septa techniques. $^1$H NMR spectra were measured at 400 MHz unless stated otherwise and data were reported as follows in ppm (δ) from the internal standard (TMS, 0.0 ppm): chemical shift (multiplicity, integration, coupling constant in Hz).

General Scheme 1

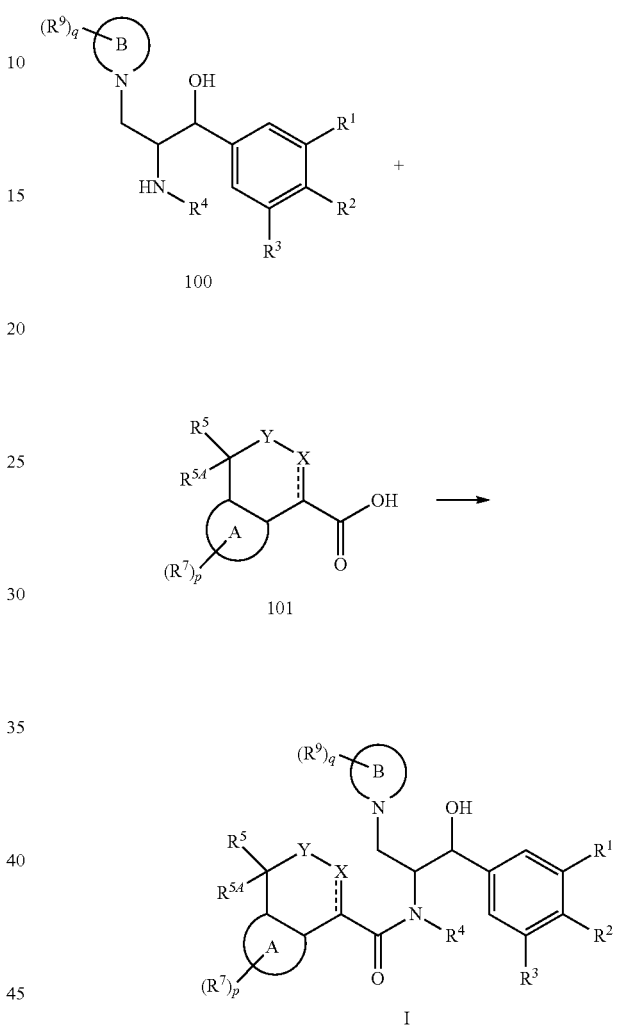

A Compound of Formula I (where all groups are as defined according to any of the embodiments disclosed herein) can be prepared according to General Scheme 1.

A Compound of Formula I can be prepared using standard amide coupling conditions. More specifically, an intermediate of formula 100, which can be prepared using procedures disclosed herein or are known to one of ordinary skill in the art, is treated with 101 in a solvent such as DMF, DCM or THF, optionally in the presence of a base such as DIPEA or TEA, and in the presence of a coupling agent such as EDCI and/or HOBt to yield a compound of Formula I. The mixture can optionally be purified using procedures known to one of ordinary skill in the art. Alternatively, the intermediate of formula 101 can be treated with a chlorinating agent such as oxalyl chloride in a solvent such as DMF followed by treatment with the intermediate of formula 100 to yield a compound of Formula I. The mixture can optionally be purified (or individual isomers optionally resolved) using procedures known to one of ordinary skill in the art.

SYNTHETIC EXAMPLES

Intermediate A

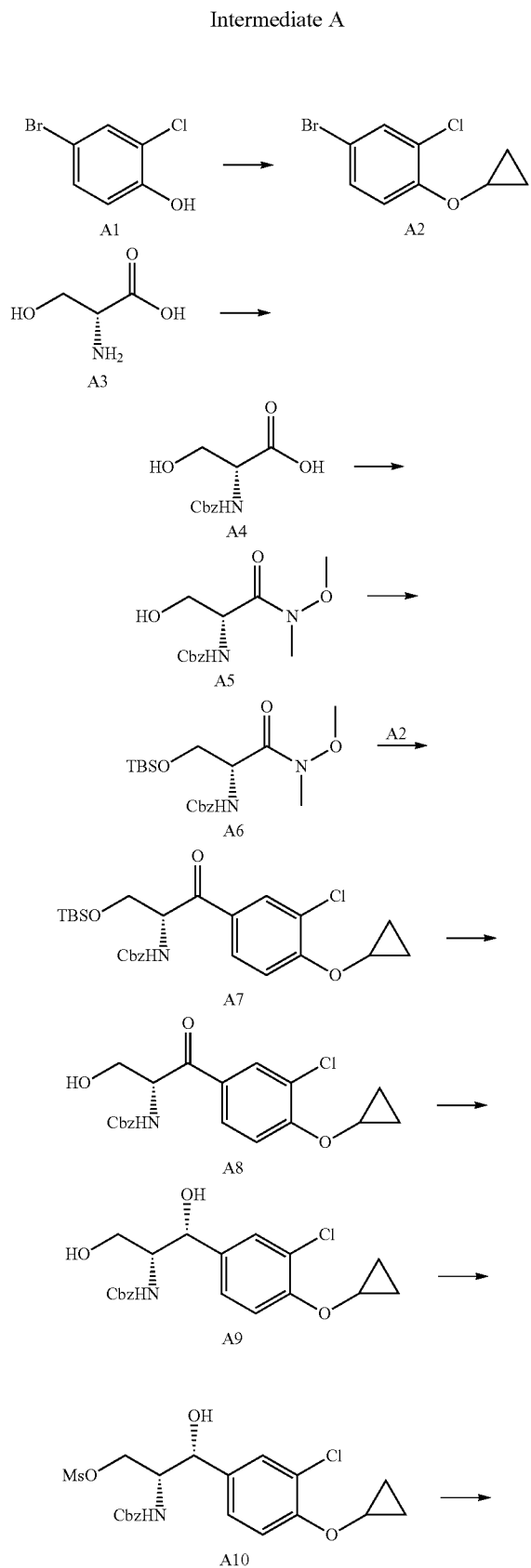

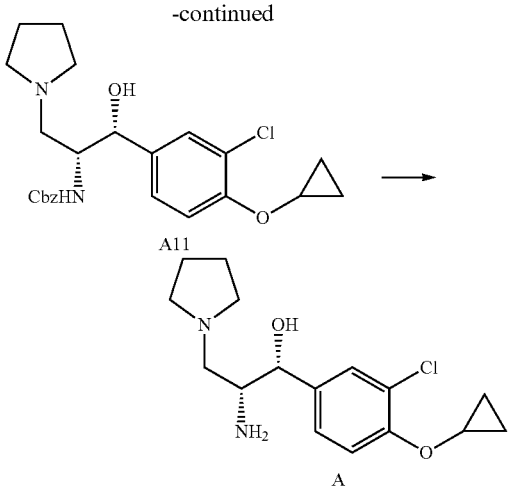

To a solution of Intermediate A1 (20 g, 96 mmol) in 1-methyl-2-pyrrolidinone (300 mL) was added cesium carbonate (62.8 g, 193 mmol) and bromocyclopropane (24 mL, 289 mmol). The mixture was stirred for 24 h while keeping internal temperature between 145° C. and 155° C. The reaction mixture was cooled to room temperature, diluted with water (400 mL), and extracted with a mixture of ethyl acetate in petroleum ether (15% v/v) (300 mL×3). The combined organic phases were washed with brine (150 mL×4), dried over anhydrous sodium sulfate, filtered, and concentrated to afford a crude product. The crude product was purified with flash column chromatography on silica gel (petroleum ether) to furnish Intermediate A2. HPLC: Rt: 1.96 minute. $^1$H-NMR (CDCl$_3$, 400 MHz): δ (ppm) 0.80-0.88 (m, 4H), 3.67-3.82 (m, 1H), 7.15 (d, J=8.8 Hz, 1H), 7.32 (dd, J=8.8, 2.4 Hz, 1H), 7.47 (d, J=2.4 Hz, 1H).

Benzyl chloroformate (50 w.t. % solution in toluene, 50 mL, 148 mmol) was added to a solution of (R)-2-amino-3-hydroxypropanoic acid (A3, 10.5 g, 100 mmol) in sat. aq NaHCO$_3$ solution (400 mL). The mixture was stirred vigorously at 20° C. for 4 h. and the aqueous solution was extracted with ether (400 mL×2). The aqueous phase was acidified with conc. hydrochloric acid to pH=2 and extracted with ethyl acetate (300 mL×3). The combined organic phases were dried with Na$_2$SO$_4$ and concentrated to afford Intermediate A4. LC-MS (m/z): 240 [M+1]$^+$; $^1$H-NMR (DMSO-d$_6$, 400 MHz) peaks: δ (ppm) 3.653 (m, 2H), 4.051 (m, 1H), 4.884 (m, 1H), 5.038 (s, 2H), 7.303-7.373 (m, 6H), 12.658 (s, 1H).

To a mixture of EDCI.HCl (2.4 g, 12.5 mmol), HOBt (1.7 g, 12.5 mmol), DIPEA (2.7 g, 20 mmol) in DCM (50 mL) was added Intermediate A4 (1 g, 4 mmol) and N,O-dimethylhydroxylamine hydrochloride (1.2 g, 12.5 mmol) and the reaction mixture was stirred at room temperature overnight. The reaction mixture was washed with hydrochloric acid solution (1 M, 50 mL×2), saturated aqueous NaHCO$_3$ (20 mL), brine (20 mL), and dried over Na$_2$SO$_4$, and concentrated. The crude product was purified by silica gel column chromatography (ethyl acetate in petroleum, 30% v/v) to give Intermediate A5. LC-MS (m/z): 283 [M+1]$^+$; $^1$H-NMR (CDCl$_3$, 400 MHz) peaks: δ (ppm) 3.113 (s, 3H), 3.673 (s, 3H), 3.743 (t, J=4.8 Hz, 2H), 4.766 (m, 1H), 4.959-5.044 (m, 2H), 6.046 (d, J=8.0 Hz, 1H), 7.200-7.254 (m 5H).

To a solution of Intermediate A5 (500 mg, 1.77 mmol) and imidazole (602 mg, 8.86 mmol) in THF (20 mL) at 0° C. was added dropwise a solution of TBDMS-Cl (800 mg, 5.31 mmol) in THF (10 mL) and the reaction mixture was stirred at room temperature for 2 h. The reaction mixture was filtered, washed with 1N HCl (50 mL×2) and brine (50 mL), and dried over $Na_2SO_4$, and concentrated. The crude product was purified with silica gel column chromatography (ethyl acetate in petroleum, 13% v/v) to give Intermediate A6. LC-MS (m/z): 396 [M+1]$^+$; $^1$H-NMR (CDCl$_3$, 400 MHz) peaks: δ (ppm) 0.012 (s, 3H), 0.085 (s, 6H), 0.852 (s, 9H), 3.211 (s, 3H), 3.756 (s, 3H), 3.794-3.896 (m, 2H), 4.809 (m, 1H), 5.085 (q, J=11.2 Hz, 2H), 5.662 (d, J=8.8 Hz, 1H), 7.286-7.351 (m 5H).

To a solution of Intermediate A2 (70 g, 283 mmol) in dry THF (700 mL) at −70° C. under nitrogen atmosphere was added dropwise n-BuLi (2.4 M in hexane, 118 mL) over a period of 20 minutes. After the mixture was stirred at −70° C. for 40 minutes, to the mixture was slowly added a solution of Intermediate A6 (44.8 g, 113 mmol) in dry THF (50 mL) at a rate that maintained the internal temperature between −70° C. and −50° C. The mixture was stirred for 1 h. The reaction mixture was quenched with saturated ammonium chloride solution (400 mL) and extracted with ethyl acetate (300 mL×3). The organic phase was washed with water (200 mL) and brine (200 mL), dried over anhydrous sodium sulfate, filtered, and concentrated to furnish a crude product. The crude product was purified with flash column chromatography on silica gel (ethyl acetate in petroleum ether, from 5% to 10% v/v) to furnish Intermediate A7. LC-MS (ESI) m/z: 504 [M+H]$^+$; $^1$H-NMR (CDCl$_3$, 400 MHz): δ (ppm) 0.01 (d, J=6.0 Hz, 6H), 0.87 (s, 9H), 1.02 (d, J=4.8 Hz, 4H), 1.36-1.40 (m, 1H), 3.99-4.03 (m, 1H), 4.09 (dd, J=10.0, 3.6 Hz, 1H), 5.26 (s, 2H), 5.42-5.44 (m, 1H), 6.04 (d, J=8.0 Hz, 1H), 7.44-7.50 (m, 6H), 8.00 (dd, J=8.8, 1.6 Hz, 1H), 8.11 (s, 1H).

A solution of Intermediate A7 (6.0 g, 11.9 mmol) in a mixture of THF, water, and glacial acetic acid (125 mL, 1/1/3, v/v/v) was stirred at 25° C. for 30 h. The reaction mixture was concentrated under reduced pressure to remove excess solvent. The residue was poured into ice water (20 g) and its pH was adjusted to 7~8 with aqueous sodium hydroxide (1 N) and saturated aqueous sodium bicarbonate. The mixture was extracted with ethyl acetate (60 mL×3). The combined organic phases were washed with brine (50 mL), dried over anhydrous sodium sulfate, filtered, and concentrated to afford a crude product, which was further purified with flash column chromatography on silica gel (ethyl acetate in petroleum ether, from 30% to 50% v/v) to give Intermediate A8. LC-MS (ESI) m/z: 390 [M+H]$^+$, 412 [M+Na]$^+$; $^1$H-NMR (CDCl$_3$, 400 MHz): δ (ppm) 0.89 (d, J=4.5 Hz, 4H), 2.78 (s, 1H), 3.81-3.92 (m, 2H), 4.01 (d, J=9.4 Hz, 1H), 5.08-5.17 (m, 2H), 5.26-5.38 (m, 1H), 6.12 (d, J=6.9 Hz, 1H), 7.25-7.45 (m, 6H), 7.92 (d, J=8.5 Hz, 1H), 8.02 (s, 1H).

To a solution of Intermediate A8 (3.3 g, 7.7 mmol) in dry THF (140 mL) under nitrogen atmosphere at −78° C. was added dropwise a solution of diisobutylaluminum hydride (1.0 M in toluene, 31 mL) over a period of 15 minutes. After the reaction was stirred at −70° C. for 1 h, a solution of HCl (2 N, 40 mL) was slowly added. The reaction mixture was extracted with ethyl acetate (30 mL×3), dried over anhydrous sodium sulfate, filtered, and concentrated to afford a crude product, which was further purified with flash column chromatography on silica gel (ethyl acetate in petroleum ether, from 50% to 150% v/v) to furnish Intermediate A9. LC-MS (ESI) m/z: 374 [M−OH]$^+$; $^1$H-NMR (CDCl$_3$, 400 MHz): δ (ppm) 0.80-0.83 (m, 4H), 1.23-1.27 (m, 1H), 2.79 (s, 1H), 3.45 (d, J=2.0 Hz, 1H), 3.74-3.81 (m, 4H), 4.93-5.08 (m, 2H), 5.52-5.54 (m, 1H), 7.16-7.37 (m, 8H).

To a solution of Intermediate A9 (900 mg, 2.30 mmol) in THF (20 mL) was added triethylamine (698 mg, 6.89 mmol). To the mixture at −30° C. was added dropwise methanesulfonyl chloride (290 mg, 2.53 mmol) over a period of 15 minutes. The reaction mixture was stirred at −30° C. for 1.5 h, diluted with water (50 mL), and extracted with ethyl acetate (50 mL×2). The combined organic layers were washed with brine (50 mL), dried over anhydrous sodium sulfate, filtered, and concentrated to afford Intermediate A10, which was directly used for the next step without further purification. LC-MS (ESI) m/z: 452 [M−OH]$^+$.

To a solution of Intermediate A10 (1.12 g, 2.83 mmol) in THF (60 mL) was added pyrrolidine (2 g, 28 mmol) and the reaction mixture was heated at 50° C. for 16 h. The reaction mixture was diluted with water (30 mL), extracted with ethyl acetate (150 mL×2), washed with brine (50 mL), dried over anhydrous sodium sulfate, filtered, and concentrated. The crude product was purified with flash column chromatography on silica gel (methanol in dichloromethane, 5% v/v) to give Intermediate A11. LC-MS (ESI) m/z: 445 [M+H]$^+$.

To a solution of Intermediate A1 (520 mg, 1.17 mmol) in ethanol (12 mL) and water (2 mL) was added LiOH.H$_2$O (197 mg, 4.68 mmol) and the reaction mixture was heated at 80° C. for 16 h. The reaction mixture was diluted with water (15 mL) and extracted with dichloromethane (50 mL×2). The combined organic phases were washed with water (50 mL) and brine (50 mL), dried over anhydrous sodium sulfate, filtered, and concentrated to furnish Intermediate A, which was directly used for the next step without further purification. LC-MS (ESI) m/z: 311 [M+H]$^+$.

Intermediate B

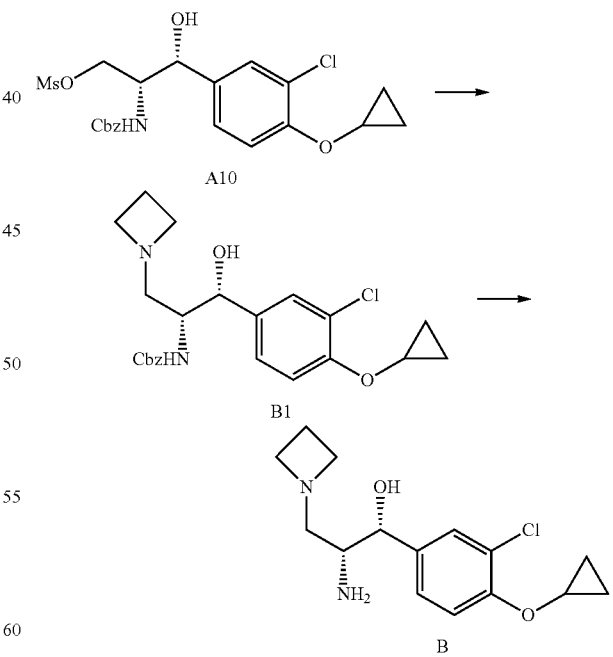

Intermediates B1 and B were synthesized by employing the procedures described for Intermediates A11 and A using azetidine and Intermediates B1 in lieu of pyrrolidine and Intermediate A11.

Intermediate B1. LC-MS (ESI) m/z: 431 [M+H]$^+$.

Intermediate B, which was directly used for the next step without further purification. LC-MS (ESI) m/z: 297 [M+H]$^+$.

Intermediate C

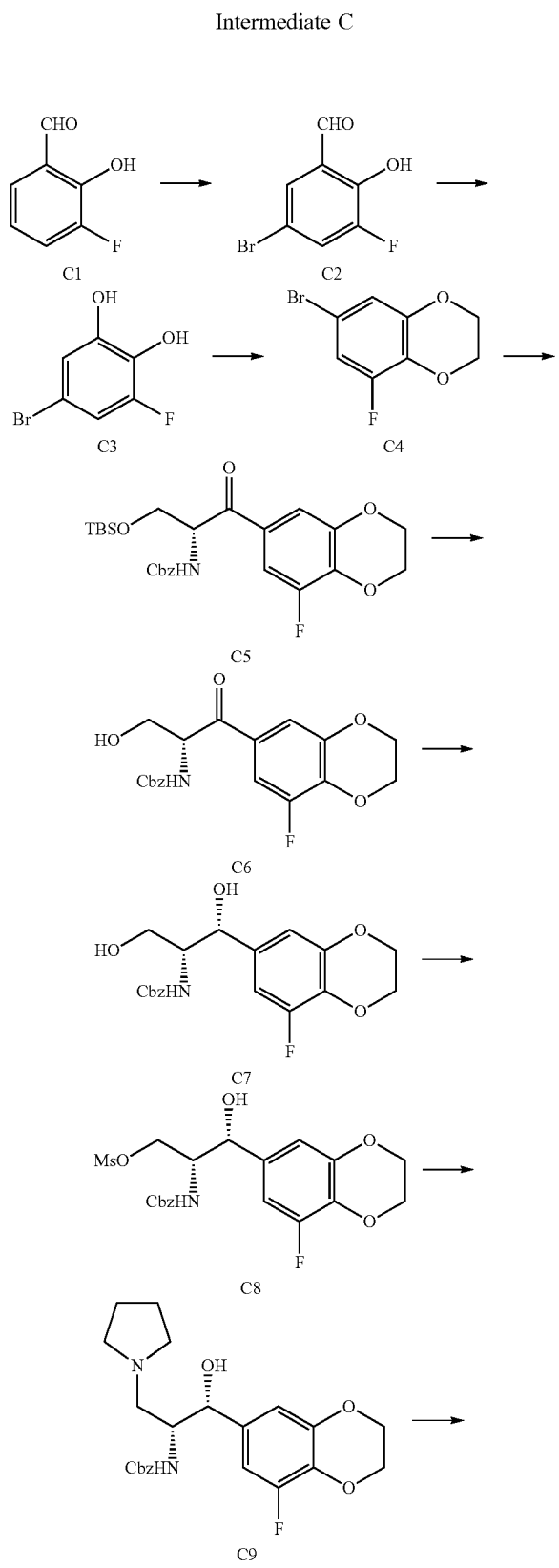

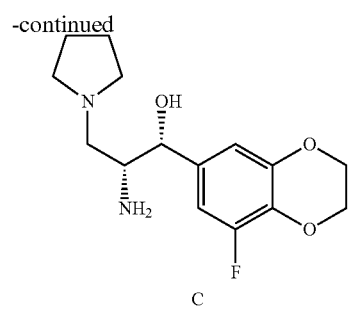

To a solution of Intermediate C1 (50 g, 357 mmol) in MeCN (400 mL) was added NBS (60.08 g, 360 mmol) and HCOONH$_4$ (2.47 mg, 39 mmol) at room temperature and the reaction mixture was stirred at room temperature for 2 h. After removal of the solvent, the mixture was diluted with ethyl acetate (200 mL), washed with brine, dried over anhydrous Na$_2$SO$_4$, and concentrated to give Intermediate C2. $^1$H-NMR (CDCl$_3$, 400 MHz): δ (ppm) 7.48-7.23 (m, 2H), 9.87 (s, 1H), 10.89 (s, 1H).

To a solution of Intermediate C2 (40 g, 183 mmol) in THF (260 mL) at 0° C. was added dropwise aq. NaOH solution (0.05 N, 720 mL, 37 mmol), followed by 30% H$_2$O$_2$ solution (90 mL). The mixture was stirred at room temperature 2 h., followed by addition of a second portion of 30% H$_2$O$_2$ (90 mL). After stirring for 4 h, it was cooled to 0° C. and aq. NaOH solution (2 N, 112 mL) was added until pH 10~11. The mixture was stirred for 0.5 h., quenched with conc. HCl at 0° C. to pH 2~3, extracted with dichloromethane (250 mL×3), washed with brine (300 mL×2), dried over Na$_2$SO$_4$, and concentrated to give Intermediate C3. LC-MS (m/z): 205 [M−1]$^-$.

To a mixture of Intermediate C3 (30 g, 146 mol) and K$_2$CO$_3$ (60.3 g, 437 mol) in DMF (450 mL) was added 1,2-dibromoethane (63 mL, 730 mol) and the reaction mixture was stirred at 80° C. for 4 h. After the reaction mixture was cooled to room temperature, it was filtered and the cake was washed with EtOAc (100 mL). The filtrate was diluted with water (900 mL) and extracted with EtOAc (400 mL×3). The organic layer was washed with water (900 mL×5) and brine (900 ml×1), dried, concentrated, and purified by column chromatography on silica gel (ethyl acetate in petroleum, 5% v/v) to afford Intermediate C4. $^1$H-NMR (CDCl$_3$, 400 MHz): δ (ppm) 4.35 (s, 4H), 6.91 (t, J=8 Hz, 1H), 7.33 (s, 1H).

Intermediates C5, C6, C7, C8, and C9 were synthesized by employing the procedures described correspondingly for Intermediates A7, A8, A9, A10, and A11 using Intermediates C4, C5, C6, C7, and C8 in lieu of Intermediates A2, A7, A8, A9, and A10.

Intermediate C5. LC-MS (m/z): 490 [M+1]$^+$.

Intermediate C6. LC-MS (ESI) m/z: 376 [M+H]$^+$; $^1$H-NMR (CDCl$_3$, 400 MHz): δ (ppm) 2.50-2.53 (m, 1H), 3.78-3.83 (m, 1H), 3.91-3.97 (m, 1H), 4.25-4.27 (m, 2H), 4.31-4.33 (m, 2H), 5.07 (s, 2H), 6.00 (d, J=4 Hz, 1H), 7.24-7.31 (m, 7H).

Intermediate C7. LC-MS (ESI) m/z: 360 [M−OH]$^+$; $^1$H-NMR (CDCl$_3$, 400 MHz): δ (ppm) 3.45-3.59 (m, 3H), 4.23-4.24 (m, 4H), 4.84 (s, 1H), 5.00 (s, 2H), 5.54 (d, J=8 Hz, 1H), 6.69 (t, J=8 Hz, 2H), 7.27-7.35 (m, 5H).

Intermediate C8. LC-MS (m/z): 438 [M+1-18]$^+$.

Intermediate C9. LC-MS (m/z): 431 [M+1]$^+$.

To a solution of Intermediate C9 (2.15 g, 5 mmol) in ethanol (60 mL) was added 10% Pd(OH)$_2$ (200 mg). The solution was stirred under H$_2$ atmosphere at 25° C. for 24 h, filtered, and concentrated to yield Intermediate C, which was directly used for the next step. LC-MS (ESI) m/z: 297 [M+H]+; 1H-NMR (CDCl3, 400 MHz): δ (ppm) 1.75-1.79 (m, 4H), 2.46-2.89 (m, 6H), 3.06-3.10 (m, 1H), 4.28 (s, 4H), 4.50 (d, J=4 Hz, 1H), 6.65-6.77 (m, 2H).

Intermediate D

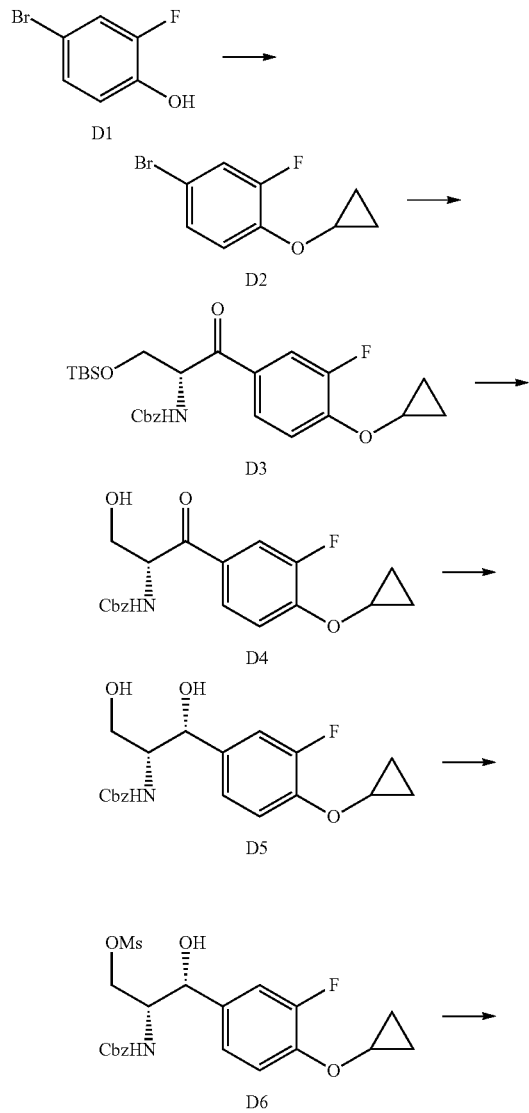

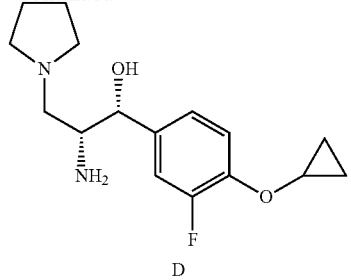

Intermediates D2, D3, D4, D5, D6, and D7 were synthesized by employing the procedures described for Intermediates A2, A7, A8, A9, A10, and A11 using Intermediates D1, D2, D3, D4, D5, and D6 in lieu of Intermediates A1, A2, A7, A8, A9, and A10.

Intermediate D2. 1H-NMR (CDCl3, 400 MHz): δ (ppm) 0.79-0.84 (m, 4H), 3.78-3.80 (m, 1H), 7.14-7.23 (m, 3H).

Intermediate D3. LC-MS (ESI) m/z: 488 [M+H]; 1H-NMR (DMSO-d6, 400 MHz): δ (ppm) −0.08 (s, 6H), 0.82 (m, 11H), 0.84-0.88 (m, 2H), 3.81-3.90 (m, 2H), 4.05-4.09 (m, 1H), 5.03 (s, 2H), 5.13-5.18 (m, 1H), 7.27-7.36 (m, 5H), 7.53 (t, J=8.4 Hz, 1H), 7.64 (d, J=8.4 Hz, 1H), 7.74 (dd, J=12.0, 2.4 Hz, 1H), 7.86 (d, J=8.4 Hz, 1H).

Intermediate D4. LC-MS (ESI) m/z: 374 [M+H]+; 1H-NMR (DMSO-d6, 400 MHz): δ (ppm) 0.75-0.89 (m, 4H), 3.62-3.78 (m, 2H), 4.07-4.09 (m, 1H), 4.91 (t, J=5.6 Hz, 1H), 5.03 (s, 2H), 5.10-5.14 (m, 1H), 7.26-7.38 (m, 5H), 7.55 (t, J=8.8 Hz, 1H), 7.60 (d, J=8.0 Hz, 1H), 7.79 (dd, J=12.0, 1.6 Hz, 1H), 7.90 (d, J=8.4 Hz, 1H).

Intermediate D5. LC-MS (ESI) m/z: 376 [M+H]+; 1H-NMR (DMSO-d6, 400 MHz): δ (ppm) 0.38-0.81 (m, 4H), 3.25-3.31 (m, 1H), 3.47-3.53 (m, 1H), 3.64-3.65 (m, 1H), 3.88-3.91 (m, 1H), 4.72-4.77 (m, 2H), 4.87-5.01 (m, 2H), 5.37 (d, J=5.2 Hz, 1H), 6.75 (d, J=10.0 Hz, 1H), 7.05-7.34 (m, 8H).

Intermediate D6, which was used for the next step without further purification. LC-MS (ESI) m/z: 436 [M−OH]+.

Intermediate D7. LC-MS (ESI) m/z: 429 [M+H]+; 1H-NMR (DMSO-d6, 400 MHz): δ (ppm) 0.68-0.81 (m, 4H), 1.66 (s, 4H), 2.24-2.50 (m, 5H), 2.59-2.64 (m, 1H), 3.75-3.81 (m, 1H), 3.88-3.91 (m, 1H), 4.72 (s, 1H), 4.87-5.00 (m, 2H), 5.52 (brs, 1H), 6.79 (d, J=9.2 Hz, 1H), 7.05-7.13 (m, 2H), 7.17-7.34 (m, 6H).

Intermediate D was synthesized by employing the procedure described for Intermediate C using Intermediate D7 in lieu of Intermediate C9. LC-MS (ESI) m/z: 295 [M+H]+; 1H-NMR (DMSO-d6, 400 MHz): δ (ppm) 0.67-0.79 (m, 4H), 1.23 (s, 2H), 1.65 (s, 4H), 2.16-2.20 (m, 1H), 2.29-2.36 (m, 6H), 2.86-2.89 (m, 1H), 3.89-3.93 (m, 1H), 4.38 (d, J=4.8 Hz, 1H), 7.06-7.15 (m, 2H), 7.32 (t, J=8.4 Hz, 1H).

Intermediate E

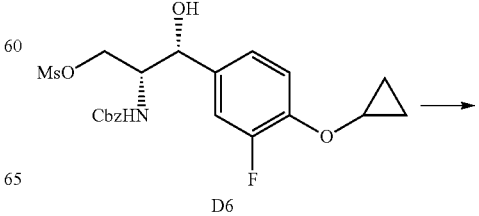

-continued

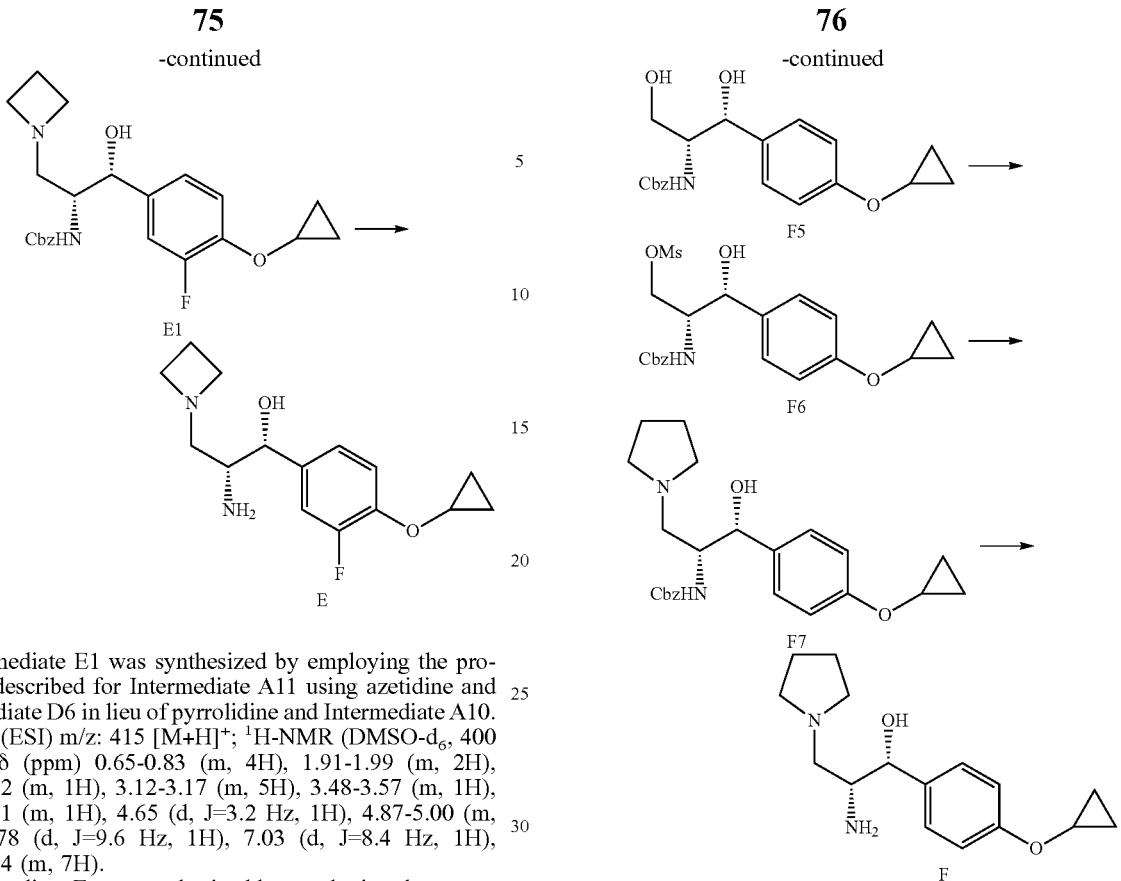

Intermediate E1 was synthesized by employing the procedure described for Intermediate A11 using azetidine and Intermediate D6 in lieu of pyrrolidine and Intermediate A10. LC-MS (ESI) m/z: 415 [M+H]$^+$; $^1$H-NMR (DMSO-d$_6$, 400 MHz): δ (ppm) 0.65-0.83 (m, 4H), 1.91-1.99 (m, 2H), 2.27-2.32 (m, 1H), 3.12-3.17 (m, 5H), 3.48-3.57 (m, 1H), 3.87-3.91 (m, 1H), 4.65 (d, J=3.2 Hz, 1H), 4.87-5.00 (m, 2H), 6.78 (d, J=9.6 Hz, 1H), 7.03 (d, J=8.4 Hz, 1H), 7.07-7.34 (m, 7H).

Intermediate E was synthesized by employing the procedure described for Intermediate C using Intermediate E1 in lieu of Intermediate C9. LC-MS (ESI) m/z: 281 [M+H]$^+$; $^1$H-NMR (DMSO-d$_6$, 400 MHz): δ (ppm) 0.67-0.81 (m, 4H), 1.89-1.96 (m, 2H), 2.15-2.26 (m, 2H), 2.61-2.65 (m, 1H), 3.03-3.13 (m, 4H), 3.87-3.93 (m, 1H), 4.34 (d, J=4.8 Hz, 1H), 7.01-7.12 (m, 2H), 7.26-7.34 (m, 1H).

Intermediate F

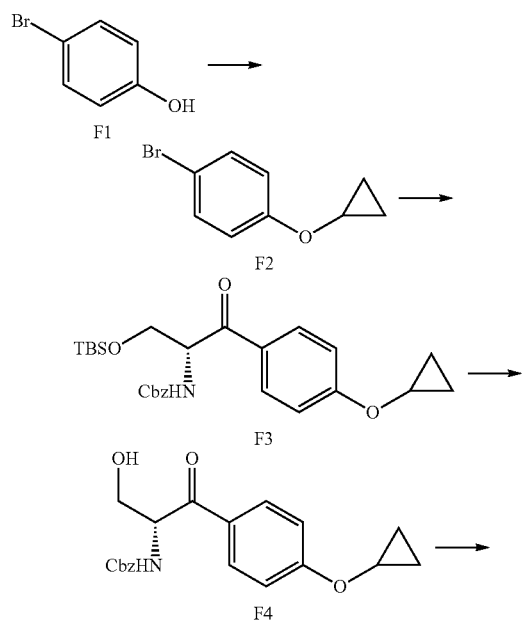

Intermediates F2, F3, F4, F5, F6, F7, and F, were synthesized by employing the procedures described for Intermediates A2, A7, A8, A9, A10, A11, and A using Intermediates F1, F2, F3, F4, F5, F6, and F7, in lieu of Intermediates A1, A2, A7, A8, A9, A10, and A11.

Intermediate F2. LC-MS (ESI) m/z: retention time: 2.19 minute; $^1$H-NMR (CDCl$_3$, 400 MHz): δ (ppm) 0.66-0.75 (m, 4H), 3.60-3.71 (m, 1H), 6.82-7.02 (m, 2H), 7.28-7.41 (m, 2H).

Intermediate F3. LC-MS (ESI) m/z: 470 [M+H]$^+$.

Intermediate F4. LC-MS (ESI) m/z: 356 [M+H]$^+$, 378 [M+Na]$^+$; $^1$H NMR (DMSO-d$_6$, 400 MHz): δ (ppm) 0.65-0.72 (m, 2H), 0.78-0.88 (m, 2H), 3.58-3.71 (m, 1H), 3.75-3.80 (m, 1H), 3.94-3.99 (m, 1H), 4.89 (t, J=5.8 Hz, 1H), 5.04 (s, 2H), 5.16 (dd, J=13.0, 5.5 Hz, 1H), 7.17 (d, J=8.7 Hz, 2H), 7.32-7.38 (m, 4H), 7.51 (d, J=7.9 Hz, 1H), 8.00 (d, J=8.7 Hz, 2H).

Intermediate F5. LC-MS (ESI) m/z: 340 [M−OH]$^+$. $^1$H-NMR (CDCl$_3$, 400 MHz): δ (ppm) 0.74-0.77 (m, 4H), 1.81 (s, 1H), 2.76 (s, 1H), 3.23 (s, 1H), 3.65-3.90 (m, 4H), 4.92-5.08 (m, 2H), 5.51 (d, J=7.8 Hz, 1H), 6.99 (d, J=8.6 Hz, 2H), 7.27-7.38 (m, 7H).

Intermediate F6. LC-MS (ESI) m/z: 418 [M−OH]$^+$, 458 [M+Na]$^+$. $^1$H-NMR (CDCl$_3$, 400 MHz): δ (ppm) 0.66-0.84 (m, 4H), 1.76 (s, 1H), 2.92-2.96 (m, 3H), 3.69-3.74 (m, 1H), 4.07-4.17 (m, 2H), 4.34-4.39 (m, 1H), 4.89 (s, 1H), 5.00-5.03 (m, 2H), 5.40 (d, J=7.1 Hz, 1H), 7.00 (d, J=8.6 Hz, 2H), 7.16-7.75 (m, 7H).

Intermediate F7. LC-MS (ESI) m/z: 411 [M+H]$^+$.

Intermediate F, which was directly used for the next step without further purification. LC-MS (ESI) m/z: 277 [M+H]$^+$; $^1$H-NMR (DMSO-d$_6$, 400 MHz): δ (ppm) 0.60-0.64 (m, 2H), 0.74-0.78 (m, 2H), 1.23 (s, 1H), 1.65 (s, 4H), 2.10-2.14 (m, 1H), 2.28-2.49 (m, 6H), 2.87-2.90 (m, 1H), 3.77-3.82 (m, 1H), 4.33 (d, J=5.0 Hz, 1H), 6.98 (d, J=8.4 Hz, 2H), 7.22 (d, J=8.8 Hz, 2H).

Intermediate G

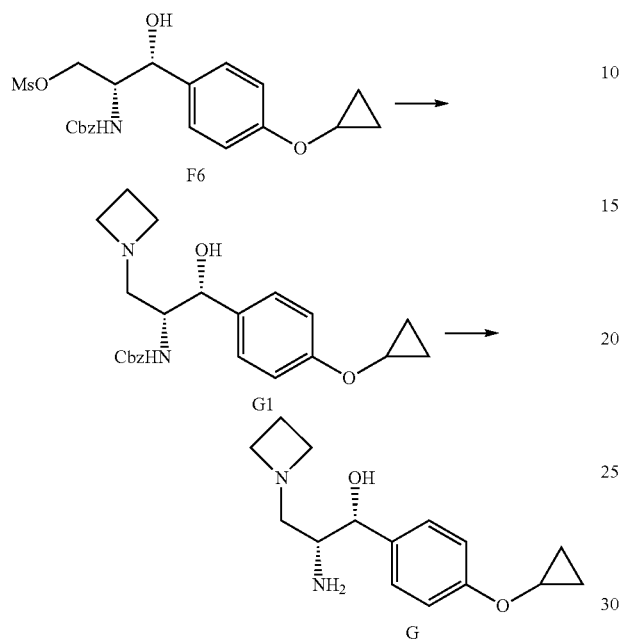

Intermediate G1 and G were synthesized by employing the procedures described for Intermediate A11 and A using azetidine and Intermediate F6 in lieu of pyrrolidine and Intermediate A10.

Intermediate G1. LC-MS (ESI) m/z: 397 [M+H]$^+$.

Intermediate G, which was directly used for the next step without further purification. LC-MS (ESI) m/z: 263 [M+H]$^+$.

Intermediate H

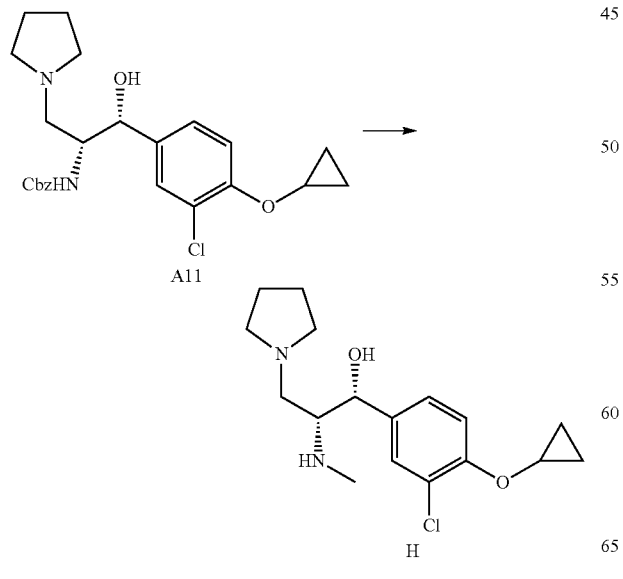

To a solution of Intermediate A11 (111 mg, 0.25 mmol) in THF (15 mL) under nitrogen was added LiAlH$_4$ (38 mg, 1 mmol). The resulting mixture was stirred at 60° C. for 3 h., quenched with NH$_3$.H$_2$O (3 mL), and filtered. The filtrate was treated with water (20 mL) and extracted with ethyl acetate (20 mL×2). The combined organic layers were washed with brine (40 mL), dried over anhydrous sodium sulfate, and concentrated to afford a crude product. It was purified with prep-HPLC to give Intermediate H, which was used without further purification. LC-MS (ESI) m/z: 325 [M+H]$^+$.

Intermediate I

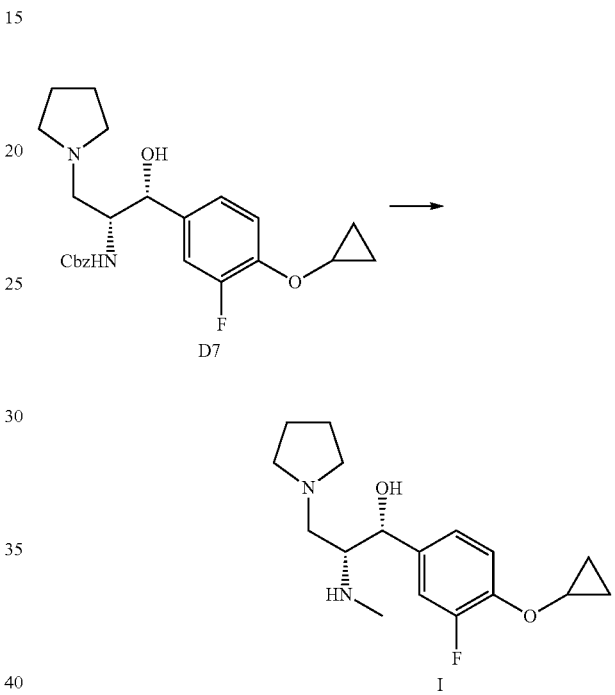

Intermediate I was synthesized by employing the procedure described for Intermediate H using Intermediate D7 in lieu of Intermediate A11, which was used without further purification. LC-MS (ESI) m/z: 309 [M+H]$^+$; $^1$H-NMR (CDCl$_3$, 400 MHz): δ (ppm) 0.75-0.85 (m, 4H), 1.76-1.79 (m, 4H), 2.34 (s, 3H), 2.43-2.59 (m, 6H), 2.87-2.91 (m, 1H), 3.77-3.82 (m, 1H), 4.63-4.69 (m, 1H), 7.02-7.12 (m, 2H), 7.22-7.26 (m, 1H).

Intermediate J

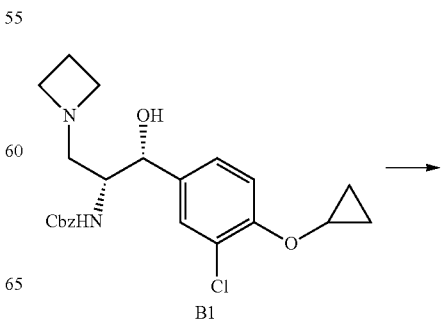

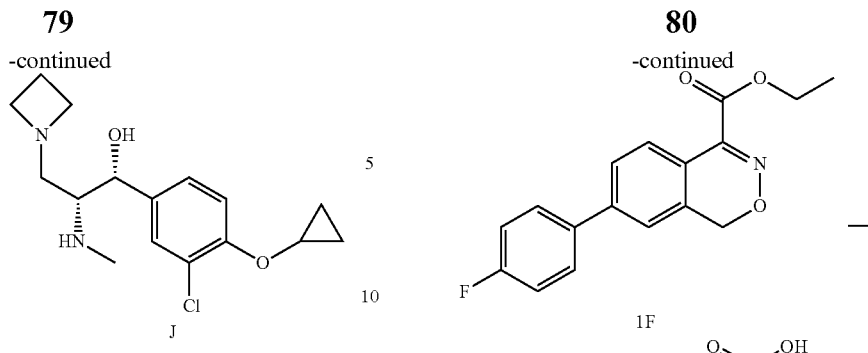

Intermediate J was synthesized by employing the procedure described for Intermediate H using Intermediate B1 in lieu of Intermediate A11, which was used without further purification. LC-MS (ESI) m/z: 311 [M+H]+.

Example 1

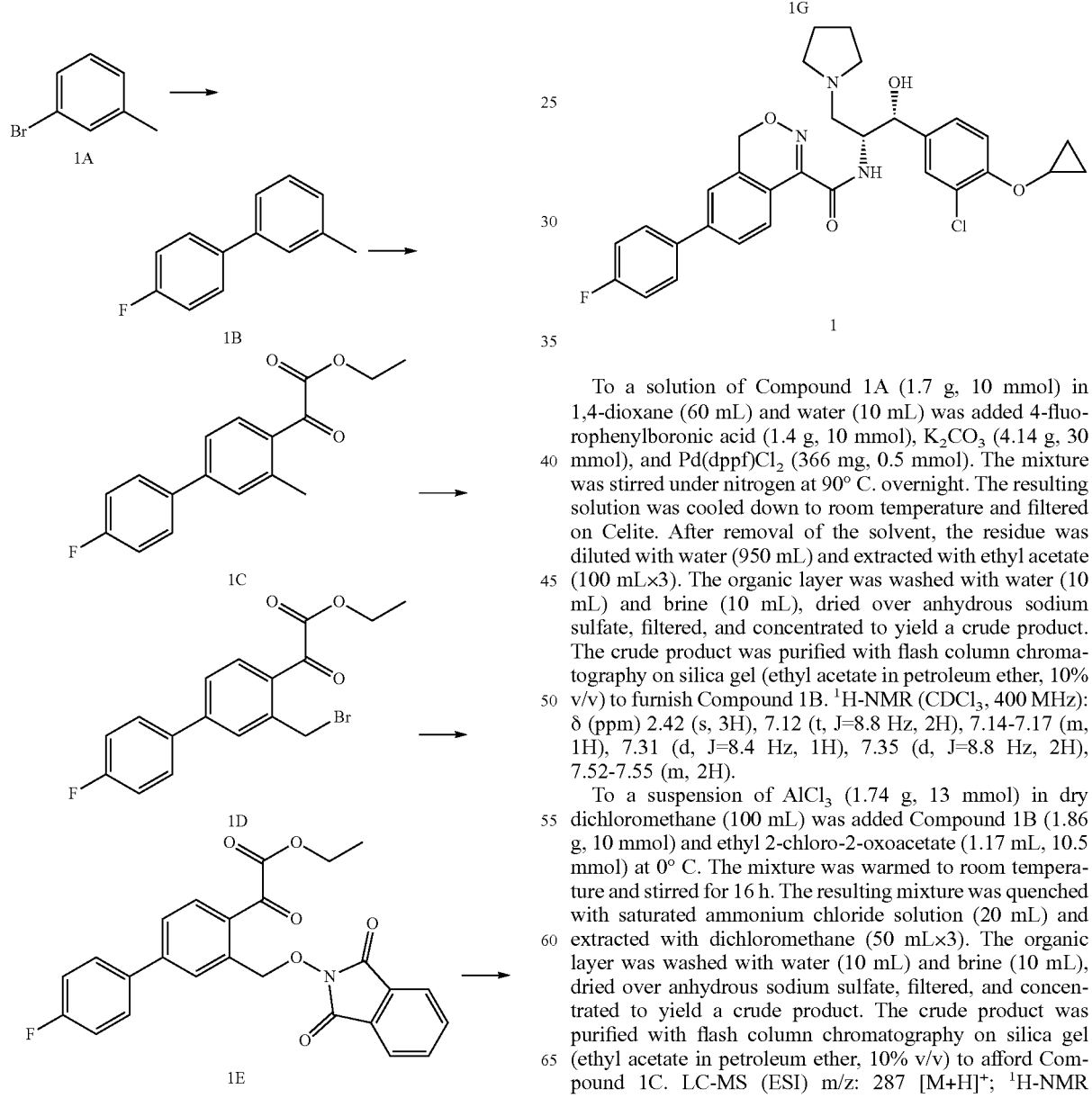

To a solution of Compound 1A (1.7 g, 10 mmol) in 1,4-dioxane (60 mL) and water (10 mL) was added 4-fluorophenylboronic acid (1.4 g, 10 mmol), $K_2CO_3$ (4.14 g, 30 mmol), and Pd(dppf)Cl$_2$ (366 mg, 0.5 mmol). The mixture was stirred under nitrogen at 90° C. overnight. The resulting solution was cooled down to room temperature and filtered on Celite. After removal of the solvent, the residue was diluted with water (950 mL) and extracted with ethyl acetate (100 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate in petroleum ether, 10% v/v) to furnish Compound 1B. $^1$H-NMR (CDCl$_3$, 400 MHz): δ (ppm) 2.42 (s, 3H), 7.12 (t, J=8.8 Hz, 2H), 7.14-7.17 (m, 1H), 7.31 (d, J=8.4 Hz, 1H), 7.35 (d, J=8.8 Hz, 2H), 7.52-7.55 (m, 2H).

To a suspension of AlCl$_3$ (1.74 g, 13 mmol) in dry dichloromethane (100 mL) was added Compound 1B (1.86 g, 10 mmol) and ethyl 2-chloro-2-oxoacetate (1.17 mL, 10.5 mmol) at 0° C. The mixture was warmed to room temperature and stirred for 16 h. The resulting mixture was quenched with saturated ammonium chloride solution (20 mL) and extracted with dichloromethane (50 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate in petroleum ether, 10% v/v) to afford Compound 1C. LC-MS (ESI) m/z: 287 [M+H]+; $^1$H-NMR (CDCl$_3$, 400 MHz): δ (ppm) 1.44 (t, J=6.8 Hz, 3H), 4.46 (q, J=7.2 Hz, 2H), 7.17 (t, J=8.4 Hz, 2H), 7.49-7.50 (m, 2H), 7.58-7.62 (m, 2H), 7.78 (d, J=8.8 Hz, 1H), 2.69 (s, 3H).

To a solution of Compound 1C (545 mg, 1.91 mmol) in CCl₄ (20 mL) was added NBS (373 mg, 2.1 mmol) and BPO (46 mg, 0.19 mmol). The mixture was heated to reflux for 3 h. The resulting mixture was cooling down to room temperature and extracted with dichloromethane (50 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate in petroleum ether, 10% v/v) to furnish Compound 1D. LC-MS (ESI) m/z: 365 [M+H]⁺; ¹H-NMR (CDCl₃, 400 MHz): δ (ppm) 1.44 (t, J=7.2 Hz, 3H), 4.47 (q, J=7.2 Hz, 2H), 4.88 (s, 2H), 7.19 (t, J=8.8 Hz, 2H), 7.60-7.63 (m, 3H), 7.73-7.74 (m, 1H), 7.84 (d, J=8.4 Hz, 1H).

To a solution of 2-hydroxyisoindoline-1,3-dione (1.54 g, 9.43 mmol) in DMF/acetonitrile/water (44 mL, 5/1/5 v/v) was added Na₂CO₃ (2.50 g, 23.6 mmol). After stirring for 2 h, Compound 1D (3.64 g, 10 mmol) was added to the above mixture and the resulting mixture was stirred at room temperature overnight. After filtration, the cake was washed with water (5 mL×3) and dried to furnish Compound 1E. LC-MS (ESI) m/z: 448 [M+H]⁺; ¹H-NMR (CDCl₃, 400 MHz): δ (ppm) 1.43 (t, J=7.2 Hz, 3H), 4.46 (q, J=7.2 Hz, 2H), 5.72 (s, 2H), 7.19 (t, J=8.4 Hz, 2H), 7.66 (dd, J=8.0, 1.6 Hz, 1H), 7.68-7.72 (m, 2H), 7.76 (d, J=8.0 Hz, 1H), 7.77 (d, J=6.0 Hz, 1H), 7.85-7.87 (m, 2H), 7.89 (d, J=8.4 Hz, 1H), 8.26 (s, 1H).

To a solution of Compound 1E (556 mg, 1.24 mmol) in ethanol (30 mL) was added 80% hydrazine hydrate (7 drops, 3.72 mmol). The mixture was stirred at room temperature for 1 h. The resulting mixture was adjusted to pH 7 with aqueous HCl solution (2 N, 0.5 mL) and evaporated. The residue was diluted with water (30 mL) and extracted with ethyl acetate (50 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate in petroleum ether, 10% v/v) to afford Compound 1F. LC-MS (ESI) m/z: 300 [M+H]⁺; ¹H-NMR (CDCl₃, 400 MHz): δ (ppm) 1.46 (t, J=7.2 Hz, 3H), 4.48 (q, J=7.2 Hz, 2H), 5.11 (s, 2H), 7.17 (t, J=8.8 Hz, 2H), 7.34 (s, 1H), 7.56-7.60 (m, 2H), 7.62 (d, J=1.6 Hz, 1H), 8.01 (d, J=8.4 Hz, 1H).

To a solution of Compound 1F (322 mg, 1.08 mmol) in THF (12 mL) was added dropwise a solution of LiOH.H₂O (181 mg, 4.31 mmol) in water (3 mL). The mixture was stirred at room temperature for 1 h. The reaction solution was adjusted to pH 4 with aqueous HCl solution (1 N, 1.5 mL) and separated. The organic layer was dried directly over anhydrous sodium sulfate, filtered, and concentrated to afford Compound 1G. LC-MS (ESI) m/z: 233 [M−H]⁺; ¹H-NMR (DMSO-d₆, 400 MHz): δ (ppm) 5.12 (s, 2H), 7.35 (t, J=8.8 Hz, 2H), 7.63 (d, J=1.6 Hz, 1H), 7.77-7.81 (m, 2H), 7.87 (d, J=8.0 Hz, 2H).

To a solution of Intermediate A (109 mg, 0.35 mmol) in dichloromethane (10 mL) under nitrogen was added Compound 1G (80 mg, 0.30 mmol), EDCI (85 mg, 0.44 mmol), HOBt (60 mg, 0.44 mmol), and DIPEA (114 mg, 0.88 mmol). The mixture was stirred at room temperature overnight. The resulting mixture was diluted with saturated aqueous sodium bicarbonate solution (50 mL) and extracted with dichloromethane (50 mL×3). The combined organic phases were washed with water (50 mL) and brine (50 mL), dried over anhydrous sodium sulfate, filtered, and concentrated to afford a crude product. The crude product was purified with prep-HPLC to furnish Compound 1. LC-MS (ESI) m/z: 564 [M+H]⁺; ¹H-NMR (CD₃OD, 400 MHz): δ (ppm) 0.69-0.80 (m, 4H), 2.05-2.07 (m, 2H), 2.19-2.22 (m, 2H), 3.21-3.28 (m, 2H), 3.53-3.57 (m, 1H), 3.70-3.83 (m, 4H), 4.69-4.71 (m, 1H), 4.95 (d, J=2.8 Hz, 1H), 5.11 (d, J=3.6 Hz, 2H), 7.23 (t, J=8.8 Hz, 2H), 7.35-7.39 (m, 3H), 7.48 (s, 1H), 7.53 (s, 1H), 7.56 (d, J=8.0 Hz, 1H), 7.69-7.73 (m, 2H).

Example 2

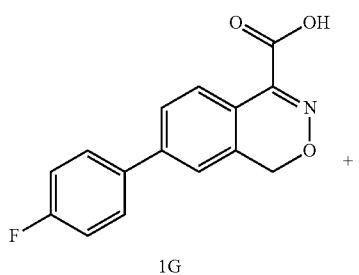

1G

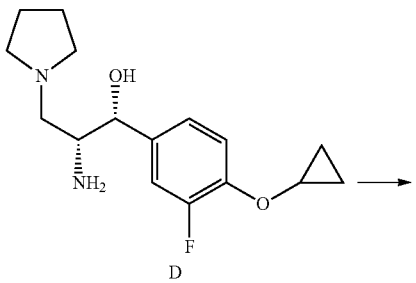

D

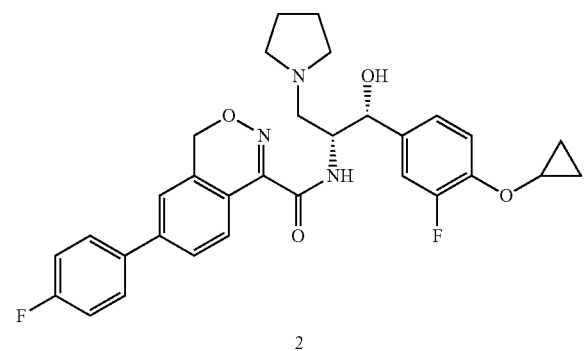 [SMILES: O=C(N[C@H](CN1CCCC1)[C@H](O)c1ccc(OC2CC2)c(Cl)c1)C1=NOCc2cc(-c3ccc(F)cc3)ccc21]

2

Compound 2 was synthesized by employing the procedure described for Compound 1 using Intermediate D in lieu of Intermediate A. LC-MS (ESI) m/z: 548 [M+H]⁺; ¹H-NMR (CD₃OD, 400 MHz): δ (ppm) 0.69-0.78 (m, 4H), 2.05-2.06 (m, 2H), 2.20-2.22 (m, 2H), 3.20-3.27 (m, 2H), 3.52-3.56 (m, 1H), 3.68-3.74 (m, 2H), 3.81-3.85 (m, 2H), 4.69-4.72 (m, 1H), 4.94 (d, J=2.8 Hz, 1H), 5.11 (d, J=4.0 Hz, 2H), 7.20-7.25 (m, 4H), 7.33 (t, J=8.4 Hz, 1H), 7.47 (d, J=8.0 Hz, 1H), 7.53 (s, 1H), 7.58 (d, J=8.4 Hz, 1H), 7.69-7.72 (m, 2H).

Example 3

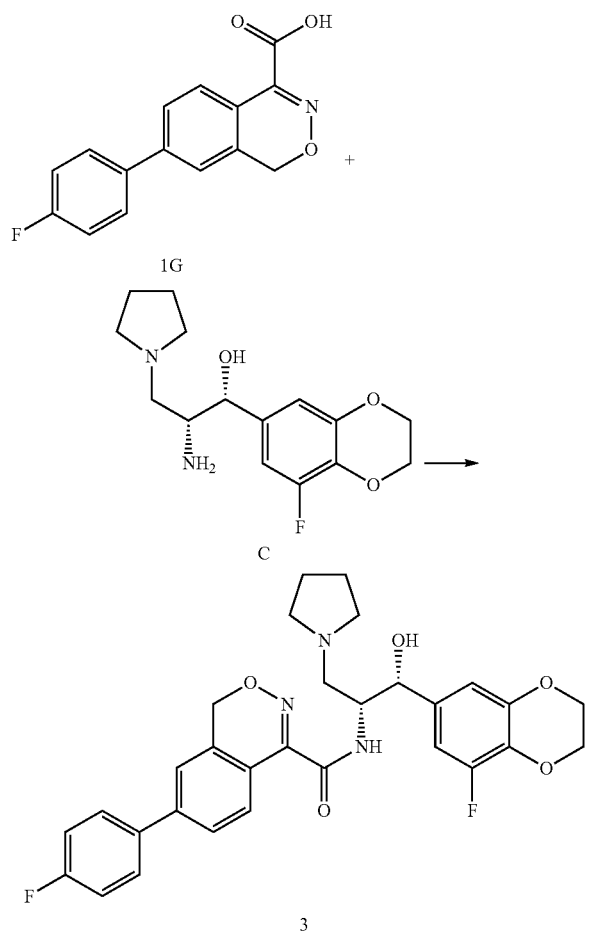

Compound 3 was synthesized by employing the procedure described for Compound 1 using Intermediate C in lieu of Intermediate A. LC-MS (ESI) m/z: 550 [M+H]$^+$; $^1$H-NMR (CD$_3$OD, 400 MHz): δ (ppm) 2.04-2.05 (m, 2H), 2.19-2.21 (m, 2H), 3.19-3.29 (m, 2H), 3.50-3.54 (m, 1H), 3.67-3.73 (m, 2H), 3.79-3.81 (m, 1H), 4.16-4.24 (m, 4H), 4.65-4.68 (m, 1H), 4.86 (d, J=2.4 Hz, 1H), 5.11 (d, J=3.6 Hz, 2H), 6.80-6.83 (m, 2H), 7.22 (t, J=8.0 Hz, 2H), 7.53-7.58 (m, 2H), 7.61-7.63 (m, 1H), 7.69-7.73 (m, 2H).

Example 4

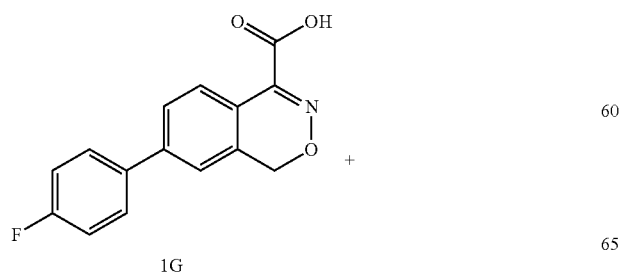

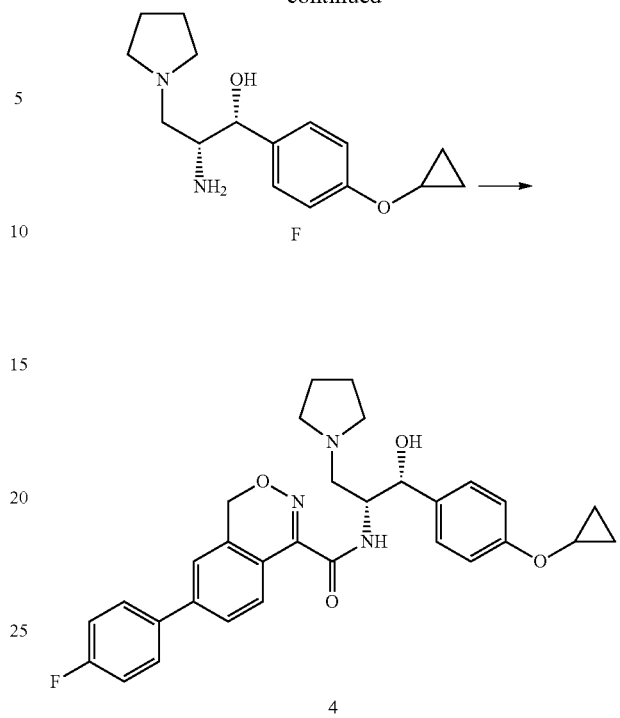

Compound 4 was synthesized by employing the procedure described for Compound 1 using Intermediate F in lieu of Intermediate A. LC-MS (ESI) m/z: 530 [M+H]$^+$; $^1$H-NMR (CD$_3$OD, 400 MHz): δ (ppm) 0.64-0.76 (m, 4H), 2.04-2.06 (m, 2H), 2.17-2.21 (m, 2H), 3.21-3.28 (m, 2H), 3.51-3.55 (m, 1H), 3.66-3.75 (m, 3H), 3.80-3.84 (m, 1H), 4.68-4.71 (m, 1H), 4.95 (d, J=3.2 Hz, 1H), 5.06-5.16 (m, 2H), 7.02 (d, J=8.4 Hz, 2H), 7.23 (t, J=8.4 Hz, 2H), 7.38 (d, J=8.4 Hz, 2H), 7.48 (d, J=8.4 Hz, 1H), 7.53 (s, 1H), 7.56 (dd, J=8.0, 1.6 Hz, 1H), 7.67-7.72 (m, 2H).

Example 5

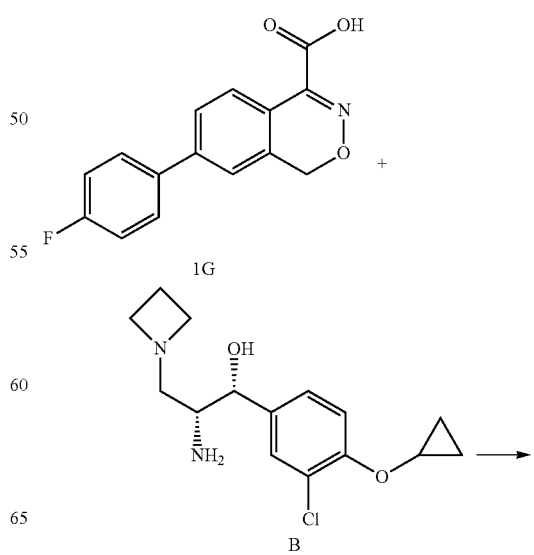

-continued

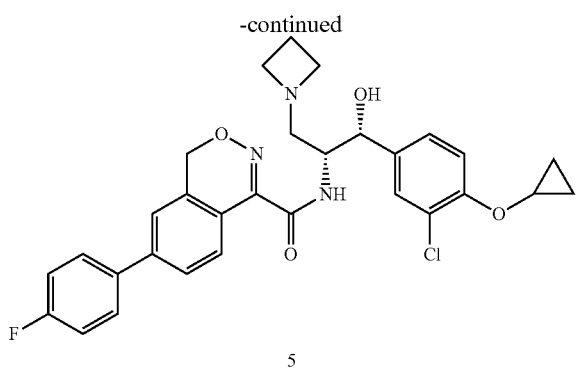

5

Compound 5 was synthesized by employing the procedure described for Compound 1 using Intermediate B in lieu of Intermediate A. LC-MS (ESI) m/z: 550 [M+H]$^+$; $^1$H-NMR (CD$_3$OD, 400 MHz): δ (ppm) 0.69-0.80 (m, 4H), 2.44-2.48 (m, 1H), 2.60-2.67 (m, 1H), 3.60-3.62 (m, 2H), 3.81-3.85 (m, 1H), 4.24-4.34 (m, 4H), 4.51-4.55 (m, 1H), 4.93 (d, J=2.8 Hz, 1H), 5.07-5.15 (m, 2H), 7.23 (t, J=8.8 Hz, 2H), 7.35-7.38 (m, 3H), 7.47 (s, 1H), 7.53 (s, 1H), 7.56 (dd, J=8.0, 1.6 Hz, 1H), 7.69-7.73 (m, 2H).

Example 6

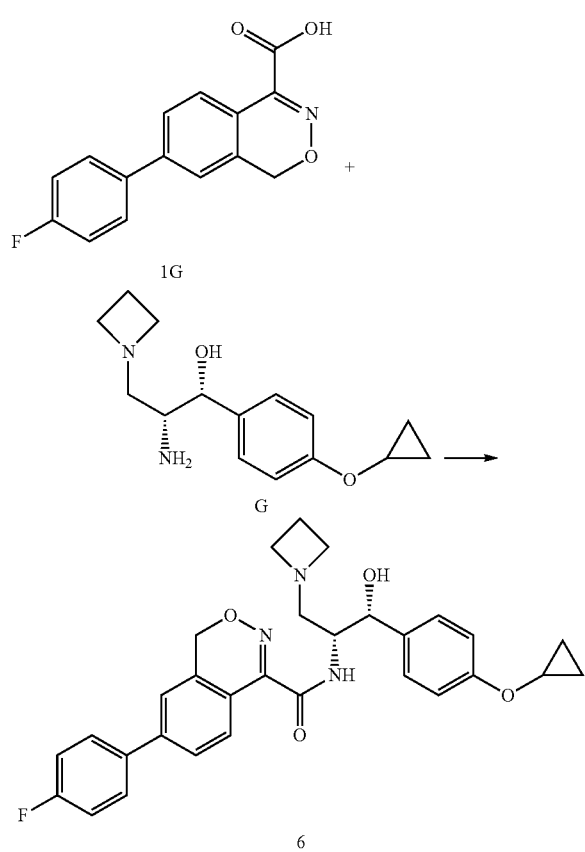

Compound 6 was synthesized by employing the procedure described for Compound 1 using Intermediate G in lieu of Intermediate A. LC-MS (ESI) m/z: 516 [M+H]$^+$; $^1$H-NMR (CD$_3$OD, 400 MHz): δ (ppm) 0.64-0.76 (m, 4H), 2.43-2.45 (m, 1H), 2.59-2.66 (m, 1H), 3.53-3.63 (m, 2H), 3.71-3.76 (m, 1H), 4.22-4.31 (m, 4H), 4.51-4.54 (m, 1H), 4.92 (d, J=3.2 Hz, 1H), 5.05-5.15 (m, 2H), 7.03 (d, J=8.8 Hz, 2H), 7.22 (t, J=8.8 Hz, 2H), 7.37 (d, J=8.8 Hz, 2H), 7.48 (d, J=8.8 Hz, 1H), 7.52 (s, 1H), 7.58 (d, J=8.4 Hz, 1H), 7.68-7.72 (m, 2H).

Example 7

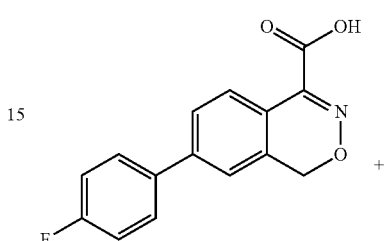

Compound 7 was synthesized by employing the procedure described for Compound 1 using Intermediate E in lieu of Intermediate A. LC-MS (ESI) m/z: 534 [M+H]$^+$; $^1$H-NMR (CD$_3$OD, 400 MHz): δ (ppm) 0.70-0.78 (m, 4H), 2.43-2.48 (m, 1H), 2.60-2.67 (m, 1H), 3.58-3.61 (m, 2H), 3.82-3.86 (m, 1H), 4.23-4.33 (m, 4H), 4.51-4.55 (m, 1H), 4.92 (d, J=2.4 Hz, 1H), 5.07-5.14 (m, 2H), 7.19-7.25 (m, 4H), 7.34 (t, J=8.8 Hz, 1H), 7.46 (d, J=8.0 Hz, 1H), 7.53 (s, 1H), 7.58 (dd, J=8.0, 1.2 Hz, 1H), 7.69-7.72 (m, 2H).

Example 8

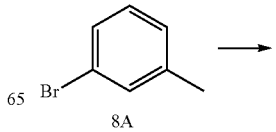

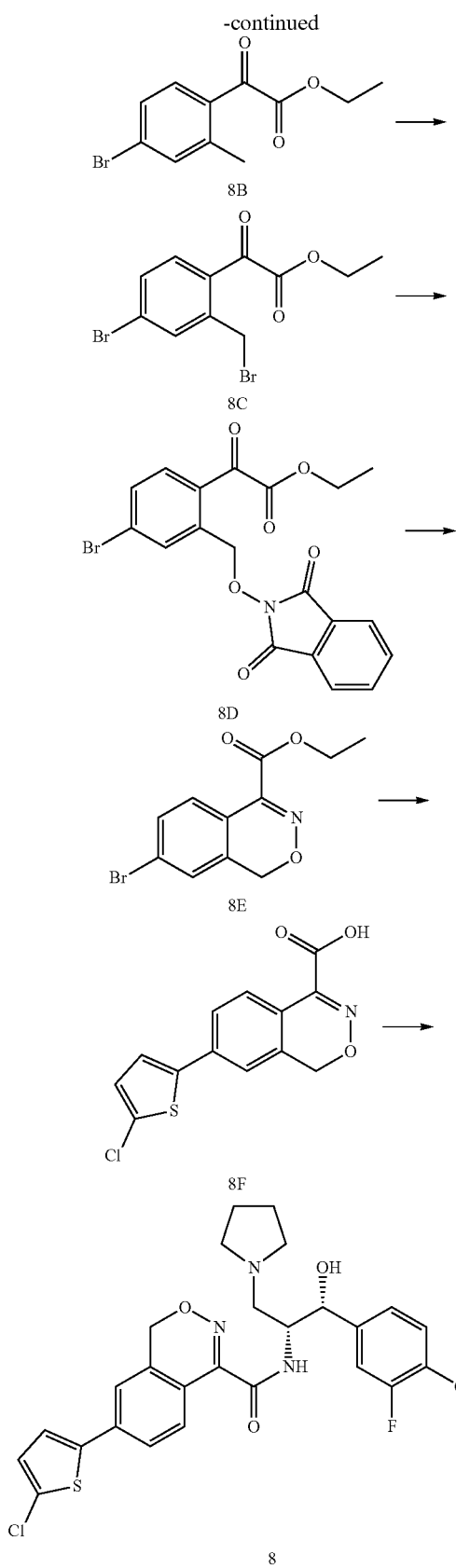

Compounds 8B, 8C, 8D, and 8E were synthesized by employing the procedure described for Compounds 1C, 1D, 1E, and 1F using Compounds 8A, 8B, 8C, and 8D in lieu of Compounds 1B, 1C, 1D, and 1E.

Compound 8B. LC-MS (ESI) m/z: 271 [M+H]$^+$; $^1$H-NMR (CDCl$_3$, 400 MHz): δ (ppm) 1.42 (t, J=8.0 Hz, 3H), 2.58 (s, 3H), 4.40-4.46 (q, J=8.0 Hz, 2H), 7.45-7.49 (m, 2H), 7.57 (d, J=8.0 Hz, 1H).

Compound 8C. LC-MS (ESI) m/z: 349 [M+H]$^+$; $^1$H-NMR (CDCl$_3$, 400 MHz): δ (ppm) 1.42 (t, J=8.0 Hz, 3H), 4.41-4.47 (q, J=8.0 Hz, 2H), 4.83 (s, 2H), 7.57-7.62 (m, 2H), 7.72-7.73 (m, 1H).

Compound 8D. LC-MS (ESI) m/z: 432 [M+H]$^+$; $^1$H-NMR (DMSO-d$_6$, 400 MHz): δ (ppm) 1.28 (t, J=6.8 Hz, 3H), 4.31-4.37 (q, J=6.8 Hz, 2H), 5.49 (s, 2H), 7.82-7.85 (m, 6H), 8.16 (s, 1H).

Compound 8D. LC-MS: (ESI) m/z: 284 [M+H]$^+$; $^1$H-NMR (CDCl$_3$, 400 MHz): δ (ppm) 1.43 (t, J=6.8 Hz, 3H), 4.42-4.48 (q, J=6.8 Hz, 2H), 5.01 (s, 2H), 7.34 (d, J=1.6 Hz, 1H), 7.56-7.60 (m, 1H), 7.85 (d, J=8.8 Hz, 1H).

Compound 8F was synthesized by employing the procedure described for Compound 1B using 5-chlorothiophen-2-ylboronic acid and Na$_2$CO$_3$ in lieu of 4-fluorophenylboronic acid and K$_2$CO$_3$. LC-MS (ESI) m/z: 294 [M–H]$^+$; $^1$H-NMR (DMSO-d$_6$, 400 MHz): δ (ppm) 4.83 (s, 2H), 7.20 (d, J=4.0 Hz, 1H), 7.49-7.51 (m, 2H), 7.63 (d, J=8.0 Hz, 1H), 7.71 (d, J=8.0 Hz, 1H).

To a solution of Intermediate D (55 mg, 0.19 mmol) in DMF (3 mL) and triethylamine (0.2 mL) was added Compound 8F (60 mg, 0.19 mmol) and HATU (106 mg, 0.28 mmol). The mixture was stirred at room temperature overnight. The resulting mixture was purified with prep-HPLC to furnish Compound 8. LC-MS (ESI) m/z: 570 [M+H]$^+$; $^1$H-NMR (CD$_3$OD, 400 MHz): δ (ppm) 0.68-0.82 (m, 4H), 2.01-2.23 (m, 4H), 3.18-3.32 (m, 2H), 3.52-3.56 (m, 1H), 3.68-3.86 (m, 4H), 4.66-4.71 (m, 1H), 4.94 (d, J=2.4 Hz, 1H), 5.07 (d, J=4.0 Hz, 2H), 7.04 (d, J=4.0 Hz, 1H), 7.19-7.22 (m, 2H), 7.30-7.43 (m, 3H), 7.51-7.54 (m, 2H).

Example 9

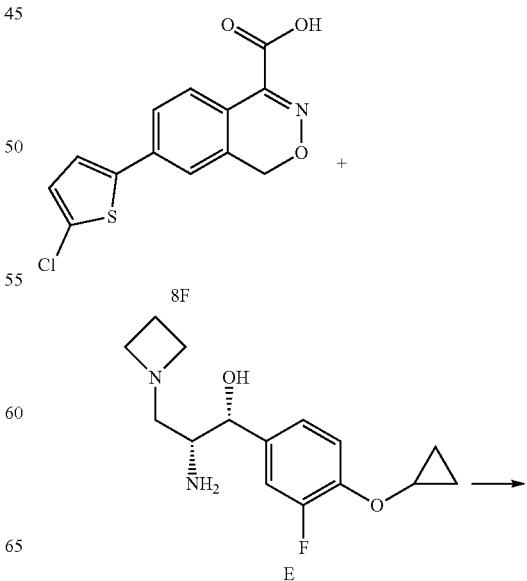

-continued

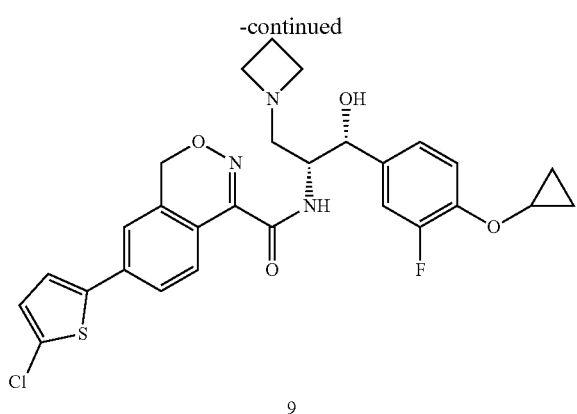

9

Compound 9 was synthesized by employing the procedure described for Compound 8 using Intermediate E in lieu of Intermediate D. LC-MS (ESI) m/z: 556 [M+H]⁺; ¹H-NMR (CD₃OD, 400 MHz): δ (ppm) 0.67-0.80 (m, 4H), 2.41-2.49 (m, 1H), 2.58-2.67 (m, 1H), 3.54-3.65 (m, 2H), 3.81-3.87 (m, 1H), 4.22-4.36 (m, 4H), 4.49-4.54 (m, 1H), 4.92 (d, J=2.4 Hz, 1H), 5.07 (d, J=4.0 Hz, 2H), 7.04 (d, J=4.0 Hz, 1H), 7.18-7.21 (m, 2H), 7.30-7.43 (m, 3H), 7.51-7.54 (m, 2H).

Example 10

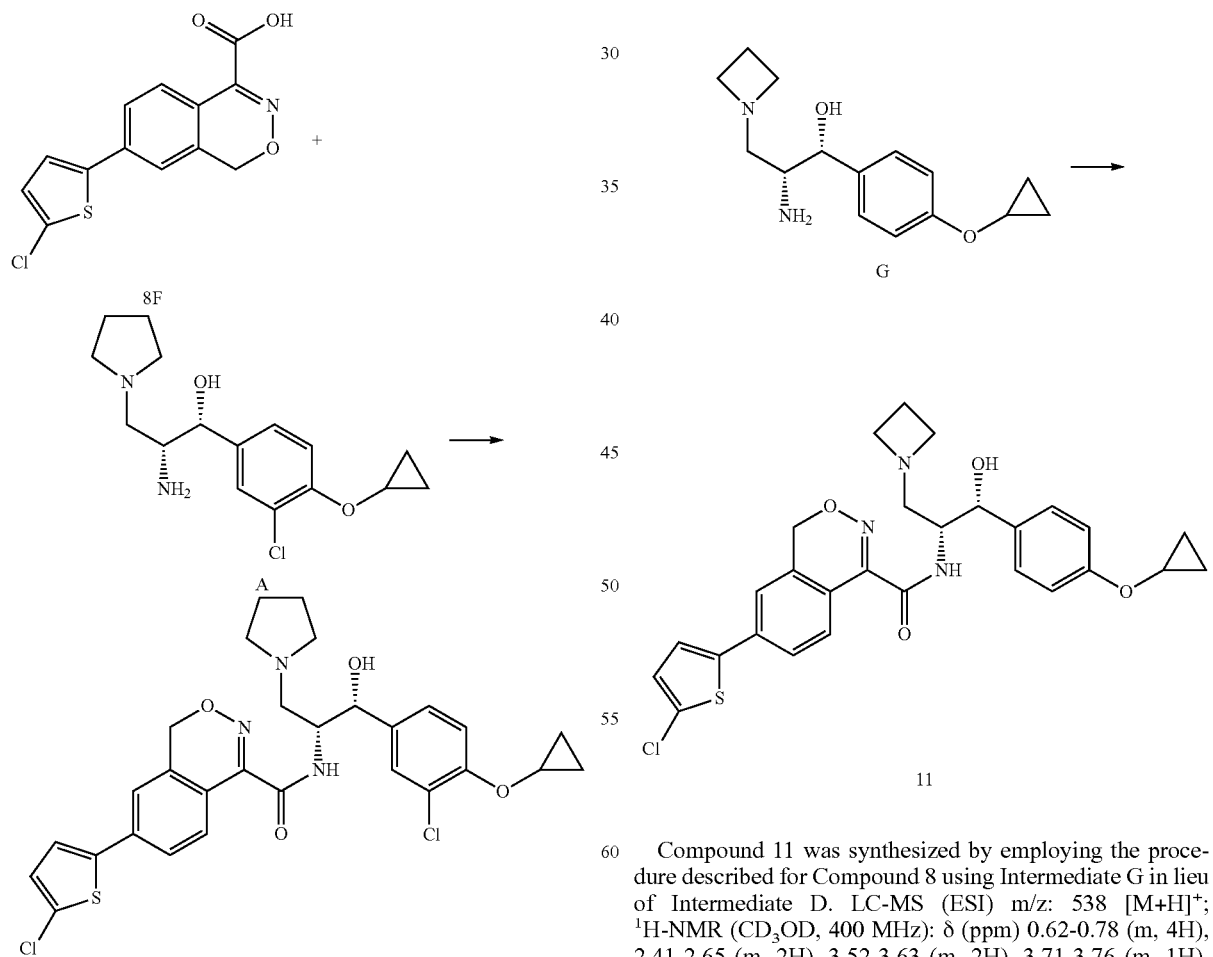

Compound 10 was synthesized by employing the procedure described for Compound 8 using Intermediate A in lieu of Intermediate D. LC-MS (ESI) m/z: 586 [M+H]⁺; ¹H-NMR (CD₃OD, 400 MHz): δ (ppm) 0.67-0.85 (m, 4H), 1.99-2.24 (m, 4H), 3.18-3.32 (m, 2H), 3.53-3.85 (m, 5H), 4.66-4.71 (m, 1H), 4.95 (d, J=2.4 Hz, 1H), 5.03-5.12 (m, 2H), 7.04 (d, J=4.4 Hz, 1H), 7.30-7.37 (m, 4H), 7.46-7.51 (m, 3H).

Example 11

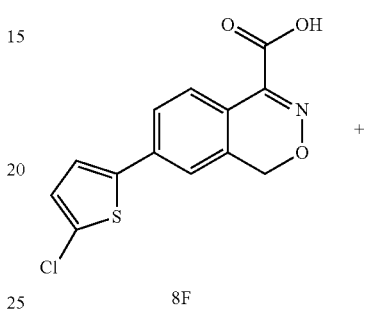

Compound 11 was synthesized by employing the procedure described for Compound 8 using Intermediate G in lieu of Intermediate D. LC-MS (ESI) m/z: 538 [M+H]⁺; ¹H-NMR (CD₃OD, 400 MHz): δ (ppm) 0.62-0.78 (m, 4H), 2.41-2.65 (m, 2H), 3.52-3.63 (m, 2H), 3.71-3.76 (m, 1H), 4.16-4.34 (m, 4H), 4.48-4.53 (m, 1H), 4.93 (d, J=3.2 Hz, 1H), 5.00-5.12 (m, 2H), 7.00-7.04 (m, 3H), 7.34-7.37 (m, 4H), 7.49-7.52 (m, 2H).

Example 12

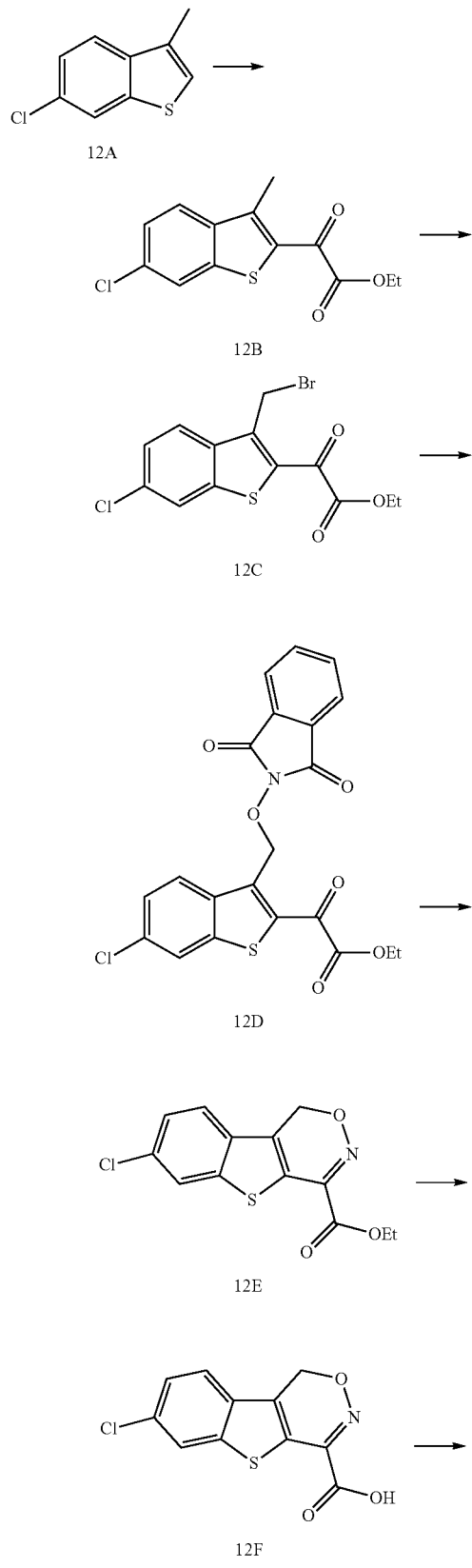

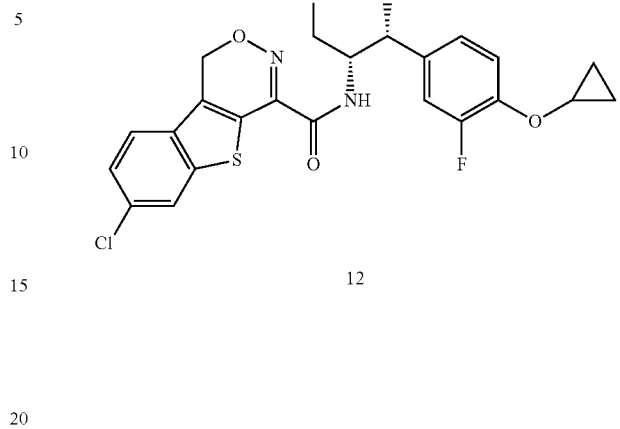

To a solution of Compound 12A (5.0 g, 27.37 mmol) in THF (50 mL) was added n-BuLi (2.4 M, 12.5 mL, 30.11 mmol) under nitrogen at −78° C. The mixture was stirred at −78° C. for 15 minutes. To the resulting mixture was quickly added diethyl oxalate (16.0 g, 109.5 mmol). The reaction mixture was stirred at −78° C. for 1 h., quenched with saturated ammonium chloride solution (30 mL), and extracted with ethyl acetate (100 mL×3). The combined organic phases were washed with water (50 mL) and brine (50 mL), dried over anhydrous sodium sulfate, filtered, and concentrated to furnish a crude product, which was further purified with flash column chromatography on silica gel (petroleum ether, 100% v/v) to furnish Compound 12B. LC-MS (ESI) m/z: 283 [M+H]$^+$, 305 [M+Na]$^+$; $^1$H-NMR (CDCl$_3$, 400 MHz): δ (ppm) 1.44 (t, J=7.2 Hz, 3H), 2.75 (s, 3H), 4.45 (q, J=7.1 Hz, 2H), 7.39 (d, J=9.0 Hz, 1H), 7.80-7.83 (m, 2H).

Compounds 12C, 12D, 12E, and 12F were synthesized by employing the procedure described for Compounds 1D, 1E, 1F, and 1G using Compounds 12B, 12C, 12D, and 12E in lieu of Compounds 1C, 1D, 1E, and 1F.

Compound 12C. LC-MS (ESI) m/z: 361 [M+H]$^+$, 383 [M+Na]$^+$; $^1$H-NMR (CDCl$_3$, 400 MHz): δ (ppm) 1.46 (t, J=7.2 Hz, 3H), 4.47 (q, J=7.2 Hz, 2H), 5.14 (s, 2H), 7.49 (dd, J=8.8, 2.0 Hz, 1H), 7.88 (d, J=2.0 Hz, 1H), 7.95 (d, J=8.8 Hz, 1H).

Compound 12D. LC-MS (ESI) m/z: 466 [M+Na]$^+$.

Compound 12E. LC-MS (ESI) m/z: 296 [M+H]$^+$.

Compound 12F. LC-MS (ESI) m/z: 268 [M+H]$^+$; $^1$H-NMR (DMSO-d$_6$, 400 MHz): δ (ppm) 5.55 (s, 2H), 7.55 (d, J=8.6 Hz, 1H), 7.97 (d, J=8.6 Hz, 1H), 8.30 (s, 1H).

Compound 12 was synthesized by employing the procedure described for Compound 8 using Compound 12F in lieu of Compound 8F. LC-MS (ESI) m/z: 544 [M+H]$^+$; $^1$H-NMR (CD$_3$OD, 400 MHz): δ (ppm) 0.57-0.81 (m, 4H), 1.96-2.07 (m, 2H), 2.15-2.22 (m, 2H), 3.18-3.32 (m, 2H), 3.36-3.49 (m, 1H), 3.63-3.84 (m, 4H), 4.61 (dt, J=11.2, 3.2 Hz, 1H), 4.92-4.96 (m, 1H), 5.45-5.57 (m, 2H), 7.16-7.19 (m, 2H), 7.31 (t, J=8.4 Hz, 1H), 7.45-7.48 (m, 1H), 7.83 (d, J=8.8 Hz, 1H), 8.03 (s, 1H).

Example 13

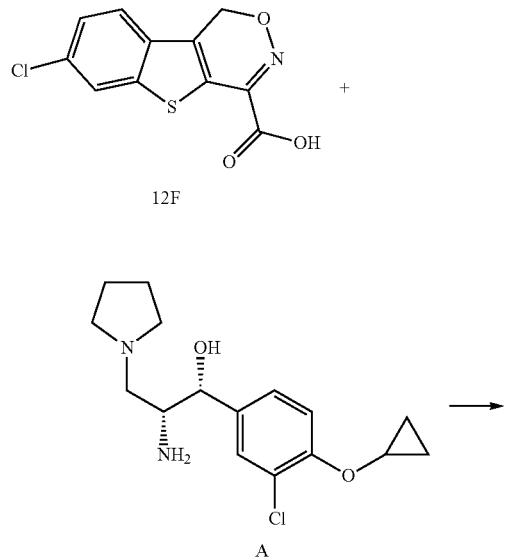

Compound 13 was synthesized by employing the procedure described for Compound 8 using Compound 12F and Intermediate A in lieu of Compound 8F and Intermediate D. LC-MS (ESI) m/z: 560 [M+H]+; $^1$H-NMR (CD$_3$OD, 400 MHz): δ (ppm) 0.61-0.75 (m, 4H), 2.00-2.03 (m, 2H), 2.16-2.20 (m, 2H), 3.19-3.31 (m, 2H), 3.48-3.51 (m, 1H), 3.65-3.80 (m, 4H), 4.57-5.59 (m, 1H), 4.92-4.96 (m, 1H), 5.46-5.56 (m, 2H), 7.28-7.32 (m, 2H), 7.43-7.47 (m, 2H), 7.80-7.83 (m, 1H), 8.00-8.02 (m, 1H).

Example 14

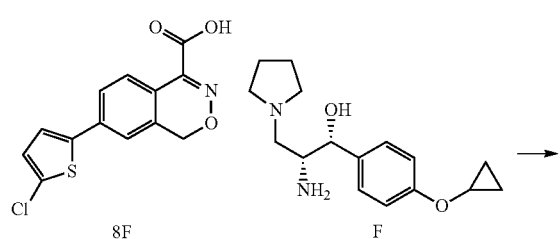

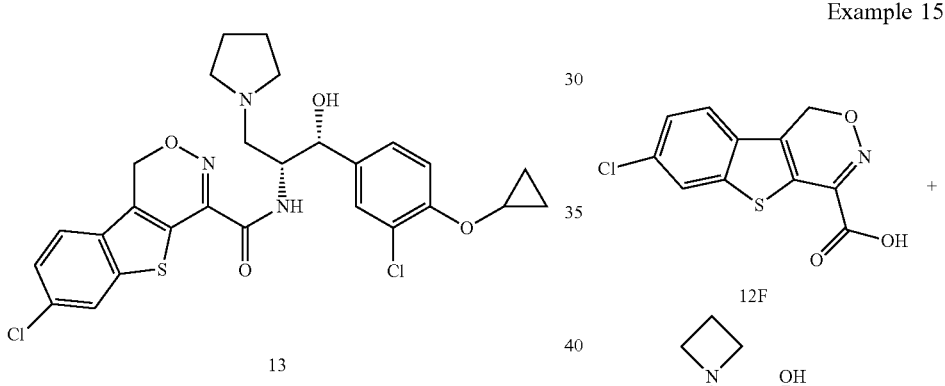

Compound 14 was synthesized by employing the procedure described for Compound 8 using Intermediate F in lieu of Intermediate D. LC-MS (ESI) m/z: 552 [M+H]+; $^1$H-NMR (CD$_3$OD, 400 MHz): δ (ppm) 0.62-0.79 (m, 4H), 1.99-2.25 (m, 4H), 3.18-3.31 (m, 2H), 3.48-3.55 (m, 1H), 3.66-3.85 (m, 4H), 4.64-4.71 (m, 1H), 4.93 (d, J=3.2 Hz, 1H), 5.02-5.12 (m, 2H), 7.00-7.04 (m, 3H), 7.34-7.41 (m, 4H), 7.51-7.54 (m, 2H).

Example 15

Compound 15 was synthesized by employing the procedure described for Compound 8 using Compound 12F and Intermediate E in lieu of Compound 8F and Intermediate D. LC-MS (ESI) m/z: 530 [M+H]+; $^1$H-NMR (CD$_3$OD, 400

MHz): δ (ppm) 0.59-0.73 (m, 4H), 2.42-2.44 (m, 1H), 2.54-2.59 (m, 1H), 3.54-3.57 (m, 2H), 3.76-3.79 (m, 1H), 4.18-4.31 (m, 4H), 4.40-4.45 (m, 1H), 4.96-4.98 (m, 1H), 5.44-5.55 (m, 2H), 7.15-7.18 (m, 2H), 7.30 (t, J=8.4 Hz, 1H), 7.44-7.46 (m, 1H), 7.79-7.82 (m, 1H), 7.79-8.01 (m, 1H).

Example 16

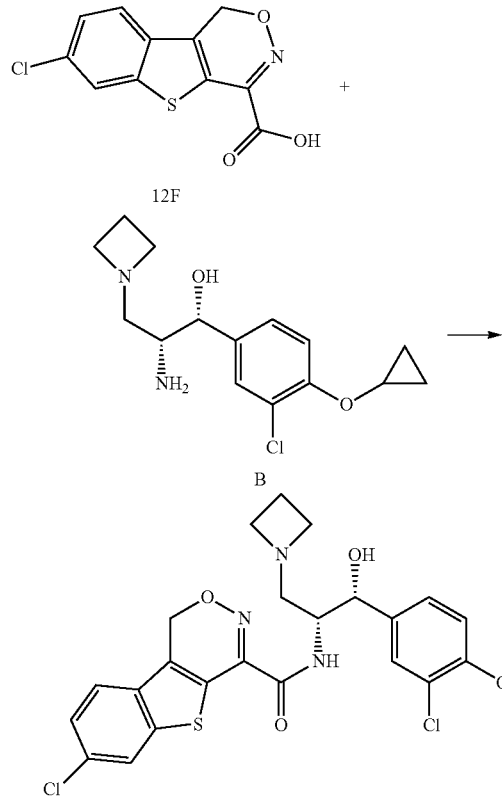

Compound 16 was synthesized by employing the procedure described for Compound 8 using Compound 12F and Intermediate B in lieu of Compound 8F and Intermediate D. LC-MS (ESI) m/z: 546 [M+H]+; 1H-NMR (CD3OD, 400 MHz): δ (ppm) 0.59-0.77 (m, 4H), 2.42-2.44 (m, 1H), 2.56-2.59 (m, 1H), 3.56-3.59 (m, 2H), 3.77-3.79 (m, 1H), 4.24-4.27 (m, 4H), 4.40-4.44 (m, 1H), 4.96-4.98 (m, 1H), 5.46-5.55 (m, 2H), 7.32 (s, 2H), 7.43-7.47 (m, 2H), 7.80-7.82 (m, 1H), 8.00 (d, J=1.7 Hz, 1H).

Example 17

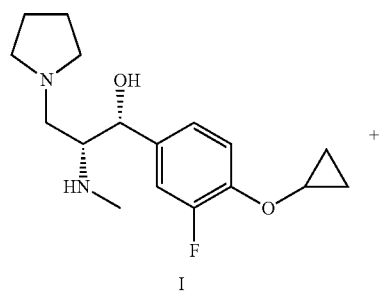

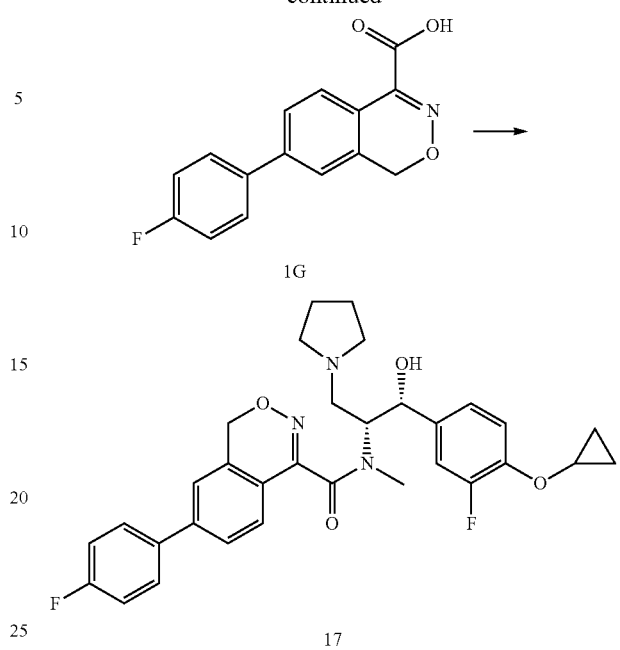

Compound 17 was synthesized by employing the procedure described for Compound 8 using Compound 1G and Intermediate I in lieu of Compound 8F and Intermediate D. LC-MS (ESI) m/z: 562 [M+H]+; 1H-NMR ((CD3)2CO, 400 MHz): δ (ppm) 0.56-0.87 (m, 4H), 2.10-2.34 (m, 4H), 3.19-3.28 (m, 3H), 3.36-3.58 (m, 2H), 3.68-4.56 (m, 5H), 4.96-5.70 (m, 4H), 6.44-7.00 (m, 1H), 7.06-7.62 (m, 7H), 7.73-7.81 (m, 2H), 8.64-9.31 (m, 1H).

Example 18

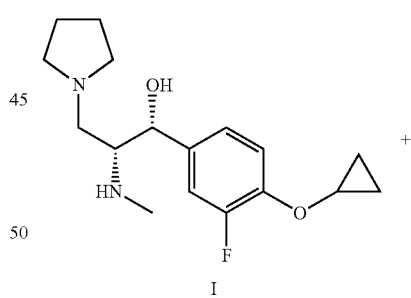

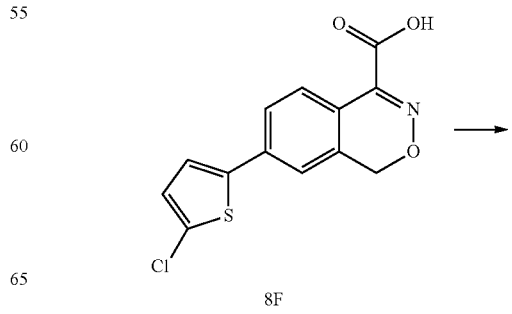

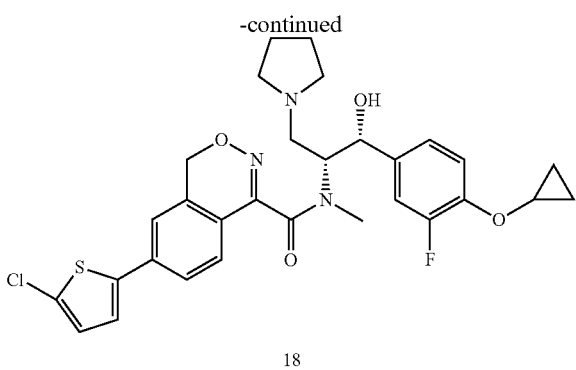

18

Compound 18 was synthesized by employing the procedure described for Compound 8 using Intermediate I in lieu of Intermediate D. LC-MS (ESI) m/z: 585 [M+H]+; 1H-NMR ((CD3)2CO, 400 MHz): δ (ppm) 0.62-0.86 (m, 4H), 2.06-2.15 (m, 4H), 3.09-3.19 (m, 5H), 3.64-4.14 (m, 5H), 5.00-5.39 (m, 3H), 5.58-6.30 (m, 1H), 6.95-7.85 (m, 8H), 11.14-11.60 (m, 1H).

Example 19

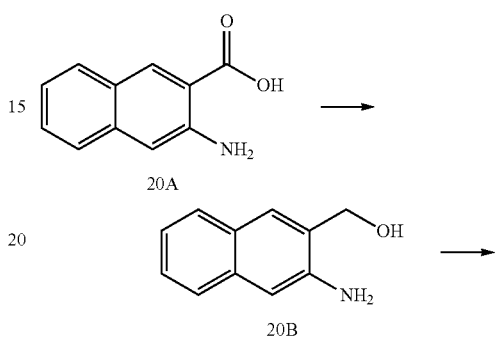

19

Compound 19 was synthesized by employing the procedure described for Compound 8 using Compound 1G and Intermediate H in lieu of Compound 8F and Intermediate D. LC-MS (ESI) m/z: 578 [M+H]+. 1H-NMR (CD3OD, 400 MHz): δ (ppm) 0.56-0.84 (m, 4H), 2.07-2.21 (m, 4H), 3.16-3.34 (m, 3H), 3.44 (s, 1H), 3.53-4.18 (m, 5H), 4.84-5.18 (m, 4H), 5.51-6.11 (m, 1H), 6.99-7.08 (m, 1H), 7.15-7.17 (m, 1H), 7.22-7.28 (m, 2H), 7.41-7.57 (m, 4H), 7.69-7.77 (m, 2H).

Example 20

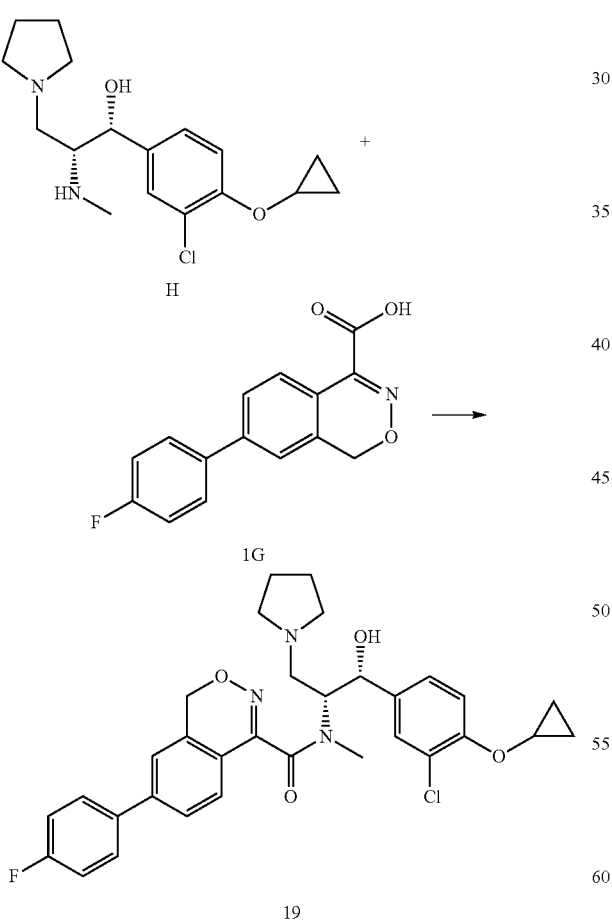

night. The reaction mixture was quenched with water (2.54 mL), aq. NaOH (15%, 2.54 mL), and water (7.62 mL). After stirring for 30 min, the mixture was filtered and the filtrate was extracted with ethyl acetate (100 mL×3). The combined organic layers were washed with water (10 mL) and brine (10 mL), dried over anhydrous sodium sulfate, filtered, and concentrated to afford Compound 20B. LC-MS (ESI) m/z: 174 [M+H]$^+$; $^1$H-NMR (CDCl$_3$, 400 MHz): δ (ppm) 1.59 (s, 2H), 4.36 (s, 1H), 4.85 (s, 2H), 7.04 (s, 1H), 7.24 (t, J=7.2 Hz, 1H), 7.38 (t, J=8.0 Hz, 1H), 7.59-7.61 (m, 2H), 7.69 (d, J=8.0 Hz, 1H).

To a solution of Compound 20B (1.0 g, 10 mmol) in water (6 mL), acetone (6 mL), and concentrated HCl (3.2 mL) at 0° C. was added a solution of NaNO$_2$ (439 mg, 6.36 mmol) in water (1.4 mL). After the mixture was stirred at 0° C. for 2 h, to it was added a solution of KI (1.44 g, 8.67 mmol) and concentrated H$_2$SO$_4$ (0.32 mL) in water (2.4 mL). The mixture was stirred at 60° C. for 3 h. The reaction mixture was cooled down to room temperature and a saturated solution of Na$_2$S$_2$O$_3$ (10 mL) was added. The mixture was extracted with ethyl acetate (100 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate in petroleum ether, 20% v/v) to furnish Compound 20C. LC-MS (ESI) m/z: 285 [M+H]$^+$; $^1$H-NMR (CDCl$_3$, 400 MHz): δ (ppm) 2.17 (t, J=6.0 Hz, 1H), 4.83 (d, J=6.4 Hz, 2H), 7.48-7.53 (m, 2H), 7.72-7.74 (m, 1H), 7.81-7.84 (m, 1H), 7.90 (s, 1H), 8.38 (s, 1H).

To a solution of Compound 20C (568 g, 2.0 mmol) in dichloromethane (20 mL) was added triphenylphosphine (786 mg, 3.0 mmol), iodine (762 mg, 3.0 mmol), and imidazole (204 mg, 3.0 mmol). The mixture was stirred at room temperature overnight. The resulting solution was quenched with saturated Na$_2$S$_2$O$_3$ solution (10 mL) and extracted with dichloromethane (50 mL×3). The organic layer was washed with water (10 mL) and brine (10 mL), dried over anhydrous sodium sulfate, filtered, and concentrated to yield a crude product. The crude was purified with flash column chromatography on silica gel (ethyl acetate in petroleum ether, 3% v/v) to give Compound 20D. $^1$H-NMR (CDCl$_3$, 400 MHz): (ppm) 4.74 (s, 2H), 7.49-7.51 (m, 2H), 7.69-7.72 (m, 1H), 7.76-7.78 (m, 1H), 7.98 (s, 1H), 8.38 (s, 1H).

To a suspension of Compound 20D (3.8 g, 9.64 mmol) in AcOH (60 mL) was added zinc powder (6.27 g, 96.4 mmol). The mixture was stirred at 80° C. for 2 h. The resulting solution was cooled down to room temperature and filtered with Celite. After removal of the solvent, the residue was extracted with ethyl acetate (100 mL×3). The organic layer was washed with water (10 mL) and brine (10 mL), dried over anhydrous sodium sulfate, filtered, and concentrated to yield a crude product. The crude was purified with flash column chromatography on silica gel (petroleum ether, 100%) to furnish Compound 20E. $^1$H-NMR (CDCl$_3$, 400 MHz): δ (ppm) 2.59 (s, 3H), 7.41-7.49 (m, 2H), 7.69-7.74 (m, 3H), 8.38 (s, 1H).

Compound 20F was synthesized by employing the procedure described for Compound 12B using Compound 20E in lieu of Compound 12A. LC-MS (ESI) m/z: 243 [M+H]$^+$; $^1$H-NMR (CDCl$_3$, 400 MHz): δ (ppm) 1.46 (t, J=7.2 Hz, 3H), 2.75 (s, 3H), 4.50 (q, J=7.2 Hz, 2H), 7.51 (t, J=8.4 Hz, 1H), 7.62 (t, J=8.4 Hz, 1H), 7.71 (s, 1H), 7.80 (d, J=8.0 Hz, 1H), 7.90 (d, J=8.0 Hz, 1H), 8.28 (s, 1H).

Compounds 20G, 20H, 20I, 20J, and 20 were synthesized by employing the procedure described for Compounds 1D, To a suspension of LiAlH$_4$ (2.54 g, 66.8 mmol) in anhydrous THF (100 mL) at 0° C. was added dropwise a solution of Compound 20A (5.0 g, 26.7 mmol) in THF (100 mL) over 30 min. The mixture was stirred at room temperature over- 1E, 1F, 1G, and 1 using Compounds 20F, 20G, 20H, 20I, and 20J in lieu of Compounds 1C, 1D, 1E, 1F, and 1G.

Compound 20G. LC-MS (ESI) m/z: 321 [M+H]$^+$; 1.47 (t, J=7.2 Hz, 3H), 4.52 (q, J=7.2 Hz, 2H), 5.11 (s, 2H), 7.59-7.73 (m, 2H), 7.88 (d, J=8.0 Hz, 1H), 7.94 (s, 1H), 7.98 (d, J=8.0 Hz, 1H), 8.36 (s, 1H).

Compound 20H. LC-MS (ESI) m/z: 404 [M+H]$^+$; $^1$H-NMR (CDCl$_3$, 400 MHz): δ (ppm) 1.47 (t, J=7.2 Hz, 3H), 4.52 (q, J=7.2 Hz, 2H), 5.79 (s, 2H), 7.61 (t, J=8.0 Hz, 1H), 7.68 (t, J=8.4 Hz, 1H), 7.73-7.75 (m, 2H), 7.82-7.84 (m, 2H), 7.92 (d, J=8.0 Hz, 1H), 7.96 (d, J=8.0 Hz, 1H), 8.28 (s, 1H), 8.44 (s, 1H).

Compound 20I. LC-MS (ESI) m/z: 256 [M+H]$^+$.

Compound 20J. LC-MS (ESI) m/z: 228 [M+H.

Compound 20. LC-MS (ESI) m/z: 520 [M+H]$^+$; $^1$H-NMR (CD$_3$OD, 400 MHz): δ (ppm) 0.39-0.64 (m, 4H), 1.96-2.11 (m, 4H), 3.13-3.17 (m, 2H), 3.45-3.71 (m, 5H), 4.66-4.69 (m, 1H), 4.87 (d, J=2.4 Hz, 1H), 5.02-5.14 (m, 2H), 7.17 (d, J=8.4 Hz, 1H), 7.27 (dd, J=8.4, 2.0 Hz, 1H), 7.41-7.51 (m, 3H), 7.60 (s, 1H), 7.69 (s, 1H), 7.75 (d, J=8.0 Hz, 1H), 7.79 (d, J=8.0 Hz, 1H).

Example 21

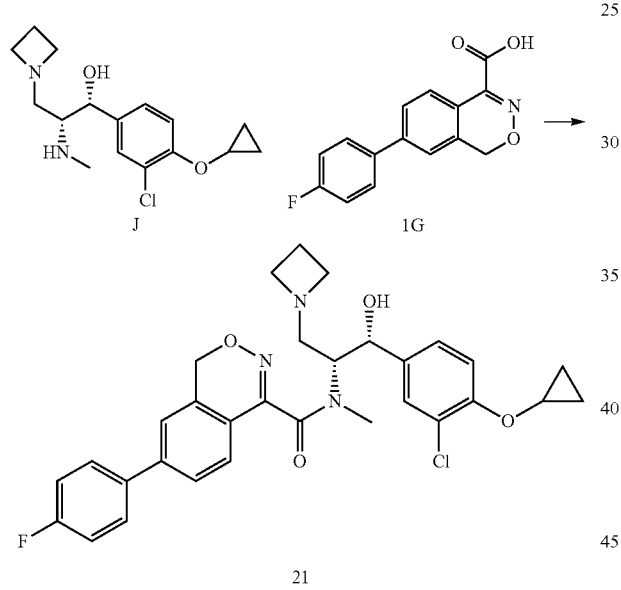

Compound 21 was synthesized by employing the procedure described for Compound 8 using Compound 1G and Intermediate J in lieu of Compound 8F and Intermediate D. LC-MS (ESI) m/z: 564 [M+H]$^+$; $^1$H-NMR ((CD$_3$)$_2$CO, 400 MHz): δ (ppm) 0.54-0.87 (m, 4H), 2.55-2.72 (m, 2H), 3.12-3.25 (m, 3H), 3.67-4.12 (m, 3H), 4.41-4.64 (m, 4H), 4.83-5.16 (m, 3H), 5.28-5.49 (m, 1H), 6.36-7.60 (m, 8H), 7.73-7.80 (m, 2H).

Example 22

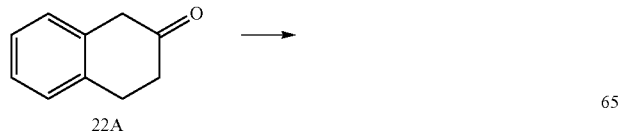

22A

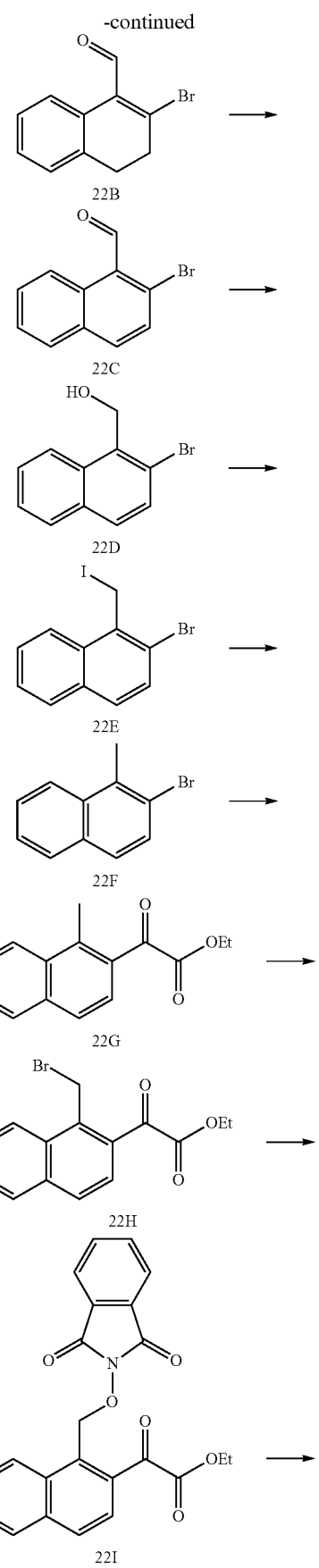

-continued

22B

22C

22D

22E

22F

22G

22H

22I

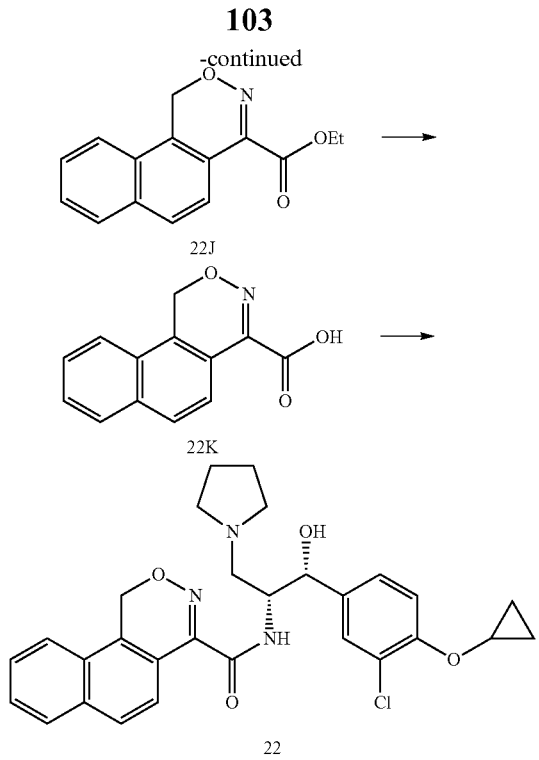

Dimethylformamide (8.0 mL, 100 mmol) was added dropwise to a solution of phosphorus tribromide (8.0 mL, 84 mmol) in dry chloroform (200 mL) at 0° C. The mixture was stirred at 0° C. for 1 h to give a suspension. A solution of β-tetralone (22A, 5.0 g, 34 mmol) in dry chloroform (200 mL) was added to the suspension and the reaction mixture was heated at reflux for 1 h. The reaction mixture was cooled to 0° C. and basified with saturated aqueous sodium bicarbonate solution. The resulting mixture was extracted with dichloromethane, dried over anhydrous sodium sulfate, filtered, and evaporated under vacuum. The residue was purified with flash column chromatography on silica gel (ethyl acetate in petroleum ether, 25% v/v) to give Compound 22B. $^1$H-NMR (DMSO-d$_6$, 400 MHz): δ (ppm) 2.85-2.89 (m, 2H), 3.00-3.04 (m, 2H), 7.21-7.27 (m, 3H), 7.79-7.81 (m, 1H), 10.18 (s, 1H).

A mixture of Compound 22B (3.1 g, 13 mmol) and DDQ (2.9 g, 13 mmol) in toluene (100 mL) was refluxed for 72 h. After the reaction mixture was cooled to room temperature, the mixture was filtered through Celite and the filtrate was evaporated to dryness. The residue was purified with flash column chromatography on silica gel (ethyl acetate in petroleum ether, 25% v/v) to give Compound 22C. LC-MS (ESI) m/z: No; $^1$H-NMR (DMSO-d$_6$, 400 MHz): δ (ppm) 7.65-7.80 (m, 3H), 8.06-8.08 (m, 1H), 8.15-8.17 (m, 1H), 8.85-8.87 (m, 1H), 10.62 (s, 1H).

To a solution of Compound 22C (2.44 g, 10.4 mmol) in EtOH (50 mL) at room temperature was added NaBH$_4$ (395 mg, 10.4 mmol) in several portions. The mixture was stirred at room temperature for 2 h. The reaction mixture was quenched with 1 N HCl, evaporated, and purified with flash column chromatography on silica gel (ethyl acetate in petroleum ether, 50% v/v) to give Compound 22D. LC-MS (ESI) m/z: 219 [M−OH]$^+$; $^1$H-NMR (CDCl$_3$, 400 MHz): δ (ppm) 5.30 (d, J=6.0 Hz, 2H), 7.50-7.68 (m, 4H), 7.83 (d, J=7.6 Hz, 1H), 8.24 (d, J=8.4 Hz, 1H).

Compounds 22E and 22F were synthesized by employing the procedure described for Compounds 20D and 20E using Compounds 22D and 22E in lieu of Compounds 20C and 20D.

Compound 22E. $^1$H-NMR (CDCl$_3$, 400 MHz): δ (ppm) 5.04 (s, 2H), 7.53-7.58 (m, 2H), 7.66-7.69 (m, 2H), 7.85-7.87 (m, 1H), 8.05-8.07 (m, 1H).

Compound 22F. $^1$H-NMR (CDCl$_3$, 400 MHz): δ (ppm) 2.80 (s, 3H), 7.49-7.62 (m, 4H), 7.81 (d, J=8.0 Hz, 1H), 8.04 (d, J=8.0 Hz, 1H).

Compound 22G was synthesized by employing the procedure described for Compound 12B using Compound 22F in lieu of Compound 12A. LC-MS (ESI) m/z: 243 [M+H]$^+$.

Compounds 22H, 22I, 22J, 22K, and 22 were synthesized by employing the procedures described for Compounds 1D, 1E, 1F, 1G, and 1 using Compounds 22G, 22H, 22I, 22J, and 22K in lieu of Compounds 1C, 1D, 1E, 1F, and 1G.

Compound 22H. LC-MS (ESI) m/z: 321 [M+H]$^+$; $^1$H-NMR (CDCl$_3$, 400 MHz): δ (ppm) 1.43 (t, J=7.2 Hz, 3H), 4.48 (q, J=7.2 Hz, 2H), 5.32 (s, 2H), 7.65-7.73 (m, 3H), 7.91-7.94 (m, 2H), 8.33-8.35 (m, 1H).

Compound 22I. LC-MS (ESI) m/z: 404 [M+H]$^+$.

Compound 22J. LC-MS (ESI) m/z: 256 [M+H]$^+$.

Compound 22K. LC-MS (ESI) m/z: 228 [M+H]$^+$.

Compound 22. LC-MS (ESI) m/z: 520 [M+H]$^+$; $^1$H-NMR (acetone-d$_6$, 400 MHz): δ (ppm) 0.68-0.69 (m, 2H), 0.79-0.80 (m, 2H), 2.07-2.09 (m, 4H), 3.08 (brs, 2H), 3.75-3.79 (m, 2H), 3.93-3.97 (m, 3H), 4.81-4.82 (m, 1H), 5.20 (d, J=1.6 Hz, 1H), 5.53 (q, J=15.2 Hz, 2H), 7.33-7.35 (m, 1H), 7.43-7.45 (m, 1H), 7.54-7.55 (m, 1H), 7.64-7.66 (m, 2H), 7.77-7.78 (m, 1H), 7.87-7.97 (m, 1H), 7.96-8.03 (m, 2H), 8.11-8.14 (m, 1H).

Example 23

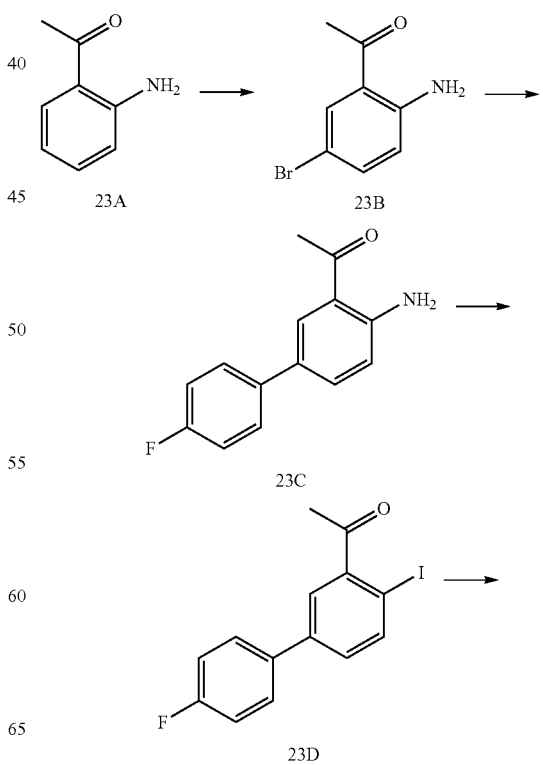

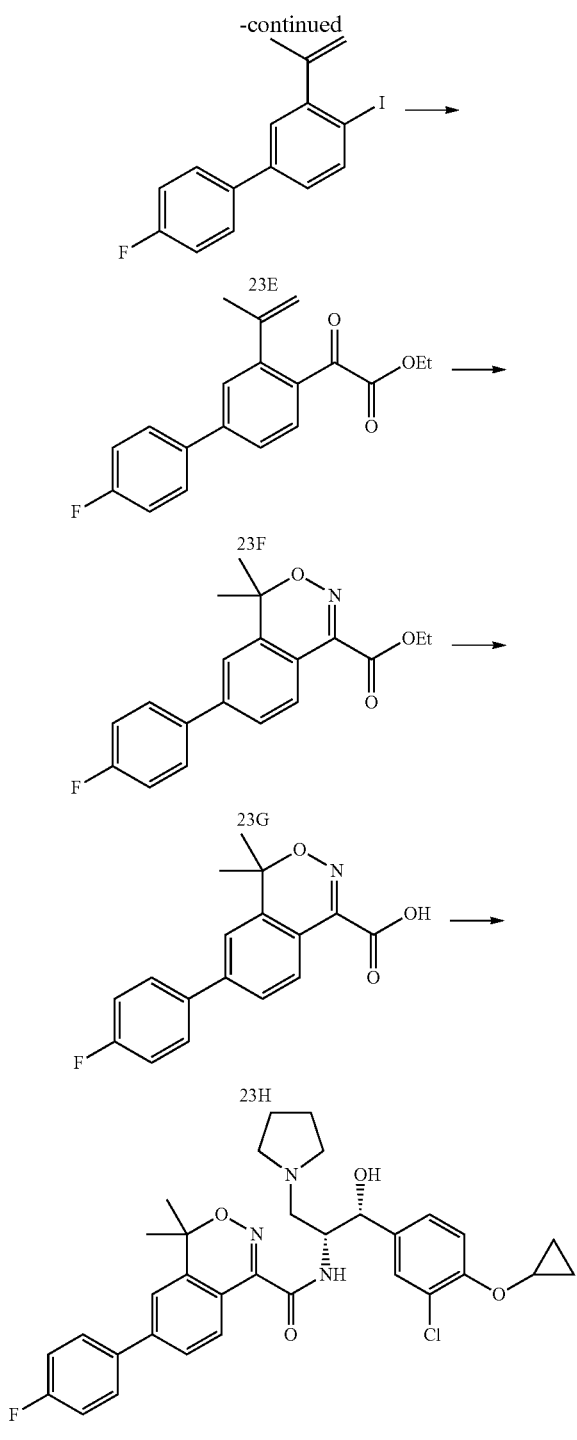

Compound 23C was synthesized by employing the procedure described for Compound 1B using Intermediate 23B in lieu of Intermediate 1A. LC-MS (ESI) m/z: 230 [M+H]$^+$; $^1$H-NMR (CDCl$_3$, 400 MHz): δ (ppm) 2.65 (s, 3H), 6.35 (s, 2H), 6.74 (d, J=8.8 Hz, 1H), 7.12 (t, J=8.4 Hz, 2H), 7.46-7.50 (m, 3H), 7.86 (d, J=2.4 Hz, 1H).

To a stirred solution of p-TsOH (1.03 g, 6.0 mmol) in MeCN (7.2 mL) was added Compound 23C (458 mg, 2.0 mmol). To the resulting suspension at 0° C. was slowly added dropwise an aqueous solution of KI (830 mg, 5.0 mmol) and NaNO$_2$ (276 mg, 4.0 mmol) in water (2 mL). The mixture was stirred at room temperature for 4.5 h. and water (15 mL) and saturated Na$_2$S$_2$O$_3$ solution (10 mL) were added. The mixture was extracted with ethyl acetate (100 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate in petroleum ether, 10% v/v) to furnish Compound 23D. LC-MS (ESI) m/z: 341 [M+H]$^+$; $^1$H-NMR (CDCl$_3$, 400 MHz): δ (ppm) 2.68 (s, 3H), 7.16 (t, J=8.4 Hz, 2H), 7.30 (dd, J=8.0, 2.4 Hz, 1H), 7.51-7.55 (m, 2H), 7.58 (d, J=2.4 Hz, 1H), 7.98 (d, J=8.8 Hz, 1H).

To a solution of methyltriphenylphosphonium bromide (1.76 g, 4.94 mmol) in THF (40 mL) at 0° C. was added n-BuLi (2.5 M in hexane, 1.98 mL, 4.94 mmol). After stirring at 0° C. for 1 h, to the mixture was added a solution of Compound 23D (1.12 g, 3.31 mmol) in THF (5 mL). The mixture was stirred at room temperature for 2 h. The reaction mixture was quenched with saturated ammonium chloride solution (10 mL) and extracted with ethyl acetate (100 mL×3). The organic layer was washed with water (10 mL) and brine (10 mL), dried over anhydrous sodium sulfate, filtered, and concentrated to yield a crude product. The crude was purified with flash column chromatography on silica gel (petroleum ether, 100%) to give Compound 23E. $^1$H-NMR (CDCl$_3$, 400 MHz): δ (ppm) 2.11 (s, 3H), 4.95 (s, 1H), 5.27 (t, J=1.6 Hz, 1H), 7.11-7.15 (m, 3H), 7.35 (d, J=2.0 Hz, 1H), 7.51-7.55 (m, 2H), 7.88 (d, J=8.0 Hz, 1H).

Compound 23F was synthesized by employing the procedure described for Compound 12B using Compound 23E in lieu of Compound 12A. LC-MS (ESI) m/z: 313 [M+H]$^+$; $^1$H-NMR (CDCl$_3$, 400 MHz): δ (ppm) 1.38 (t, J=7.2 Hz, 3H), 2.21 (s, 3H), 4.33 (q, J=7.2 Hz, 2H), 4.86 (s, 1H), 5.27 (s, 1H), 7.18 (t, J=8.4 Hz, 2H), 7.52 (t, J=1.6 Hz, 1H), 7.59-7.62 (m, 3H), 7.83 (d, J=8.4 Hz, 1H).

To a solution of Compound 23F (550 mg, 1.76 mmol) in ethanol (20 mL) was added sodium acetate (444 mg, 5.28 mmol) and hydroxylamine hydrochloride (364 mg, 5.28 mmol). The mixture was heated at 50° C. for 3 h. After removal of the solvent, it was extracted with ethyl acetate (50 mL×3). The organic layer was washed with water (10 mL) and brine (10 mL), dried over anhydrous sodium sulfate, filtered, and concentrated to yield a crude product. The crude was purified with flash column chromatography on silica gel (ethyl acetate in petroleum ether, 10% v/v) to furnish Compound 23G. LC-MS (ESI) m/z: 328 [M+H]$^+$; $^1$H-NMR (DMSO-d$_6$, 400 MHz): δ (ppm) 1.37 (t, J=7.2 Hz, 3H), 1.54 (s, 6H), 4.38 (q, J=7.2 Hz, 2H), 7.34 (t, J=8.8 Hz, 2H), 7.75 (dd, J=8.4, 1.6 Hz, 1H), 7.78-7.82 (m, 2H), 7.90 (d, J=8.4 Hz, 1H), 7.92 (d, J=1.2 Hz, 1H).

Compounds 23H and 23 were synthesized by employing the procedures described for Compounds 1G and 1 using Compounds 23G and 22K in lieu of Compounds 1F and 1G.

Compound 23H. LC-MS (ESI) m/z: 300 [M+H]$^+$.

Compound 23. LC-MS (ESI) m/z: 592 [M+H]$^+$; $^1$H-NMR (CD$_3$OD, 400 MHz): δ (ppm) 0.54-0.76 (m, 4H), 1.66 (s, To a solution of Compound 23A (1.35 g, 10 mmol) in MeCN (10 mL) at 0° C. was added dropwise a solution of NBS (1.78 g, 10 mmol) in MeCN (10 mL) over 3 min. and the reaction mixture was stirred at room temperature for 3 h. After removal of solvent, the residue was filtered through a short plug of silica (eluting with ethyl acetate in petroleum ether, 20% v/v). The filtrate was concentrated to yield Compound 23B. LC-MS (ESI) m/z: 214 [M+H]$^+$; $^1$H-NMR (CDCl$_3$, 400 MHz): δ (ppm) 2.57 (s, 3H), 6.30 (s, 2H), 6.57 (d, J=8.8 Hz, 1H), 7.33 (dd, J=8.8, 2.4 Hz, 1H), 7.81 (d, J=2.0 Hz, 1H).

3H), 1.72 (s, 3H), 2.02-2.19 (m, 4H), 3.21-3.28 (m, 2H), 3.55-3.84 (m, 4H), 3.96-3.99 (m, 1H), 4.62-4.65 (m, 1H), 4.97 (d, J=1.6 Hz, 1H), 7.21 (t, J=8.8 Hz, 2H), 7.32-7.35 (m, 1H), 7.49 (d, J=1.6 Hz, 1H), 7.64-7.74 (m, 5H), 8.16 (d, J=8.0 Hz, 1H).

Example 24

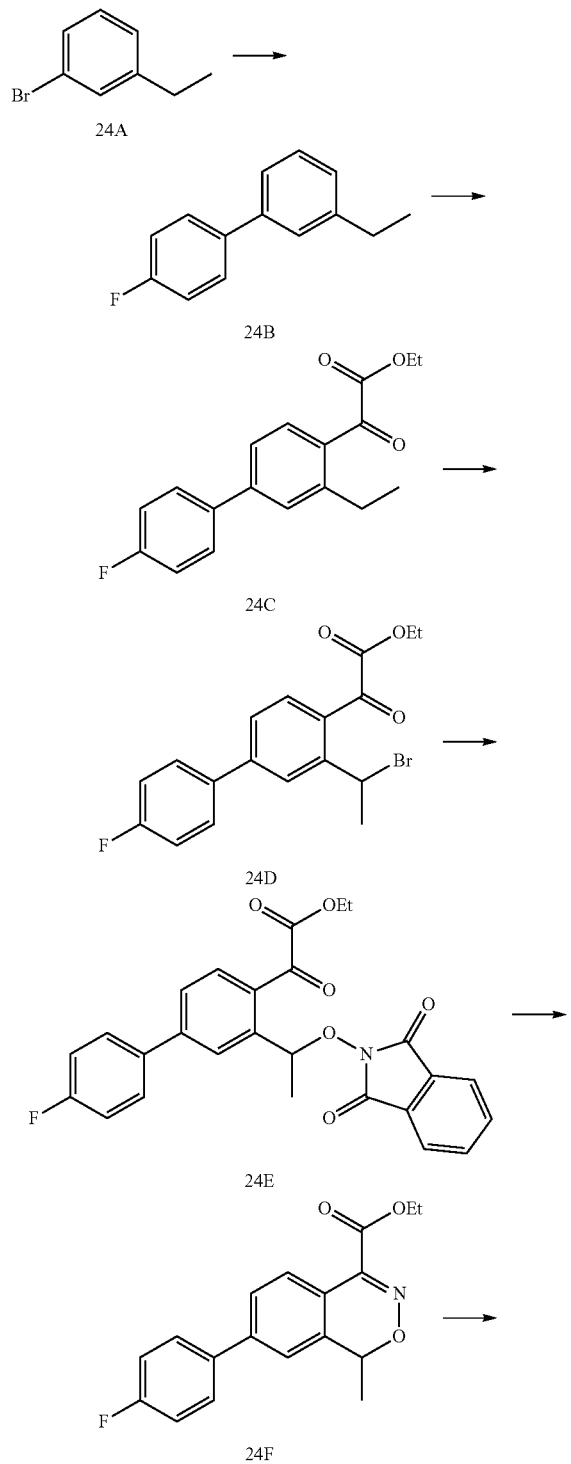

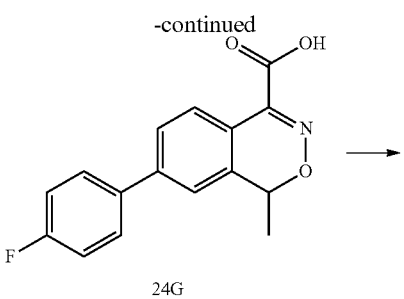

Compounds 24B, 24C, 24D, 24E, 24F, 24G, and 24 were synthesized by employing the procedure described for Compounds 1B, 1C, 1D, 1E, 1F, 1G, and 1 using Compounds 24A, 24B, 24C, 24D, 24E, 24F, and 24G in lieu of Compounds 1A, 1B, 1C, 1D, 1E, 1F, and 1G.

Compound 24B. $^1$H-NMR (CDCl$_3$, 400 MHz): δ (ppm) 1.28 (t, J=7.6 Hz, 3H), 2.68-2.74 (m, 2H), 7.11 (t, J=8.8 Hz, 2H), 7.18-7.20 (m, 1H), 7.34-7.37 (m, 3H), 7.53-7.54 (m, 2H).

Compound 24C. LC-MS: (ESI) m/z: 301 [M+H]$^+$.

Compound 24D. $^1$H-NMR (CDCl$_3$, 400 MHz): δ (ppm) 1.42-1.46 (m, 3H), 2.07 (d, J=6.8 Hz, 3H), 4.44-4.49 (m, 2H), 6.19-6.25 (m, 1H), 7.17-7.21 (m, 2H), 7.55-7.64 (m, 3H), 7.71-7.73 (d, J=8.4 Hz, 1H), 8.08-8.09 (d, J=2.0 Hz, 1H).

Compound 24E. LC-MS: (ESI) m/z: 484 [M+Na]$^+$; $^1$H-NMR (CDCl$_3$, 400 MHz): δ (ppm) 1.39 (t, J=7.2 Hz, 3H), 1.74 (d, J=6.4 Hz, 3H), 4.39-4.44 (m, 2H), 6.26-6.31 (m, 2H), 7.20-7.25 (m, 1H), 7.59-7.62 (m, 1H), 7.70-7.86 (m, 7H), 8.49 (d, J=1.6 Hz, 1H).

Compound 24F. LC-MS: (ESI) m/z: 314 [M+H]$^+$; $^1$H-NMR (CDCl$_3$, 400 MHz): δ (ppm) 1.45 (t, J=7.6 Hz, 3H), 1.72 (d, J=6.4 Hz, 3H), 4.50 (m, 2H), 5.15-5.19 (m, 1H), 7.16 (t, J=8.8 Hz, 2H), 7.33 (s, 1H), 7.55-7.61 (m, 3H), 7.99 (d, J=8.0 Hz, 1H).

Compound 24G. LC-MS: (ESI) m/z: 286 [M+H]$^+$.

Compound 24. LC-MS (ESI) m/z: 578 [M+H]$^+$; $^1$H-NMR (CD$_3$OD, 400 MHz): δ (ppm) 0.54-0.69 (m, 4H), 1.56-1.58 (m, 3H), 1.95-2.10 (m, 4H), 3.10-3.15 (m, 2H), 3.43-3.47 (m, 1H), 3.60-3.71 (m, 4H), 4.59-4.62 (m, 1H), 4.84 (t, J=2.8 Hz, 1H), 5.08-5.15 (m, 1H), 7.10 (t, J=8.4 Hz, 2H), 7.21-7.27 (m, 3H), 7.37-7.45 (m, 3H), 7.58-7.62 (m, 2H).

Example 25

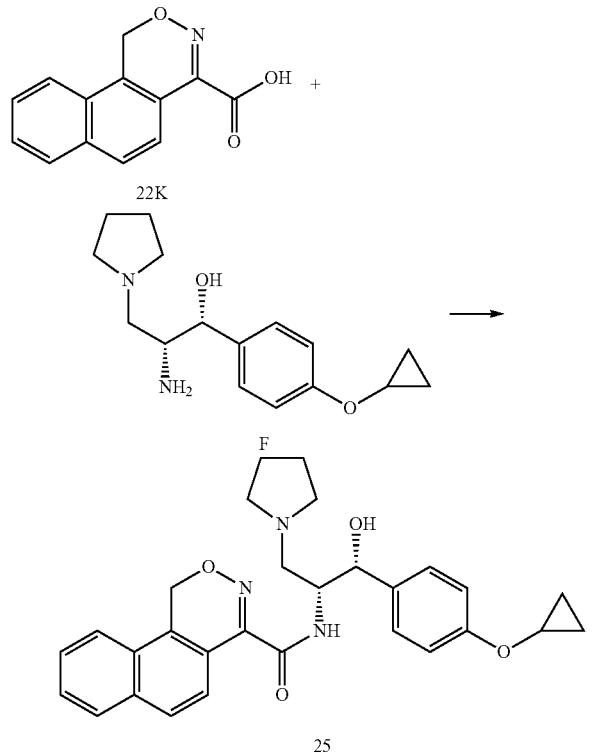

Compound 25 was synthesized by employing the procedure described for Compound 1 using Compound 22K and Intermediate F in lieu of Compound 1G and Intermediate A. LC-MS (ESI) m/z: 486 [M+H]+; 1H-NMR (acetone-d6, 400 MHz): δ (ppm) 0.73-0.75 (m, 4H), 2.13 (s, 4H), 3.01-3.10 (m, 2H), 3.38-3.40 (m, 2H), 3.68-3.93 (m, 3H), 4.65 (s, 1H), 5.08 (s, 1H), 5.38-5.56 (m, 2H), 7.01-7.03 (m, 2H), 7.31-7.35 (m, 2H), 7.58-7.63 (m, 3H), 7.77-7.80 (m, 1H), 7.87-7.88 (m, 2H).

Example 26

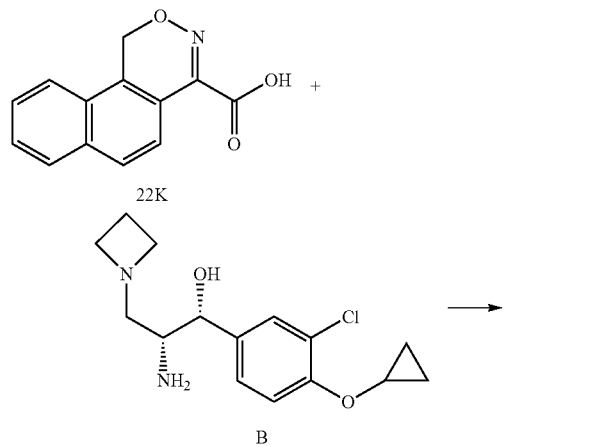

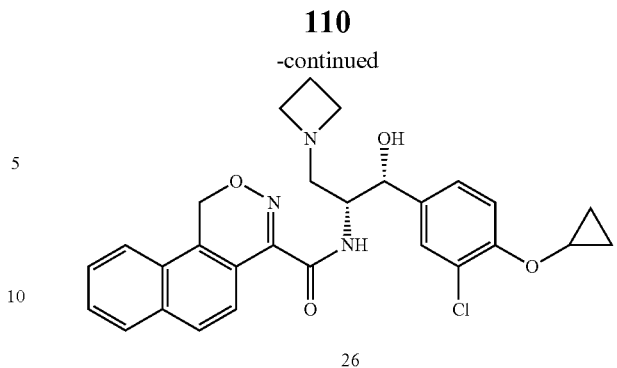

Compound 26 was synthesized by employing the procedure described for Compound 1 using Compound 22K and Intermediate B in lieu of Compound 1G and Intermediate A. LC-MS (ESI) m/z: 506 [M+H]+; 1H-NMR (acetone-d6, 400 MHz): δ (ppm) 0.67-0.82 (m, 4H), 2.48-2.66 (m, 2H), 3.70-3.77 (m, 2H), 3.85-3.88 (m, 1H), 4.36-4.42 (m, 4H), 4.66-4.67 (m, 1H), 5.15 (s, 1H), 5.49-5.55 (m, 2H), 7.33-7.35 (m, 1H), 7.41-7.44 (m, 1H), 7.52-7.53 (m, 1H), 7.64-7.67 (m, 2H), 7.80-7.82 (m, 1H), 7.87-7.93 (m, 2H), 7.98-8.01 (m, 1H), 8.11-8.14 (m, 1H).

Example 27

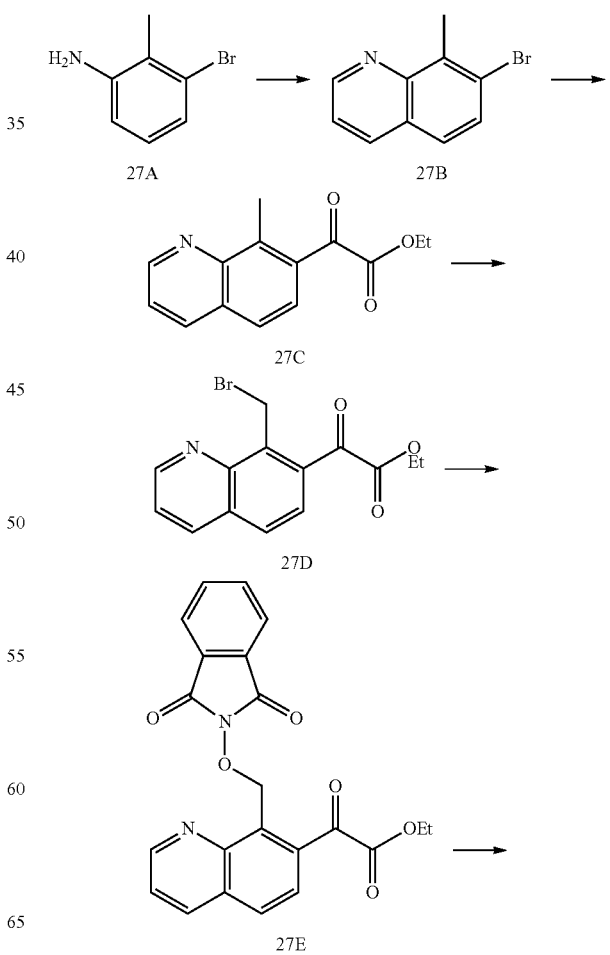

-continued

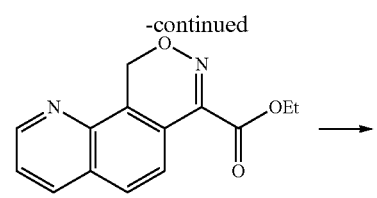

27F

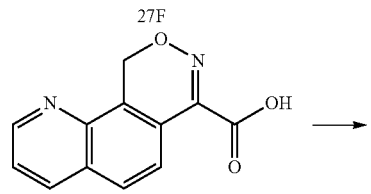

27G

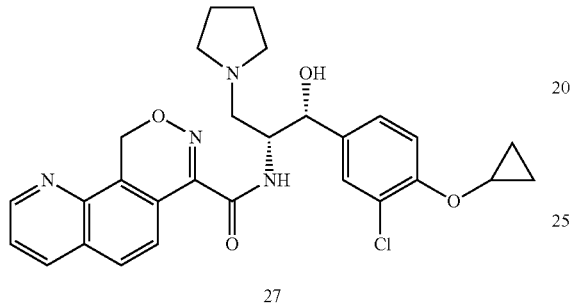

27

A mixture of Compound 27A (13.50 g, 70.58 mmol), propane-1,2,3-triol (7.98 g, 86.74 mmol), and NaI (1.06 g, 7.06 mmol) in $H_2SO_4$ (80%, 39.90 g) was stirred at 140° C. for 4 hours. The reaction mixture was cooled down to room temperature, adjusted pH to 11 with aqueous NaOH solution (40%, 60 mL), and extracted with dichloromethane (200 mL×3). The combined organic phases were washed with water (200 mL) and brine (200 mL), dried over anhydrous sodium sulfate, concentrated, and purified with flash column chromatography on silica gel (ethyl acetate in petroleum ether, from 0% to 10%) to furnish Compound 27B. LC-MS (ESI) m/z: 222 [M+H]$^+$; $^1$H-NMR (CDCl$_3$, 400 MHz): δ (ppm) 2.94 (s, 3H), 7.42 (dd, J=8.0, 4.0 Hz, 1H), 7.53 (d, J=8.8 Hz, 1H), 7.69 (d, J=8.4 Hz, 1H), 8.11 (dd, J=8.4, 2.0 Hz, 1H), 8.94 (dd, J=4.0, 1.6 Hz, 1H).

Compound 27C was synthesized by employing the procedure described for Compound 12B using Compound 27B in lieu of Compound 12A. LC-MS (ESI) m/z: 244 [M+H]$^+$; $^1$H-NMR (CDCl$_3$, 400 MHz): δ (ppm) 1.44 (t, J=7.2 Hz, 3H), 3.04 (s, 3H), 4.47 (q, J=6.8 Hz, 2H), 7.52 (dd, J=8.0, 2.0 Hz, 1H), 7.72-7.75 (m, 2H), 8.17 (dd, J=8.4, 2.0 Hz, 1H), 9.03 (dd, J=4.0, 1.6 Hz, 1H).

Compounds 27D, 27E, 27F, and 27G were synthesized by employing the procedure described for Compounds 1D, 1E, 1F, and 1G using Compounds 27C, 27D, 27E, and 24F in lieu of Compounds 1C, 1D, 1E, and 1F.

Compound 27D. LC-MS (ESI) m/z: 322 [M+H]$^+$; $^1$H-NMR (CDCl$_3$, 400 MHz): δ (ppm) 1.45 (t, J=7.6 Hz, 3H), 4.49 (q, J=7.6 Hz, 2H), 5.67 (s, 2H), 7.57 (dd, J=8.0, 4.0 Hz, 1H), 7.78 (d, J=8.8 Hz, 1H), 7.90 (d, J=8.8 Hz, 1H), 8.21 (dd, J=8.4, 1.6 Hz, 1H), 9.12 (dd, J=4.0, 1.6 Hz, 1H).

Compound 27E. LC-MS (ESI) m/z: 405 [M+H]$^+$; $^1$H-NMR (CDCl$_3$, 400 MHz): δ (ppm) 1.39 (t, J=7.6 Hz, 3H), 4.46 (q, J=7.2 Hz, 2H), 6.27 (s, 2H), 7.48 (dd, J=8.4, 4.4 Hz, 1H), 7.67-7.74 (m, 4H), 7.77 (d, J=8.4 Hz, 1H), 7.94 (d, J=8.4 Hz, 1H), 8.19 (dd, J=8.4, 1.6 Hz, 1H), 8.90 (dd, J=4.4, 1.6 Hz, 1H).

Compound 27F. LC-MS (ESI) m/z: 257 [M+H]$^+$; $^1$H-NMR (CDCl$_3$, 400 MHz): δ (ppm) 1.47 (t, J=6.8 Hz, 3H), 4.50 (q, J=7.2 Hz, 2H), 5.80 (s, 2H), 7.52 (dd, J=8.4, 4.4 Hz, 1H), 7.87 (d, J=8.4 Hz, 1H), 8.09 (d, J=8.4 Hz, 1H), 8.20 (dd, J=8.0, 1.6 Hz, 1H), 8.98 (dd, J=4.0, 1.2 Hz, 1H).

Compound 27G. LC-MS (ESI) m/z: 229 [M+H]$^+$.

Compound 27 was synthesized by employing the procedure described for Compound 8 using Compound 27G and Intermediate A in lieu of Compound 8F and Intermediate D. LC-MS (ESI) m/z: 521 [M+H]$^+$; $^1$H-NMR (DMSO-d$_6$, 400 MHz): δ (ppm) 0.65-0.81 (m, 4H), 1.88-2.05 (m, 4H), 3.12-3.21 (m, 2H), 3.44-3.57 (m, 4H), 3.88-3.91 (m, 1H), 4.58-4.61 (m, 1H), 4.83 (d, J=2.8 Hz, 1H), 5.52 (d, J=14.0 Hz, 1H), 5.83 (d, J=14.0 Hz, 1H), 7.32-7.38 (m, 2H), 7.44 (d, J=2.0 Hz, 1H), 7.69-7.74 (m, 2H), 8.02 (d, J=8.4 Hz, 1H), 8.48-8.50 (m, 2H), 9.03 (dd, J=4.0, 1.6 Hz, 1H), 9.25 (brs, 1H).

Example 28

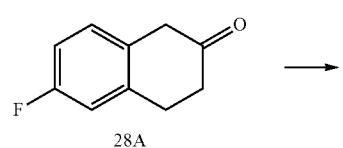

28A

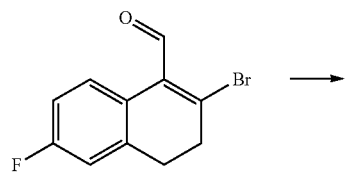

28B

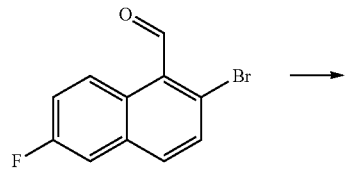

28C

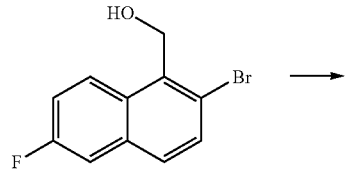

28D

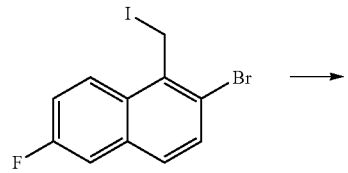

28E

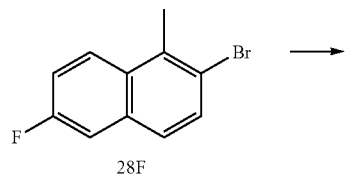

28F

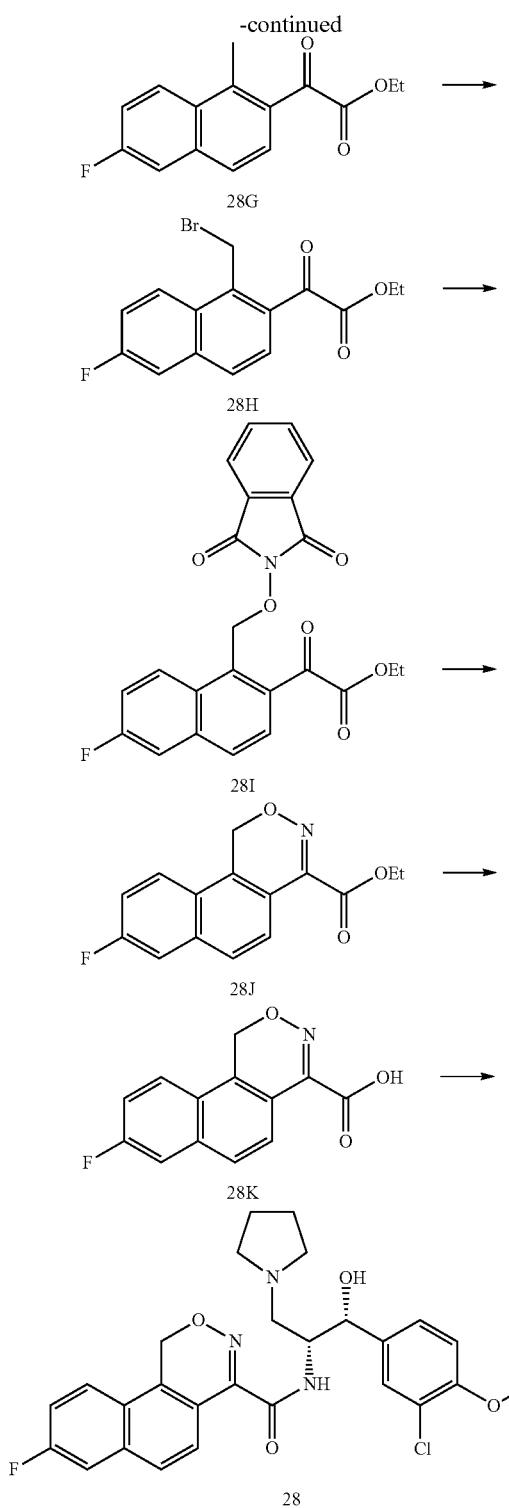

Compounds 28B, 28C, and 28D were synthesized by employing the procedures described for Compounds 22B, 22C, and 22D using Compounds 28A, 28B, and 28C in lieu of Compounds 22A, 22B, and 22C.

Compound 28B. LC-MS (ESI) m/z: No; ¹H-NMR (CDCl₃, 400 MHz): δ (ppm) 2.87-2.91 (m, 2H), 3.00-3.04 (m, 2H), 6.85-6.88 (m, 1H), 6.91-6.96 (m, 1H), 7.99-8.02 (m, 1H), 10.30 (s, 1H).

Compound 28C. LC-MS (ESI) m/z: No; ¹H-NMR (DMSO-d₆, 400 MHz): δ (ppm) 7.44-7.47 (m, 2H), 7.71 (d, J=8.8 Hz, 1H), 7.81 (d, J=8.8 Hz, 1H), 9.13-9.17 (m, 1H), 10.74 (s, 1H).

Compound 28D. LC-MS (ESI) m/z: 237 [M–OH]⁺.

Compounds 28E and 28F were synthesized by employing the procedure described for Compounds 20D and 22E using Compounds 28D and 28E in lieu of Compounds 20C and 20D.

Compound 28E. ¹H-NMR (CDCl₃, 400 MHz): δ (ppm) 4.99 (s, 2H), 7.41-7.46 (m, 2H), 7.56-7.62 (m, 2H), 8.04-8.07 (m, 1H).

Compound 28F. ¹H-NMR (CDCl₃, 400 MHz): δ (ppm) 2.78 (s, 3H), 7.27-7.32 (m, 1H), 7.39-7.42 (m, 1H), 7.48 (d, J=8.8 Hz, 1H), 7.61 (d, J=8.8 Hz, 1H), 8.00-8.04 (m, 1H).

Compound 28G was synthesized by employing the procedure described for Compound 12B using Compound 28F in lieu of Compound 12A. LC-MS (ESI) m/z: 261 [M+H]⁺; ¹H-NMR: (CDCl₃, 400 MHz): δ (ppm) 1.43 (t, J=8.4 Hz, 3H), 2.90 (s, 3H), 4.46 (q, J=6.8 Hz, 2H), 7.35-7.40 (m, 1H), 7.46-7.49 (m, 1H), 7.64 (d, J=8.4 Hz, 1H), 7.71 (d, J=8.4 Hz, 1H), 8.22-8.26 (m, 1H).

Compounds 28H, 28I, 28J, and 28K were synthesized by employing the procedures described for Compounds 1D, 1E, 1F, and 1G using Compounds 28G, 28H, 28I, and 28J in lieu of Compounds 1C, 1D, 1E, and 1F.

Compound 28H. ¹H-NMR (CDCl₃, 400 MHz): δ (ppm) 1.37 (t, J=6.8 Hz, 3H), 4.41 (q, J=7.2 Hz, 2H), 5.23 (s, 2H), 7.40-7.47 (m, 2H), 7.62 (d, J=8.8 Hz, 1H), 7.80 (d, J=8.4 Hz, 1H), 8.28-8.31 (m, 1H).

Compound 28I. LC-MS (ESI) m/z: 422 [M+H]⁺.

Compound 28J. LC-MS (ESI) m/z: 274 [M+H]⁺; ¹H-NMR (CDCl₃, 400 MHz): δ (ppm) 1.47 (t, J=6.8 Hz, 3H), 4.50 (q, J=6.8 Hz, 2H), 5.51 (s, 2H), 7.37-7.42 (m, 1H), 7.52-7.55 (m, 1H), 7.83 (d, J=8.4 Hz, 1H), 7.90-7.93 (m, 1H), 7.99 (d, J=8.8 Hz, 1H).

Compound 28K. LC-MS (ESI) m/z: 246 [M+H]⁺.

Compound 28 was synthesized by employing the procedure described for Compound 8 using Compound 28K and Intermediate A in lieu of Compound 8F and Intermediate D. LC-MS (ESI) m/z: 538 [M+H]⁺; ¹H-NMR (MeOD, 400 MHz): δ (ppm) 0.74-0.82 (m, 4H), 1.85-1.86 (m, 4H), 2.68-3.09 (m, 6H), 3.81-3.87 (m, 1H), 4.43-4.49 (m, 1H), 4.94-4.95 (m, 1H), 5.51 (s, 2H), 7.27-7.34 (m, 2H), 7.44-7.53 (m, 2H), 7.52 (d, J=8.8 Hz, 1H), 7.63-7.66 (m, 1H), 7.77-7.83 (m, 1H), 8.11-8.16 (m, 1H).

Example 29

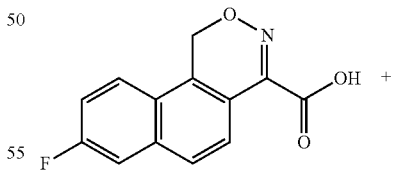

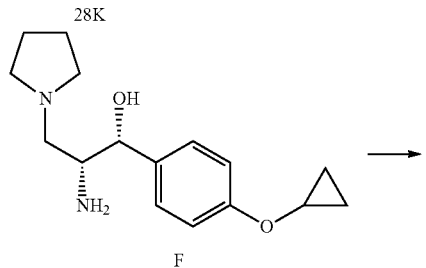

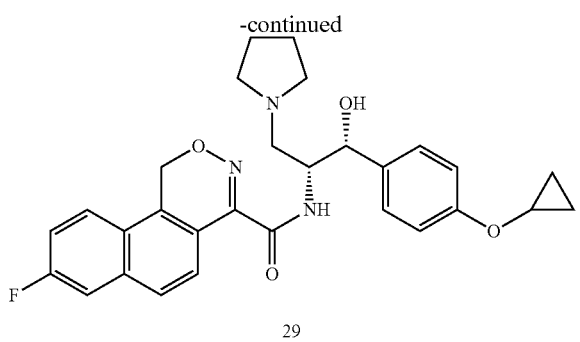

29

Compound 29 was synthesized by employing the procedure described for Compound 8 using Compound 28K and Intermediate F in lieu of Compound 8F and Intermediate D. LC-MS (ESI) m/z: 504 [M+H]+; ¹H-NMR (MeOD, 400 MHz): δ (ppm) 0.67-0.77 (m, 4H), 1.86 (br, 4H), 2.72-2.90 (m, 6H), 3.73-3.78 (m, 1H), 4.43-4.53 (m, 1H), 4.93-4.94 (m, 1H), 5.45-5.57 (m, 2H), 7.02 (d, J=8.8 Hz, 2H), 7.36 (d, J=8.4 Hz, 2H), 7.44-7.49 (m, 1H), 7.57 (d, J=8.4 Hz, 1H), 7.63-7.66 (m, 1H), 7.82 (d, J=8.8 Hz, 1H), 8.13-8.16 (m, 1H).

Example 30

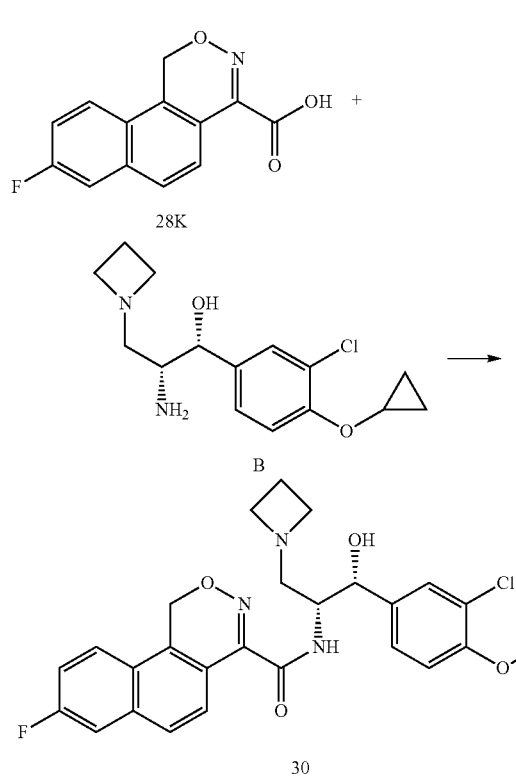

Compound 30 was synthesized by employing the procedure described for Compound 8 using Compound 28K and Intermediate B in lieu of Compound 8F and Intermediate D. LC-MS (ESI) m/z: 524 [M+H]+; ¹H-NMR (MeOD, 400 MHz): δ (ppm) 0.73-0.82 (m, 4H), 2.14-2.17 (m, 2H), 2.80-2.94 (m, 2H), 3.45-3.50 (m, 4H), 3.82-3.87 (m, 1H), 4.29-4.33 (m, 1H), 4.87-4.88 (m, 1H), 5.46-5.56 (m, 2H), 7.31-7.36 (m, 2H), 7.45-7.51 (m, 3H), 7.63-7.66 (m, 1H), 7.80-7.82 (m, 1H), 8.12-8.16 (m, 1H).

Example 31

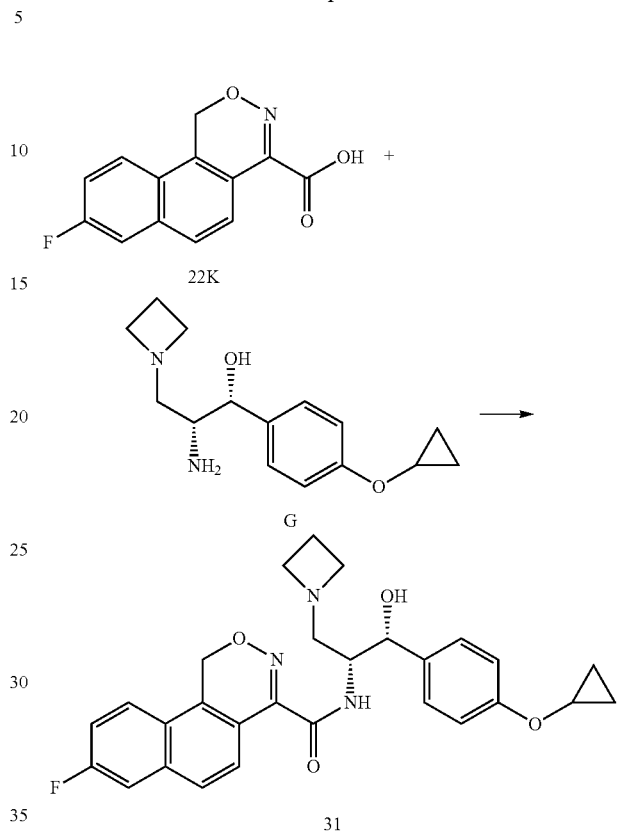

Compound 31 was synthesized by employing the procedure described for Compound 8 using Compound 28K and Intermediate G in lieu of Compound 8F and Intermediate D. LC-MS (ESI) m/z: 490 [M+H]+; ¹H-NMR (MeOD, 400 MHz): δ (ppm) 0.67-0.78 (m, 4H), 2.10-2.17 (m, 2H), 2.71-2.85 (m, 2H), 3.36-3.42 (m, 4H), 3.73-3.77 (m, 1H), 4.28-4.33 (m, 1H), 4.85-4.86 (m, 1H), 5.41-5.57 (m, 2H), 7.02 (d, J=8.4 Hz, 2H), 7.34 (d, J=8.8 Hz, 2H), 7.46-7.56 (m, 1H), 7.57 (d, J=8.4 Hz, 1H), 7.62-7.65 (m, 1H), 7.81 (d, J=8.8 Hz, 1H), 8.12-8.15 (m, 1H).

Example 32

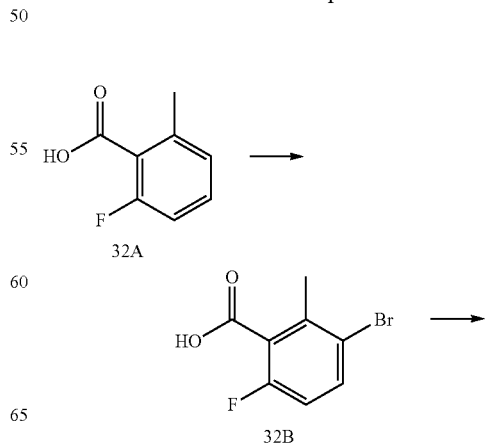

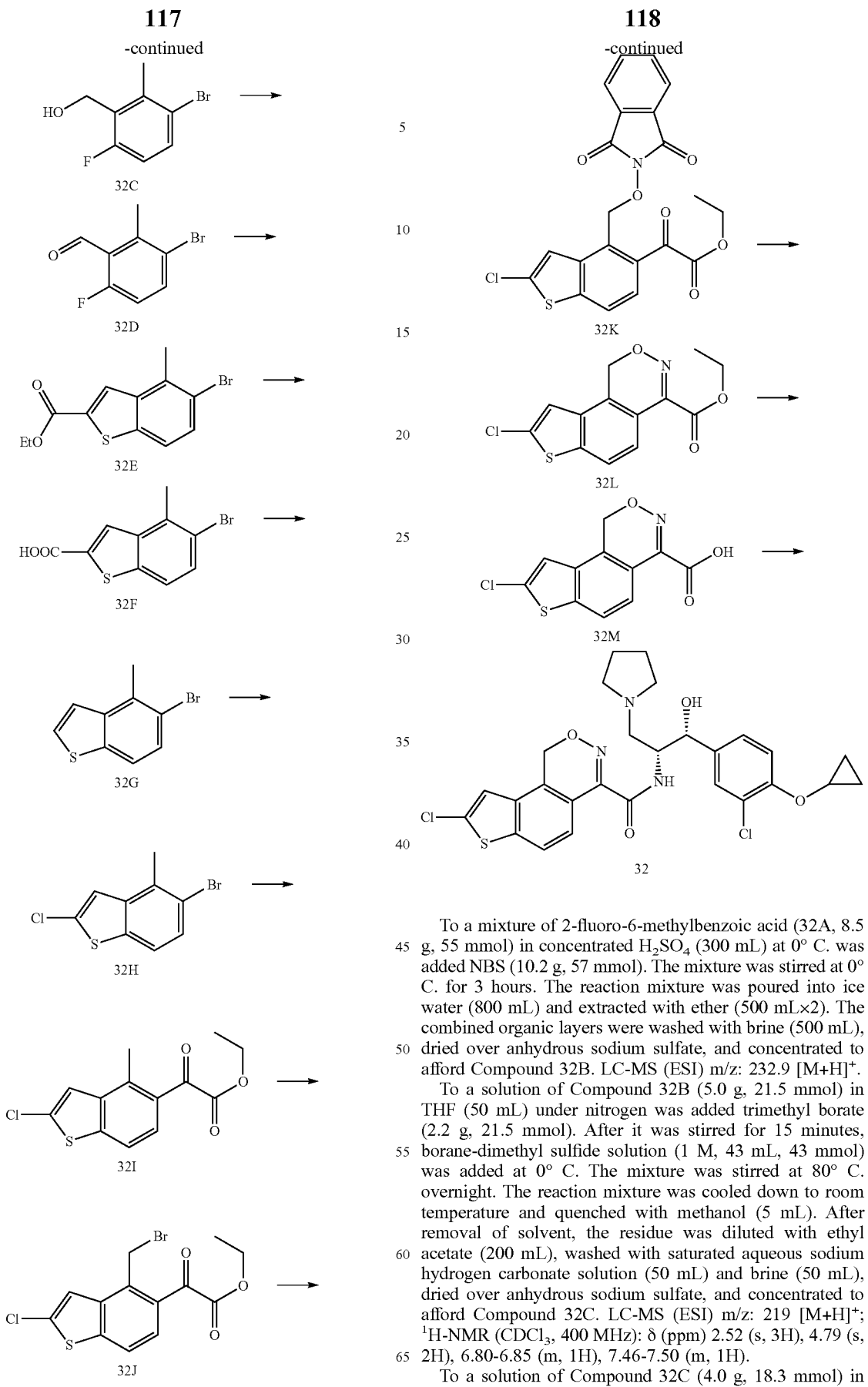

To a mixture of 2-fluoro-6-methylbenzoic acid (32A, 8.5 g, 55 mmol) in concentrated H$_2$SO$_4$ (300 mL) at 0° C. was added NBS (10.2 g, 57 mmol). The mixture was stirred at 0° C. for 3 hours. The reaction mixture was poured into ice water (800 mL) and extracted with ether (500 mL×2). The combined organic layers were washed with brine (500 mL), dried over anhydrous sodium sulfate, and concentrated to afford Compound 32B. LC-MS (ESI) m/z: 232.9 [M+H]$^+$.

To a solution of Compound 32B (5.0 g, 21.5 mmol) in THF (50 mL) under nitrogen was added trimethyl borate (2.2 g, 21.5 mmol). After it was stirred for 15 minutes, borane-dimethyl sulfide solution (1 M, 43 mL, 43 mmol) was added at 0° C. The mixture was stirred at 80° C. overnight. The reaction mixture was cooled down to room temperature and quenched with methanol (5 mL). After removal of solvent, the residue was diluted with ethyl acetate (200 mL), washed with saturated aqueous sodium hydrogen carbonate solution (50 mL) and brine (50 mL), dried over anhydrous sodium sulfate, and concentrated to afford Compound 32C. LC-MS (ESI) m/z: 219 [M+H]$^+$; $^1$H-NMR (CDCl$_3$, 400 MHz): δ (ppm) 2.52 (s, 3H), 4.79 (s, 2H), 6.80-6.85 (m, 1H), 7.46-7.50 (m, 1H).

To a solution of Compound 32C (4.0 g, 18.3 mmol) in dichloromethane (100 mL) at 0° C. was added Dess-Martin periodinane (11.7 g, 27.5 mmol) in several small portions. The mixture was stirred at 10° C. for 16 hours. The reaction mixture was diluted with diethyl ether (300 mL) and poured into a saturated aqueous sodium hydrogen carbonate solution (200 mL) at 0° C. To the mixture was added saturated aqueous $Na_2S_2O_3$ solution (300 mL) and the reaction mixture was stirred vigorously for 0.5 h. The organic phase was separated and the aqueous layer was extracted with diethyl ether (200 mL×2). The combined organic layers were dried over anhydrous sodium sulfate and evaporated to give Compound 32D. $^1$H-NMR (CDCl$_3$, 400 MHz): δ (ppm) 2.63 (s, 3H), 6.86-6.88 (m, 1H), 7.66-7.69 (m, 1H), 10.39 (s, 1H).

To a mixture of Compound 32D (6.05 g, 28 mmol) and potassium carbonate (5.02 g, 36.4 mmol) in DMF (30 mL) with ice cooling was added dropwise ethyl thioglycolate (3.36 g, 28 mmol). The mixture was stirred at ambient temperature for 30 minutes and at 60° C. for 12 hours, until LCMS showed full conversion of starting material. The reaction mixture was poured into water (500 mL) and extracted with ethyl acetate (500 mL×2). The extracts were washed with H$_2$O (500 mL), dried, and concentrated under vacuum. The residue was slurried in ethyl alcohol and collected by filtration to give Compound 32E. $^1$H-NMR (CDCl$_3$, 400 MHz): δ (ppm) 1.42 (t, J=6.8 Hz, 3H), 2.70 (s, 3H), 4.42 (q, J=6.8 Hz, 2H), 7.58 (m, 2H), 8.13 (s, 1H).

A mixture of Compound 32E (5.3 g, 18 mmol) and LiOH.H$_2$O (1.49 g, 36 mmol) in THF (40 mL) and H$_2$O (5 mL) was heated at 40° C. overnight. The reaction mixture was cooled down to room temperature and concentrated under vacuum. The residue was dissolved in H$_2$O (50 mL), adjusted to pH 4 with aqueous HCl solution (1 N), and extracted with ethyl acetate (100 mL×3). The combined organic layers were dried over anhydrous sodium sulfate, filtered, and concentrated to afford Compound 32F. LC-MS (ESI) m/z: 270 [M+H]$^+$.

To a solution of Compound 32F (810 mg, 2.98 mmol) in quinoline (6 mL) was added Cu powder (95 mg, 1.49 mmol). The mixture was stirred at 200° C. under nitrogen for 4 hours. The reaction mixture was cooled down to room temperature and filtered to remove the Cu powder. The filtrate was diluted with ethyl acetate (100 mL), washed with diluted HCl (50 mL×2) and brine (50 mL), dried over anhydrous sodium sulfate, and concentrated to give a crude product, which was purified with flash column chromatography on silica gel (petroleum ether, 100% v/v) to afford Compound 32G. $^1$H-NMR (CDCl$_3$, 400 MHz): δ (ppm) 2.69 (s, 3H), 7.69 (d, J=8.4 Hz, 1H), 7.45-7.49 (m, 2H), 7.56 (d, J=8.4 Hz, 1H).

To a solution of diisopropylamine (1.71 g, 17 mmol) in THF (30 mL) under nitrogen at −60° C. was added a solution of n-BuLi in hexane (2.5 M, 6.76 mL, 17 mmol). After the mixture was stirred at −60° C. for 10 minutes, a solution of Compound 32G (3.48 g, 15.3 mmol) in THF (10 mL) was added dropwise. The resulting mixture was stirred for 0.5 hour and a solution of CCl$_4$ (6 mL) in THF (2 mL) was added in one portion. After stirring at −60° C. for 1.5 hour, the reaction mixture was quenched with saturated ammonium chloride solution (60 mL) and extracted with ethyl acetate (100 mL×3). The combined organic layers were washed with brine (100 mL), dried over anhydrous sodium sulfate, and concentrated to give a crude product, which was purified with flash column chromatography on silica gel (petroleum ether, 100% v/v) to furnish Compound 32H. $^1$H-NMR (CDCl$_3$, 400 MHz): δ (ppm) 2.60 (s, 3H), 7.25 (d, J$_1$=6.0 Hz, 1H), 7.40 (s, 1H), 7.47 (d, J=6.0 Hz, 1H).

Compound 32I was synthesized by employing the procedure described for Compound 12B using Compound 32H in lieu of Compound 12A. LC-MS (ESI) m/z: 305 [M+Na]$^+$.

Compounds 32J, 32K, 32L, and 32M were synthesized by employing the procedures described for Compounds 1D, 1E, 1F, and 1G using Compounds 32I, 32J, 32K, and 32L in lieu of Compounds 1C, 1D, 1E, and 1F.

Compound 32J. $^1$H-NMR (CDCl$_3$, 400 MHz): δ (ppm) 1.45 (t, J=6.4 Hz, 3H), 4.46 (q, J=6.4 Hz, 2H), 5.13 (s, 2H), 7.52 (s, 1H), 7.64 (d, J=8.4 Hz, 1H), 7.78 (d, J=8.4 Hz, 1H).

Compound 32K. LC-MS (ESI) m/z: 444 [M+H]$^+$.

Compound 32L. LC-MS (ESI) m/z: 296 [M+H]$^+$.

Compound 32M. LC-MS (ESI) m/z: 268 [M+H]$^+$.

Compound 32 was synthesized by employing the procedure described for Compound 8 using Compound 32M and Intermediate A in lieu of Compound 8F and Intermediate D. LC-MS (ESI) m/z: 560 [M+H]$^+$; $^1$H-NMR (MeOD, 400 MHz): δ (ppm). 0.67-0.82 (m, 4H), 2.04-2.22 (m, 4H), 3.33 (m, 2H), 3.53-3.57 (m, 1H), 3.70-3.83 (m, 4H), 4.68-4.71 (m, 1H), 4.94 (m, 1H), 5.29-5.35 (m, 2H), 7.29-7.36 (m, 3H), 7.48 (d, J=2 Hz, 1H), 7.55 (s, 1H), 7.77 (d, J=8.8 Hz, 1H).

Example 33

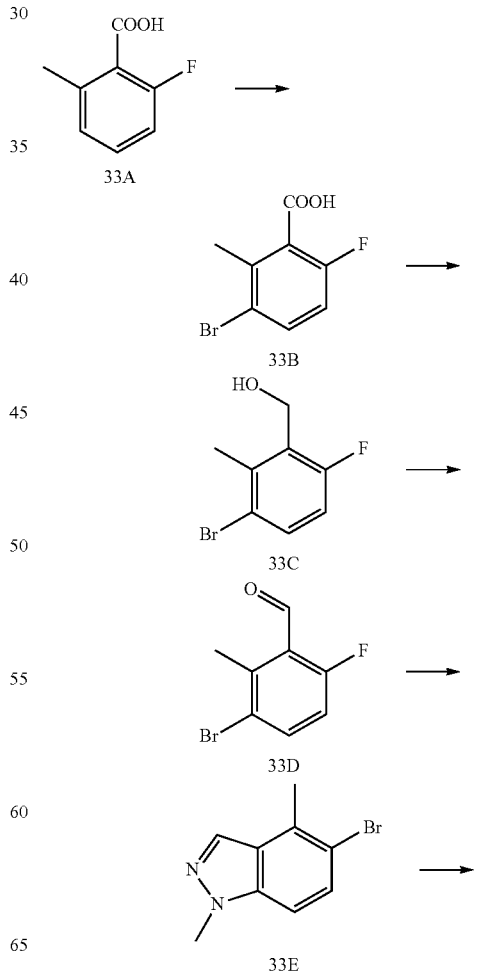

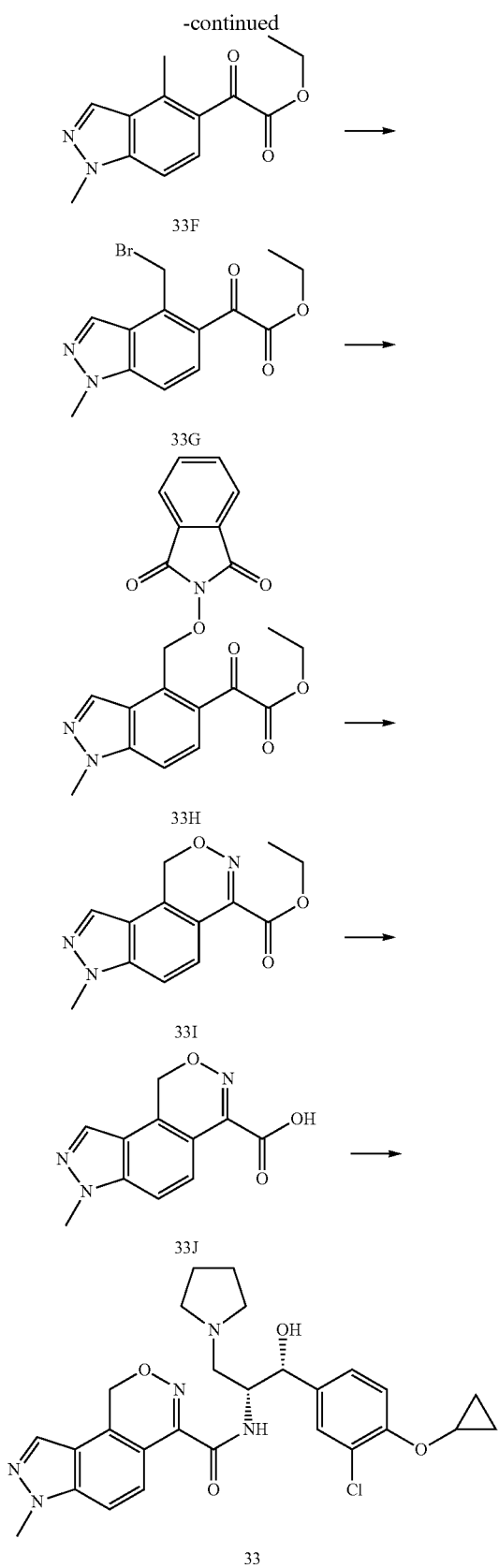

32C, and 32D using Compounds 33A, 33B, and 33C in lieu of Compounds 32A, 32B, and 32C.

Compound 33B. LC-MS (ESI) m/z: 233 [M+H]$^+$; $^1$H-NMR (CDCl$_3$, 400 MHz): δ (ppm) 2.51 (s, 3H), 6.78-6.91 (m, 1H), 7.60-7.63 (m, 1H).

Compound 33C. LC-MS (ESI) m/z: 219 [M+H]$^+$; $^1$H-NMR (CDCl$_3$, 400 MHz): δ (ppm) 2.52 (s, 3H), 4.79 (s, 2H), 6.80-6.85 (m, 1H), 7.46-7.50 (m, 1H).

Compound 33D. $^1$H-NMR (CDCl$_3$, 400 MHz): δ (ppm) 2.63 (s, 3H), 6.86-6.88 (m, 1H), 7.66-7.69 (m, 1H), 10.39 (s, 1H).

A solution of Compound 33D (1 g, 4.6 mmol) and methylhydrazine (0.6 g, 13.8 mmol) in 1-methylpyrrolidin-2-one (10 mL) was stirred at 20° C. for 0.5 hour, and then heated at 200° C. for 2 hours in a microwave oven. The reaction mixture was cooled down to room temperature, diluted with brine (20 mL), and extracted with diethyl ether (30 mL×2). The combined organic layers were washed with water (30 mL×2) and brine (30 mL), dried over anhydrous sodium sulfate, and concentrated to afford a crude product. The crude was purified with flash column chromatography on silica gel (ethyl acetate in petroleum ether, from 5% to 30% v/v) to yield Compound 33E. LC-MS (ESI) m/z: 225 [M+H]$^+$; $^1$H-NMR (CDCl$_3$, 400 MHz): δ (ppm) 2.61 (s, 3H), 4.04 (s, 3H), 7.08 (d, J=8.8 Hz, 1H), 7.47 (d, J=8.8 Hz, 1H), 7.95 (s, 1H).

Compound 33F was synthesized by employing the procedure described for Compound 12B using Compound 33E in lieu of Compound 12A. LC-MS (ESI) m/z: 247 [M+H]$^+$; $^1$H-NMR (CDCl$_3$, 400 MHz): δ (ppm) 1.43 (t, J=7.2 Hz, 3H), 2.90 (s, 3H), 4.09 (s, 3H), 4.45 (q, J=6.8 Hz, 2H), 7.27 (d, J=8.0 Hz, 1H), 7.71 (d, J=8.0 Hz, 1H), 7.20 (s, 1H).

Compounds 33G, 33H, 33I, 33J, and 33 were synthesized by employing the procedures described for Compounds 1D, 1E, 1F, 1G, and 8 using Compounds 33F, 33G, 33H, 33I, 33J, and Intermediate A in lieu of Compounds 1C, 1D, 1E, 1F, 8F, and Intermediate D.

Compounds 33G. LC-MS: (ESI) m/z: 325 [M+H]$^+$; $^1$H-NMR (CDCl$_3$, 400 MHz): δ (ppm) 1.44 (t, J=6.8 Hz, 3H), 4.14 (s, 3H), 4.47 (q, J=7.2 Hz, 2H), 5.23 (s, 2H), 7.42 (d, J=8.8 Hz, 1H), 7.73 (d, J=8.8 Hz, 1H), 8.32 (s, 1H).

Compounds 33H. LC-MS: (ESI) m/z: 408 [M+H]$^+$; $^1$H-NMR (CDCl$_3$, 400 MHz): δ (ppm) 1.41 (t, J=7.2 Hz, 3H), 4.13 (s, 3H), 4.45 (q, J=7.2 Hz, 2H), 5.96 (s, 2H), 7.45 (t, J=8.8 Hz, 1H), 7.75-7.78 (m, 3H), 7.84-7.86 (m, 2H), 8.72 (s, 1H).

Compounds 33I LC-MS: (ESI) m/z: 260 [M+H]$^+$; $^1$H-NMR (CDCl$_3$, 400 MHz): δ (ppm) 1.47 (t, J=7.6 Hz, 3H), 4.12 (s, 3H), 4.48 (q, J=7.2 Hz, 2H), 5.36 (s, 2H), 7.42 (d, J=9.2 Hz, 1H), 7.95 (d, J=8.4 Hz, 1H), 8.03 (s, 1H).

Compounds 33J. LC-MS (ESI) m/z: 232 [M+H]$^+$.

Compounds 33. LC-MS (ESI) m/z: 524 [M+H]$^+$; $^1$H-NMR (CD$_3$OD, 400 MHz): δ (ppm) 0.69-0.81 (m, 4H), 2.04-2.23 (m, 4H), 3.27-3.31 (m, 2H), 3.58-3.59 (m, 1H), 3.71-3.83 (m, 4H), 4.09 (s, 3H), 4.70 (d, J=10.8 Hz, 1H), 4.97 (s, 1H), 5.37 (s, 2H), 7.32-7.49 (m, 5H), 8.19 (s, 1H).

Example 34

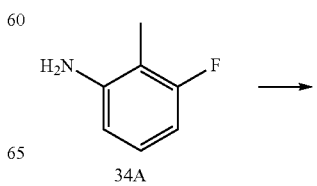

Compounds 33B, 33C, and 33D were synthesized by employing the procedures described for Compounds 32B,

123

-continued

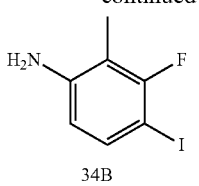
34B

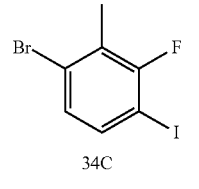
34C

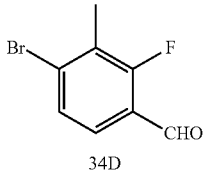
34D

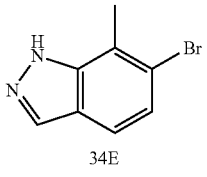
34E

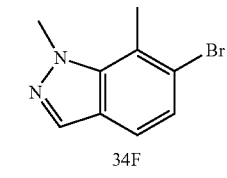
34F

+

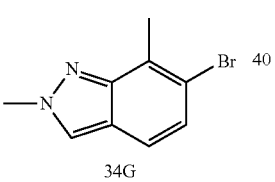
34G

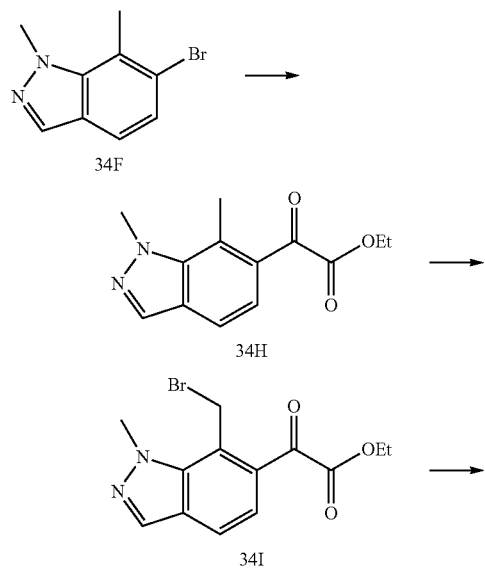

124

-continued

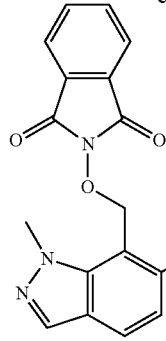
34J

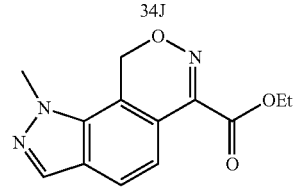
34K

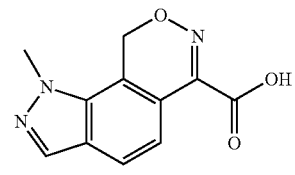
34L

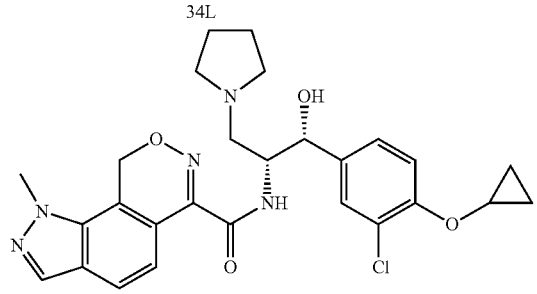
34

To a solution of 3-fluoro-2-methylaniline (34A) (4.0 g, 32 mmol) and NaBO$_3$.4H$_2$O (4.9 g, 32 mmol) in a mixture of acetic acid and water (20 mL, 1/1 v/v) at 5-10° C. was added dropwise a solution of KI (5.3 g, 32 mmol) in water (20 mL) over 30 minutes. After stirring at 20° C. for 1 hour, to the mixture was added dropwise water (15 mL) over 30 minutes. The reaction mixture was filtered, washed with water (50 mL), and dried to afford Compound 34B. LC-MS (ESI) m/z: 252 [M+H]$^+$; $^1$H-NMR (CDCl$_3$, 400 MHz): δ (ppm) 2.09 (s, 3H), 3.74 (s, 2H), 6.28-6.30 (m, 1H), 7.28-7.31 (m, 1H).

To a solution of Compound 34B (5.0 g, 19.9 mmol) in hydrobromic acid (40%, 50 mL) at 0° C. was added dropwise a solution of sodium nitrite (1.6 g, 22.9 mmol) in water (10 mL) over 1.5 hour. After addition, the mixture was stirred at 0° C. for 1.5 hour and CuBr (8.5 g, 59.7 mmol) was added, and then stirred at 0° C. for 0.5 hour and at 25° C. overnight. The reaction mixture was quenched with water (300 mL) and extracted with ethyl acetate (200 mL×3). The combined organic layers were washed with saturated sodium hydrogen carbonate solution (100 mL) and brine (100 mL), dried over anhydrous sodium sulfate, and concentrated to give a crude product, which was purified with flash column chromatography on silica gel (ethyl acetate in petroleum ether, from 0% to 5% v/v) to yield Compound 34C.

¹H-NMR (CDCl₃, 400 MHz): δ (ppm) 2.36-2.37 (m, 3H), 7.10 (d, J=8.4 Hz, 1H), 7.41-7.45 (m, 1H).

To a solution of Compound 34C (4 g, 12.7 mmol) in dry THF (40 mL) under nitrogen at −78° C. was added n-BuLi solution (2.5 N in n-hexane, 6.1 mL, 15.3 mmol). After it was stirred at −78° C. for 0.5 hour, anhydrous DMF (4.4 g, 63.7 mmol) was added. The resultant mixture was stirred at −78° C. for 0.5 hour, quenched with saturated aqueous NH₄Cl solution (20 mL), and extracted with ethyl acetate (50 mL×2). The combined organic layer was washed with brine (50 mL), dried over anhydrous sodium sulfate, and concentrated to give a crude product, which was purified with flash column chromatography on silica gel (ethyl acetate in petroleum ether, 5% v/v) to afford Compound 34D. ¹H-NMR (CDCl₃, 400 MHz): δ (ppm) 2.40-2.41 (m, 3H), 7.47-7.49 (m, 1H), 7.56-7.58 (m, 1H), 10.32 (s, 1H).

A solution of Compound 34D (1 g, 4.6 mmol) and hydrazine monohydrate (1.1 g, 23 mmol) in 1-methylpyrrolidin-2-one (10 mL) was stirred at 20° C. for 0.5 hour, and then heated at 200° C. for 1 hour in a microwave oven. The reaction mixture was cooled down to room temperature, diluted with brine (20 mL), and extracted with diethyl ether (30 mL×2). The combined organic layers were washed with water (30 mL×2) and brine (30 mL), dried over anhydrous sodium sulfate, and concentrated to give a crude product, which was purified with flash column chromatography on silica gel (ethyl acetate in petroleum ether, from 5% to 30% v/v) to yield Compound 34E. LC-MS (ESI) m/z: 211 [M+H]⁺; ¹H-NMR (CDCl₃, 400 MHz): δ (ppm) 2.61 (s, 3H), 7.33 (d, J=8.4 Hz, 1H), 7.45 (d, J=8.4 Hz, 1H), 8.06 (s, 1H), 10.36 (s, 1H).

To an ice-cooled solution of Compound 34E (0.2 g, 0.9 mmol) in DMF (5 mL) was added sodium hydride (60% in mineral, 57 mg, 1.4 mmol). After the mixture was stirred at room temperature for 30 minutes, iodomethane (0.67 g, 4.5 mmol) was added. The reaction mixture was stirred at room temperature for 1 hour, quenched with ammonium chloride solution (10 mL), and extracted with ethyl acetate (40 mL×3). The combined organic layers were washed with water (50 mL×4) and brine (50 mL), dried over anhydrous sodium sulfate, and concentrated to give a crude product, which was purified with flash column chromatography on silica gel (ethyl acetate in petroleum ether, from 0% to 40% v/v) to afford Compound 34F and Compound 34G. Compound 34F: LC-MS (ESI) m/z: 225 [M+H]⁺; ¹H-NMR (CDCl₃, 400 MHz): δ (ppm) 2.85 (s, 3H), 4.32 (s, 3H), 7.28 (d, J=8.4 Hz, 1H), 7.36 (d, J=8.4 Hz, 1H), 7.87 (s, 1H). Compound 34G: LC-MS (ESI) m/z: 225 [M+H]⁺; ¹H-NMR (CDCl₃, 400 MHz): δ (ppm) 2.67 (s, 3H), 4.20 (s, 3H), 7.19 (d, J=8.8 Hz, 1H), 7.33 (d, J=8.8 Hz, 1H), 7.84 (s, 1H).

Compound 34H is synthesized by employing the procedure described for Compound 12B using Compound 34F in lieu of Compound 12A. LC-MS (ESI) m/z: 247 [M+H]⁺; ¹H-NMR (CDCl₃, 400 MHz): δ (ppm) 1.43 (t, J=7.2 Hz, 3H), 2.98 (s, 3H), 4.42 (s, 3H), 4.46 (q, J=6.8 Hz, 2H), 7.31 (d, J=8.4 Hz, 1H), 7.62 (d, J=8.4 Hz, 1H), 7.98 (s, 1H).

Compounds 34I, 34J, 34K, 34L, and 34 were synthesized by employing the procedures described for Compounds 1D, 1E, 1F, 1G, and 8 using Compounds 34H, 34I, 34J, 34K, 34L, and Intermediate A in lieu of Compounds 1C, 1D, 1E, 1F, 8F, and Intermediate D.

Compounds 34I. LC-MS: (ESI) m/z: 325 [M+H]⁺; ¹H-NMR (CDCl₃, 400 MHz): δ (ppm) 1.43 (t, J=7.2 Hz, 3H), 4.47 (q, J=7.2 Hz, 2H), 4.59 (s, 3H), 5.32 (s, 2H), 7.39 (d, J=8.4 Hz, 1H), 7.78 (d, J=8.4 Hz, 1H), 8.06 (s, 1H).

Compounds 34J. LC-MS: (ESI) m/z: 408 [M+H]⁺; ¹H-NMR (CDCl₃, 400 MHz): δ (ppm) 1.33 (t, J=7.2 Hz, 3H), 4.33 (q, J=7.6 Hz, 2H), 4.63 (s, 3H), 5.88 (s, 2H), 7.25-7.27 (m, 1H), 7.70-7.78 (m, 4H), 7.85-7.87 (m, 1H), 8.11 (s, 1H).

Compounds 34K. LC-MS: (ESI) m/z: 260 [M+H]⁺; ¹H-NMR (CDCl₃, 400 MHz): δ (ppm) 1.46 (t, J=6.8 Hz, 3H), 4.27 (s, 3H), 4.48 (q, J=7.2 Hz, 2H), 5.60 (s, 2H), 7.58 (d, J=8.4 Hz, 1H), 7.76 (d, J=8.4 Hz, 1H), 8.01 (s, 1H).

Compounds 34L. LC-MS: (ESI) m/z: 232 [M+H]⁺.

Compounds 34. LC-MS (ESI) m/z: 524 [M+H]⁺; ¹H-NMR (CD₃OD, 400 MHz): δ (ppm) 0.69-0.82 (m, 4H), 2.05-2.23 (m, 4H), 3.21-3.31 (m, 2H), 3.57-3.61 (m, 1H), 3.71-3.84 (m, 4H), 4.26 (s, 3H), 4.73 (d, J=10.8 Hz, 1H), 4.97 (s, 1H), 5.6 (q, J=13.6 Hz, 2H), 6.9 (d, J=8.4 Hz, 1H), 7.36-7.37 (m, 2H), 7.49 (s, 1H), 7.65 (d, J=8.8 Hz, 1H), 8.04 (s, 1H).

Example 35

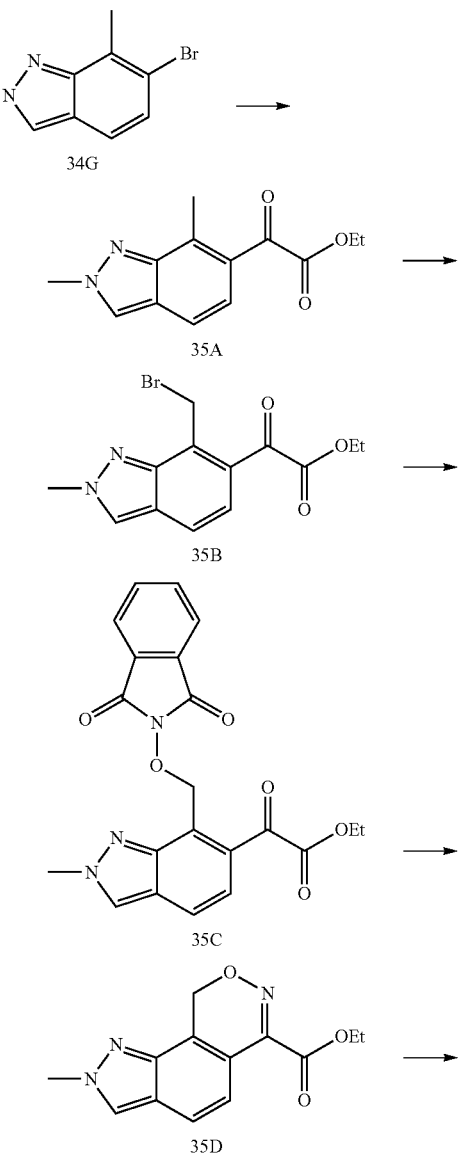

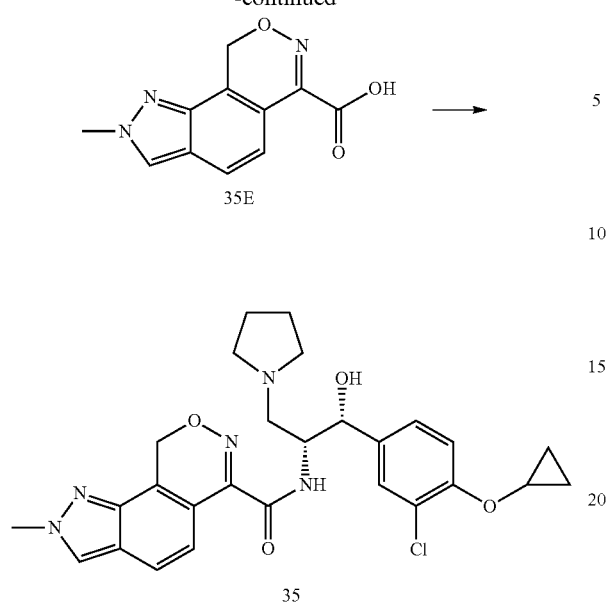
Compound 35A is synthesized by employing the procedure described for Compound 12B using Compound 34G in lieu of Compound 12A.
Compounds 35B, 35C, 35D, 35E, and 35 are synthesized by employing the procedures described for Compounds 1D, 1E, 1F, 1G, and 1 using Compounds 35A, 35B, 35C, 35D, and 35E in lieu of Compounds 1C, 1D, 1E, 1F, and 1G.
Example 36
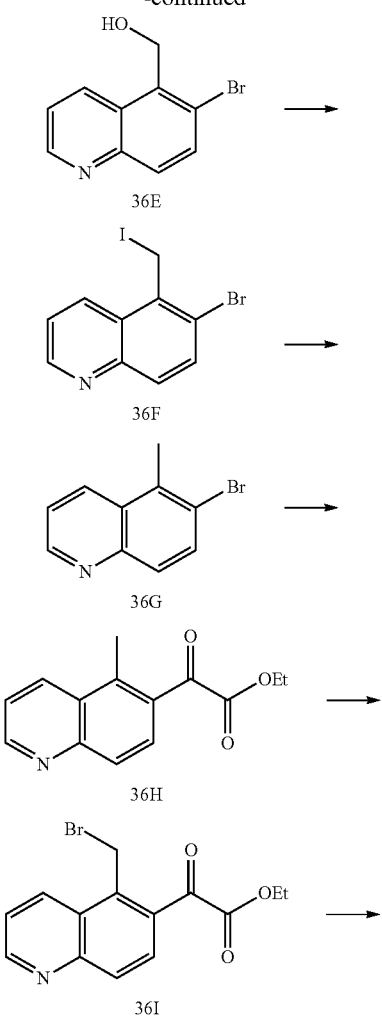
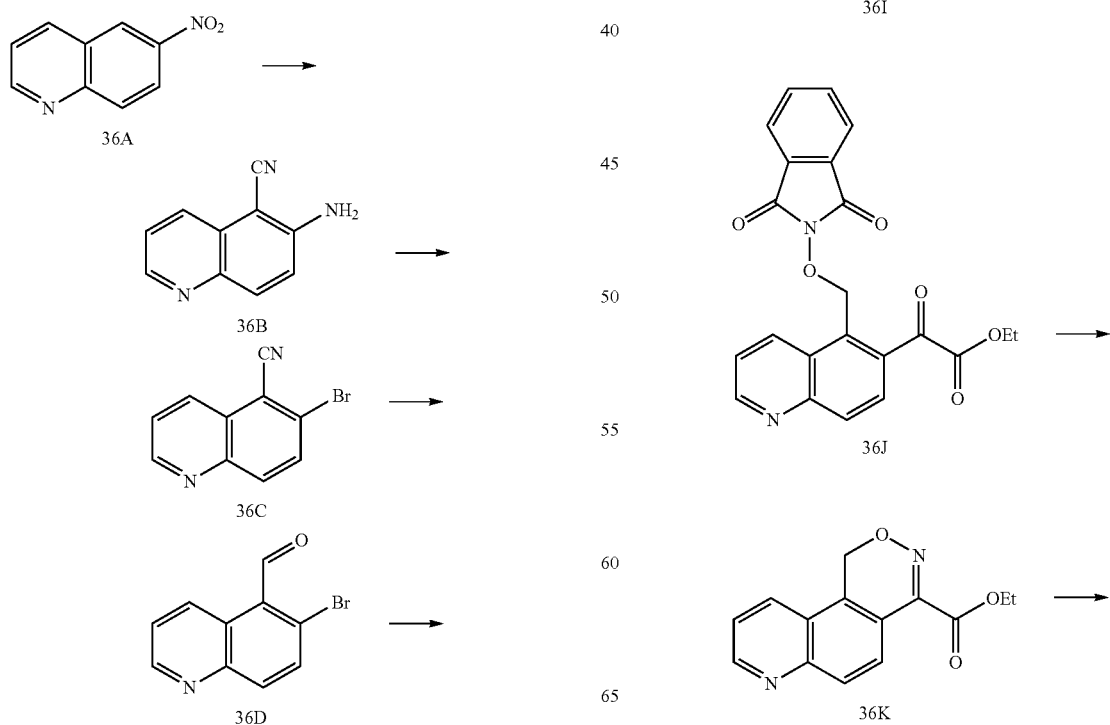

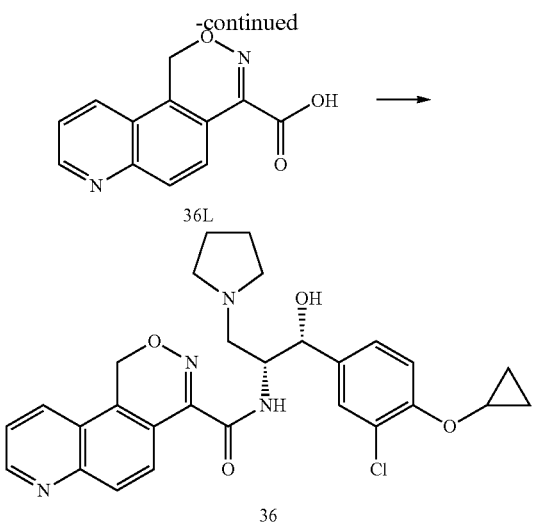

To a solution of ethyl cyanoacetate (11.53 g, 102 mmol) and potassium hydroxide (5.7 g, 102 mmol) in DMF (87 mL) was added nitroquinoline (36A, 5.96 g, 34 mmol) and the reaction mixture was stirred at 25° C. for 22 hours. The mixture was concentrated in vacuo. The residue was treated with 10% hydrochloric acid (100 mL) and heated at reflux for 3 hours. The reaction mixture was basified with 10% aqueous sodium hydroxide and extracted with chloroform and methanol (20:1, 100 mL×3). The combined organic layer was washed with brine, dried over sodium sulfate, filtered, and evaporated to give a crude product, which was purified by flash chromatography on silica gel (methanol in dichloromethane, 5% to 10% v/v) to furnish Compound 36B. LC-MS (ESI) m/z: 170 [M+H]$^+$; $^1$H-NMR (DMSO-d$_6$, 400 MHz): δ (ppm) 6.90 (s, 2H), 7.23 (d, J=9.6 Hz, 1H), 7.48-7.51 (m, 1H), 7.88 (d, J=9.6 Hz, 1H), 8.01 (d, J=8.8 Hz, 1H), 8.58 (m, 1H).

To a solution of Compound 36B (5.07 g, 30 mmol) in acetonitrile (150 mL) under nitrogen was added cupper bromide (8 g, 36 mmol) and the reaction mixture was stirred at room temperature for 10 minutes. To the mixture was added tert-butyl nitrite (4.7 mL, 39 mmol) and the reaction mixture was heated at 60° C. for 15 hours. Hydrochloric acid (1 N, 100 mL) was added to the mixture and the reaction mixture was stirred for another 4 hours. The mixture was basified to pH 6 with solid NaHCO$_3$ and extracted with ethyl acetate (100 mL×3). The combined organic layers were washed with saturated NH$_4$Cl solution (100 mL) and brine (100 mL), dried over sodium sulfate, and evaporated to give a crude Compound 36C. LC-MS (ESI) m/z: 233 [M+H]$^+$; $^1$H-NMR (CDCl$_3$, 400 MHz): δ(ppm) 7.63-7.66 (m, 1H), 7.94 (d, J=8.8 Hz, 1H), 8.21 (d, J=8.8 Hz, 1H), 8.52 (d, J=8.8 Hz, 1H), 9.06 (s, 1H).

To a solution of Compound 36C (2.4 g, 10 mmol) in toluene (80 mL) at −5° C. under nitrogen was slowly added a solution of diisobutylaluminum hydride (25% in toluene, 10 mL, 17 mmol) and the reaction mixture was stirred at 10° C. for 3 hours. After the reaction mixture was cooled to −5° C., the reaction mixture was quenched with a solution of 5% sulfuric acid and stirred at room temperature for 1 hour. The mixture was basified with saturated NaHCO$_3$ solution and extracted with ethyl acetate (100 mL×3). The combined organic layers were washed with brine (100 mL), dried over sodium sulfate, and evaporated to give a crude product, which was purified by flash chromatography on silica gel (methanol in dichloromethane, 5% to 10% v/v) to furnish Compound 36D. LC-MS (ESI) m/z: 236 [M+H]$^+$; $^1$H-NMR (CDCl$_3$, 400 MHz): δ (ppm) 7.56-7.59 (m, 1H), 7.94 (d, J=8.8 Hz, 1H), 8.16 (d, J=8.8 Hz, 1H), 8.97-8.98 (m, 1H), 9.46 (d, J=8.8 Hz, 1H), 10.71 (s, 1H).

Compound 36E was synthesized by employing the procedure described for Compound 22D using Compound 36D in lieu of Compound 22C, which was used without further purification. LC-MS (ESI) m/z: 238 [M+H]$^+$.

To a solution of Compound 36E (2.17 g, 9.2 mmol) in CH$_3$CN (150 mL) at 0° C. was added NaI (6.9 mg, 46 mmol) and TMSCl (4 mL, 46 mmol) and the reaction mixture was stirred at 50° C. for 24 hours. The reaction mixture was evaporated under vacuum to give a crude product, which was purified by flash chromatography on silica gel (methanol in dichloromethane, 0% to 20% v/v) to furnish Compound 36F, which was used without further purification. LC-MS (ESI) m/z: 348 [M+H]$^+$.

Compound 36G was synthesized by employing the procedure described for Compound 20E using Compound 36F in lieu of Compound 20D. LC-MS (ESI) m/z: 222 [M+H]$^+$; $^1$H-NMR (CDCl$_3$, 400 MHz): δ (ppm) 2.77 (s, 3H), 7.43-7.46 (m, 1H), 7.83 (s, 2H), 8.37 (d, J$_1$=8.8 Hz, J$_2$=1.6 Hz, 1H), 8.91 (d, J$_1$=4.4 Hz, J$_2$=1.6 Hz, 1H).

Compound 36H was synthesized by employing the procedure described for Compound 12B using Compound 36G in lieu of Compound 12A. LC-MS (ESI) m/z: 244 [M+H]$^+$; $^1$H-NMR (CDCl$_3$, 400 MHz): δ (ppm) 1.44 (t, J=7.6 Hz, 3H), 2.89 (s, 3H), 4.44-4.50 (m, 2H), 7.52-7.55 (m, 1H), 7.87 (d, J=8.8 Hz, 1H), 8.05 (d, J=8.4 Hz, 1H), 8.56 (d, J=8.8 Hz, 1H), 9.02-9.03 (m, 1H). Compounds 36I, 36J, 36K, 36L, and 36 were synthesized by employing the procedures described for Compounds 1D, 1E, 1F, 1G, and 1 using Compounds 36H, 36I, 36J, 36K, 36L, and Intermediate A in lieu of Compounds 1C, 1D, 1E, 1F, 8F, and Intermediate D.

Compounds 36I. LC-MS (ESI) m/z: 322 [M+H]$^+$.
Compounds 36J. LC-MS (ESI) m/z: 405 [M+H]$^+$.
Compounds 36K. LC-MS (ESI) m/z: 257 [M+H]$^+$.
Compounds 36L. LC-MS (ESI) m/z: 229 [M+H]$^+$.
Compounds 36. LC-MS (ESI) m/z: 521 [M+H]$^+$; $^1$H-NMR (CD$_3$OD, 400 MHz): δ (ppm) 0.68-0.84 (m, 4H), 1.29-1.32 (m, 2H), 2.06-2.21 (m, 4H), 2.87-3.00 (m, 1H), 3.19-3.27 (m, 2H), 3.57-3.61 (m, 1H), 3.70-3.86 (m, 4H), 4.73-4.75 (m, 1H), 4.98 (s, 1H), 5.54-5.63 (m, 2H), 7.34-7.40 (m, 2H), 7.50 (s, 1H), 7.65-7.72 (m, 2H), 7.98 (d, J=8.8 Hz, 1H), 8.63 (d, J=8.4 Hz, 1H), 9.00 (s, 1H).

Example 37

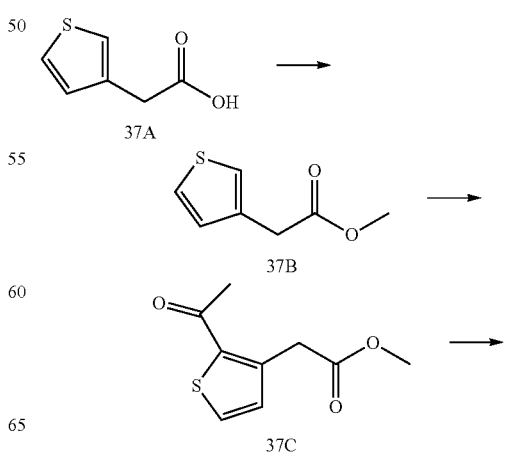

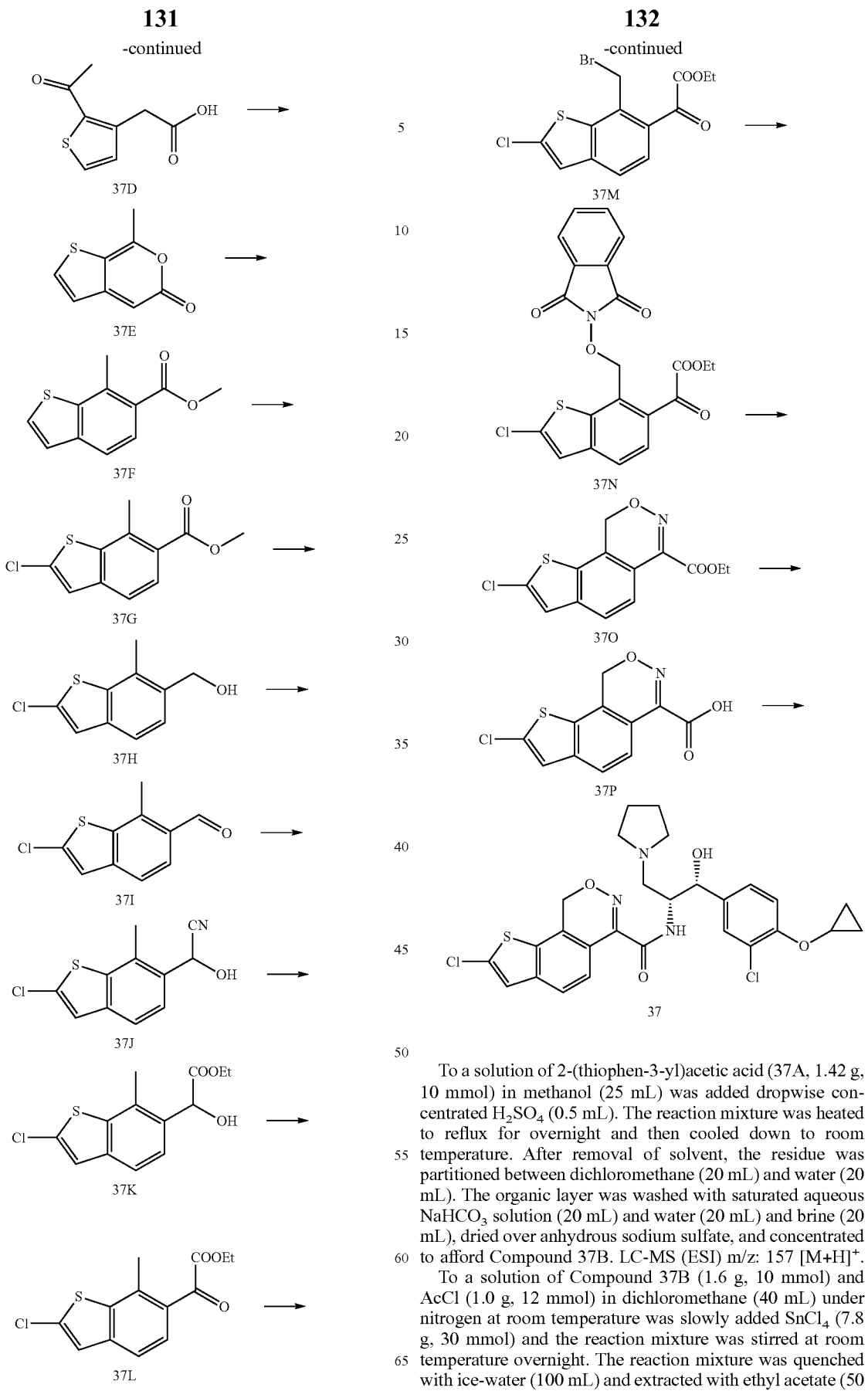

To a solution of 2-(thiophen-3-yl)acetic acid (37A, 1.42 g, 10 mmol) in methanol (25 mL) was added dropwise concentrated $H_2SO_4$ (0.5 mL). The reaction mixture was heated to reflux for overnight and then cooled down to room temperature. After removal of solvent, the residue was partitioned between dichloromethane (20 mL) and water (20 mL). The organic layer was washed with saturated aqueous $NaHCO_3$ solution (20 mL) and water (20 mL) and brine (20 mL), dried over anhydrous sodium sulfate, and concentrated to afford Compound 37B. LC-MS (ESI) m/z: 157 [M+H]$^+$.

To a solution of Compound 37B (1.6 g, 10 mmol) and AcCl (1.0 g, 12 mmol) in dichloromethane (40 mL) under nitrogen at room temperature was slowly added $SnCl_4$ (7.8 g, 30 mmol) and the reaction mixture was stirred at room temperature overnight. The reaction mixture was quenched with ice-water (100 mL) and extracted with ethyl acetate (50 mL×3). The combined organic layers were washed with saturated aqueous NaHCO$_3$ solution (30 mL) and water (30 mL) and brine (30 mL), dried over anhydrous sodium sulfate, and concentrated to give a crude product, which was purified with flash column chromatography on silica gel (ethyl acetate in petroleum ether, from 10% to 50% v/v) to furnish Compound 37C. LC-MS (ESI) m/z: 199 [M+H]$^+$; $^1$H-NMR (CDCl$_3$, 400 MHz): δ (ppm) 2.54 (s, 3H), 3.71 (s, 3H), 4.07 (s, 2H), 7.06 (d, J=4.8 Hz, 1H), 7.46 (d, J=4.8 Hz, 1H).

To a solution of Compound 37C (0.75 g, 3.55 mmol) in THF/MeOH (9 mL/1 mL) was added aqueous KOH solution (2 M, 5 mL). The mixture was stirred at room temperature for about 2 hours until the reaction was completed as shown by thin layer chromatography. The reaction mixture was acidified to pH 2 with diluted aqueous HCl solution (1.0 N, 40 mL) and extracted with ethyl acetate (30 mL×2). The combined organic layers were washed with water (100 mL) and brine (100 mL), dried over anhydrous sodium sulfate, and concentrated to yield Compound 37D. LC-MS (ESI) m/z: 185 [M+H]$^+$; $^1$H-NMR (DMSO-d$_6$, 400 MHz): δ (ppm) 2.50 (s, 3H), 3.94 (s, 2H), 7.14 (d, J=4.8 Hz, 1H), 7.82 (d, J=4.8 Hz, 1H), 12.32 (s, 1H).

A mixture of Compound 37D (1.84 g, 10 mmol) and Ac$_2$O (30 mL) was heated to reflux for 4 hours. After removal of the reagent, the residue was dissolved in ether (100 mL), washed with water (100 mL) and brine (100 mL), dried over anhydrous sodium sulfate, and evaporated to give Compound 37E. LC-MS (ESI) m/z: 167 [M+H]$^+$; $^1$H-NMR (CDCl$_3$, 400 MHz): δ (ppm) 2.50 (s, 3H), 6.26 (s, 1H), 6.78 (d, J=5.6 Hz, 1H), 7.53 (d, J=5.6 Hz, 1H).

A mixture of Compound 37E (1.66 g, 10 mmol) and methyl propiolate (3.2 g, 38 mmol) in PhBr (50 mL) was refluxed under nitrogen for 4 hours. After evaporation, the residue was purified with flash column chromatography on silica gel (ethyl acetate in petroleum ether, from 10% to 50% v/v) to furnish Compound 37F. LC-MS (ESI) m/z: 207 [M+H]$^+$.

To a solution of Compound 37F (200 mg, 1 mmol) in THF (10 mL) was added LAH (50 mg, 1.3 mmol) and the reaction mixture was stirred at room temperature for 2 hours. The reaction mixture was quenched with Na$_2$SO$_4$.10H$_2$O, filtered, and concentrated to give a crude Compound 37G. LC-MS (ESI) m/z: 179 [M+H]$^+$.

Compound 37H was synthesized by employing the procedure described for Compound 32D using Compound 37G in lieu of Compound 32C. LC-MS (ESI) m/z: 177 [M+H]$^+$.

To a solution of diisopropylamine (0.408 mL, 2.92 mmol) in anhydrous THF (10 mL) was added a solution of n-BuLi in n-hexane (2.5 M, 1.16 mL, 2.92 mmol) at −60° C. under nitrogen and stirred at −60° C. for 1 hour. To it was added dropwise a solution of Compound 37F (548 mg, 2.65 mmol) in anhydrous THF (3 mL). After the mixture was stirred at −60° C. for 1 hour, a solution of CCl$_4$ (1.64 g, 10.6 mmol) in anhydrous THF (4 mL) was added in one portion. The reaction mixture was stirred at −60° C. for 2 hours, quenched with saturated annonium chloride solution (26 mL), and extracted with ethyl acetate (50 mL×2). The combined organic layers was washed with water (50 mL) and brine (50 mL), dried over anhydrous sodium sulfate, filtered, and concentrated under reduced pressure. The residue was purified with flash column chromatography on silica gel (ethyl acetate in petroleum ether, from 10% to 50% v/v) to furnish Compound 37G. LC-MS (ESI) m/z: 241 [M+H]$^+$; $^1$H-NMR (CDCl$_3$, 400 MHz): δ (ppm) 2.78 (s, 3H), 3.75 (s, 3H), 7.20 (s, 1H), 7.26 (s, 1H), 7.92 (d, J=8.8 Hz, 1H).

To a solution of Compound 37G (240 mg, 1 mmol) in anhydrous THF (10 mL) was added LiAlH$_4$ (50 mg, 1.3 mmol). The reaction mixture was stirred at room temperature for 2 hours, quenched with Na$_2$SO$_4$.10H$_2$O, and filtered. The filtrate was concentrated to give a crude Compound 37H. LC-MS (ESI) m/z: 213 [M+H]$^+$.

To a solution of Compound 37H (212 mg, 1 mmol) in dichloromethane (10 mL) was added Dess-Martin periodinane (551 mg, 1.3 mmol) and stirred at room temperature overnight. The reaction mixture was quenched with saturated aqueous Na$_2$S$_2$O$_3$ solution (20 mL), followed by addition of dichloromethane (50 mL) and water (30 mL). The organic layer was separated, washed with brine (30 mL), dried over anhydrous sodium sulfate, filtered, and concentrated to give a crude product, which was purified with flash column chromatography on silica gel (ethyl acetate in petroleum ether, from 10% to 50% v/v) to furnish Compound 37I. LC-MS (ESI) m/z: 211 [M+H]$^+$.

To a solution of Compound 37I (211 mg, 1 mmol) and NaCN (103 mg, 1.5 mmol) in methanol (10 mL) was dropped AcOH (0.5 mL) and stirred at room temperature overnight. The reaction mixture was poured into water (20 mL) and extracted with ethyl acetate (20 mL×2). The combined organic layers was washed with water (20 mL) and brine (30 mL), dried over anhydrous sodium sulfate, filtered, and concentrated to give a crude product, which was purified with flash column chromatography on silica gel (ethyl acetate in petroleum ether, from 10% to 50% v/v) to afford Compound 37J. LC-MS (ESI) m/z: 238 [M+H]$^+$.

To a mixture of Compound 37J (237 mg, 1 mmol) in anhydrous ethanol (10 mL) was bubbled with a stream of HCl gas at 0° C. for 6 hours. The mixture was stirred at 20° C. for 16 hours. After removal of most of solvent, the residue was diluted with ice water (100 mL) and stirred at 20° C. for 1 hour. The mixture was extracted with dichloromethane (100 mL×3). The combined organic layers was washed with water (200 mL) and brine (200 mL), dried over anhydrous sodium sulfate, filtered, and concentrated to give a crude product, which was purified with flash column chromatography on silica gel (ethyl acetate in petroleum, from 0% to 30% v/v) to yield Compound 37K. LC-MS (ESI) m/z: 285 [M+H]$^+$.

Compound 37L was synthesized by employing the procedure described for Compound 37I using Compound 37K in lieu of Compound 37H. LC-MS (ESI) m/z: 283 [M+H]$^+$.

Compounds 37M, 37N, 37O, 37P, and 37 were synthesized by employing the procedures described for Compounds 1D, 1E, 1F, 1G, and 8 using Compounds 37L, 37M, 37N, 37O, 37P, and Intermediate A in lieu of Compounds 1C, 1D, 1E, 1F, 8F, and Intermediate D.

Compounds 37M. LC-MS (ESI) m/z: 361 [M+H]$^+$.

Compounds 37N. LC-MS (ESI) m/z: 444 [M+H]$^+$.

Compounds 37O. LC-MS (ESI) m/z: 296 [M+H]$^+$; $^1$H-NMR (CDCl$_3$, 400 MHz): δ (ppm) 1.38 (t, J=6.8 Hz, 3H), 1.43 (q, J=6.8 Hz, 2H), 5.12 (s, 2H), 7.20 (s, 1H), 7.63 (d, J=8.8 Hz, 1H), 7.74 (d, J=8.8 Hz, 1H).

Compounds 37P. LC-MS (ESI) m/z: 268 [M+H]$^+$.

Compounds 37. LC-MS (ESI) m/z: 560 [M+H]$^+$; $^1$H-NMR (DMSO-d$_6$, 400 MHz): δ (ppm) 0.67-0.82 (m, 4H), 1.71-2.04 (m, 4H), 3.14-3.21 (m, 2H), 3.51-3.54 (m, 4H), 3.88-3.89 (m, 1H), 4.53-4.55 (m, 1H), 4.80-4.81 (m, 1H), 5.17-5.32 (m, 2H), 6.01-6.03 (m, 1H), 7.31-7.37 (m, 2H), 7.42 (s, 1H), 7.54 (d, J=8.8 Hz, 1H), 7.72 (s, 1H), 7.81 (d, J=8.8 Hz, 1H), 8.42-8.44 (m, 1H), 9.26 (brs, 1H).

Example 38

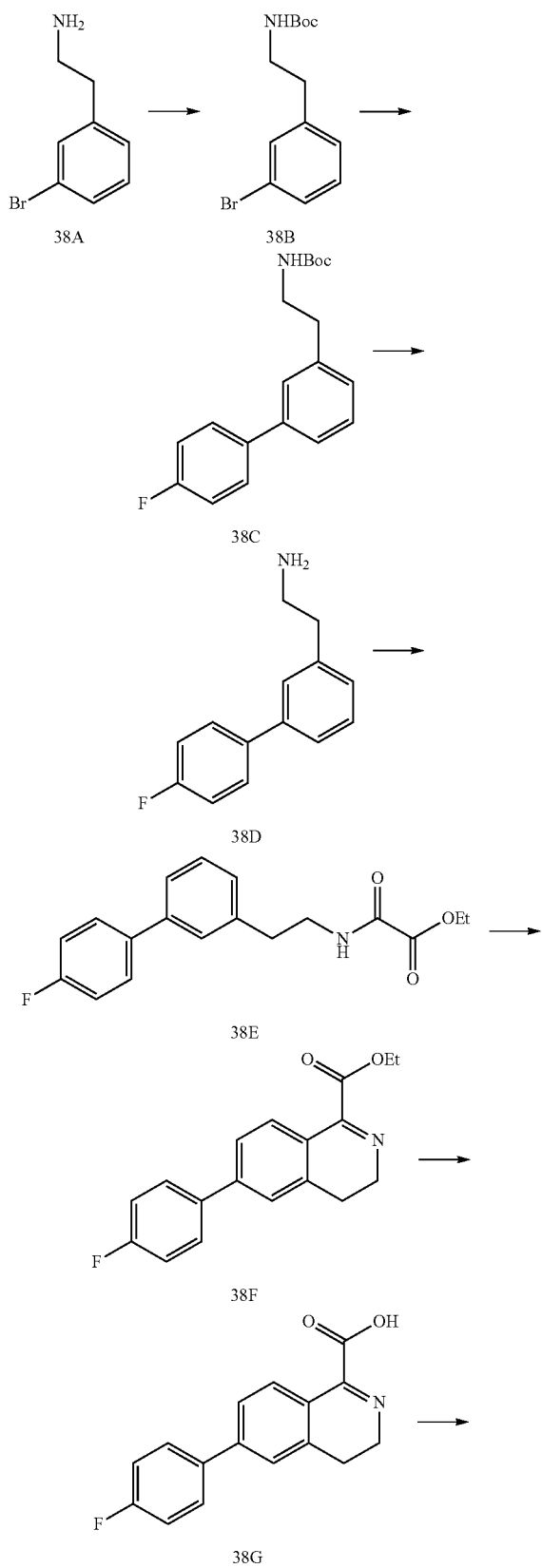

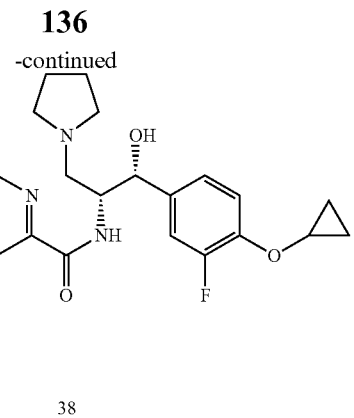

To a solution of Compound 38A (2 g, 10 mmol) in THF (20 mL) and water (5 mL) was added sodium bicarbonate (5.1 g, 60 mmol) and Boc$_2$O (4.4 g, 20 mmol) and the reaction mixture was stirred at room temperature overnight. The reaction mixture was quenched with water (50 mL), extracted with ethyl acetate (50 mL×2), washed with water (50 mL×2) and brine (50 mL), dried over anhydrous sodium sulfate, and concentrated to furnish Compound 38B, which was used without further purification. LC-MS (ESI) m/z: 244 [M−55]$^+$.

Compound 38C was synthesized by employing the procedure described for Compound 1B using Intermediate 38B in lieu of Intermediate 1A. LC-MS (ESI) m/z: 316 [M+H]$^+$; $^1$H-NMR (CDCl$_3$, 400 MHz): δ (ppm) 1.43 (s, 9H), 2.86 (t, J=6.8 Hz, 2H), 3.41-3.43 (m, 2H), 7.09-7.18 (m, 3H), 7.36-7.41 (m, 3H), 7.51-7.55 (m, 2H).

To a solution of Compound 38C (2.5 g, 7.9 mmol) in dichloromethane (20 mL) was added a solution of hydrogen chloride in 1,4-dioxane (4 M, 4 mL) and the reaction mixture was stirred at room temperature overnight. The reaction mixture was treated with saturated aqueous of sodium bicarbonate (50 mL), extracted with dichloromethane (50 mL×2), washed with brine (50 mL), dried over anhydrous sodium sulfate, and concentrated to furnish Compound 38D. LC-MS (ESI) m/z: 216 [M+H]$^+$.

To a solution of diethyl oxalate (876 mg, 6.0 mmol) in toluene (10 mL) was added Compound 38D (860 mg, 4.0 mmol) dropwise. The mixture was stirred at room temperature for 45 min and 60° C. for 2 h. The resulting mixture was concentrated. The residue was purified with prep-TLC (ethyl acetate in petroleum ether, 30% v/v) to give Compound 38E. LC-MS (ESI) m/z: 316 [M+H]$^+$; $^1$H-NMR (CDCl$_3$, 400 MHz): δ (ppm) 1.36 (t, J=6.8 Hz, 3H), 2.93 (q, J=6.8 Hz, 2H), 3.65 (q, J=6.8 Hz, 2H), 4.33 (q, J=6.8 Hz, 2H), 7.10-7.19 (m, 4H), 7.37-7.55 (m, 5H).

To a solution of Compound 38E (315 mg, 1.0 mmol) in POCl$_3$ (459 mg, 3.0 mmol) was added zinc chloride (272 mg, 2.0 mmol). The reaction mixture was stirred under nitrogen atmosphere at 90° C. for 2 hours. To the mixture at 60° C. was added toluene (2 mL). After the mixture was cooled down to a room temperature, to it was added ethanol (1 mL), water (4 mL), aqueous sodium hydroxide solution (25%, 8 mL), and ethyl acetate (4 mL). The mixture was filtered with Celite and washed with ethyl acetate (6 mL). The organic layer was separated and the aqueous layer was extracted with ethyl acetate (10 mL). The organic layers were combined, dried over anhydrous sodium sulfate, and concentrated to furnish Compound 38F. LC-MS (ESI) m/z: 298 [M+H]$^+$; $^1$H-NMR (DMSO-d$_6$, 400 MHz): δ (ppm) 1.34

(t, J=7.2 Hz, 3H), 2.93 (t, J=8.0 Hz, 2H), 3.86 (t, J=8.0 Hz, 2H), 4.40 (q, J=7.2 Hz, 2H), 7.33-7.37 (m, 2H), 7.72-7.75 (m, 3H), 7.80-7.84 (m, 2H).

Compound 38G was synthesized by employing the procedure described for Compound 1G using Compound 38F in lieu of Compound 1F. LC-MS (ESI) m/z: 270 [M+H]⁺.

Compound 38 was synthesized by employing the procedure described for Compound 8 using Compound 38G in lieu of Compound 8F. LC-MS (ESI) m/z: 546 [M+H]⁺; ¹H-NMR (CD₃OD, 400 MHz): δ (ppm) 0.74-0.82 (m, 4H), 2.09-2.22 (m, 4H), 3.00-3.03 (m, 2H), 3.21-3.28 (m, 2H), 3.51-3.54 (m, 1H), 3.77-3.94 (m, 5H), 4.82-4.85 (m, 2H), 5.00 (s, 1H), 6.32 (d, J=8.4 Hz, 1H), 7.21-7.27 (m, 4H), 7.36-7.42 (m, 2H), 7.60 (s, 1H), 7.71-7.74 (m, 2H).

Example 39

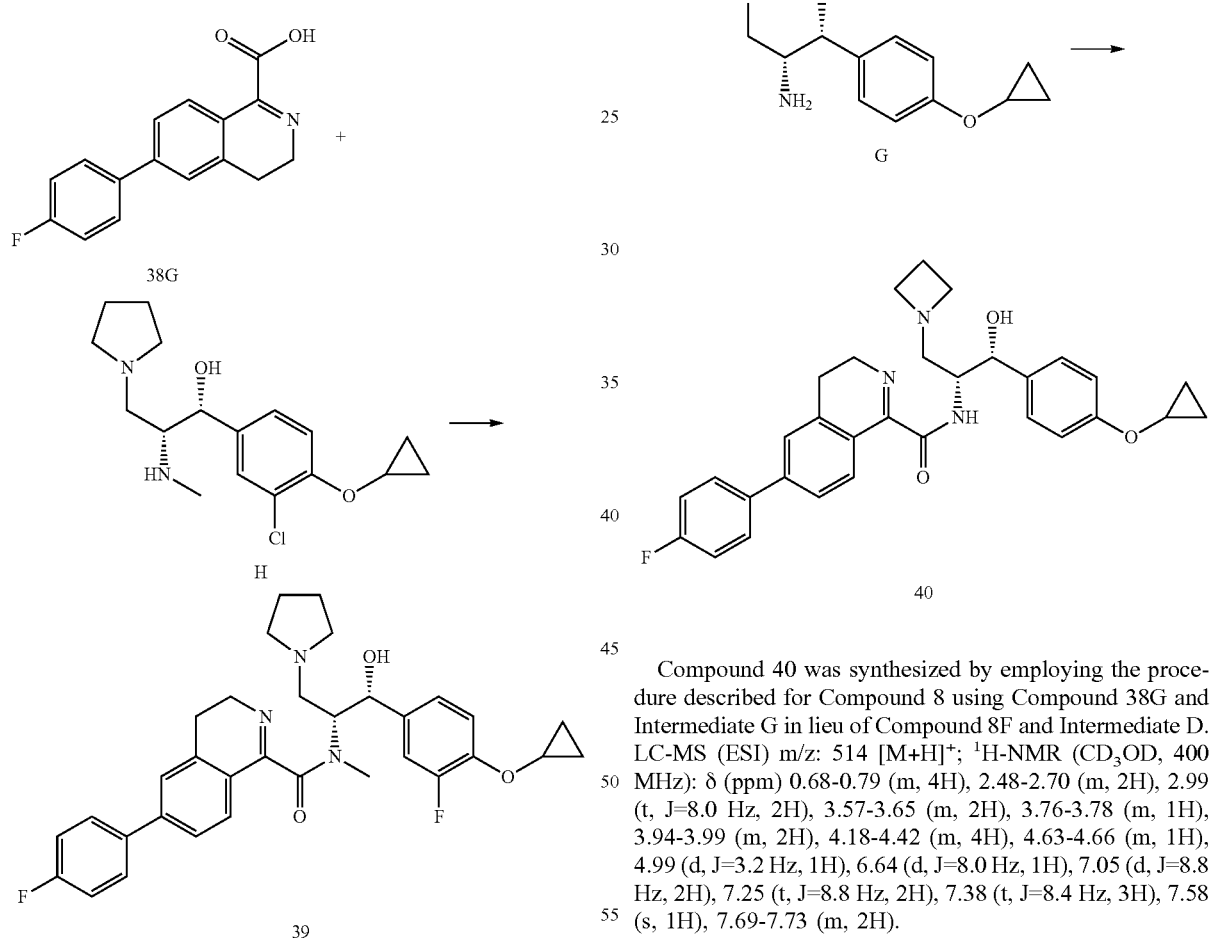

Compound 39 was synthesized by employing the procedure described for Compound 8 using Compound 38G and Intermediate H in lieu of Compound 8F and Intermediate D. LC-MS (ESI) m/z: 576 [M+H]⁺. ¹H-NMR (CD₃OD, 400 MHz): δ (ppm) 0.73-0.84 (m, 4H), 2.10-2.22 (m, 4H), 2.87-3.09 (m, 5H), 3.41-3.95 (m, 7H), 4.14-4.21 (m, 1H), 5.17 (d, J=4.4 Hz, 1H), 5.53-5.55 (m, 1H), 6.03 (s, 1H), 7.24-7.33 (m, 4H), 7.47 (s, 2H), 5.58-5.59 (m, 2H), 7.71-7.74 (m, 2H).

Example 40

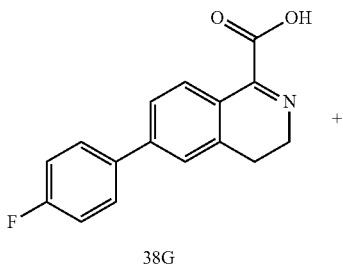

Compound 40 was synthesized by employing the procedure described for Compound 8 using Compound 38G and Intermediate G in lieu of Compound 8F and Intermediate D. LC-MS (ESI) m/z: 514 [M+H]⁺; ¹H-NMR (CD₃OD, 400 MHz): δ (ppm) 0.68-0.79 (m, 4H), 2.48-2.70 (m, 2H), 2.99 (t, J=8.0 Hz, 2H), 3.57-3.65 (m, 2H), 3.76-3.78 (m, 1H), 3.94-3.99 (m, 2H), 4.18-4.42 (m, 4H), 4.63-4.66 (m, 1H), 4.99 (d, J=3.2 Hz, 1H), 6.64 (d, J=8.0 Hz, 1H), 7.05 (d, J=8.8 Hz, 2H), 7.25 (t, J=8.8 Hz, 2H), 7.38 (t, J=8.4 Hz, 3H), 7.58 (s, 1H), 7.69-7.73 (m, 2H).

Example 41

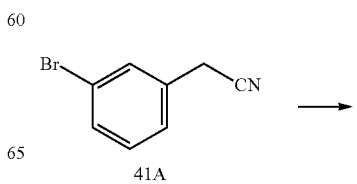

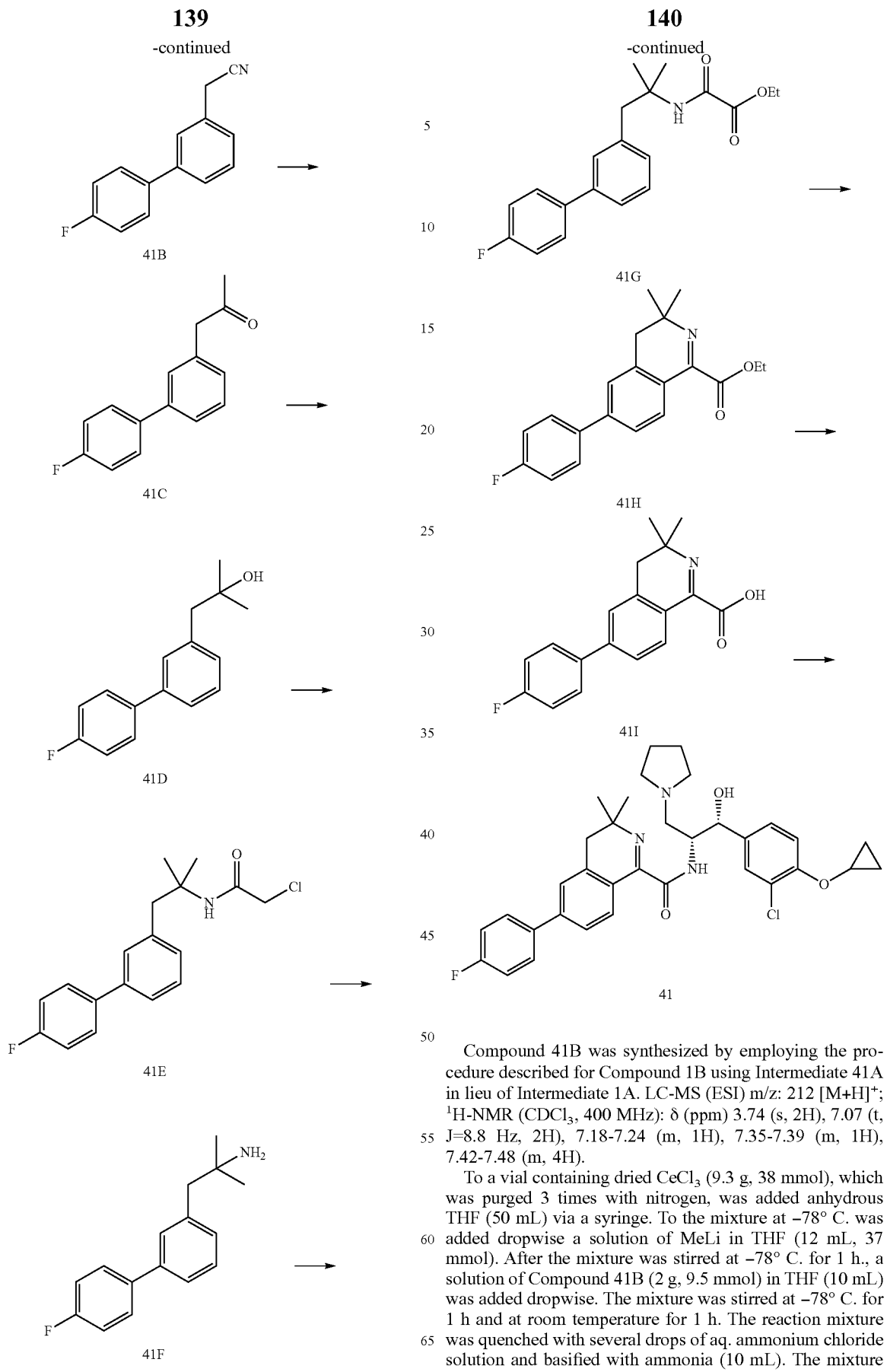

Compound 41B was synthesized by employing the procedure described for Compound 1B using Intermediate 41A in lieu of Intermediate 1A. LC-MS (ESI) m/z: 212 [M+H]$^+$; $^1$H-NMR (CDCl$_3$, 400 MHz): δ (ppm) 3.74 (s, 2H), 7.07 (t, J=8.8 Hz, 2H), 7.18-7.24 (m, 1H), 7.35-7.39 (m, 1H), 7.42-7.48 (m, 4H).

To a vial containing dried CeCl$_3$ (9.3 g, 38 mmol), which was purged 3 times with nitrogen, was added anhydrous THF (50 mL) via a syringe. To the mixture at −78° C. was added dropwise a solution of MeLi in THF (12 mL, 37 mmol). After the mixture was stirred at −78° C. for 1 h., a solution of Compound 41B (2 g, 9.5 mmol) in THF (10 mL) was added dropwise. The mixture was stirred at −78° C. for 1 h and at room temperature for 1 h. The reaction mixture was quenched with several drops of aq. ammonium chloride solution and basified with ammonia (10 mL). The mixture was filtered and washed with ethyl acetate (50 mL). The filtrate was extracted with ethyl acetate (50 mL×2), washed with brine (50 mL), dried over anhydrous sodium sulfate, concentrated, and purified with flash column chromatography on silica gel (ethyl acetate in petroleum ether, 10%, v/v) to furnish Compound 41C. LC-MS (ESI) m/z: 229 [M+H]$^+$; $^1$H-NMR (CDCl$_3$, 400 MHz): δ (ppm) 2.19 (s, 3H), 3.76 (s, 2H), 7.12 (t, J=7.2 Hz, 2H), 7.18 (d, J=5.6 Hz, 1H), 7.37-7.38 (m, 1H), 7.40-7.41 (m, 1H), 7.44-7.45 (m, 1H), 7.51-7.54 (m, 2H).

To a solution of Compound 41C (1.5 g, 6.5 mmol) in THF (20 mL) under nitrogen at −10° C. was added a solution of CH$_3$MgBr in THF (1 M, 13 mL, 13.1 mmol). The mixture was stirred at room temperature for 2 h. The reaction mixture was treated with sat. ammonium chloride solution and extracted with ethyl acetate (50 mL×2), washed with water (50 mL×2) and brine (50 mL), dried over anhydrous sodium sulfate, concentrated, and purified with flash column chromatography on silica gel (ethyl acetate in petroleum ether, 10%, v/v) to furnish Compound 41D. LC-MS (ESI) m/z: 227 [M−OH]$^+$; $^1$H-NMR (CDCl$_3$, 400 MHz): δ (ppm) 1.27 (s, 6H), 2.83 (s, 2H), 7.12 (t, J=8.8 Hz, 2H), 7.19-7.21 (m, 1H), 7.36-7.39 (m, 2H), 7.42-7.44 (m, 1H), 7.52-7.56 (m, 2H).

To a mixture of Compound 41D (700 mg, 2.86 mmol) and ClCH$_2$CN (645 mg, 8.60 mmol) was added AcOH (516 mg, 8.6 mmol). The mixture was cooled to 0-3° C. and concentrated H$_2$SO$_4$ (843 mg, 8.6 mmol) was added dropwise at a rate of keeping the temperature below 10° C. The reaction mixture was stirred for 5 h. and allowed to reach room temperature. It was poured into ice water, extracted with ethyl acetate (50 mL×2), washed with sat. sodium bicarbonate (50 mL) and brine (50 mL), dried over anhydrous sodium sulfate, and concentrated to afford Compound 41E. LC-MS (ESI) m/z: 320 [M+H]$^+$.

A solution of Compound 41E (800 mg, 2.5 mmol) and thiourea (229 mg, 3 mmol) in ethanol (5 mL) and AcOH (1 mL) was refluxed for 10 h. It was treated with water and 20% NaOH, extracted with dichloromethane (50 mL×2), washed with sodium bicarbonate (50 mL) and brine (50 mL), dried over anhydrous sodium sulfate, concentrated, and furnish Compound 41F. LC-MS (ESI) m/z: 244 [M+H]$^+$; $^1$H-NMR (CDCl$_3$, 400 MHz): δ (ppm) 1.09 (s, 6H), 2.66 (s, 2H), 7.03-7.11 (m, 3H), 7.28-7.36 (m, 3H), 7.45-7.48 (m, 2H).

To a solution of Compound 41F (330 mg, 1.36 mmol) in THF (15 mL) at 0° C. was added triethylamine (411 mg, 4.07 mmol) and ethyl 2-chloro-2-oxoacetate (277 mg, 2.04 mmol) and was stirred at room temperature for 1.5 h. The mixture was treated with water (50 mL), extracted with ethyl acetate (50 mL×2), washed with sat. sodium bicarbonate (50 mL) and brine (50 mL), dried over anhydrous sodium sulfate, concentrated, and purified with flash column chromatography on silica gel (ethyl acetate in petroleum ether, 10%, v/v) to furnish Compound 41G. LC-MS (ESI) m/z: 344 [M+H]$^+$; $^1$H-NMR (CDCl$_3$, 400 MHz): δ (ppm) 1.35 (t, J=7.2 Hz, 3H), 1.43 (s, 6H), 3.11 (s, 2H), 4.30 (q, J=7.2 Hz, 2H), 7.09-7.13 (m, 3H), 7.29 (s, 1H), 7.34-7.38 (m, 1H), 7.41-7.43 (m, 1H), 7.49-7.53 (m, 2H).

Compound 41H was synthesized by employing the procedure described for Compound 38F using Compound 41G in lieu of Compound 38E. LC-MS (ESI) m/z: 326 [M+H]$^+$.

Compound 41I was synthesized by employing the procedure described for Compound 1G using Compound 41H in lieu of Compound 1F. LC-MS (ESI) m/z: 298 [M+H]$^+$.

Compound 41 was synthesized by employing the procedure described for Compound 8 using Compound 41I and Intermediate A in lieu of Compound 8F and Intermediate D. LC-MS (ESI) m/z: 590 [M+H]$^+$; $^1$H-NMR (CD$_3$OD, 400 MHz): δ (ppm) 0.73-0.83 (m, 4H), 1.29 (s, 3H), 1.37 (s, 3H), 2.11-2.24 (m, 4H), 2.87-2.96 (m, 2H), 3.27 (s, 2H), 3.49-3.53 (m, 1H), 3.78-3.89 (m, 4H), 4.82-4.85 (m, 1H), 4.99 (d, J=2.4 Hz, 1H), 6.54 (d, J=8.0 Hz, 1H), 7.24 (t, J=8.8 Hz, 2H), 7.29-7.31 (m, 1H), 7.39 (s, 2H), 7.47-7.50 (m, 2H), 7.70-7.74 (m, 2H).

Example 42

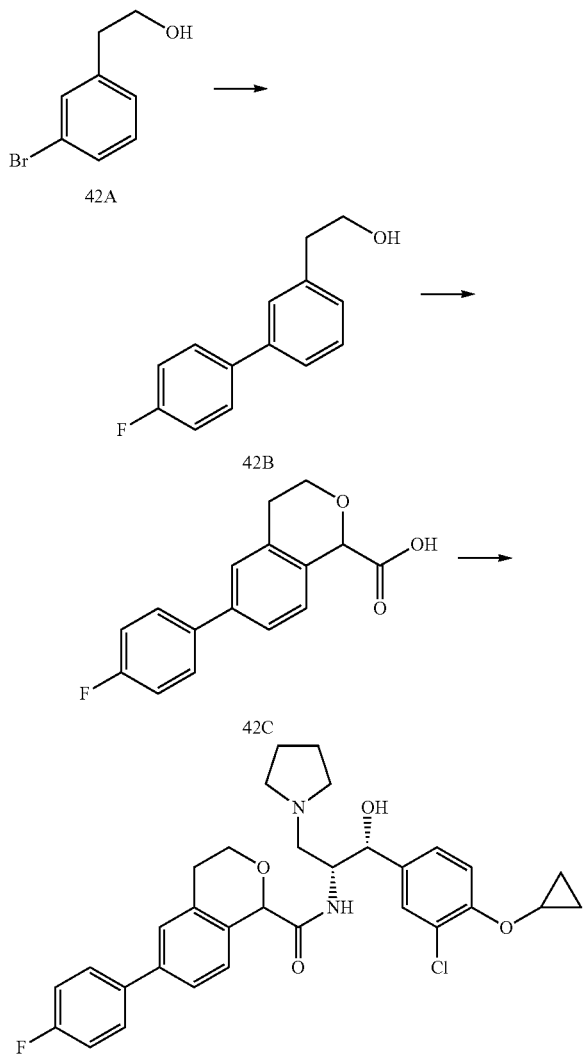

Compound 42B was synthesized by employing the procedure described for Compound 1B using Intermediate 42A in lieu of Intermediate 1A. LC-MS (ESI) m/z: 199 [M−−OH]$^+$; $^1$H-NMR (CDCl$_3$, 400 MHz): δ (ppm) 1.49 (t, J=5.2 Hz, 1H), 2.93 (t, J=6.8 Hz, 1H), 3.88-3.93 (m, 2H), 7.12 (t, J=8.8 Hz, 2H), 7.21 (d, J=7.2 Hz, 2H), 7.36-7.42 (m, 3H), 7.52-7.55 (m, 2H).

A mixture of Compound 42B (1 g, 4.6 mmol) and 2-oxoacetic acid hydrate (468 mg, 5.1 mmol) in CF$_3$COOH (5 mL) was stirred at reflux for 24 h. The resulting mixture was concentrated to remove CF$_3$COOH, adjusted to pH 8 with NH$_4$OH, and extracted with ethyl acetate (50 mL×2). The aqueous phase was adjusted to pH 2 with diluted HCl solution and extracted with ethyl acetate (50 mL×2). The organic layer was concentrated, washed with ether, and filtered to furnish Compound 42C. LC-MS (ESI) m/z: 227 [M-COOH]⁺; ¹H-NMR (DMSO-d₆, 400 MHz): δ (ppm) 2.79-2.93 (m, 2H), 3.91-3.97 (m, 1H), 4.12-4.18 (m, 1H), 5.32 (s, 1H), 7.29 (t, J=9.2 Hz, 2H), 7.41-7.49 (m, 3H), 7.68-7.71 (m, 2H), 13.01 (s, 1H).

Compound 42 was synthesized by employing the procedure described for Compound 8 using Compound 42C and Intermediate A in lieu of Compound 8F and Intermediate D. LC-MS (ESI) m/z: 565 [M+H]⁺; ¹H-NMR (DMSO-d₆, 400 MHz): δ (ppm) 0.44-0.79 (m, 4H), 1.82-2.09 (m, 4H), 2.78-3.14 (m, 4H), 3.37-3.56 (m, 6H), 4.08-4.11 (m, 1H), 4.42-4.45 (m, 1H), 4.74-4.87 (m, 1H), 5.15 (t, J=7.2 Hz, 1H), 6.92-7.17 (m, 2H), 7.23-7.27 (m, 3H), 7.34-7.48 (m, 3H), 7.56-8.06 (m, 3H).

Example 43

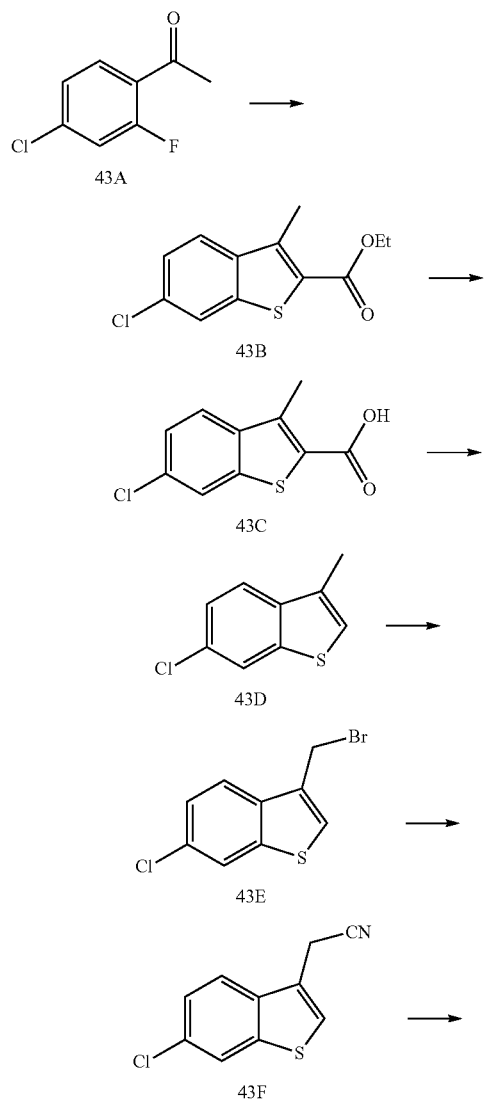

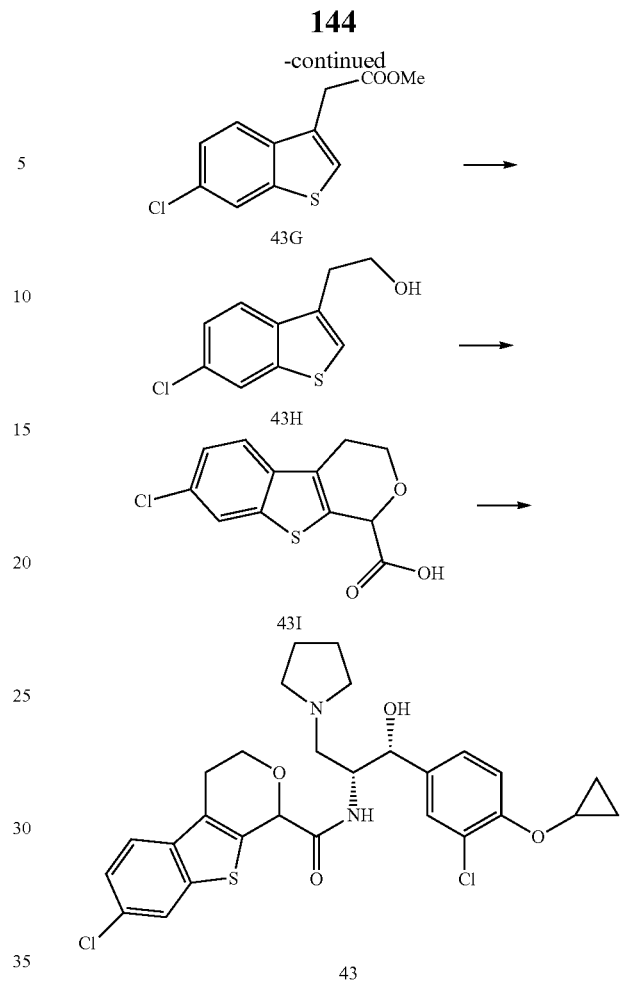

To a mixture of Compound 43A (25 g, 0.145 mol) and K₂CO₃ (26 g, 0.188 mol) in dry DMF (150 mL) at 0° C. was added ethyl 2-mercaptoacetate (16 mL, 0.146 mmol) in small portions over 1 h. The mixture was slowly warmed to room temperature and stirred for 16 h. The reaction mixture was heated at 80° C. for 24 h. After it was cooled, to it was added water (300 mL). The resulting mixture was stirred at room temperature for 30 min. and filtered. The filtrate was diluted with ethyl acetate (200 mL), washed with water (100 mL) and brine (100 mL), dried over anhydrous sodium sulfate, concentrated, and offer the Compound 43B. LC-MS (ESI) m/z: 255 [M+H]⁺; ¹H-NMR (CDCl₃, 400 MHz): δ (ppm) 1.41 (t, J=7.6 Hz, 3H), 2.74 (s, 3H), 4.39 (q, J=6.8 Hz, 2H), 7.35-7.38 (m, 1H), 7.72 (d, J=8.4 Hz, 1H), 7.78 (d, J=1.6 Hz, 1H).

To a solution of Compound 43B (35 g, 0.14 mol) in THF (100 mL) was added a solution of LiOH.H₂O (6.9 g, 0.17 mol) in water (10 mL). The resulting mixture was stirred at room temperature for 12 h. and its pH was adjusted to about 1 with diluted HCl solution. The mixture was extracted with ethyl acetate (100 mL×2). The organic layer was concentrated, filtered, and washed with petroleum ether to afford Compound 43C. LC-MS (ESI) m/z: 225 [M–H]⁺; ¹H-NMR (DMSO, 400 MHz): δ (ppm) 2.70 (s, 3H), 7.48-7.51 (m, 1H), 7.94 (d, J=8.4 Hz, 1H), 8.16 (d, J=1.6 Hz, 1H).

A suspension of Compound 43C (25 g, 0.11 mol) and Cu powder (3.5 g, 55 mmol) in quinoline (100 mL) was stirred at 210° C. for 4 h. After the reaction mixture was cooled to room temperature, it was filtered and washed with ethyl acetate (100 mL×3) and diluted HCl (100 mL×3) and brine (100 mL), dried over anhydrous sodium sulfate, concentrated, and purified with flash column chromatography on silica gel (petroleum ether 100%, v/v) to furnish Compound 43D. ¹H-NMR (CDCl₃, 400 MHz): δ (ppm) 2.39 (s, 3H), 7.03 (s, 1H), 7.31-7.34 (m, 1H), 7.58 (d, J=8.8 Hz, 1H), 7.79 (d, J=2.0 Hz, 1H).

To a solution of Compound 43D (3 g, 16 mmol) in CCl₄ (20 mL) was added NBS (3.2 g, 18 mmol) and BPO (398 mg, 1.6 mmol). The mixture was heated to reflux for 3 h., cooled down to room temperature, and extracted with dichloromethane (50 mL×3). The extracts were washed with water (50 mL×2) and brine (50 mL), dried over anhydrous sodium sulfate, concentrated, and purified with flash column chromatography on silica gel (ethyl acetate in petroleum ether, 10%, v/v) to furnish Compound 43E. ¹H-NMR (CDCl₃, 400 MHz): δ (ppm) 4.71 (s, 2H), 7.41-7.43 (m, 1H), 7.49 (s, 1H), 7.79-7.84 (m, 2H).

To a solution of Compound 43E (3.4 g, 13 mmol) in DMF (10 mL) was added NaCN (1.3 g, 26 mmol) in water (5 mL). The resulting mixture was stirred at room temperature for 2 h. The reaction was quenched with water (50 mL), extracted with ethyl acetate (50 mL×3), washed with water (50 mL×3) and brine (50 mL), dried over anhydrous sodium sulfate, concentrated, and purified with flash column chromatography on silica gel (ethyl acetate in petroleum ether, 10%, v/v) to furnish Compound 43F. LC-MS (ESI) m/z: 208 [M+H]⁺; ¹H-NMR (CDCl₃, 400 MHz): δ (ppm) 3.89 (s, 2H), 7.41-7.43 (m, 1H), 7.49 (s, 1H), 7.62 (d, J=8.8 Hz, 1H), 7.87 (d, J=1.6 Hz, 1H).

To a solution of Compound 43F (2 g, 9.6 mmol) in methanol (10 mL) was added concentrated HCl (10 mL). The resulting mixture was stirred at reflux for 48 h. The reaction mixture was cooled to room temperature, extracted with dichloromethane (50 mL×2), washed with brine (50 mL), dried over anhydrous sodium sulfate, concentrated, and purified with flash column chromatography on silica gel (ethyl acetate in petroleum ether, 10%, v/v) to furnish Compound 43G. LC-MS (ESI) m/z: 241 [M−H]⁺; ¹H-NMR (CDCl₃, 400 MHz): δ (ppm) 3.70 (s, 3H), 3.83 (s, 2H), 7.34-7.37 (m, 2H), 7.65 (d, J=8.8 Hz, 1H), 7.82 (d, J=1.6 Hz, 1H).

To a solution of LiAlH₄ (221 mg, 5.8 mmol) in THF (20 mL) under nitrogen at −60° C. was added dropwise a solution of Compound 43G (1.4 g, 5.8 mmol) in THF (5 mL). It was stirred under nitrogen at −60° C. for 1 h. The reaction mixture was diluted with ethyl acetate (50 mL) and added Na₂SO₄.10H₂O. The mixture was filtered, concentrated, and purified with flash column chromatography on silica gel (ethyl acetate in petroleum ether, 20%, v/v) to furnish Compound 43H. LC-MS (ESI) m/z: 213 [M+H]⁺; ¹H-NMR (CDCl₃, 400 MHz): δ (ppm) 2.33 (t, J=6.4 Hz, 1H), 3.09 (t, J=6.8 Hz, 2H), 3.95 (t, J=6.8 Hz, 2H), 7.21 (s, 1H), 7.34-7.36 (m, 1H), 7.66 (d, J=8.4 Hz, 1H), 7.83 (d, J=2.0 Hz, 1H).

A mixture of Compound 43H (1.2 g, 5.6 mmol), 2-oxoacetic acid hydrate (571 mg, 6.2 mmol) in CF₃COOH (5 mL) was stirred at reflux for 24 h. The mixture was evaporated to remove CF₃COOH. The mixture was diluted with ethyl acetate (100 mL), washed with sat. sodium bicarbonate (50 mL×3) and brine (50 mL), dried over anhydrous sodium sulfate, concentrated, and purified with reverse phase chromatography using eluent (acetonitrile in NH₄OH and water, from 10% to 100% v/v) to furnish Compound 43I. LC-MS (ESI) m/z: 269 [M+H]⁺.

A mixture of Compound 43I (80 mg, 0.30 mmol), Intermediate A (93 mg, 0.30 mmol), and HATU (170 mg, 0.45 mmol) in DMF (5 mL) was stirred at room temperature for 12 h. The mixture was treated with water (50 mL), extracted with dichloromethane (20 mL×2), washed with water (20 mL×3) and brine (50 mL), dried over anhydrous sodium sulfate, concentrated, and purified with prep-HPLC to furnish Compound 43. LC-MS (ESI) m/z: 561 [M+H]⁺; ¹H-NMR (CD₃OD, 400 MHz): δ (ppm) 0.34-0.83 (m, 4H), 1.86-2.23 (m, 4H), 2.82-3.26 (m, 5H), 3.48-3.67 (m, 4H), 3.83-4.07 (m, 2H), 4.46-4.55 (m, 2H), 5.16-5.27 (m, 1H), 6.63-7.18 (m, 1H), 7.31-7.48 (m, 3H), 7.65-7.91 (m, 3H).

Example 44

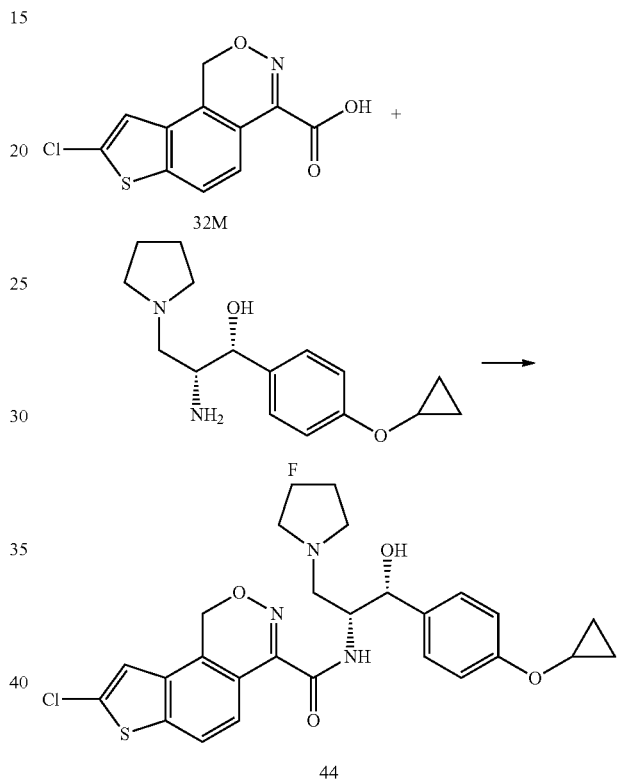

Compound 44 was synthesized by employing the procedure described for Compound 8 using Compound 33M and Intermediate F in lieu of Compound 8F and Intermediate D. LC-MS (ESI) m/z: 526 [M+H]⁺; ¹H-NMR (CD₃OD, 400 MHz): δ (ppm) 0.63-0.77 (m, 4H), 2.02-2.05 (m, 2H), 2.16-2.21 (m, 2H), 3.33-3.35 (m, 2H), 3.51-3.55 (m, 1H), 3.66-3.81 (m, 4H), 4.68-4.71 (m, 1H), 4.94 (m, 1H), 5.34 (m, 2H), 7.0-7.03 (m, 2H), 7.35-7.38 (m, 3H), 7.54 (s, 1H), 7.78 (d, J=8.4 Hz, 1H).

Example 45

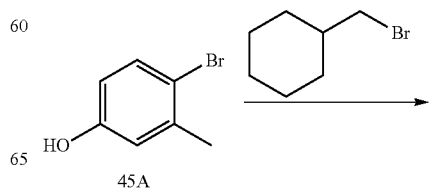

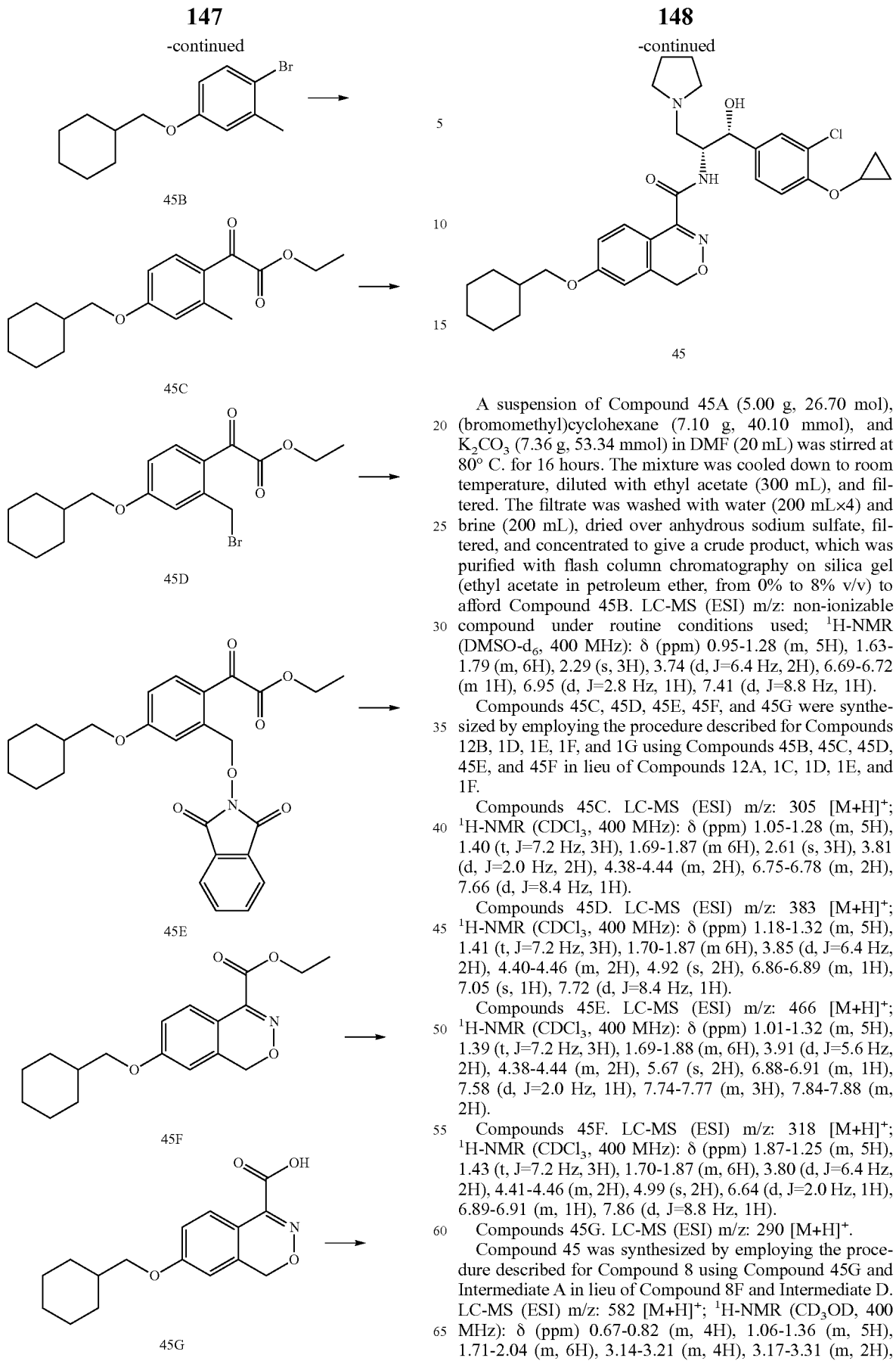

A suspension of Compound 45A (5.00 g, 26.70 mol), (bromomethyl)cyclohexane (7.10 g, 40.10 mmol), and $K_2CO_3$ (7.36 g, 53.34 mmol) in DMF (20 mL) was stirred at 80° C. for 16 hours. The mixture was cooled down to room temperature, diluted with ethyl acetate (300 mL), and filtered. The filtrate was washed with water (200 mL×4) and brine (200 mL), dried over anhydrous sodium sulfate, filtered, and concentrated to give a crude product, which was purified with flash column chromatography on silica gel (ethyl acetate in petroleum ether, from 0% to 8% v/v) to afford Compound 45B. LC-MS (ESI) m/z: non-ionizable compound under routine conditions used; $^1$H-NMR (DMSO-$d_6$, 400 MHz): δ (ppm) 0.95-1.28 (m, 5H), 1.63-1.79 (m, 6H), 2.29 (s, 3H), 3.74 (d, J=6.4 Hz, 2H), 6.69-6.72 (m 1H), 6.95 (d, J=2.8 Hz, 1H), 7.41 (d, J=8.8 Hz, 1H).

Compounds 45C, 45D, 45E, 45F, and 45G were synthesized by employing the procedure described for Compounds 12B, 1D, 1E, 1F, and 1G using Compounds 45B, 45C, 45D, 45E, and 45F in lieu of Compounds 12A, 1C, 1D, 1E, and 1F.

Compounds 45C. LC-MS (ESI) m/z: 305 [M+H]$^+$; $^1$H-NMR (CDCl$_3$, 400 MHz): δ (ppm) 1.05-1.28 (m, 5H), 1.40 (t, J=7.2 Hz, 3H), 1.69-1.87 (m 6H), 2.61 (s, 3H), 3.81 (d, J=2.0 Hz, 2H), 4.38-4.44 (m, 2H), 6.75-6.78 (m, 2H), 7.66 (d, J=8.4 Hz, 1H).

Compounds 45D. LC-MS (ESI) m/z: 383 [M+H]$^+$; $^1$H-NMR (CDCl$_3$, 400 MHz): δ (ppm) 1.18-1.32 (m, 5H), 1.41 (t, J=7.2 Hz, 3H), 1.70-1.87 (m 6H), 3.85 (d, J=6.4 Hz, 2H), 4.40-4.46 (m, 2H), 4.92 (s, 2H), 6.86-6.89 (m, 1H), 7.05 (s, 1H), 7.72 (d, J=8.4 Hz, 1H).

Compounds 45E. LC-MS (ESI) m/z: 466 [M+H]$^+$; $^1$H-NMR (CDCl$_3$, 400 MHz): δ (ppm) 1.01-1.32 (m, 5H), 1.39 (t, J=7.2 Hz, 3H), 1.69-1.88 (m, 6H), 3.91 (d, J=5.6 Hz, 2H), 4.38-4.44 (m, 2H), 5.67 (s, 2H), 6.88-6.91 (m, 1H), 7.58 (d, J=2.0 Hz, 1H), 7.74-7.77 (m, 3H), 7.84-7.88 (m, 2H).

Compounds 45F. LC-MS (ESI) m/z: 318 [M+H]$^+$; $^1$H-NMR (CDCl$_3$, 400 MHz): δ (ppm) 1.87-1.25 (m, 5H), 1.43 (t, J=7.2 Hz, 3H), 1.70-1.87 (m, 6H), 3.80 (d, J=6.4 Hz, 2H), 4.41-4.46 (m, 2H), 4.99 (s, 2H), 6.64 (d, J=2.0 Hz, 1H), 6.89-6.91 (m, 1H), 7.86 (d, J=8.8 Hz, 1H).

Compounds 45G. LC-MS (ESI) m/z: 290 [M+H]$^+$.

Compound 45 was synthesized by employing the procedure described for Compound 8 using Compound 45G and Intermediate A in lieu of Compound 8F and Intermediate D. LC-MS (ESI) m/z: 582 [M+H]$^+$; $^1$H-NMR (CD$_3$OD, 400 MHz): δ (ppm) 0.67-0.82 (m, 4H), 1.06-1.36 (m, 5H), 1.71-2.04 (m, 6H), 3.14-3.21 (m, 4H), 3.17-3.31 (m, 2H), 3.49-3.55 (m, 1H), 3.66-3.85 (m, 6H), 4.66-4.70 (m, 1H), 4.92-5.03 (m, 3H), 6.79-6.82 (m, 2H), 7.16 (d, J=8.8 Hz, 1H), 7.34 (s, 2H), 7.46 (s, 1H).

Example 46

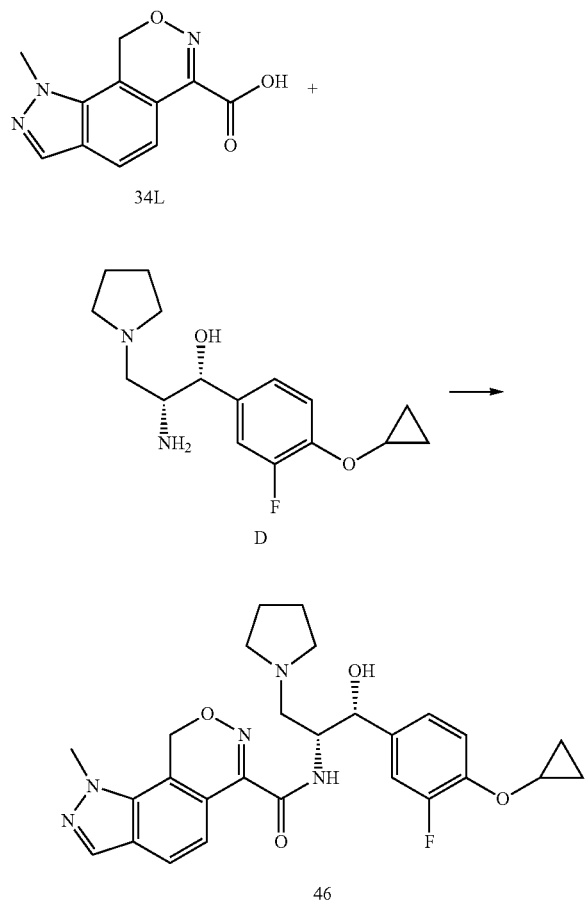

Compound 46 was synthesized by employing the procedure described for Compound 8 using Compound 34L in lieu of Compound 8F. LC-MS (ESI) m/z: 508 [M+H]+; 1H-NMR (CD3OD, 400 MHz): δ (ppm) 0.72-0.80 (m, 4H), 2.05-2.23 (m, 4H), 3.21-3.31 (m, 2H), 3.56-3.59 (m, 1H), 3.69-3.86 (m, 4H), 4.25 (s, 3H), 4.73 (d, J=10.8 Hz, 1H), 4.97 (s, 1H), 5.62 (q, J=13.6 Hz, 2H), 6.94 (d, J=8.4 Hz, 1H), 7.22-7.24 (m, 2H), 7.34 (t, J=6.4 Hz, 1H), 7.65 (d, J=8.8 Hz, 1H), 8.04 (s, 1H).

Example 47

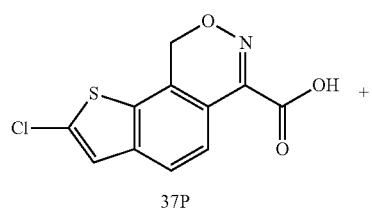

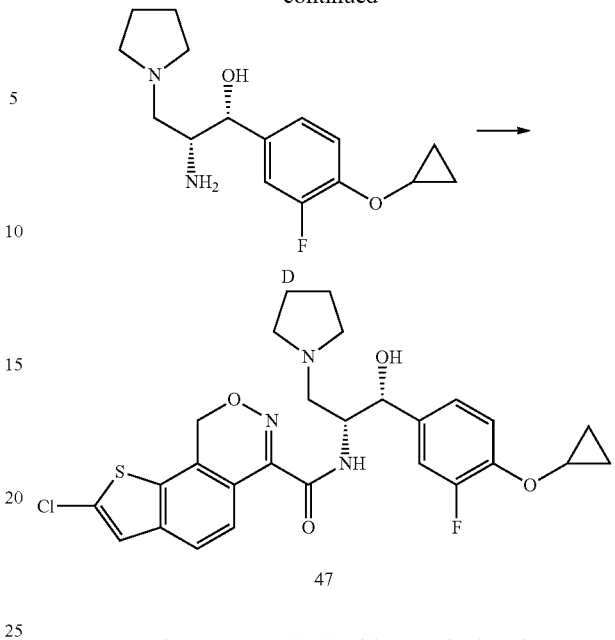

Compound 47 was synthesized by employing the procedure described for Compound 8 using Compound 37P in lieu of Compound 8F. LC-MS (ESI) m/z: 544 [M+H]+; 1H-NMR (CD3OD, 400 MHz): δ (ppm) 0.70-0.78 (m, 4H), 2.06-2.22 (m, 4H), 3.22-3.32 (m, 2H), 3.57-3.58 (m, 1H), 3.68-3.84 (m, 4H), 4.68-4.73 (m, 1H), 4.95 (s, 1H), 5.17-5.24 (m, 2H), 7.20-7.23 (m, 2H), 7.31-7.37 (m, 2H), 7.46 (s, 1H), 7.70 (d, J=8.8 Hz, 1H).

BIOLOGICAL EXAMPLES

The following describes ways in which the compounds described herein were tested to measure in vitro activity in enzymatic and cell-based assays. A person of ordinary skill in the art would know that variations in the assay conditions could be used to determine the activity of the compounds.

Assay 1: GCS Enzymatic Assay

This assay was modified based on the study by Larsen et al. (*J. Lipid Res.* 2011, 53, 282). Madin-Darby canine kidney (MDCK) cell lysate was prepared using M-PER Mammalian Protein Extraction Reagent (Thermal Scientific) in the presence of a protease inhibitor cocktail (Roche). Protein concentration was determined using BCA assay kit (Pierce). Sixty micrograms of MDCK cell lysate was incubated with various concentrations of a compound described herein from 0.001 µM-10 µM, respectively, or as indicated in Table 2, in 100 mM Tris buffer (pH 7.5) containing 10 mM MgCl2, 1 mM dithiothreitol, 1 mM EGTA, 2 mM NAD, 100 µM UDP-glucose, 10 µM C6-NBD-Ceramide (Matreya LLC, Pleasant Gap, Pa.), 35 µM dioleoylphosphatidylcholine and 5 µM sulfatide (Sigma) in a final reaction volume of 100 µL at 37° C. for 1 hour. 0.1% DMSO was used as mock treatment or control. The reaction was terminated by adding 100 µL acetonitrile solution and subjected to LC/MS analysis.

The quantitative analysis of NBD-Ceramide and glucosylceramide was performed on a Shimadzu ultra-fast liquid chromatography (Shimadzu, Japan) coupled with API 4000 triple quadrupole mass spectrometer (Applied Biosystems, Concord, Ontario, Canada). Sample separation was conducted on a Waters Xbridge™ BEH130 C18, 100 mm×4.6 mm i.d, 3.5 μm (Milford, Mass., USA). The mobile phase consisted of water and acetonitrile supplemented with 0.1% formic acid (v/v). The flow rate was 1.0 mL/min. The initial mobile phase was 20% acetonitrile and was ramped in a linear fashion to 50% acetonitrile in 0.4 min. From 0.4 to 1.5 min, the gradient was ramped to 98% acetonitrile, and then was held at 100% until 8.0 min. Acetonitrile was reset to 20% in 1.5 min, and maintained until 10.0 min. The total run time was 10.0 min. The MS/MS detection was performed in ESI positive mode. The mass transition of NBD-Ceramide was m/z 576.36→558.40 under the collision energy of 15 V, and the mass transition of glucosylceramide was m/z 738.35-558.40 under 21V collision energy. The cell lysate was diluted with equal volume of acetonitrile. Aliquots of 50 μL diluted samples were added to 1.5 mL tubes, and 100 μL of acetonitrile containing internal standard (100 ng/mL tolbutamide) were added for protein precipitation. The mixture were vortexed and then centrifuged at 13000 rpm for 10 min. 70 μL of supernatant were mixed with 140 μL of $H_2O$ and the final solution were injected for LC/MS/MS analysis and $IC_{50}$'s and/or percent inhibitions calculated.

Assay 2: K562 Cell-Based Assay

This assay was modified based on the study by Gupta et al. (*J. Lipid Res.* 2010, 51, 866). K562 cells were seeded into 12-well plates at 3×10⁵ cells/well/mL in RPMI-1640 medium with 5% FBS and incubated at 37° C. for 24 h. One μL of a compound described herein at desired concentration (10 mM, 1 mM, 0.1 mM, 0.01 mM, 0.001 mM and 0.0001 mM in DMSO) or DMSO was added into the corresponding well and mixed. Cells were incubated at 37° C. for 4 h. Then 100 μL of RPMI-1640 medium containing 110 μM of NBD-Ceramide, 11% BSA, 5% FBS, and corresponding concentration of a compound described herein was added into each well and mixed. Cells were incubated for additional 0.5 h at 37° C., followed by washing the cells with ice-cold PBS (pH 7.4) twice with centrifugation and resuspended with 50 μL cold PBS+1% Triton X-100. The cell lysate was sonicated for 15 min before adding equal volume of methanol for LCMS analysis. A small aliquot of cell lysate was used to determine protein concentration by BCA assay kit. The HPLC equipment and methods used in Assay 1 were used in this assay as well and $IC_{50}$'s were calculated.

Assay 3: NCI/ADR-Res Cell-Based Assay

NCI/ADR-RES cells are seeded into 12-well plates (4×10⁵ cells/well) in RPMI-1640 medium with 10% FBS and incubated at 37° C. for 24 h. Before treatment with a compound described herein, cell culture media are removed and replaced with 1 mL per well RPMI-1640 medium containing 5% FBS and a compound as described herein at desired concentrations (10 μM, 1 μM, 0.1 μM, 0.01 μM, 0.001 μM, and 0.0001 μM), respectively, or 0.1% DMSO only. Cells are cultured for 4 hours at 37° C. followed by replacing the media with RPMI-1640 containing 1% BSA and 10 μM of C6-NBD-Ceramide in the present of a compound described herein, and incubated for additional 0.5 hour at 37° C. Cells are then washed twice with ice-cold PBS (pH 7.4), scraped with 50 μL cold PBS+1% Trition X-100. The cell lysate is sonicated for 15 min before adding equal volume of methanol for LCMS analysis. A small aliquot of cell lysate is used to determine protein concentration by BCA assay kit. The HPLC equipment and methods used in Assay 1 are used in this assay as well and $IC_{50}$'s are calculated.

Using the above assays, the following compounds were tested.

TABLE 2

| Example No. | Assay 1 (Enzyme Assay; MDCK lysates) $IC_{50}$ | Assay 2 (Cellular Assay; K562 cells) $IC_{50}$ |
|---|---|---|
| 1 | A | A |
| 2 | A | A |
| 3 | A | A |
| 4 | B | A |
| 5 | B | A |
| 6 | B | A |
| 7 | A | A |
| 8 | A | A |
| 9 | A | A |
| 10 | B | A |
| 11 | B | A |
| 12 | B | B |
| 13 | B | ND |
| 14 | A | A |
| 15 | C | ND |
| 16 | C | ND |
| 17 | A | A |
| 18 | B | A |
| 19 | B | A |
| 20 | A | A |
| 21 | B | A |
| 22 | A | A |
| 23 | C | ND |
| 24 | B | B |
| 25 | A | A |
| 26 | A | A |
| 27 | A | B |
| 28 | A | A |
| 29 | A | A |
| 30 | A | B |
| 31 | B | B |
| 32 | A | A |
| 33 | A | B |
| 34 | A | B |
| 36 | A | B |
| 37 | A | A |
| 38 | B | A |
| 39 | B | A |
| 40 | B | ND |
| 41 | C | ND |
| 42 | C | ND |
| 43 | C | ND |
| 44 | B | A |
| 45 | A | B |
| 46 | A | A |
| 47 | A | A |

In Table 2, biological data is provided as follows: $IC_{50}$ values:
A: ≤1 nM-10 nM;
B: >10-100 nM;
C: >100-1000 nM;
ND: not determined.

Sandhoff Disease Mouse Model

The murine model of Sandhoff disease is a knock out (KO) of the HEXB gene, which codes for beta-hexosaminidase in mice, as it does in humans. This KO mouse displays a phenotype closely resembling that seen in humans, although at a more advanced age, compared to humans. At ~3 months of age, the animals develop tremor and increased limb tone, which is worse in the hind legs. These manifestations become progressively more severe until 4-5 months of age, when the animals become moribund and rapidly lose weight. The motor phenotype has been quantified by activity monitor, bar-crossing, and inverted screen tests (Jayakumar M et al *Blood* 2001, 97, 327-329; Cachon-Gonzalez et al *PNAS* 2006, 103(27), 1037-10378). Histologically, the mouse neurons appear to be distended by lysosomal storage material, and signs of neuroinflammation are present. Biochemically, levels of beta-hexosaminidase are absent, and accumulations of gangliosides GM2, GA2, as well as sialic acid, can be demonstrated (Cachon-Gonzalez et al 2006; Arthur et al *Neurochem Res* 2013, DOI 10.1007/s11064-013-0992-5).

To evaluate the potential efficacy of different compounds described herein in Sandhoff disease, homozygous male mice are mated with heterozygous females. All pups (approximately 50% KO and 50% het) in a litter are treated by daily IP or SC injection with the same test (or control) article for 14 days, beginning at 3 days old. The chosen route of administration is determined based on pharmacokinetic/pharmacodynamic properties of the compound to be tested. At the end of the dosing period, pups are deeply anesthetized using isoflurane through nose cones (4% for induction and 1.5% for maintenance), blood is collected by cardiac puncture method, then the mice are euthanized. Brains and livers are collected and snap frozen. These tissues are used for analysis of experimental endpoints (GM2 and sialic acid in brain, GA2 and sialic acid in liver). An additional tissue sample (tail tip or toe) is collected and snap frozen, then sent for genotyping.

If tested compounds are found which have a marked effect on the experimental endpoints, an additional experiment is performed looking at effects on activity, inverted screen, and bar crossing tests, as well as average survival time, compared to vehicle-treated mice.

Polycystic Kidney Disease Mouse Model

To jck mice is administered a compound described herein ad libitum in food (standard chow) from 26-64 days of age. Control jck mice are fed a control diet from 26-64 days of age. At 63 days of age, the animals are transferred to metabolic cages for 24 hour urine collection. At 64 days of age, animals are sacrificed, weighed, and blood is collected by heart puncture for serum isolation. Kidneys are isolated, bisected, and weighed and half of each kidney is fixed in 4% paraformaldehyde in PBS overnight for paraffin embedding and hematoxylin and eosin staining. Kidney weight to body weight ratio is used to determine activity of the compound. Cyst volume is measured by quantitating the percentage of cystic area in histological sections of kidneys from the treated and control animals and multiplied by the kidney/body weight ratio. Kidney function is assessed by measuring blood urea nitrogen (BUN) levels in serum samples derived from animals at sacrifice. BUN levels are elevated in untreated controls while the treated animals demonstrated a significant reduction of BUN levels.

Other objects, features and advantages of the compounds, methods and compositions described herein will become apparent from the following description. It should be understood, however, that the description and the specific examples, while indicating specific embodiments, are given by way of illustration only, since various changes and modifications within the spirit and scope of the present description will become apparent from this detailed description.

All publications including patents, patent applications and published patent applications cited herein are hereby incorporated by reference for all purposes.

I claim:
1. A compound of Formula I:

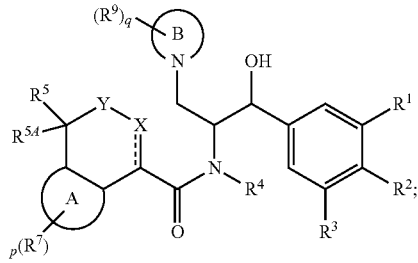

Formula I wherein
$R^1$ is H; or $R^1$ and $R^2$ together form —OCH$_2$CH$_2$O—;
$R^2$ is $C_{3-6}$ cycloalkyloxy or 3-6 membered heterocycloalkyloxy;
$R^3$ is H or halogen;
$R^4$ is H or $C_{1-4}$ alkyl;
$R^5$ and $R^{5A}$ are each independently H or $C_{1-4}$ alkyl;
X is N or O, and when X is N, the dashed line is a bond to form a double bond, and when X is O, the dashed line is not a bond to form a single bond;
Y is $C(R^6)_2$ or O; with the proviso that X and Y are not both O;
$R^6$ at each occurrence is independently H or $C_{1-4}$ alkyl;
Ring A is phenylene, naphthylene, or 5-10 membered heteroarylene;
$R^7$ at each occurrence is independently halogen, $C_{1-6}$ alkyl, $C_{1-6}$ alkoxy, $C_{3-6}$ cycloalkyloxy, $(C_{3-6}$ cycloalkyl)$C_{1-6}$ alkoxy, phenyl, or 5-6 membered heteroaryl, wherein the phenyl and heteroaryl are each optionally substituted with 1, 2, or 3 $R^8$;
p is 0, 1, or 2;
$R^8$ at each occurrence is independently halogen, cyano, amino, $C_{1-6}$ alkylamino, $C_{1-6}$ dialkylamino, $C_{1-6}$ alkyl, $C_{1-6}$ alkoxy, $C_{1-6}$ haloalkoxy, aminocarbonyl, $C_{1-6}$ alkylaminocarbonyl, or $C_{1-6}$ dialkylaminocarbonyl;
Ring B is a 4-6 membered heterocycloalkyl ring;
$R^9$ at each occurrence is independently halogen, $OR^{10}$, or $N(R^{10})_2$;
$R^{10}$ at each occurrence is independently H or $C_{1-4}$ alkyl;
q is 0, 1, 2, 3, or 4; and
optionally a single stereoisomer or mixture of stereoisomers thereof and additionally optionally a pharmaceutically acceptable salt thereof.

2. The compound of claim 1, wherein
$R^1$ is H; or $R^1$ and $R^2$ together form —OCH$_2$CH$_2$O—;
$R^2$ is $C_{3-6}$ cycloalkyloxy;
$R^3$ is H, Cl, or F;
$R^4$ is H or $C_{1-4}$ alkyl;
$R^5$ and $R^{5A}$ are each independently H or $C_{1-4}$ alkyl;
X is N or O, and when X is N, the dashed line is a bond to form a double bond, and when X is O, the dashed line is not a bond to form a single bond;
Y is CH$_2$, CH($C_{1-4}$ alkyl), C($C_{1-4}$ alkyl)$_2$, or O; with the proviso that X and Y are not both O;
Ring A is phenylene, naphthylene, benzothiophenylene, indazolylene, or quinolylene;

$R^7$ is Cl, F, $C_{1-6}$ alkyl, $(C_{3-6}$ cycloalkyl$)C_{1-6}$ alkoxy, phenyl, or thienyl, wherein the phenyl and thienyl are each optionally substituted with $R^8$;

$R^8$ is Cl, F, or $C_{1-6}$ alkyl; and optionally a single stereoisomer or mixture of stereoisomers thereof and additionally optionally a pharmaceutically acceptable salt thereof.

3. The compound of claim 1, wherein $R^7$ at each occurrence is independently halogen, $C_{1-6}$ alkyl, phenyl, or 5-6 membered heteroaryl, wherein the phenyl and heteroaryl are each optionally substituted with 1, 2, or 3 $R^8$; and optionally a single stereoisomer or mixture of stereoisomers thereof and additionally optionally a pharmaceutically acceptable salt thereof.

4. The compound of claim 3, wherein

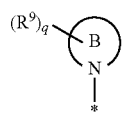

is selected from the group consisting of

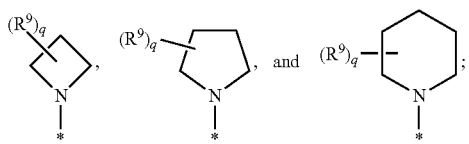

wherein the asterix indicates the point of attachment to the rest of the molecule.

5. The compound of claim 3, wherein Ring A is bicyclic.

6. The compound of claim 3, wherein Ring A is phenylene, naphthylene, benzothiophenylene, indazolylene, or quinolylene.

7. The compound of claim 3, wherein Ring A is phenylene and $R^7$ is phenyl or thienyl, each substituted with halogen.

8. The compound of claim 7, wherein $R^7$ is phenyl substituted with Cl or F, or $R^7$ is thienyl substituted with Cl.

9. The compound of claim 3, wherein the compound of Formula I is according to Formula I(a):

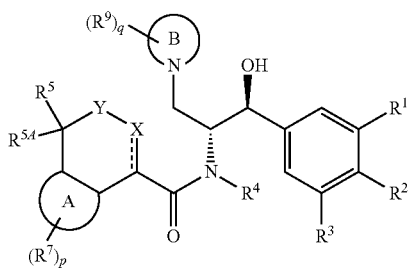

Formula I(a)

optionally as a single stereoisomer or mixture of stereoisomers thereof and additionally optionally as a pharmaceutically acceptable salt thereof.

10. The compound of claim 3, wherein the compound of Formula I is according to Formula I(b):

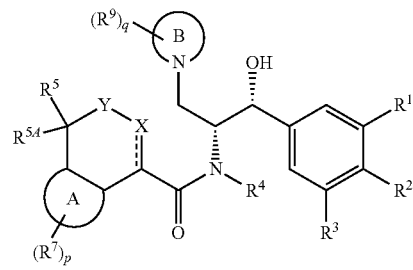

Formula I(b)

optionally as a single stereoisomer or mixture of stereoisomers thereof and additionally optionally as a pharmaceutically acceptable salt thereof.

11. The compound of claim 3, wherein the compound of Formula I is according to Formula II:

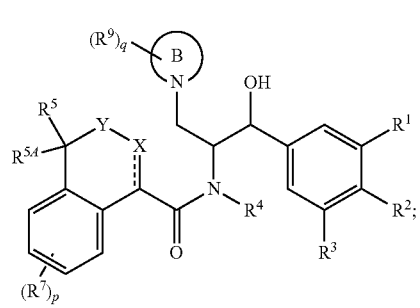

Formula II optionally as a single stereoisomer or mixture of stereoisomers thereof and additionally optionally as a pharmaceutically acceptable salt thereof.

12. The compound of claim 3, wherein p is 0 or 1.

13. The compound of claim 12, wherein q is 0.

14. The compound of claim 1, wherein the compound of Formula I is according to Formula XIII:

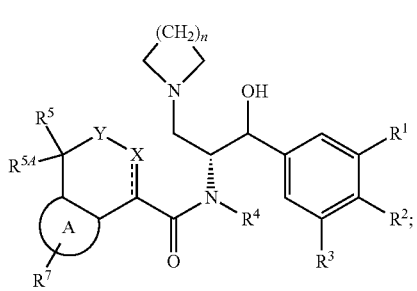

Formula XIII wherein $R^1$ is H; or $R^1$ and $R^2$ together form —$OCH_2CH_2O$—;

$R^2$ is $C_{3-6}$ cycloalkyloxy;

$R^3$ is H, Cl, or F;

$R^4$ is H or $C_{1-4}$ alkyl;

$R^5$ and $R^{5A}$ are each independently H or $C_{1-4}$ alkyl;

X is N or O, and when X is N, the dashed line is a bond to form a double bond, and when X is O, the dashed line is not a bond to form a single bond;

Y is $CH_2$, $CH(C_{1-4}$ alkyl), $C(C_{1-4}$ alkyl$)_2$, or O; with the proviso that X and Y are not both O;

Ring A is phenylene, naphthylene, benzothiophenylene, indazolylene, or quinolylene;

$R^7$ is Cl, F, $C_{1-6}$ alkyl, phenyl, or thienyl, where the phenyl and thienyl are each optionally substituted with $R^8$;

$R^8$ is Cl, F, or $C_{1-6}$ alkyl;

n is 1 or 2; and optionally a single stereoisomer or mixture of stereoisomers thereof and additionally optionally a pharmaceutically acceptable salt thereof.

15. The compound of claim 14, wherein the Ring A is phenylene, naphthylene or benzothiophenylene.

16. The compound of claim 1 selected from the group consisting of:

N-((1R,2R)-1-(3-chloro-4-cyclopropoxyphenyl)-1-hydroxy-3-(pyrrolidin-1-yl)propan-2-yl)-7-(4-fluorophenyl)-1H-benzo[d][1,2]oxazine-4-carboxamide;

N-((1R,2R)-1-(4-cyclopropoxy-3-fluorophenyl)-1-hydroxy-3-(pyrrolidin-1-yl)propan-2-yl)-7-(4-fluorophenyl)-1H-benzo[d][1,2]oxazine-4-carboxamide;

N-((1R,2R)-1-(8-fluoro-2,3-dihydrobenzo[b][1,4]dioxin-6-yl)-1-hydroxy-3-(pyrrolidin-1-yl)propan-2-yl)-7-(4-fluorophenyl-1H-benzo[d][1,2]oxazine-4-carboxamide;

N-((1R,2R)-1-(4-cyclopropoxyphenyl)-1-hydroxy-3-(pyrrolidin-1-yl)propan-2-yl)-7-(4-fluorophenyl)-1H-benzo[d][1,2]oxazine-4-carboxamide;

N-((1R,2R)-3-(azetidin-1-yl)-1-(3-chloro-4-cyclopropoxyphenyl)-1-hydroxypropan-2-yl)-7-(4-fluorophenyl)-1H-benzo[d][1,2]oxazine-4-carboxamide;

N-((1R,2R)-3-(azetidin-1-yl)-1-(4-cyclopropoxyphenyl)-1-hydroxypropan-2-yl)-7-(4-fluorophenyl)-1H-benzo[d][1,2]oxazine-4-carboxamide;

N-((1R,2R)-3-(azetidin-1-yl)-1-(4-cyclopropoxy-3-fluorophenyl)-1-hydroxypropan-2-yl)-7-(4-fluorophenyl)-1H-benzo[d][1,2]oxazine-4-carboxamide;

7-(5-chlorothiophen-2-yl)-N-((1R,2R)-1-(4-cyclopropoxy-3-fluorophenyl)-1-hydroxy-3-(pyrolidin-1-yl)propan-2-yl)-1H-benzo[d][1,2]oxazine-4-carboxamide;

N-((1R,2R)-3-(azetidin-1-yl)-1-(4-cyclopropoxy-3-fluorophenyl)-1-hydroxypropan-2-yl)-7-(5-chlorothiophen-2-yl)-1H-benzo[d][1,2]oxazine-4-carboxamide;

N-((1R,2R)-1-(3-chloro-4-cyclopropoxyphenyl)-1-hydroxy-3-(pyrrolidin-1-yl)propan-2-yl)-7-(5-chlorothiophen-2-yl)-1H-benzo[d][1,2]oxazine-4-carboxamide;

N-((1R,2R)-3-(azetidin-1-yl) 1-(4-cyclopropoxyphenyl)-1-hydroxypropan-2-yl-7-(5-chlorothiophen-2 yl)-1H-benzo[d][1,2]oxazine-4-carboxamide;

7-chloro-N-((1R,2R)-1-(4-cyclopropoxy-3-fluorophenyl)-1-hydroxy-3-(pyrrolidin-1-yl)propan-2-yl)-1H-benzo[4,5]thieno[2,3-d][1,2]oxazine-4-carboxamide;

7-chloro-N-((1R,2R)-1-(3-chloro-4-cyclopropoxyphenyl)-1-hydroxy-3-(pyrrolidin-1-yl)propan-2-yl)-1H-benzo[4,5]thieno[2,3-d][1,2]oxazine-4-carboxamide;

7-(5-chlorothiophen-2-yl)-N-((1R,2R)-1-(4-cyclopropoxyphenyl)-1-hydroxy-3-(pyrrolidin-1-yl)propan-2-yl)-1H-benzo[d][1,2]oxazine-4-carboxamide;

N-((1R,2R)-3-(azetidin-1-yl)-1-(4-cyclopropoxy-3-fluorophenyl)-1-hydroxypropan-2-yl)-7-chloro-1H-benzo[4,5]thieno[2,3-d][1,2]oxazine-4-carboxamide;

N-((1R,2R)-3-(azetidin-1-yl)-1-(3-chloro-4-cyclopropoxyphenyl)-1-hydroxypropan-2-yl)-7-chloro-1H-benzo[4,5]thieno[2,3-d][1,2]oxazine-4-carboxamide;

N-((1R,2R)-1-(4-cyclopropoxy-3-fluorophenyl)-1-hydroxy-3 (pyrrolidin-1-yl)propan-2-yl)-7-(4-fluorophenyl)-N-methyl-1H-benzo[d][1,2]oxazine-4-carboxamide;

7-(5-chlorothiophen-2-yl)-N-((1R,2R)-1-(4-cyclopropoxy-3-fluorophenyl)-1-hydroxy-3-(pyrolidin-1-yl)propan-2-yl)-N-methyl-1H-benzo[d][1,2]oxazine-4-carboxamide;

N-((1R,2R)-1-(3-chloro-4-cyclopropoxyphenyl)-1-hydroxy-3-(pyrrolidin-1-yl)propan-2-yl)-7-(4-fluorophenyl)-N-methyl-1H-benzo[d][1,2]oxazine-4-carboxamide;

N-((1R,2R)-1-(3-chloro-4-cyclopropoxyphenyl)-1-hydroxy-3-(pyrrolidin-1-yl)propan-2-yl)-1H-naphtho[2,3-d][1,2]oxazine-4-carboxamide;

N-((1R,2R)-3-(azetidin-1-yl)-1-(3-chloro-4-cyclopropoxyphenyl)-1-hydroxypropan-2-yl)-7-(4-fluorophenyl)-N-methyl-1H-benzo[d][1,2]oxazine-4-carboxamide;

N-((1R,2R)-(3-chloro-4-cyclopropoxyphenyl)-1-hydroxy-3-(pyrrolidin-1-yl)propan-2-yl)-1H-naphtho[2,1-d][1,2]oxazine-4-carboxamide;

N-((1R,2R)-1-(3-chloro-4-cyclopropoxyphenyl)-1-hydroxy-3-(pyrrolidin-1-yl)propan-2-yl)-7-(4-fluorophenyl)-1-methyl-1H-benzo[d][1,2]oxazine-4-carboxamide;

N-((1R,2R)-1-(3-chloro-4-cyclopropoxyphenyl)-1-hydroxy-3-(pyrrolidin-1-yl)propan-2-yl)-7-(4-fluorophenyl)-1-methyl-1H-benzo[d][1,2]oxazine-4-carboxamide;

N-((1R,2R)-1-(4-cyclopropoxyphenyl)-hydroxy-3-(pyrrolidin-1-yl)propan-2-yl)-1H-naphtho[2,1-d][1,2]oxazine-4-carboxamide;

N-((1R,2R)-3-(azetidin-1-yl)-1-(3-chloro-4-cyclopropoxyphenyl)-1-hydroxypropan-2-yl)-1H-naphtho[2,1-d][1,2]oxazine-4-carboxamide;

N-((1R,2R)-1-(3-chloro-4-cyclopropoxyphenyl)-1-hydroxy-3-(pyrrolidin-1-yl)propan-2-yl)-10H-[1,2]oxazino[4,5-h]quinoline-7-carboxamide;

N-((1R,2R)-1-(3-chloro-4-cyclopropoxyphenyl)-1-hydroxy-3-(pyrrolidin-1-yl)propan-2-yl)-8-fluoro-1H-naphtho[2,1-d][1,2]oxazine-4-carboxamide;

N-((1R,2R)-1-(4-cyclopropoxyphenyl)-1-hydroxy-3 (pyrrolidin-1-yl)propan-2-yl)-8-fluoro-1H-naphtho[2,1-d][1,2]oxazine-4-carboxamide;

N-((1R,2R)-3-(azetidin-1-yl)-1-(3-chloro-4-cyclopropoxyphenyl)-1-hydroxypropan-2-yl)-8-fluoro-1H-naphtho[2,1-d][1,2]oxazine-4-carboxamide;

N-((1R,2R)-3-(azetidin-1-yl)-1-(4-cyclopropoxyphenyl)-1-hydroxypropan-2-yl)-8-fluoro-1H-naphtho[2,1-d][1,2]oxazine-4-carboxamide;

8-chloro-N-((1R,2R)-1-(3-chloro-4-cyclopropoxyphenyl)-1-hydroxy-3-(pyrrolidin-1-yl)propan-2-yl)-1H-thieno[3',2':3,4]benzo[1,2-d][1,2]oxazine-4-carboxamide;

N-((1R,2R)-1-(3-chloro-4-cyclopropoxyphenyl)-1-hydroxy-3-(pyrrolidin-1-yl)propan-2-yl)-7-methyl-1,7-dihydro-[1,2]oxazino[5,4-e]indazole-4-carboxamide;

N-((1R,2R)-1-(3-chloro-4-cyclopropoxyphenyl)-1-hydroxy-3-(pyrrolidin-1-yl)propan-2-yl)-1-methyl-1,9-dihydro-[1,2]oxazino[4,5-g]indazole-6-carboxamide;

N-((1R,2R)-1-(3-chloro-4-cyclopropoxyphenyl)-1-hydroxy-3-(pyrrolidin-1-yl)propan-2-yl)-2-methyl-2,9-dihydro-[1,2]oxazino[4,5-g]indazole-6-carboxamide;

N-((1R,2R)-1-(3-chloro-4-cyclopropoxyphenyl)-1-hydroxy-3-(pyrrolidin-1-yl)propan-2-yl)-1H-[1,2]oxazino[5,4-f]quinoline-4-carboxamide;

2-chloro-N-((1R,2R)-1-(3-chloro-4-cyclopropoxyphenyl)-1-hydroxy-3-(pyrrolidin-1-ylpropan-2-yl)-9H-1-thieno[2',3':3,4]benzo[1,2-d][1,2]oxazine-6-carboxamide;

N-((1R,2R)-1-(4-cyclopropoxy-3-fluorophenyl)-1-hydroxy-3-(pyrrolidin-1-yl)propan-2-yl)-6-(4-fluorophenyl)-3,4-dihydroisoquinoline-1-carboxamide;

N-((1R,2R)-1-(3-chloro-4-cyclopropoxyphenyl)-1-hydroxy-3-(pyrrolidin-1 yl)propan-2-yl)-6-(4-fluorophenyl)-N-methyl-3,4-dihydroisoquinoline-1-carboxamide;

N-((1R,2R)-3-(azetidin-1-yl)-1-(4-cyclopropoxyphenyl)-1-hydroxypropan-2-yl)-6-(4-fluorophenyl)-3,4-dihydroisoquinoline-1-carboxamide;

N-((1R,2R)-1-(3-chloro-4-cyclopropoxyphenyl)-1-hydroxy-3-(pyrrolidin-1-yl)propan-2-yl-6-(4-fluorophenyl)-3,3-dimethyl-3,4-dihydroisoquinoline-1-carboxamide;

N-((1R,2R)-1-(3-chloro-4-cyclopropoxyphenyl)-1-hydroxy-3-(pyrrolidin-1-yl)propan-2-yl)-6-(4-fluorophenyl)isochroman-1-carboxamide;

7-chloro-N-(1R,2R)-1-(3-chloro-4-cyclopropoxyphenyl)-1-hydroxy-3-(pyrolidin-1-yl)propan-2-yl)-3,4-dihydro-1H-benzo[4,5]thieno[2,3-c]pyran-1-carboxamide;

8-chloro-N-((1R,2R)-1-(4-cyclopropoxyphenyl)-1 hydroxy-3-(pyrrolidin-1-yl)propan-2-yl)-1H-thieno[3',2':3,4]benzo[1,2-d][1,2]oxazine-4-carboxamide;

N-((1R,2R)-1-(3-chloro-4-cyclopropoxyphenyl)-1-hydroxy-3-(pyrrolidin-1-yl)propan-2-yl)-7-(cyclohexylmethoxy)-1H-benzo[d][1,2]oxazine-4-carboxamide;

N-(1R,2R)-1-(4-cyclopropoxy-3-fluorophenyl)-1-hydroxy-3-(pyrrolidin-1 yl)propan-2-yl)-1-methyl-1,9-dihydro-[1,2]oxazino[4,5-g]indazole-6-carboxamide; and 2-chloro-N-((1R,2R)-1-(4-cyclopropoxy-3-fluorophenyl)-1-hydroxy-3-(pyrrolidin-1-yl)propan-2-yl)-9H-thieno[2,3':3,4]benzo[1,2-d][1,2]oxazine-6-carboxamide; and optionally as a single stereoisomer or mixture of stereoisomers thereof and additionally optionally as a pharmaceutically acceptable salt thereof.

17. A pharmaceutical composition comprising i) a compound of claim 1 optionally as a single stereoisomer or mixture of stereoisomers thereof and additionally optionally as a pharmaceutically acceptable salt thereof, and ii) a pharmaceutically acceptable excipient.

18. A method of treating a disease or disorder comprising administering a compound of claim 1 or the pharmaceutical composition of claim 17, wherein the disease or disorder is Tay Sachs, Sandhoff's, GM1 gangliosidosis, Fabry, Gaucher, Niemanns-Pick, or polycystic kidney disease.

* * * * *